(12) United States Patent
Tiwari et al.

(10) Patent No.: US 11,260,153 B2
(45) Date of Patent: Mar. 1, 2022

(54) HOME RENAL THERAPY MACHINE

(71) Applicants: Baxter International Inc., Deerfield, IL (US); Baxter Healthcare SA, Glattpark (CH)

(72) Inventors: Neil Tiwari, Wood Dale, IL (US); Joshua James Miller, Wilmette, IL (US); Marc Steven Minkus, Bannockburn, IL (US); Matthew R. Muller, Lindenhurst, IL (US); Derek Wiebenson, Zurich (CH); Douglas L. Wilkerson, Gurnee, IL (US); Timothy G. Robinson, Easton, PA (US); Anders J. Wellings, Belleair Beach, FL (US); Kathryn Louise Hansbro, Bala Cynwyd, PA (US); Borut Cizman, Highwood, IL (US); Brian S. Kunzeman, Grayslake, IL (US); Robin D. Cooper, Wauconda, IL (US); Timothy L. Kudelka, Lindehurst, IL (US); Angelo A. Sarto, Franksville, WI (US); Steve Joseph Lindo, Chicago, IL (US); Jostein Baustad, Evanston, IL (US); Duston Mounts, The Colony, TX (US); Shafali Hill, Gurnee, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 187 days.

(21) Appl. No.: 16/429,781

(22) Filed: Jun. 3, 2019

(65) Prior Publication Data
US 2019/0287668 A1    Sep. 19, 2019

Related U.S. Application Data

(63) Continuation of application No. 15/709,714, filed on Sep. 20, 2017, now Pat. No. 10,311,970, which is a
(Continued)

(51) Int. Cl.
*A61M 1/14* (2006.01)
*A61M 1/28* (2006.01)
(Continued)

(52) U.S. Cl.
CPC ............ *A61M 1/14* (2013.01); *A61M 1/1603* (2014.02); *A61M 1/28* (2013.01); *A61M 1/282* (2014.02);
(Continued)

(58) Field of Classification Search
CPC . G06F 19/3468; A61M 1/1603; A61M 1/282; A61M 1/288; A61M 1/34
(Continued)

(56) References Cited

U.S. PATENT DOCUMENTS 3,769,964 A    11/1973   Smith
3,811,040 A    5/1974    Weinfurt et al.
(Continued)

FOREIGN PATENT DOCUMENTS

EP    2288397    3/2011
EP    2445395    5/2012
(Continued)

OTHER PUBLICATIONS

Notice of Opposition for related European Application No. 13727442.9; action dated Oct. 14, 2020; (49 pages).
(Continued)

*Primary Examiner* — Phillip A Gray
(74) *Attorney, Agent, or Firm* — K&L Gates LLP

(57) ABSTRACT

A renal therapy system is disclosed. In an example, a renal therapy system includes a dialysis fluid pump, a control
(Continued)

processor for controlling a treatment performed by the dialysis fluid pump, and a user interface device in operable communication with the control processor.

20 Claims, 101 Drawing Sheets

Related U.S. Application Data continuation of application No. 15/489,227, filed on Apr. 17, 2017, now Pat. No. 10,061,899, which is a continuation of application No. 13/828,900, filed on Mar. 14, 2013, now Pat. No. 10,089,443.

(60) Provisional application No. 61/647,340, filed on May 15, 2012.

(51) Int. Cl.
| | |
|---|---|
| *G06F 8/65* | (2018.01) |
| *G16H 40/63* | (2018.01) |
| *G16H 40/40* | (2018.01) |
| *G16H 10/60* | (2018.01) |
| *G06Q 30/06* | (2012.01) |
| *A61M 1/16* | (2006.01) |
| *A61M 1/34* | (2006.01) |
| *A61M 1/36* | (2006.01) |
| *G16H 20/17* | (2018.01) |
| *G16H 20/40* | (2018.01) |
| *G16H 40/67* | (2018.01) |
| *G16H 20/10* | (2018.01) |

(52) U.S. Cl.
CPC .............. *A61M 1/288* (2014.02); *A61M 1/34* (2013.01); *A61M 1/36* (2013.01); *G06F 8/65* (2013.01); *G06Q 30/0601* (2013.01); *G16H 10/60* (2018.01); *G16H 20/10* (2018.01); *G16H 20/17* (2018.01); *G16H 20/40* (2018.01); *G16H 40/40* (2018.01); *G16H 40/63* (2018.01); *G16H 40/67* (2018.01); *A61M 2205/3553* (2013.01); *A61M 2205/3584* (2013.01); *A61M 2205/50* (2013.01)

(58) Field of Classification Search
USPC .......................................................... 604/29
See application file for complete search history.

(56) References Cited

U.S. PATENT DOCUMENTS

| | | | |
|---|---|---|---|
| 3,831,816 A | 8/1974 | Pauliukonis | |
| 3,983,871 A | 10/1976 | Gurtovoi et al. | |
| 4,262,674 A | 4/1981 | Uemura et al. | |
| 4,324,662 A | 4/1982 | Schnell | |
| 4,356,827 A | 11/1982 | Uemura et al. | |
| 4,540,413 A | 9/1985 | Russo | |
| 4,698,057 A | 10/1987 | Joishy | |
| 4,889,132 A | 12/1989 | Hutcheson et al. | |
| 4,890,625 A | 1/1990 | Sorensen | |
| 5,022,403 A | 6/1991 | LaViola | |
| 5,247,434 A | 9/1993 | Peterson et al. | |
| 5,326,476 A | 7/1994 | Grogan et al. | |
| 5,411,472 A | 5/1995 | Steg, Jr. et al. | |
| 5,486,286 A | 1/1996 | Peterson et al. | |
| 5,487,827 A | 1/1996 | Peterson et al. | |
| 5,640,960 A | 6/1997 | Jones et al. | |
| 5,702,606 A | 12/1997 | Peter, Jr. et al. | |
| 5,744,027 A | 4/1998 | Connell et al. | |
| 5,853,005 A | 12/1998 | Scanlon | |
| 5,997,496 A | 12/1999 | Sekiguchi et al. | |
| 6,066,261 A | 5/2000 | Spickermann | |
| 6,134,458 A | 10/2000 | Rosenthal | |
| 6,162,181 A | 12/2000 | Hynson et al. | |
| 6,341,229 B1 | 1/2002 | Akiva | |
| 6,554,789 B1 | 4/2003 | Brugger et al. | |
| 6,582,365 B1 | 6/2003 | Hines et al. | |
| 6,623,443 B1 | 9/2003 | Polaschegg | |
| 6,638,477 B1 | 10/2003 | Treu et al. | |
| 6,638,478 B1 | 10/2003 | Treu et al. | |
| 6,736,789 B1 | 5/2004 | Spickermann | |
| 6,786,872 B2 | 9/2004 | Narimatsu et al. | |
| 6,830,553 B1 | 12/2004 | Burbank et al. | |
| 6,852,090 B2 | 2/2005 | Burbank et al. | |
| 6,880,404 B2 | 4/2005 | Uberreiter | |
| 6,881,194 B2 | 4/2005 | Miyata et al. | |
| 6,979,309 B2 | 12/2005 | Burbank et al. | |
| 7,044,927 B2 | 5/2006 | Mueller et al. | |
| 7,147,613 B2 | 12/2006 | Burbank et al. | |
| 7,172,570 B2 | 2/2007 | Cavalcanti et al. | |
| 7,207,944 B2 | 4/2007 | Fumuro et al. | |
| 7,264,730 B2 | 9/2007 | Connell et al. | |
| 7,267,658 B2 | 9/2007 | Treu et al. | |
| 7,300,413 B2 | 11/2007 | Burbank et al. | |
| 7,303,680 B2 | 12/2007 | Connell et al. | |
| 7,309,323 B2 | 12/2007 | Gura et al. | |
| 7,318,892 B2 | 1/2008 | Connell et al. | |
| 7,338,460 B2 | 3/2008 | Burbank et al. | |
| 7,347,849 B2 | 3/2008 | Brugger et al. | |
| 7,351,340 B2 | 4/2008 | Connell et al. | |
| 7,473,238 B2 | 1/2009 | Brugger et al. | |
| 7,537,688 B2 | 5/2009 | Tarumi et al. | |
| 7,575,562 B2 | 8/2009 | Oishi et al. | |
| 7,648,474 B2 | 1/2010 | Paolini et al. | |
| 7,780,619 B2 | 8/2010 | Brugger et al. | |
| 7,890,341 B2 | 2/2011 | McNally et al. | |
| 7,892,196 B2 | 2/2011 | Gura et al. | |
| 7,896,829 B2 | 3/2011 | Gura et al. | |
| 8,038,640 B2 | 10/2011 | Orr | |
| 8,152,751 B2 | 4/2012 | Roger et al. | |
| 8,192,388 B2 | 6/2012 | Hogard | |
| 8,197,231 B2 | 6/2012 | Orr | |
| 8,197,431 B2 | 6/2012 | Bennison | |
| 8,197,439 B2 | 6/2012 | Wang et al. | |
| 8,303,807 B2 | 11/2012 | Zhang | |
| 8,418,696 B2 | 4/2013 | Marasco | |
| 8,419,646 B2 | 4/2013 | Saito et al. | |
| 8,580,112 B2 | 11/2013 | Updyke et al. | |
| 8,684,927 B2 | 4/2014 | Basaglia | |
| 8,702,614 B2 | 4/2014 | Baym et al. | |
| 8,702,683 B2 | 4/2014 | Baym et al. | |
| 8,715,216 B2 | 5/2014 | Olde et al. | |
| 8,718,957 B2 | 5/2014 | Furmanski et al. | |
| 8,795,517 B2 | 8/2014 | Lannoy | |
| 8,932,032 B2 | 1/2015 | Orr | |
| 9,060,697 B2 | 6/2015 | Uesaka et al. | |
| 9,078,971 B2 | 7/2015 | Scarpaci et al. | |
| 9,117,012 B2 | 8/2015 | Basaglia | |
| 9,138,536 B2 | 9/2015 | Stefani et al. | |
| 9,192,702 B2 | 11/2015 | Orejola et al. | |
| 9,289,544 B2 | 3/2016 | Olde et al. | |
| 2002/0077557 A1 | 6/2002 | Cheng | |
| 2004/0111294 A1 | 6/2004 | McNally et al. | |
| 2005/0234385 A1 | 10/2005 | Vandlik | |
| 2006/0270530 A1 | 11/2006 | Santo | |
| 2010/0010426 A1* | 1/2010 | Childers ................ | A61M 1/28 604/29 |
| 2011/0066692 A1 | 3/2011 | Basaglia | |
| 2011/0066693 A1 | 3/2011 | Basaglia | |
| 2011/0072422 A1 | 3/2011 | Brauer | |
| 2011/0246220 A1 | 10/2011 | Albert | |
| 2011/0320216 A1 | 12/2011 | Kasmark | |
| 2013/0006128 A1 | 1/2013 | Olde et al. | |
| 2013/0006130 A1 | 1/2013 | Olde et al. | |
| 2013/0023776 A1 | 1/2013 | Olde et al. | |
| 2013/0096402 A1 | 4/2013 | Olde et al. | |
| 2014/0231319 A1 | 8/2014 | Olde et al. | |
| 2014/0243612 A1 | 8/2014 | Li et al. | |
| 2016/0022158 A1 | 1/2016 | Lee et al. | |
| 2016/0206804 A1 | 7/2016 | Holmer et al. | |

(56) References Cited

U.S. PATENT DOCUMENTS

| | | |
|---|---|---|
| 2016/0217265 A1 | 7/2016 | Miller et al. |
| 2016/0270733 A1 | 9/2016 | Hansson et al. |
| 2017/0153191 A1 | 6/2017 | Jones et al. |

FOREIGN PATENT DOCUMENTS

| | | |
|---|---|---|
| EP | 2519276 | 11/2012 |
| EP | 2519278 | 11/2012 |
| EP | 2519280 | 11/2012 |
| EP | 2723419 | 4/2014 |
| EP | 2872193 | 5/2015 |
| EP | 2934622 | 10/2015 |
| EP | 2976006 | 1/2016 |
| EP | 3043698 | 7/2016 |
| JP | 2010-152878 | 7/2010 |
| JP | 2011-527617 | 11/2011 |
| KR | 100730991 | 6/2007 |
| KR | 20090061806 | 6/2009 |
| WO | 93/01845 | 2/1993 |
| WO | WO2004053768 A2 | 6/2004 |
| WO | 2016206946 | 12/2016 |
| WO | 2016206948 | 12/2016 |
| WO | 2016206949 | 12/2016 |
| WO | 2016206950 | 12/2016 |

OTHER PUBLICATIONS

Department of Heath and Human Services; "Federal Register, Part II"; Feb. 20, 2003; (49 pages).
Network Working Group; "Post Office Protocol—Version 3"; May 1996; (23 pages).
Peter Mell, et al.; "Procedures for Handling Security Patches"; National Institute of Standards and Technology; Aug. 2002; (100 pages).
Network Working Group; "ECML v1.1: Field Specifications for E-Commerce"; Apr. 2001; (20 pages).
Carzaniga, et al.; "A Characterization Framework for Software Deployment Technologies"; Apr. 1998; University of Colorado, Department of Computer Science; (24 pages).
Defense Advanced Research Projects Agency; "Internet Protocol—DARPA Internet Program Protocol Specification"; Sep. 1981; (50 pages).
Wikipedia; "Datenbank"; http://web.archive.org/web/20120504194220/https://de.wikipedia.org; Aug. 31, 2020; (7 pages).
Australian Examination Report for related Australian Application No. 2019279973; action dated Jun. 4, 2020; (5 pages).
Chinese Office Action for related Chinese Application No. 201380031530.6; action dated Dec. 15, 2017 (17 pages).
Mexican Office Action for related Mexican Application No. MX/a/2014/013920; action dated Jan. 30, 2018.
Canadian Office Action for related Canadian Applicaiton No. 2,873,621; action dated Nov. 29, 2017 ( 5 pages).
Extended European Search Report dated Feb. 18, 2020, issued in related European Patent Application No. 19206745.2—12 Pages.

* cited by examiner

HOME RENAL THERAPY MACHINE

PRIORITY CLAIM

This application claims priority to and the benefit as a continuation application of U.S. patent application Ser. No. 15/709,714, now U.S. Pat. No. 10,311,970, entitled "RENAL THERAPY MACHINE AND SYSTEM WITH BLOOD PRESSURE MONITOR", filed Sep. 20, 2017, which is a continuation of U.S. patent application Ser. No. 15/489,227, now U.S. Pat. No. 10,061,899, entitled "HOME THERAPY MACHINE", filed Apr. 17, 2017, which is a continuation application of U.S. patent application Ser. No. 13/828,900, now U.S. Pat. No. 10,089,443, entitled "HOME MEDICAL DEVICE SYSTEMS AND METHODS FOR THERAPY PRESCRIPTION AND TRACKING, SERVICING AND INVENTORY", filed Mar. 14, 2013, which claims priority to U.S. Provisional Patent Application No. 61/647,340, entitled "HOME MEDICAL DEVICE SYSTEMS AND METHODS FOR THERAPY PRESCRIPTION AND TRACKING, SERVICING AND INVENTORY", filed May 15, 2012, the entire contents of each of which are incorporated herein by reference and relied upon.

CROSS REFERENCE TO COMMONLY OWNED RELATED PATENTS AND APPLICATIONS

This patent application is related to U.S. patent application Ser. No. 12/170,184 filed Jul. 9, 2008 (now U.S. Pat. No. 7,981,281), U.S. patent application Ser. No. 12/170,172 filed Jul. 9, 2008 (now U.S. Pat. No. 8,168,063), U.S. patent application Ser. No. 12/170,204 filed Jul. 9, 2008 (published on Jan. 14, 2010 as U.S. Patent Publication No. 2010/0010426), U.S. patent application Ser. No. 13/274,012 filed Oct. 14, 2011 (now U.S. Pat. No. 8,313,642), which is a continuation of U.S. patent application Ser. No. 12/170,220 filed Jul. 9, 2008 (now U.S. Pat. No. 8,057,679), U.S. patent application Ser. No. 13/251,901 filed Oct. 3, 2011 (now U.S. Pat. No. 8,257,582), which is a continuation of U.S. patent application Ser. No. 12/170,230 filed Jul. 9, 2008 (now U.S. Pat. No. 8,062,513), and U.S. Patent Application Ser. No. 61/647,340 filed May 15, 2012, the contents of each of which are herein incorporated by reference in their entirety and relied upon.

BACKGROUND

The present disclosure relates generally to renal therapy systems and more specifically to systems and methods for prescribing, tracking, servicing and organizing home medical devices.

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

Hemodialysis and peritoneal dialysis are two types of dialysis therapies commonly used to treat loss of kidney function. Hemodialysis treatment uses the patient's blood to remove waste, toxins and excess water from the patient. The patient is connected to a hemodialysis machine and the patient's blood is pumped through the machine. Catheters are inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood back to the patient. A large amount of dialysate, for example about one-hundred twenty liters, is used to dialyze the blood during a single hemodialysis treatment. The spent dialysate is then discarded. Hemodialysis treatment lasts several hours and is generally performed in a treatment center about three or four times per week.

Peritoneal dialysis uses a dialysis solution or "dialysate", which is infused into a patient's peritoneal cavity through a catheter implanted in the cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, i.e., an osmotic gradient occurs across the membrane. The spent dialysate drains from the patient's peritoneal cavity and removes the waste, toxins and excess water from the patient. This cycle is repeated.

There are various types of peritoneal dialysis therapies, including continuous ambulatory peritoneal dialysis ("CAPD"), automated peritoneal dialysis and continuous flow peritoneal dialysis. CAPD is a manual dialysis treatment, in which the patient connects an implanted catheter to a drain and allows a spent dialysate fluid to drain from the peritoneal cavity. The patient then connects the catheter to a bag of fresh dialysate and manually infuses fresh dialysate through the catheter and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient repeats the manual dialysis procedure.

In CAPD the patient performs several drain, fill, and dwell cycles during the day, for example, about four times per day. Each treatment cycle typically takes about an hour. Manual peritoneal dialysis performed by the patient requires a significant amount of time and effort from the patient. This inconvenient procedure leaves ample room for improvement and therapy enhancements to improve patient quality of life.

Automated peritoneal dialysis ("APD") is similar to CAPD in that the dialysis treatment includes a drain, fill, and dwell cycle. APD machines, however, automatically perform three to four cycles of peritoneal dialysis treatment, typically overnight while the patient sleeps. The APD machines fluidly connect to an implanted catheter. The APD machines also fluidly connect to a source or bag of fresh dialysate and to a fluid drain.

The APD machines pump fresh dialysate from the dialysate source, through the catheter, into the patient's peritoneal cavity and allow the dialysate to dwell within the cavity so that the transfer of waste, toxins and excess water from the patient's bloodstream to the dialysate solution can take place. The APD machines then pump spent dialysate from the peritoneal cavity, though the catheter, to the drain. APD machines are typically computer controlled so that the dialysis treatment occurs automatically when the patient is connected to the dialysis machine, for example, when the patient sleeps. That is, the APD systems automatically and sequentially pump fluid into the peritoneal cavity, allow for a dwell, pump fluid out of the peritoneal cavity and repeat the procedure.

As with the manual process, several drain, fill, and dwell cycles will occur during APD. A "last fill" is typically used at the end of APD, which remains in the peritoneal cavity of the patient when the patient disconnects from the dialysis machine for the day. APD frees the patient from having to manually perform the drain, dwell, and fill steps.

For patients suffering from renal diseases, frequent dialysis is a way of life. Most peritoneal dialysis patients perform dialysis once a day. Hemodialysis patients typically require dialysis several times a week. To allow patients to continue to live their lives as normally as possible, there has been an increased desire to provide home dialysis solutions. Peritoneal dialysis is typically performed at home. Hemodialysis and other blood treatment therapies, such as hemofiltration, are performed largely in centers and clinics.

Performing hemodialysis at home presents more challenges and complexity than peritoneal dialysis because blood is actually removed from a patient for cleaning. Hemodialysis may require a water treatment system to prepare dialysate online. Home hemodialysis may also require some form of patient supervision. Home hemodialysis can also be complicated by the fact that the patient's treatment prescription may change over time and that patients may have multiple treatment prescriptions. Also, consumables used in hemodialysis can be expensive. Their use, efficacy and inventory should be tightly monitored. Hemodialysis machines may also require maintenance or service from a skilled technician. It is thus desirable to have a way to manage service calls to a patient's home to keep the machines running correctly. A schedule may also be needed for the delivery of the necessary consumables without delivering more than needed and risking waste of consumables.

It is desirable to transfer the results of treatment for both home peritoneal dialysis and hemodialysis. The results should be accurate, timely and provide the level of detail that clinicians expect from in-clinic therapies. It is also desirable for clinicians to modify prescriptions.

A need accordingly exists for a home dialysis system, for both peritoneal dialysis and hemodialysis, that provides at least some of the above-described features.

SUMMARY

The present system and method involve a medical device infrastructure that integrates many aspects of providing home renal therapy. The system and method in one embodiment integrates the training of patients to properly use various medical devices, transferring data to a central repository maintained by a therapy provider, providing reports of treatment data to clinicians, integrating with billing and ordering systems, tracking consumables usage and delivering consumables as needed, and servicing and maintaining the machines on a network of the system.

In one embodiment, a home medical device system includes a plurality of home medical devices including a renal therapy machine, such as, but not limited to, a home hemodialysis ("HD") machine, a home peritoneal dialysis ("PD") machine, a home hemofiltration ("HF") machine, a home hemodiafiltration ("HDF") machine, and a home continuous renal replacement ("CRRT") machine. While renal therapy is one focus of the present disclosure, the present disclosure also contemplates the integration of any home fluid delivery therapy, such as in addition, a home drug delivery therapy or a nutritional therapy. The machine may be at the home of the patient, or any other dwelling, such as, for example, a hotel room, vacation home, temporary shelter, nursing home, etc. The medical device system includes a system hub coupled to the renal therapy machine through a connectivity server, a web portal configured to access the system hub, and an enterprise resource planning system coupled to the system hub. The enterprise resource planning system may store a doctor's prescription for example. Renal therapy, for example, according to the prescription is performed by a home medical machine on a patient.

In one embodiment, the home medical device system also includes a method for home renal therapy training. A patient is trained on a first renal therapy machine in a clinic. A unique patient identification ("ID") is generated for that patient. A second renal therapy machine is sent to the patient's home. The second renal therapy machine is linked to the patient by entering the patient ID. The second renal therapy machine is then used by the patient for home renal therapy. The second machine is at least substantially similar to the first machine so that the patient is already familiar with the machine and the corresponding therapy.

In one embodiment, the home medical device system also includes a method for obtaining and transferring treatment prescriptions. A doctor's prescription for a renal or other type of therapy is retrieved. A clinician can remotely select, based upon the doctor's prescription, supplies to send to the patient's home, such as a dialyzer. The clinician can also remotely set settings for operating the renal therapy machine according to the prescription. The settings can be in the form of parameters or ranges that allow the patient to select a value within the range. Any selection is doctor approved. Nevertheless, the patient has some input into the treatment that the home therapy machine performs. The clinician may remotely update the settings for the renal therapy machine. The supplies and the treatment program for the renal therapy machine are sent to the patient and the patient performs renal treatment at home according to the settings.

In one embodiment, the system includes a method for safely allowing network or internet access. A connectivity agent resides on each renal therapy machine. The connectivity agent is turned off before each treatment and is turned on after the renal therapy machine is finished with the treatment. This way, the network connection cannot interrupt treatment. In one embodiment, the connectivity agent is not turned on until the renal therapy machine is finished disinfecting itself. During treatment, the renal therapy machine generates log files that document events that occur during treatment. The connectivity agent sends the log files to a connectivity server after treatment is completed, or alternatively after disinfection. In one embodiment, before each treatment and before the connectivity agent is turned off, the renal therapy machine checks whether the connectivity server has any updates or modifications to the renal therapy machine settings.

In one embodiment, the system includes a method for upgrading firmware on a renal therapy machine. When upgraded firmware is generated, a director, e.g., a service director, may need to approve the upgraded firmware. The director may for example decide that renal therapy machines in only certain regions should receive the upgraded firmware. Authority is given by the director to local service personnel. The service personnel work closely with their patients and their associated renal therapy machines and are allowed leeway for when to actually upgrade the firmware on the service person's approved renal therapy machines. In one embodiment, the system includes a method for securely adding users and submitting new device programs. When certain changes are made to settings within the system, the system may require additional authentication information from the user. Or, the system may require another user to agree with certain changes before the changes are implemented.

The present systems and methods also manage and keep track of consumables at a patient's home. In one embodiment, a large number of patient prescriptions for a given patient can be supported. The duration of use of the machine and components thereof are also tracked. Machine performance is also tracked. When a machine component expires or shows signs of disrepair, a local service person assigned to monitor the particular machine notices same and schedules a service call.

The present systems and methods store large amounts of treatment and associated data. In one embodiment, sensitive patient data is stored in a Health Insurance Portability and Accountability Act ("HIPAA") compliant database, billing and ordering information is stored in a billing and ordering database, and customer management information is stored in a customer relationship database.

While dialysis, such as hemodialysis, is one type of therapy that can be implemented at home via the systems and method of the present disclosure, other blood therapies, such as hemofiltration, hemodiafiltration, continuous renal replacement therapy ("CRRT") may alternatively or additionally be implemented at the patient's home. Other dialysis treatments, such as peritoneal dialysis, may alternatively or additionally be implemented at the patient's home. Other home-related therapies, such as nutritional supplementing or medical delivery of a drug via one or more infusion pump may alternatively or additionally be implemented. With any of these therapies, it is contemplated to train the patient initially using the system and method of the present disclosure at a training facility or a hospital.

Based on the foregoing and following description, it should be appreciated that it is an advantage of the present disclosure to provide a high level of supervision and reporting for home renal therapy.

It is another advantage of the present disclosure to provide an efficient and timely inventory management system for home renal therapy consumables.

It is a further advantage of the present disclosure to provide a reliable maintenance and service infrastructure.

It is yet another advantage of the present disclosure to provide clinicians, doctors and nurses the ability to remotely review and monitor treatment data and to modify and update settings of the renal therapy machines.

It is yet a further advantage of the present disclosure to provide easy to use and secure user interfaces for specifying supplies and for specifying settings of the renal therapy machines via the development and remote transfer of one or more therapy prescriptions for the patient.

It is yet another advantage of the present disclosure to provide training to familiarize patients with the renal therapy and to allow patients flexibility in administering the treatment at home.

It is yet another advantage of the present disclosure to conveniently provide and transfer customized software for a user interface of the renal therapy machine.

It is a further advantage of the present disclosure to provide a reliable verification technique for verifying that correct types and amounts of consumables are used at home with the renal therapy machines.

Moreover, it is an advantage of the present disclosure to provide multiple home medical devices all working cohesively to reliably recreate the in-clinic dialysis experience in the convenience of a patient's home.

Additional features and advantages are described herein and will be apparent from the following Detailed Description and the figures.

BRIEF DESCRIPTION OF THE FIGURES

FIG. 14B is another screen shot of an example treatment summary screen of the present disclosure.

FIG. 18A is a screen shot of a users screen of the present disclosure.

FIG. 18B is another screen shot of a users screen of the present disclosure.

FIG. 18E is yet a further screen shot of a users screen of the present disclosure.

FIG. 28 is a screen shot of an example daily complaints report of the present disclosure.

FIG. 29 is a screen shot of an example complaints reconciliation report of the present disclosure.

FIG. 32B is a screen shot of a further example treatment summary screen of the present disclosure.

FIG. 34B is a screen shot of another example device program screen of the present disclosure.

FIG. 40C is a screen shot of a further example patient information screen of the present disclosure.

FIG. 41A is a screen shot of an example add patient screen of the present disclosure.

FIG. 41B is a screen shot of another example add patient screen of the present disclosure.

FIG. 45B is a screen shot of another example patient order screen for a patient of the present disclosure.

FIG. 45E is a screen shot of yet a further example patient order screen for a patient of the present disclosure.

DETAILED DESCRIPTION

Figure 1A:
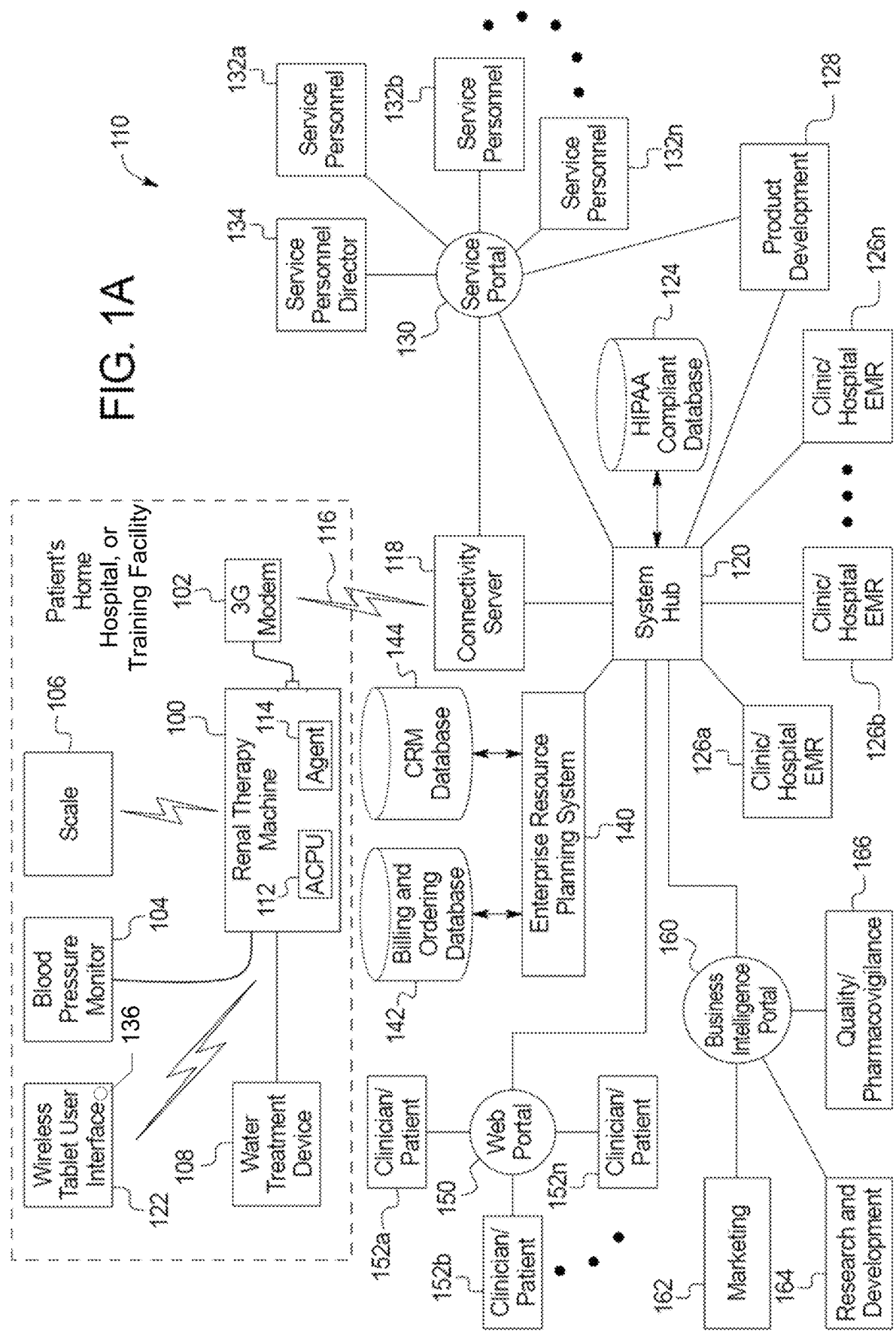
FIG. 1A is a schematic block diagram of one embodiment of a home medical device system of the present disclosure.

Referring now to the drawings and in particular to FIG. 1A, a home medical device system 110 includes, among many other features discussed below, a renal therapy machine 100, a wireless scale 106, a wireless tablet user interface 122, a blood pressure monitor 104, a water treatment device 108 and a modem 102. The components listed are in general the components located within the patient's home, as indicated by the dotted lines in FIG. 1A. Machine 100 may be located at the patient's home or any other dwelling, such as for example, a hotel room, vacation room, temporary shelter, nursing home, a vacation home or a corporate apartment provided by an employer of the patient. If renal therapy machine 100 is a home hemodialysis machine, one suitable machine is set forth in U.S. Patent Publication No. 2009/0101549, entitled, "Modular Assembly For A Hemodialysis System", filed Aug. 27, 2008, the entire contents of which are incorporated herein by reference and relied upon. One suitable water treatment device 108 is set forth in U.S. Patent Publication No. 2011/0197971, entitled, "Water Purification System And Method", filed Apr. 25, 2011, the entire contents of which are incorporated herein by reference and relied upon.

The renal therapy machine 100 is in general the nexus or hub between the components at the patient's home and can communicate with devices 104, 106, 108 and 122. The scale 106, blood pressure monitor 104, tablet 122, and water treatment device 108 communicate in one embodiment only with renal therapy machine 100. Any of components 104, 106, 108 and 122 may communicate wirelessly with renal therapy machine 100 or be in wired communication with same. Wireless communication may be via Bluetooth™ or WiFi™ wireless communication technology. Alternatively, any of components 104, 106, 108 and 122 can communicate with renal therapy machine 100 via wired communication.

The blood pressure monitor 104 may be provided with a blood pressure module that plugs into the renal therapy machine 100. For example, the blood pressure module of monitor 104 may include a printed circuit board controller that plugs into a controller bus of machine 100. The module of monitor 104 communicates thereafter via data bus communication with a primary control processor ("ACPU") 112. The blood pressure module of monitor 104 is connected pneumatically to a blood pressure cuff that extends outside of machine 100. The patient then presses a button on user interface 122, e.g., a wireless tablet user interface, to pressurize the cuff. The cuff may be pressurized via pneumatics located within therapy machine 100. Or, the module of monitor 104 may be provided with its own small pneumatic air pump that inflates the cuff. The patient's blood pressure is logged by ACPU 112 and may be read out to the patient on one or both of the cuff of monitor 104 or user interface 122. One suitable module for blood pressure monitor 104 is provided by Microlife, model 3AC1-PC, which is embedded into renal therapy machine so only the tube and the cuff of blood pressure monitor 104 are visible to a patient. Again, monitor and cuff 104 may be wireless alternatively.

The patient weighs himself or herself via scale 106. The weight is then sent to ACPU 112, e.g., via wired or wireless communication. ACPU 112 uses the weight in one embodiment to calculate how much ultrafiltration or ultrafiltrate ("UF") is removed from the patient. One suitable wireless weight scale 106 is provided by LifeSource (A&D)®, model UC-321PBT. In a further alternative embodiment, the patient weighs himself or herself and enters that value into system 110, e.g., via tablet user interface 122.

The water treatment device 108 connects to the renal therapy machine 100 through an Ethernet cable in one embodiment. The water treatment device 108 is normally powered. The renal therapy machine 100 can request water as needed from water treatment device 108. Water treatment device 108 is configured to supply, on an online basis, any amount of water that machine 100 needs. Renal therapy machine 100 controls and receives data from the water treatment device 108. In one embodiment, the tablet 122 does not control water treatment device 108. Instead, water treatment device 108 is a slave to the programmed ACPU 112. The water treatment device 108 can inform the renal therapy machine 100 of its status, such as an alarm situation, and send any other pertinent data to ACPU 112. Renal therapy machine 100 stores and acts upon the data, e.g., decides whether to raise an alarm. Water treatment device 108 in an embodiment include a small user interface and display.

In one embodiment, the renal therapy machine 100 performs hemodialysis on a patient at the patient's home and then reports the results of that treatment to clinicians, doctors and nurses who are responsible for managing the health and well-being of that patient. To generate reports, renal therapy machine 100 can use a Linux™ operating system operated by ACPU 112. Renal therapy machine 100 writes log files using the operating system. The log files document pertinent parameters and activities of the renal therapy machine 100 and the patient over the course of treatment. The log files may be any one or more of Extensible Markup Language ("XML"), comma-separated values ("CSV") or text files. The log files are placed into a file server box of the software of renal therapy machine 100. The treatment may take several hours and have many steps and sub-steps, each yielding logged data. As illustrated in FIG. 1A, in one embodiment, tablet 122 includes a camera 136. The tablet 122 may use camera 136 to take photographs or videos of the patient as the renal therapy machine 100 performs therapy. For example, a patient may be able to photograph inflammation of the skin caused by insertion of a needle into the patient's vein or artery. The log files may include photos or videos recorded with camera 136.

In one embodiment, ACPU 112 and user interface 122 of renal therapy machine 100 walk the patient through the entire treatment process and instruct the patient on a step-by-step basis to perform the treatment. The user interface screens are standardized but are populated with data that machine 100 receives from clinicians (as described in detail below). The instructions are according to a doctor's prescription and provide parameters by which machine 100 operates, such as the blood flowrate, dialysate flowrate and ultrafiltrate volume. Renal therapy machine 100 performs a treatment and records that the treatment has been performed according to the parameters. Errors, alerts, alarm conditions and whether or not treatment steps have been successfully performed are recorded. The renal therapy machine 100 records this information by creating the log files that document each treatment.

The treatment may occur over several hours. After the treatment, the renal therapy machine 100 instructs the patient to disconnect from the machine. The renal therapy machine 100 then enters into a disinfection mode and prepares itself for the next treatment, which may take place the next day or a few days later. The water treatment device 108, which provides water to the renal therapy machine 100 as needed, also records and maintains its own log files that document the actions taken by the water treatment device 108 and any alarm or alert events that occur over a treatment. The water treatment device 108 in one embodiment does not write directly to the log files of renal therapy machine 100 log files. Renal therapy machine 100 may however include some data or parameters sent from water treatment device 108 that machine 100 records in its own log files. For example, the renal therapy machine 100 may record how much water treatment device 108 has made and delivered to machine 100 and add that information to the machine's own log files. Data stored on water treatment device 108 that is not sent to machine 100 may otherwise be obtained via the Ethernet data connection to water treatment device 108. For example, a service person can access the additional data via a laptop connection to water treatment device 108 via the Ethernet connection.

In one embodiment, the user interface 122 is a tablet that runs a custom, secure interface that only allows access to the renal therapy machine 100. In one implementation, tablet 122 operates wirelessly. Tablet 122 here can plug into the renal therapy machine 100 initially for pairing the tablet 122 with the renal therapy machine 100 and for performing software (e.g., firmware) upgrades. Tablet 122 may also plug into the renal therapy machine 100 to power or charge the tablet 122. Connectivity between tablet 122 and renal therapy machine 100 may be via a serial data connection, over a universal serial bus ("USB") connection, parallel connection or via another suitable data transfer interface. Once the tablet 122 is paired to the renal therapy machine 100, the tablet 122 communicates wirelessly (e.g., using Bluetooth™ or WiFi™) with the renal therapy machine 100.

In one embodiment, renal therapy machine 100 is Bluetooth™ or WiFi™ enabled via an associated chip located with the other electronics of machine 100, e.g., with ACPU 112 discussed below. If it is found however that having a Bluetooth™ or WiFi™ chip on a renal therapy machine 100 circuit board (inside the renal therapy machine 100) causes electromagnetic interference with the circuit board, tablet 122 may alternatively use a Bluetooth™ dongle, WiFi™ dongle or other like device that plugs removably into the renal therapy machine 100, e.g., over a USB connection, which adds Bluetooth™ functionality, for example, to a non-Bluetooth™ device.

In one embodiment, tablet 122 serves as a user interface to the renal therapy machine 100 in the sense that the user can send data to and receive data from machine 100 via tablet 122. Data entered into the user interface is securely sent to the renal therapy machine 100 and processed in ACPU 112, which actually controls the machine. In one embodiment, all treatment data is stored in the renal therapy machine 100, not the tablet 122. Storing no treatment data in the tablet 122 is advantageous because if the tablet 122 is disconnected or lost no sensitive or important data is lost.

While user interface 122 is described below as a wireless user interface, mainly, user interface can alternatively be tethered to machine 100, for example, as shown and described in U.S. Patent Publication No. 2009/0114582, the entire contents of which are incorporated herein by reference and relied upon. Unless otherwise stated, however, the functional relationship between user interface 122 and machine 100 remains the same.

In one embodiment, tablet 122 runs a customized version of the Android™ operating system. The standard Android™ operating system displays a toolbar that always remains on the screen, even when applications are running on a tablet 122. The toolbar can pose a security risk for home medical device system 110 because the toolbar may allow other applications on tablet 122 to access the renal therapy machine 100. The toolbar may also allow the user to access other applications when the user interface of system 110 should be displayed. The customized tablet operating system in one embodiment removes all functionality of the Android™ operating system, including the toolbar, and only allows the use of the system application, which provides the user interface to the renal therapy machine 100. The tablet 122 in one embodiment can only communicate with the renal therapy machine 100. Tablet 122 accordingly does not need its own Internet connection.

Renal therapy machine 100 in one embodiment accesses the Internet using a separate 3G modem 102 provided as part of the home medical device system 110. The 3G modem 102 may use an Internet Service Provider ("ISP"), such as Vodafone™. In one embodiment, because the patient can potentially connect other personal devices, e.g., laptop or mobile phone, to the 3G modem 102, system 110 monitors the usage on the 3G modem 102 to ensure that only the renal therapy machine 100 uses 3G modem 102. Clinics associated with a particular patient may receive periodic reports containing usage information from a provider of the 3G modem 102. Clinicians can review the reports to determine if a particular 3G modem 102 is accessing the Internet more often than generally needed to connect renal therapy machine 100 to the connectivity server 118. The system 110 may send a signal to clinics notifying clinics that a 3G modem 102's Internet usage exceeds a predetermined amount. In an alternative embodiment, system 110 places software restrictions on the 3G modem 102 so that no device other than renal therapy machine 100 can use the 3G modem 102 to connect to the Internet. That is, a patient may be able to physically connect personal devices to the 3G modem 102, but software running on the 3G modem 102 is configured to only provide Internet connectivity to the renal therapy machine 100. Alternatively, the 3G modem 102 may be hardwired directly to the renal therapy machine 100 and no other device can physically connect to the 3G modem 102. In this embodiment, the renal therapy machine 100 and 3G modem 102 are permanently attached. The system 110 sends a signal to the associated clinic if a patient tampers with the 3G modem 102 by removing the hardwired connection to renal therapy machine 100 or trying to connect a personal device to the 3G modem 102.

It should be understood that even though modem 102 is described as being a 3G modem, the modem 102 may use other available networking technologies and protocols, such as 4G and technologies developed in the future. In one embodiment, a dedicated line is provided at each patient's home for connecting the renal therapy machine 100 to the connectivity server 118 via modem 102.

Renal therapy machine 100 in one embodiment, via the Internet, uses a connectivity service to transfer data between modem 102 and a system hub 120. There are various ways in which it is contemplated to implement the connectivity service. In one implementation, software is stored on ACPU 112 that accesses the software libraries needed to use the connectivity service. In another implementation a connectivity agent 114 developed by the connectivity service provider is installed onto the renal therapy machine 100 and run on ACPU 112. An example connectivity service provider is Axeda™. While this application is discussed primarily with connectivity agent 114, the functionality attributed to it herein is also applicable to the customized connectivity service alternative. The connectivity service provides a secure managed connection 116 between medical devices and the connectivity server 118. The connectivity service in one embodiment also maintains information about all of the renal therapy machines 100 connected to server 118 and system 110.

The connectivity agent 114 allows the renal therapy machine 100 to connect to connectivity server 118 and transfer data to and from the connectivity server 118. The connectivity service operating via agent 114 and server 118 ensures that the connection with machine 100 is secure, ensures that the data correctly passes through its firewalls, checks whether there has been a data or system crash and checks whether and ensures that the connectivity server 118 is communicating with the correct renal therapy machine 100. The renal therapy machine 100 creates the log files and provides the log files to the connectivity agent 114. The renal therapy machine 100 works with the connectivity agent 114 to transport the log files to the connectivity server 118. To send data to the connectivity server 118, the renal therapy machine 100 allows the connectivity service to run remote scripts on the renal therapy machine 100.

In one embodiment, renal therapy machine 100 can only connect to the connectivity server 118 when the connectivity agent 114 is turned on. During treatment and post-treatment disinfection, while machine 100 is functioning, connectivity agent 114 is turned off. This prevents the renal therapy machine 100 from communicating with any entity and sending or receiving data during treatment and disinfection or when machine 100 is live or running. In an alternative embodiment, the connectivity agent 114 is turned on after treatment but before post-treatment disinfection. The 3G modem 102 may or may not remain on or activated at these machine live times, but connectivity agent 114 is off. Renal therapy machine 100, however, compiles the data it has collected during treatment, encrypts that data into log files and then places the log files in a directory on the renal therapy machine 100. In one embodiment, when the renal therapy machine 100 is idle, e.g., after treatment is complete, the ACPU 112 turns connectivity agent 114 on. Connectivity agent 114 then retrieves the log files from the renal therapy machine 100 and transfers data to the connectivity server 118 using the connectivity service. The connectivity service routes data packets to their proper destination but in one embodiment does not modify, access, or encrypt the data. Indeed, the data may be sensitive patient-related data that should only be manipulated or "looked at" by authorized users.

In system 110 of FIG. 1A, the connectivity service via connectivity server 118 can communicate data to various places via a system hub 120 and a service portal 130. Connectivity server 118 allows service personnel 132a to 132n and/or clinicians to track and retrieve various assets across the network, such as appropriate renal therapy machines 100 and 3G modem 112, and their associated information, including machine or modem serial numbers. The connectivity server 118 can also be used to receive and provide firmware upgrades, approved by a director of service personnel 134, obtained remotely via service portal 130 to authorized renal therapy machines 100.

In one embodiment, the renal therapy machine 100 may be operated in a service mode for service personnel to access, diagnose and troubleshoot the renal therapy machine 100 on site and/or remotely. For example, if a patient using a renal therapy machine 100 encounters a problem, the patient may be able to call a service personnel or technician. The patient and/or service person may then be able to place the renal therapy machine 100 into a service mode that allows the service technician to remotely verify machine settings and functionality for various components of renal therapy machine 100. For example, the service person may be able to logon onto machine 100 while treatment is paused. Alternatively, machine 100 must be in an idle state, or even powered down, for the service person to be able to access the machine. Further alternatively, the machine 100 need only be disconnected from the patient for the service person to be able to access the machine. Once accessed, the service technician may be able to remotely investigate and retrieve the log files stored on the renal therapy machine 100 to determine the cause of the error. The service person may also be able to toggle valves and run a heater, for example, to see if a related sensor, e.g., pressure, conductivity or temperature sensor is operating properly and/or if the valve or heater (for example) is operating properly.

The connectivity server 118 communicates with much of home medical device system 110 via a home medical device system hub 120. System hub 120 enables data and information concerning each renal therapy machine 100 on system 110 to travel back and forth via the connectivity service between the machines 100 and the clients connected to server 118. In the illustrated embodiment, system hub 120 is connected to an enterprise resource planning system 140, a service portal 130, a web portal 150, a business intelligence portal 160, a HIPAA compliant database 124, a product development team 128 and electronic medical records databases 126a to 126n. Web portal 150 in turn enables patients and clinics 152a to 152n treating the patients to access a publicly available website for system 110. Thus while machine 100 and associated instructions and data are kept in a protected and regulated environment, the patient and patient's clinic are free to access the website. The patient may do so using the patient's own computer but not using tablet 122 or machine 100 in one embodiment. System 110 may require that the patient or clinic enter a username and password to access a patient or clinician's account on the website at portal 150. In this manner, the public is restricted from patient-specific data that the patient can receive. Clinician data is restricted to that clinic.

The enterprise resource planning system 140 obtains and compiles data generated by patient and clinician website access, such as complaints, billing information and life cycle management information. Data sent from the system hub 120 or portal 150 to the enterprise resource planning system 140 may be de-identified data, meaning the patient cannot be identified from the sent data. For example, data about complaints will not be associated with a patient. Data sent to marketing 162, research and development 164 and product development 128 may also be de-identified. Other data can be patient specific. For example, billing data over hub 120 will be associated with a patient. Or, quality/pharmacovigilance 166 data may also be associated with a patient. The enterprise resource planning system 140 is connected in the illustrated embodiment to a billing and ordering database 142. Billing and ordering database 142 contains a doctor's electronic signature authorizing certain supplies for carrying out patient prescriptions. The enterprise resource planning system 140 is also connected in the illustrated embodiment to a customer relationship management ("CRM") database 144 storing information about enterprise resource planning system 140.

The electronic medical records ("EMR") databases 126a to 126n contain electronic information about patients. The system hub 120 can send the data collected from the log files of machine 100 to hospital or clinic databases 126a to 126n to merge or supplement that patient's medical records. Databases 126a to 126n contain patient-specific treatment and prescription data and therefore access to such databases is highly restricted.

As discussed, web portal 150 is a portal for clinicians and patients to access the website and system hub 120. Clinicians can use the web portal 150 to update one or more device programs for the renal therapy machines 100. The system hub 120 scans through the renal therapy machine 100 log files to display the treatment data to a clinician through the web portal 150. Clinicians can access the web portal 150 from anywhere they can access the Internet, including their homes. A password is required in one embodiment. A clinician will see various web portal 150 administrative screens to set up an account. In one embodiment, the web portal 150 also connects to the enterprise resource planning system 140. Clinicians may also use the web portal 150 to send questionnaires or alerts to a patient. For example, a clinician may send a questionnaire to a patient asking the patient about a recent therapy. The questions may be multiple choice questions or Yes/No questions that can be easily and quickly answered by the patient. The clinician may also use web portal 150 to send reminders or alerts about an upcoming doctor's visit or the status of a shipment of supplies.

Business intelligence portal 160 collects data from the system hub 120 and provides data to marketing 162, research and development 164, and quality/pharmacovigilance 166. In one embodiment, the system hub 120 de-identifies data by removing any patient-specific information and sends de-identified data periodically, e.g., once a day, to the business intelligence portal 160. Marketing 162, research and development 164, and quality/pharmacovigilance 166 can analyze the de-identified data and provide reporting information about treatment data.

Figure 1B:
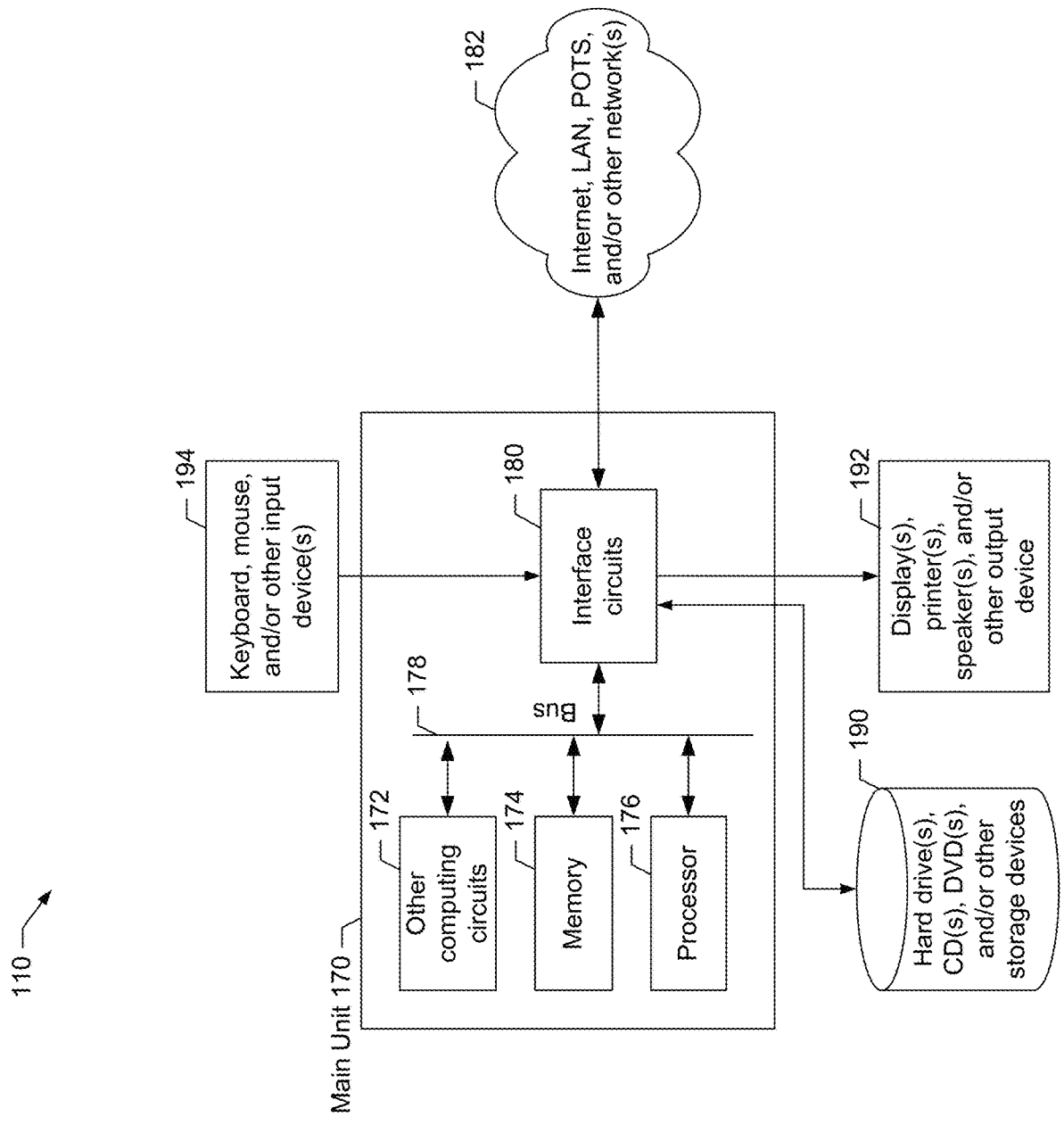
FIG. 1B is a block diagram showing one example of a computing device used in the home medical device system of the present disclosure.

A block diagram of the electrical systems of any of the devices or subsystems of the home medical device system (e.g., machine 100, modem 102, blood pressure monitor 104, scale 106, water treatment device 108, server 118, system hub 120, user interface 122, service portal 130, enterprise resource planning system 140, web portal 150, business intelligence portal 160) is illustrated in FIG. 1B. System 110, including any or all of devices or subsystems 100, 102, 104, 106, 108, 118, 120, 122, 130, 140, 150, and 160, includes a main unit 170 which preferably includes one or more processors 176 electrically coupled by an address/data bus 178 to one or more memory devices 174, other computer circuitry 172, and one or more interface circuits 180. Processor 176 may be any suitable processor, such as a microprocessor from the INTEL PENTIUM® family of microprocessors. The memory 174 preferably includes volatile memory and non-volatile memory. Memory 174 can store a software program that interacts with the other devices in the system 110 as described below. This program may be executed by the processor 176 in any suitable manner. The memory 174 may also store digital data indicative of documents, files, programs, web pages, etc. retrieved from another computing device and/or loaded via an input device 194.

The interface circuit 180 may be implemented using any suitable interface standard, such as an Ethernet interface and/or a Universal Serial Bus ("USB") interface. One or more input devices 194 may be connected to the interface circuit 180 for entering data and commands into the main unit 170. For example, the input device 194 may be a keyboard, mouse, touch screen, track pad, track ball, isopoint, and/or a voice recognition system. The interface circuit 180 may be connected to any type of network 182, such as an Internet, a local area network ("LAN"), a telephone network ("POTS"), and/or other networks.

One or more displays, printers, speakers, and/or other output devices 192 may also be connected to the main unit 170 via the interface circuit 180. The display 192 may be a cathode ray tube ("CRTs"), liquid crystal displays ("LCDs"), or any other type of display. The display 192 generates visual displays of data generated during operation of the device or subsystem 100, 102, 104, 106, 108, 118, 120, 122, 130, 150, 140, 160. For example, the display 192 may be used to display information received from the system hub 120. The visual displays may include prompts for human input, run time statistics, calculated values, data, etc.

One or more storage devices 190 may also be connected to the main unit 170 via the interface circuit 180. For example, a hard drive, CD drive, DVD drive, and/or other storage devices may be connected to the main unit 170. The storage devices 190 may store any type of suitable data.

Patient Training and Set-Up

Figure 2:
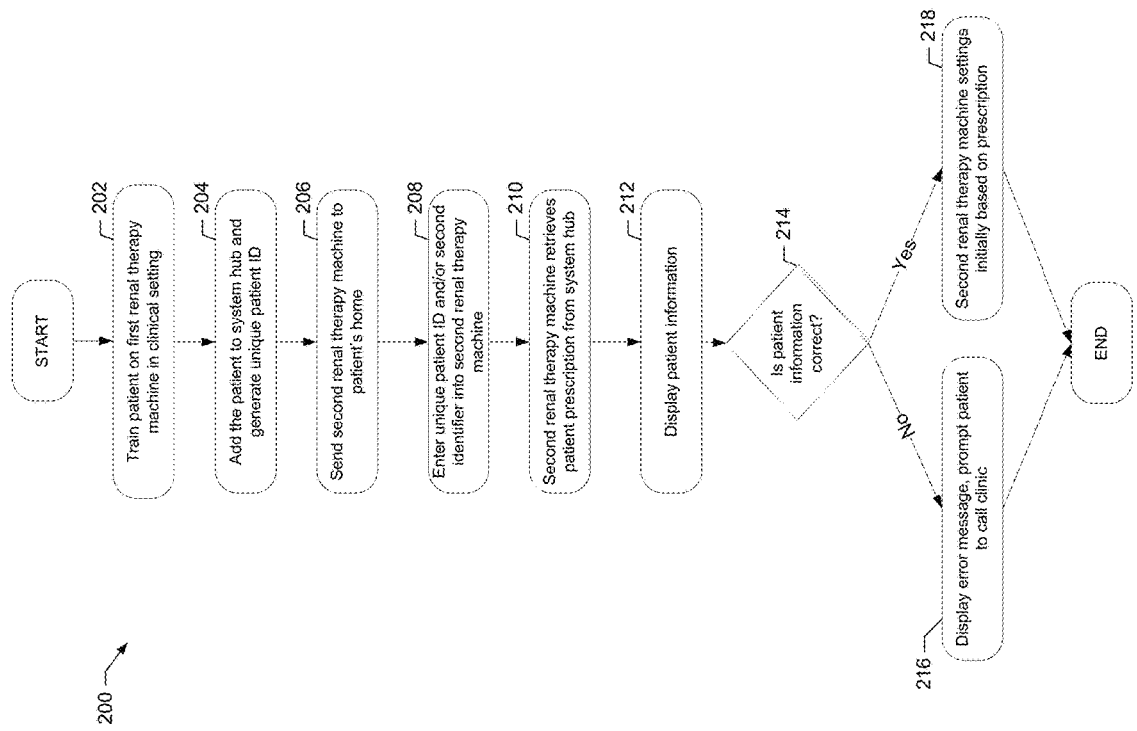
FIG. 2 is a flowchart of an example process of the present disclosure for preparing a patient to use a renal therapy machine at home.

Referring now to FIG. 2, an example process 200 for preparing a patient to use a renal therapy machine 100 at home is described. Upon starting process 200 at the start oval, the patient is first trained on a renal therapy machine 100 in a clinical setting as shown at block 202. The renal therapy machine 100 used for training is not specific to the patient and may be used by more than one patient in the clinical setting. The training machine 100 at least closely mimics the machine 100 that will be placed in the patient's home.

As shown at block 204, the patient is then set up as an account on system hub 120. As described in further detail below, a clinician, e.g., a nurse, may generate a unique patient identifier ("ID") using the web portal 150. In particular, the billing and ordering database 142 receives new patient information from the clinician and generates the unique patient ID, which identifies that patient thereafter across the entire home medical device system 110. The unique patient ID identifies that patient to all clients and subsystems that are involved in providing and supporting the home medical device system 110.

In one embodiment, a patient receives four to eight weeks of training in the clinical setting with a training machine 100 before being allowed to perform home hemodialysis. Once the patient is properly trained, a second renal therapy machine 100 is sent to the patient's home as shown at block 206. This second renal therapy machine 100 will be a personal machine intended only for that patient. The personal renal therapy machine 100 is not linked on system 110 to the patient when it is shipped to the patient's home.

At the patient's home, the patient enters the unique patient ID generated at block 204 into the personal renal therapy machine 100 as shown at block 208. In one embodiment, a second patient identifier, e.g., a birth date or other information particular to the patient, is also entered into the renal therapy machine 100 as shown at block 208. Entering the patient's unique ID and/or second patient identifier can be performed via tablet 122 and links the home renal therapy machine 100 to that patient. Based upon this entered ID and/or second patient identifier, the home renal therapy machine 100 retrieves a patient prescription prescribed previously by a doctor and/or clinician and any other information needed to run a treatment from system hub 120, as shown at block 210.

The home renal therapy machine 100 displays patient information to the patient to verify that the correct patient prescription has been retrieved, as shown at block 212. For example, the home renal therapy machine 100 may display the patient's name. The home renal therapy machine 100 prompts the patient to confirm whether the patient information is correct, as shown at block 214. If the patient information is not correct, the home renal therapy machine may display an error message and prompt the patient to call his or her clinic, as shown at block 216. If the patient information is confirmed as being correct, the home renal machine settings are set initially based upon retrieving patient prescription as shown at block 218. The home renal therapy machine 100 now has the information needed to run a treatment that is prescribed specifically for the patient and his/her associated machine 100. Process 200 is then completed as indicated at the end oval.

In one embodiment, renal therapy machine 100 does not identify or verify the patient each time a patient uses the renal therapy machine 100 because machine 100 is used only by one patient in his or her own home. Renal therapy machine 100 may however display a message such as, "Hello, Bill Smith" each time renal therapy machine 100 is turned on and/or prompted for treatment. In the unlikely event that the wrong person attempts to use a renal therapy machine 100, the welcome message serves as a reminder or warning that the renal therapy machine 100 is only intended for one specific patient, e.g., Bill Smith.

Supplies and Device Program Set-Up

Medical products and drugs are shipped or delivered to a patient's home for the renal therapy machine 100 to use during treatment. Only therapy products or drugs approved under a doctor's prescription can be shipped to the patient's home. In the U.S., prescriptions last one year. One or more prescription is stored for each patient in the system hub 120. Each renal therapy machine 100 uses supplies and settings according to the prescription. If the patient's prescription changes or if a prescription is added, the patient's clinician uses web portal 150 to update the renal therapy machine 100 settings to change or add the prescription. If the renal therapy machine 100 settings are updated, the system hub 120 sends the updated settings to the renal therapy machine 100 via the connectivity service as discussed previously.

Figure 3:
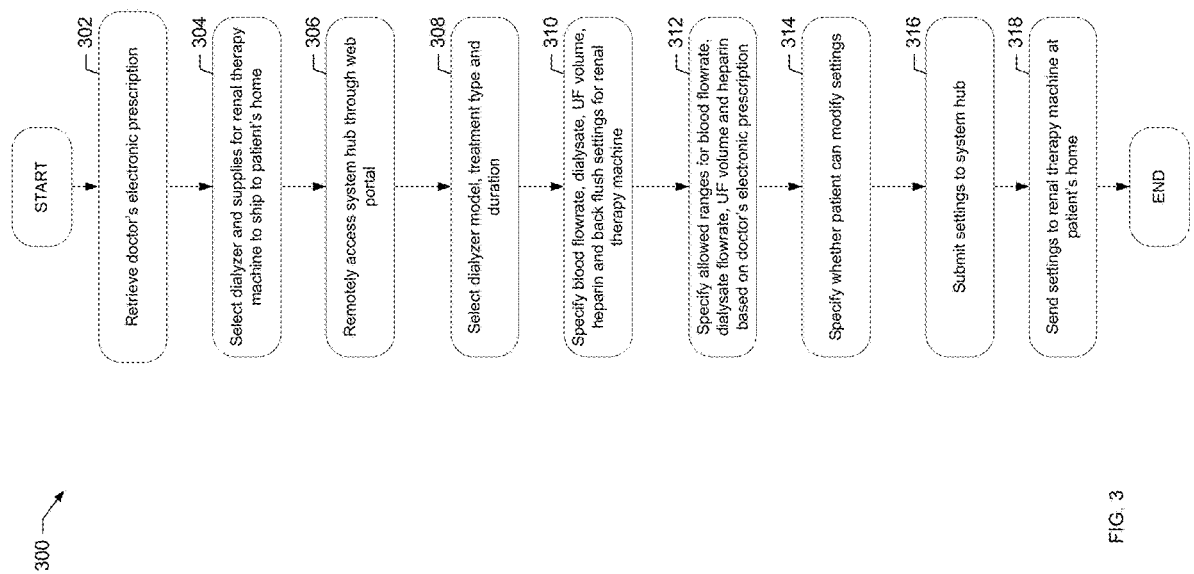
FIG. 3 is a flowchart of an example process of the present disclosure for shipping inventory and programming a renal therapy machine based upon an approved treatment prescription.

Referring now to FIG. 3, process 300 illustrates an example process for shipping inventory and programming a renal therapy machine 100 based upon a doctor's prescription for a particular patient. That is, a doctor associated with the clinic 152a to 152n can also access system hub 120 via web portal 150 to deliver a device program to the clinician for the patient. Upon starting process 300 at the start oval, the clinician retrieves an electronic prescription prescribed by a doctor using the web portal 150 as shown at block 302. At the web portal 150, the clinician selects the dialyzer, blood tubing set, acid, bicarbonate, needles, etc. and other supplies necessary to fulfill the prescription run on renal therapy machine 100. The selected dialyzer and other supplies will be shipped to the patient's home as shown at block 304. At the same or different time, the clinician may remotely access the system hub 120 through the web portal 150 to remotely program renal therapy machine 100, as shown at block 306.

To remotely program the renal therapy machine 100, the clinician selects the dialyzer model, treatment type and duration as shown at block 308. The clinician also sets various treatment parameters used to program the renal therapy machine 100 as shown at block 310, such as blood flowrate, dialysate flowrate, UF volume and heparin flowrate flush. The clinician also specifies allowed ranges for the various settings as shown at block 312. That is, the patient may be allowed to pick within a range of values for certain parameters under the specified device program. In this manner, the patient has a certain amount of control over the treatment that is performed. Dialysate temperature, for example, may be set within a range of allowable values based upon patient preference and comfort. The clinician further specifies whether or not the patient will have the ability to modify the settings at all as shown at block 314. If the patient is allowed to modify parameter settings, the setting variability is within an allowed range, such that the patient picks a value inside the range specified by the clinician at block 312. The clinician settings and parameter ranges are discussed in further detail with reference to FIGS. 16A to 16G as well as FIGS. 34A to 34G below. The clinician then submits the settings to the system hub 120 as shown at block 316. The system hub 120 then sends the settings to the renal therapy machine 100 at the patient's home as shown at block 318 via the connectivity service as discussed above. Process 300 then ends as illustrated at the end oval.

Performing Renal Therapy with an Updated Device Program

Before treatment begins, e.g., after disinfection the day before, ACPU 112 of renal therapy machine 100 checks whether the connectivity service via agent 114 has posted an updated prescription for that particular renal therapy machine 100. To do so, in one embodiment, the renal therapy machine 100 and the system hub 120, through the connectivity service, compare prescription version numbers to determine whether renal therapy machine 100 has the most updated prescription. If not, the most recent prescription version is delivered to therapy machine 100.

Figure 4:
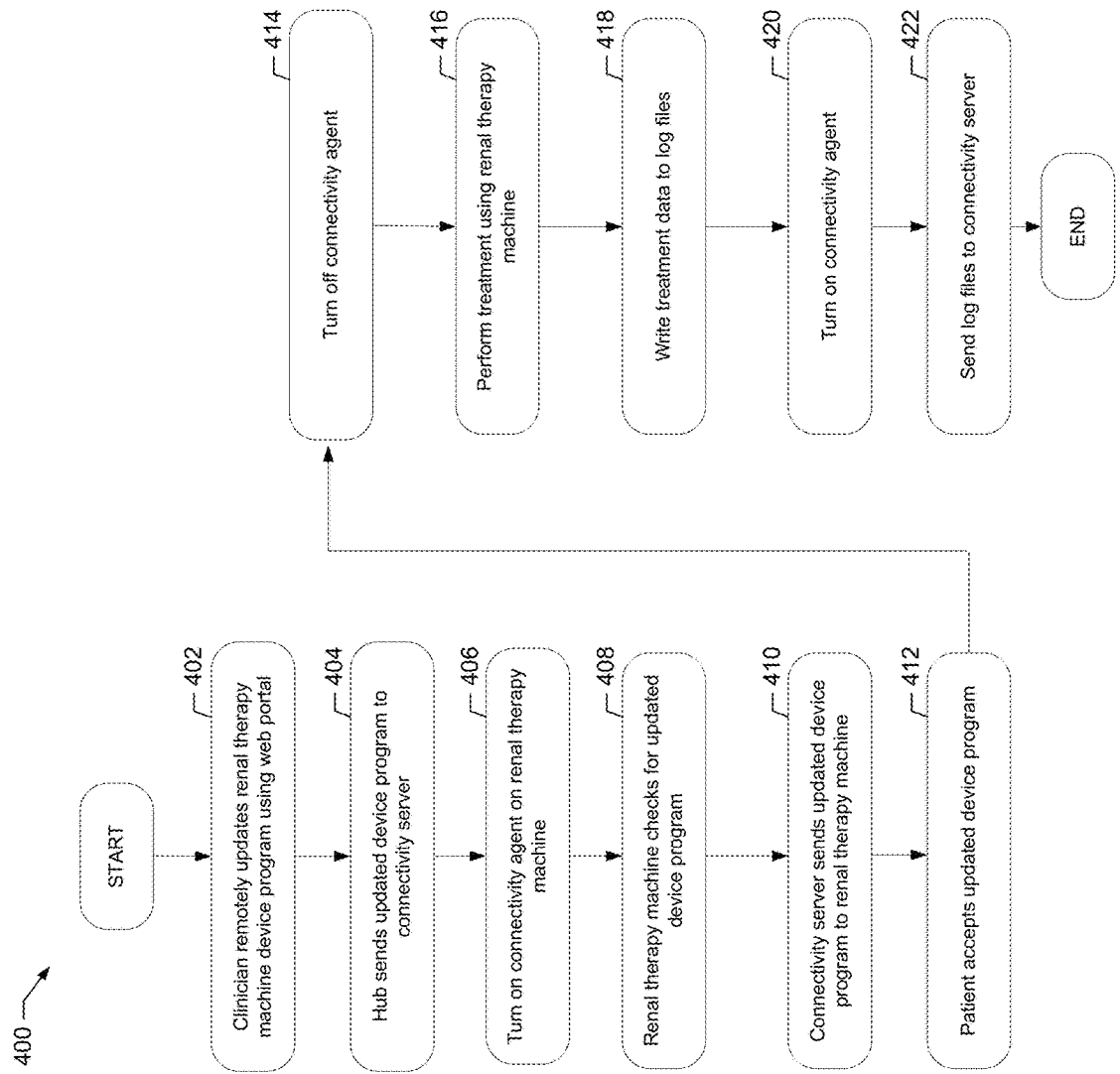
FIG. 4 is a flowchart of an example process of the present disclosure for transferring data between a renal therapy machine and a connectivity server, for example, to send a device operating program from the server to the renal therapy machine.

Referring now to FIG. 4, an example process 400 for updating the patient's device program, sending the updated device program to the renal therapy machine 100, performing therapy and transferring data between a renal therapy machine 100 and connectivity server 118 is described. The clinician at block 402 remotely updates the device program for renal therapy machine 100 using the web portal 150 as described in process 300 of FIG. 3. The system hub 120 then sends the updated device program to the connectivity server 118 as shown at block 404. When the connectivity agent 114 residing at renal therapy machine 100 is next turned on or enabled as shown at block 406, renal therapy machine 100 checks for an updated device program as shown at block 408. If one is present, connectivity server 118 sends the updated device program to the renal therapy machine 100 as shown at block 410.

Machine 100 prompts the patient to accept the new device program. In one embodiment, the patient must accept the new device program to continue using the renal therapy machine 100. In one embodiment, machine 100 will not run an old device program if a new device program is present on machine 100. However, the new device program will not overwrite the old device program until the patient accepts the new or updated device program as shown at block 412. In this manner, the patient confirms that the patient knows that his or her treatment has changed. Upon accepting the new device program, the new device program is written into the memory of therapy machine 100. In an alternative embodiment, machine 100 can store multiple device programs in memory so even when a new device program is downloaded, the old device program is kept in memory. Machine 100 may be able to store different types or categories of device programs. Each different type of device program may provide a different treatment, e.g., to remove a low amount, medium amount, or large amount of ultrafiltration for dialysis. The machine 100 may be able to store one device program in each category.

The next time the patient is about to perform treatment, the connectivity agent 114 is turned off as shown at block 414. The renal therapy machine 100 as shown at block 416 now runs a treatment using the updated device program specified at block 402. Renal therapy machine 100 writes treatment data produced by the new treatment to the log files as shown at block 418. Connectivity agent 114 is turned on as shown at block 420. In one embodiment, the renal therapy machine 100 initiates the connection to the connectivity service. In an alternative embodiment, the connectivity service may initiate the connection to the renal therapy machine 100. At block 422, the log files are uploaded to connectivity server 118. Process 400 then ends as illustrated at the end oval.

Machine 100 can perform post treatment procedures, such as a disinfection procedure that cleans the machine and the disposables used for treatment for the next treatment. In one embodiment, system 110 allows the connectivity agent to be turned on at block 420 after treatment but while post-treatment disinfection is taken place. Writing treatment data at block 418 can also be done during disinfection. Alternatively, the renal therapy machine 100 waits to write data at block 418 or turn on the connectivity agent at block 420 until disinfection is completed and the machine 100 enters an idle mode.

In the illustrated embodiment, because the connectivity agent 114 turns off before treatment and does not turn on again until after treatment, system 110 provides no real-time monitoring of a treatment. Events that occur during a treatment, including alarms and alerts, are not reported to the system hub 120 immediately. Such information is part of the log files that are sent to the system hub 120 after treatment.

In an alternative embodiment, the connectivity agent 114 may remain on during treatment and may report information about the renal therapy machine 100 and the treatment in real-time. For example, in one embodiment, system 110 may allow a clinician to remotely and simultaneously view screens being viewed by the patient on user interface 122.

Firmware Upgrades

From time to time, the software that ACPU 112 runs on renal therapy machine 100, which may also be referred to herein as firmware, may need to be upgraded. The home medical device system 110 provides a seamless and reliable manner for upgrading firmware that integrates the product development team 128 and service personnel 132a to 132n.

Figure 5:
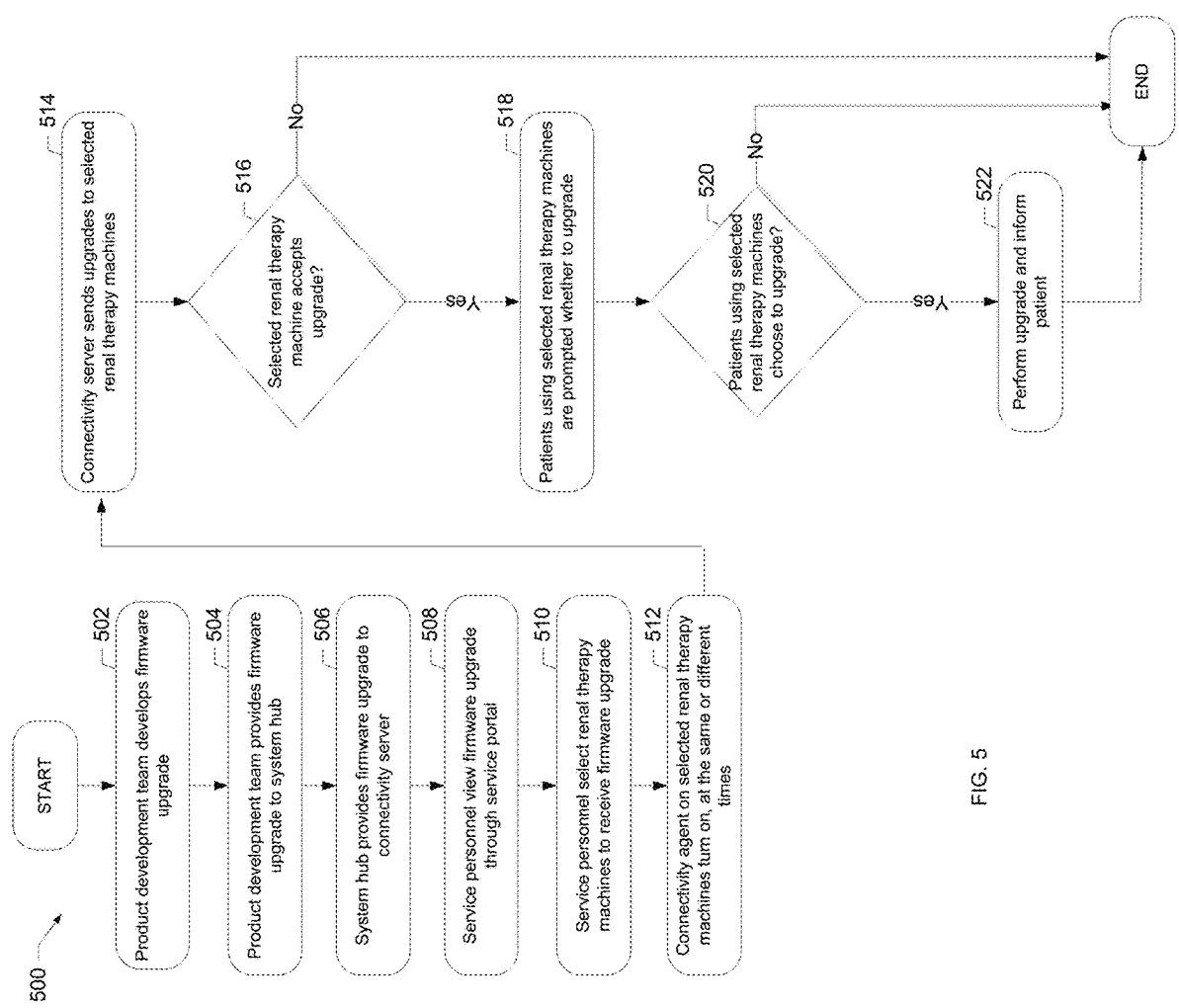
FIG. 5 is a flowchart of an example process of the present disclosure for upgrading firmware on a renal therapy machine.

FIG. 5 illustrates an example process 500 for upgrading firmware on the renal therapy machine 100. Upon starting process 500 at the start oval, a product development team 128 develops a firmware upgrade as shown at block 502. At block 504, the product development team 128 uploads the firmware upgrade to the system hub 120. The service portal 130 then allows a service personnel director or decision-maker 134 to view and approve the upgrade. Upon approving the upgrade, director 134 uploads the upgrade from system hub 120 to the connectivity server 118, as shown at block 506. In the illustrated embodiment of FIG. 1A, director 134 is separate from the service personnel 132a to 132n that are responsible for servicing and maintaining the renal therapy machines 100 and for maintaining relationships with the patients. Service personnel director 134 not only has the authority to finalize whether the upgrade is sent to the connectivity server 118, director 134 can also designate which machines 100 get the upgrade, if not all machines 100, and refuse the upgrade or return it to the product development team 128 for refinement. Once an upgrade is allowed to reach connectivity server 118, service personnel 132a to 132n, or designated ones thereof, can view the firmware upgrade through service portal 130 as illustrated at block 508. In one embodiment, the product development team 128 uploads the firmware upgrade directly to the connectivity server 118, without going through the system hub 120.

As discussed above, service personnel 132a to 132n manage the day-to-day relationship with the patients. Service personnel 132a to 132n are familiar with patient schedules and are in the best position to determine when a patient should receive the firmware upgrade. For example, service personnel 132a to 132n will know the maintenance and activity schedule for the renal therapy machines 100 they normally service. If the patient's machine 100 is scheduled to soon receive a part needed for the firmware upgrade, then the service personnel 132a to 132n can wait until the new part is installed before upgrading the firmware (needing the new part) on the patient's renal therapy machine 100.

Each service personnel 132a to 132n selects which of its designated renal therapy machines 100 should receive the firmware upgrade as shown at block 510. The next time connectivity agents 114 on the selected renal therapy machines 100 are turned on, as shown at block 512, connectivity server 118, waiting for the agents to be turned on, sends the upgrade to the selected renal therapy machines 100 as shown at block 514.

In one embodiment, the selected renal therapy machines 100 may decide whether or not to accept the upgrade, as shown at block 516. If the selected renal therapy machines 100 do not accept the upgrade, process 500 ends as shown at block 516 and the end oval. If any of the selected renal therapy machines 100 accept the upgrade, the corresponding patients are prompted as to whether they would like to install the upgrade, as shown at block 518. If the patients using the selected renal therapy machines 100 do not choose to upgrade, the process 500 ends as shown at block 520 and the end oval. If the patients using the selected renal therapy machines 100 choose to upgrade, the upgrade is performed and the renal therapy machines 100 inform the patients that the software has been upgraded as shown at block 522. Some countries require by law that patient approval must be obtained before upgrading a patient's firmware. In one embodiment, system 110 may require that only renal therapy machines 100 in countries that require patient approval prompt patients to accept the firmware upgrade at blocks 518 and 520.

Renal therapy machines 100 may be allowed to retain the ability to revert back to a previous software version. For example, if a firmware upgrade is corrupt, or if the firmware on a renal therapy machine 100 becomes corrupt, renal therapy machine 100 in an embodiment is allowed to revert back to a previous, non-corrupt software version. Alternatively, renal therapy machine 100 cannot revert back to a previous software version. Here, if the software is or becomes corrupted, new software is installed or renal therapy machine 100 is swapped with a new renal therapy machine 100.

The connectivity service at server 118 documents all events related to firmware upgrades, such as which patients have received upgrades, and which service personnel 132a to 132n have been involved in the upgrades. The connectivity server 118 stores serial numbers, tracking numbers and software versions so the various steps in the upgrade process are documented and so that at any given moment the current software version of each machine 100 on system 110 can be readily obtained. At the end oval in FIG. 5, process 500 ends.

Clinician Dashboard with Rule-Evaluation

A clinician can view a list of the clinician's patients and a file for each patient showing how treatments for the patients have transpired. The treatment files are derived from the log files in the renal therapy machine 100, including flowrates achieved, ultrafiltrate removal, ultrafiltration rates achieved, blood pressure over the course of therapy, weight, etc. A clinician can sort the list of patients by numerous categories, including the type of treatment they have received, e.g., hemodialysis (sub-categorized as for example short daily, nocturnal, every other day, and every other night), peritoneal dialysis (sub-categorized as continuous cycling peritoneal dialysis ("CCPD"), tidal, for example), the supervising doctor, or by the notifications described below. A clinician can also view a patient snapshot and an overview for the week, month or other duration.

Web portal 150 provides a clinician dashboard having notifications about events that occurred during treatment. In one embodiment, the notifications include colored flags, with different colors corresponding to different notification conditions. The clinicians can choose which events generate the red or yellow flags that appear on the dashboard. In one embodiment, the flag settings are clinic-specific, not patient-specific. Thus, choosing to be notified about certain events applies to all patients in the clinic or under the clinician's case. For example, a clinician may set a rule that a yellow flag should appear on the dashboard if a treatment lasted less than four hours. This rule would then apply to all patients at that clinic or under that clinician's care. The dashboard will indicate, e.g., with yellow flags, any patients who have undergone a treatment that lasted less than four hours.

Alternatively or additionally, there can be notifications that are patient-specific. For example, the clinician may set for patient A that a yellow flag should appear on the dashboard if a treatment lasted less than four hours. The dashboard will then only apply this rule for patient A and only generate a yellow flag if a treatment for patient A lasts less than four hours. Here, the clinician can set flags for each patient individually. The dashboard may show multiple yellow flags even in this individualized embodiment, however, the flag may not be applied to all patients of the clinic or under the clinician's care.

There may also be an indicator indicating whether the same or different clinician has already reviewed certain one or more notifications for a particular treatment. For example, if a clinician reviewing the dashboard sees a flag for a treatment and an indicator next to that flag, the clinician knows that he or she or another clinician has already reviewed that treatment flag and its corresponding cause.

The notifications are evaluated based upon rules or settings set by a clinician. If the rules or settings are changed, the flags are re-evaluated. The dashboard reflects the most current updated notification rules. For example, if a clinician previously set a notification rule that he should be notified if an alarm went off three times during treatment, but then changes that rule to be notified if an alarm went off only two times, the flags are re-evaluated upon the change. Thus here, flags may appear (indicating only two alarms) that did not appear before (when three alarms were needed). The dashboard is updated based upon the updated rule. Web portal 150 enables each clinician and each clinic to tailor the flagging of treatment conditions to meet specific needs.

Figure 6:
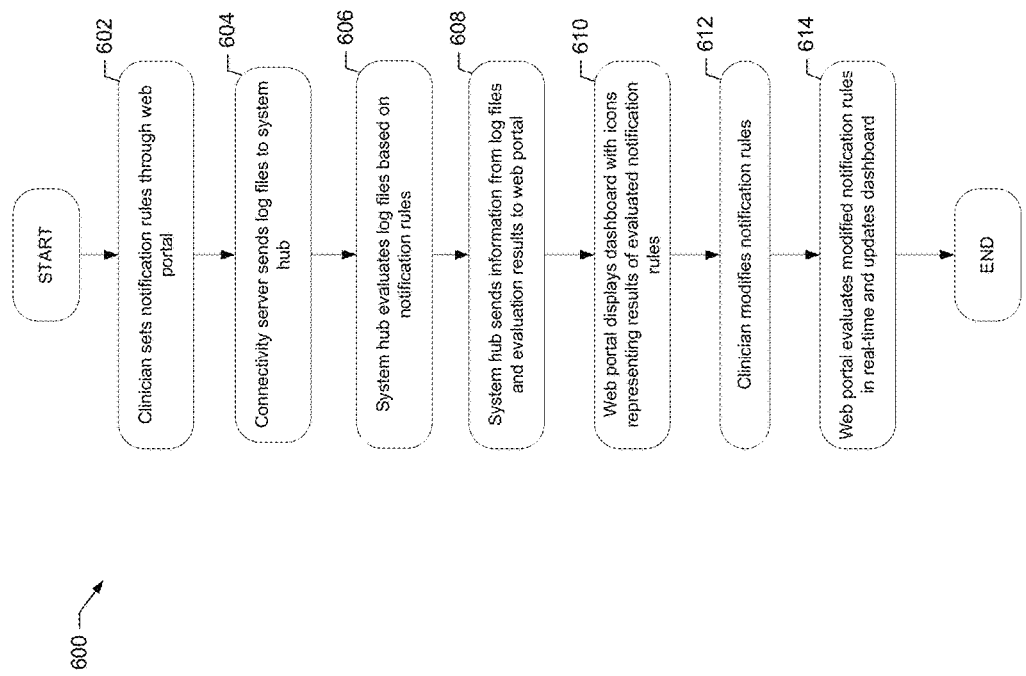
FIG. 6 is a flowchart of an example process of the present disclosure for setting and evaluating rules for notifications and presenting treatment data in a clinician dashboard.

FIG. 6 describes an example process 600 for setting rules or criteria, evaluating the rules against treatment data and presenting the data on a dashboard. Referring now to FIG. 6, the clinician beginning at the start oval sets the notification rules through the web portal 150 as shown at block 602. The connectivity server 118 then sends the log files to the system hub 120 as shown at block 604. The system hub 120 evaluates the log files based upon the notification rules as shown at block 606. The system hub 120 then sends information from the log files and the evaluation results to the web portal 150 as shown at block 608. The web portal 150 displays a dashboard such as the dashboard shown in FIG. 12A or the dashboard shown in FIG. 30A. The dashboard displays icons, e.g., check marks or exclamation points (FIG. 12A, FIG. 30A), representing the results of the evaluated notification rules as shown at block 610. The clinician can then modify the notification rules through the web portal 150 as shown at block 612 even as the clinician is viewing the dashboard. If the clinician chooses to modify the notification rules, as illustrated at block 612, the web portal 150 evaluates the modified notification rules in real-time and updates the dashboard as shown at block 614. Web portal 150 may use processing at system hub 120 for this second evaluation, or web portal 150 may evaluate the modified notification rules locally. Process 600 terminates at the end oval.

Security

In one embodiment, the system 110 provides security features by requiring verification information before certain changes can be implemented. In one example, system 110 requires that a user, already authenticated and logged into web portal 150, must enter his or her password into web portal 150 again after making a certain change before the change is actually implemented. Here, the security feature includes a second user authentication. Or, system 110 may require that a change is only implemented in the system if that change is approved by a second user. Here, the security feature is an approval entered by an authorized approver.

Figure 7:
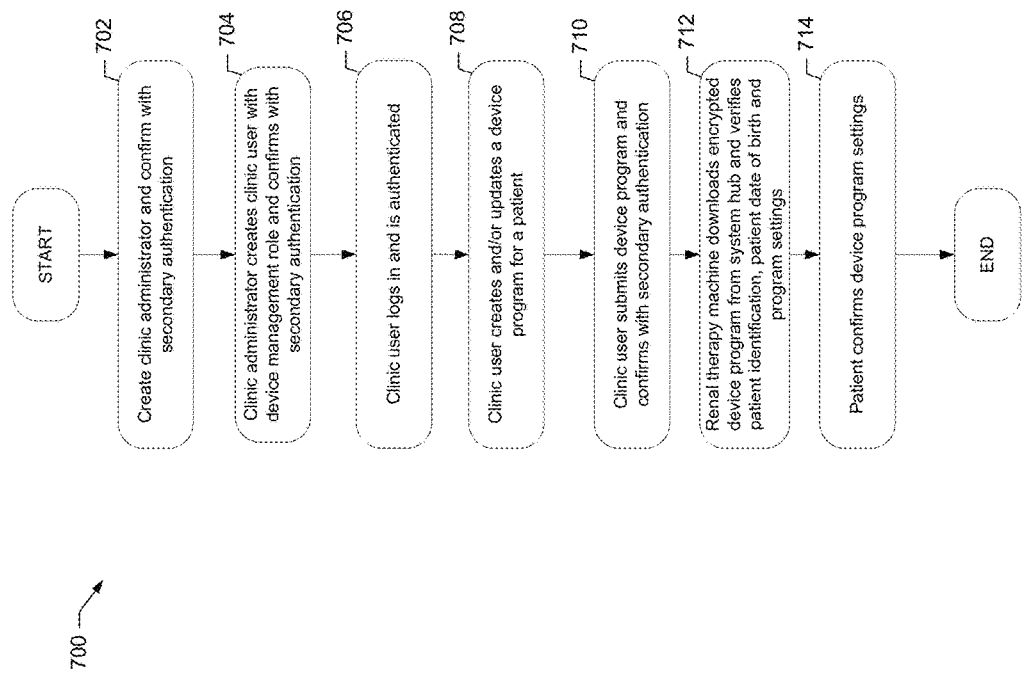
FIG. 7 is a flowchart of an example process of the present disclosure for securely creating or adding users and submitting device programs.

Referring now to FIG. 7, security and setup process 700 illustrates an example security process used for creating new users and submitting new device or treatment programs. Upon starting process 700 at the start oval, a clinic administrator is created and confirmed with a secondary authentication as shown at block 702. The clinic administrator then creates a clinic user with a device management role (explained below in connection with FIGS. 18A to 18E) and confirms the creation of the clinic user with secondary authentication as shown at block 704.

The created clinic user can then log into system 110 and is authenticated as shown at block 706 by entering verification information established at user setup block 704. The clinic user can then create and/or update a device or treatment program as shown at block 708. The clinic user submits the created or updated device program, confirming the submission with secondary authentication, as shown at block 710.

In one embodiment, system hub 120 encrypts the created or updated device program before the device program is sent to a renal therapy machine 100. The renal therapy machine 100 downloads the encrypted device program from system hub 120 via connectivity server 118 and verifies patient identification, e.g., patient date of birth, and/or program settings as shown at block 712. Renal therapy machine 100 may verify the information by matching data tagged to the device program with like data stored in the memory of renal therapy machine 100. The patient then confirms or accepts the device program settings as shown at block 714. The process then ends as shown by the end oval for security and setup process 700.

In one embodiment, system 110 may implement various rules to enhance security. For example, system hub 120 and/or connectivity server 118 may keep a record of internet protocol ("IP") addresses of all renal therapy machines 100 linked to system 110. If a renal therapy machine 100 is located at a different IP address than the IP address normally associated with that renal therapy machine 100, system 110 may require a second user, e.g., a second approver, to approve the submittal of a new device or treatment program to renal therapy machine 100.

Other events may also require approval from secondary sources. For example, if a clinic administrator tries to create a clinic user with a device management role (FIGS. 18A to 18E), system 110 may require secondary approval by a designated person. Or, if a clinic user attempts to create and/or update a device program, a secondary approval may be required by a designated person. In a further example, anytime a device program is created or updated, the clinic administrator or a person designated by the clinic administrator may receive an email informing that the clinic administrator/person about the new device program or update.

System 110 may also monitor and track the total number of changes being made to the different device programs and settings for the various renal therapy machines. System 110 may expect a certain number of changes in a given timeframe. If the number of changes to device program settings exceeds the expected number of changes by a threshold amount, system 110 may conclude that a security breach has occurred and shut itself down. The expected number may be set for a particular clinic, for the patients within the clinic, or for both.

Web Portal

Figure 8:
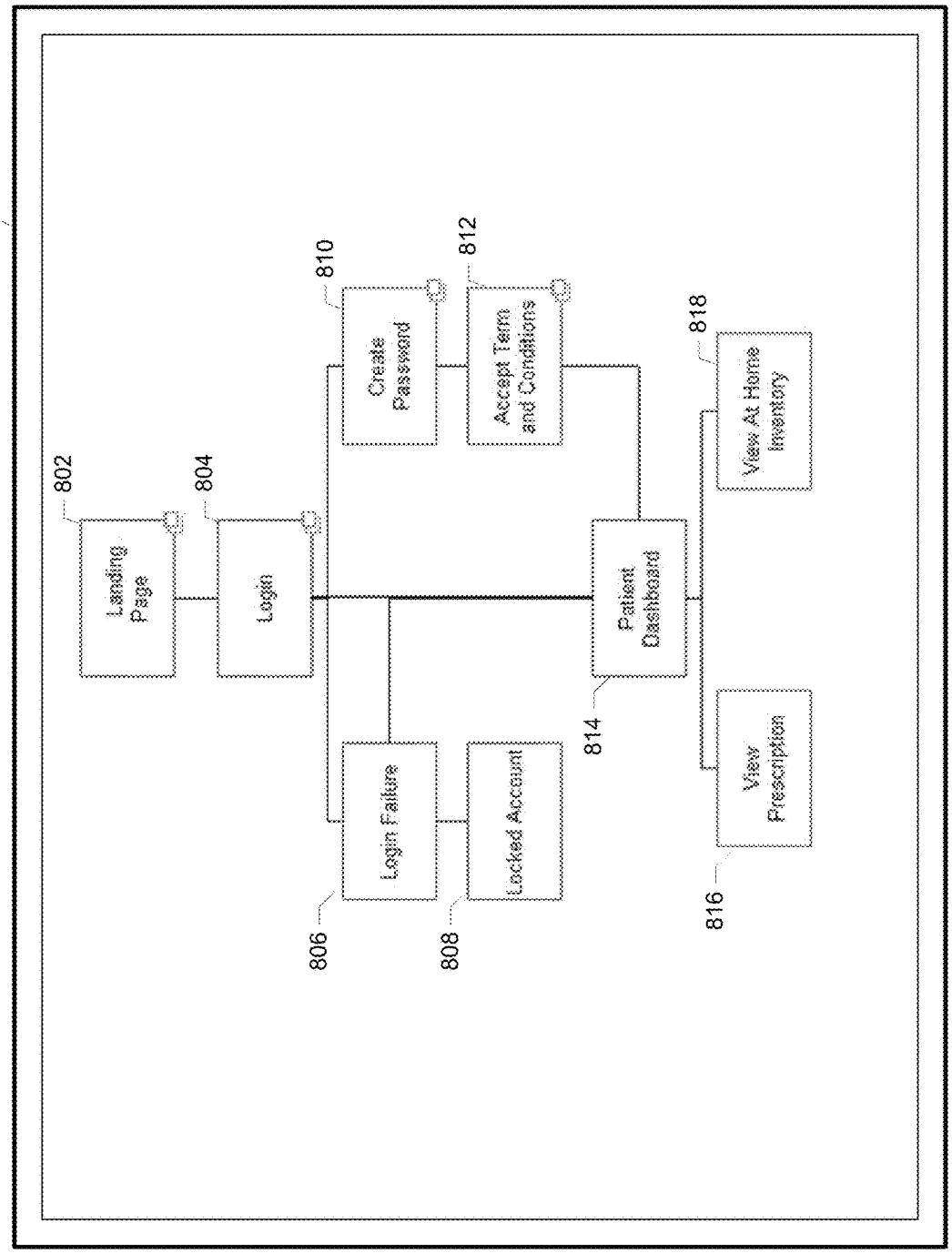
FIG. 8 is a screen shot of an example patient site map of the present disclosure.

Clinicians and patients can access information about the home medical device system 110 via the web portal 150, which links to the rest of system 110 via system hub 120. FIG. 8 illustrates an example patient site map 800 on a patient's display device 192 that describes the various pages that are accessible to a patient from the web portal 150. The patient arrives at landing page 802 of site map 800 and is prompted to login at login page 804. If the login fails, a login failure page 806 is displayed after which the patient can try to log in again. If the login fails several times, for example three times, system 110 provides a locked account page 808. If the patient has never logged in before, system 110 prompts the patient to create an account and password at page 810 and accept terms and conditions at page 812. Once the patient has successfully logged into system 110, system 110 displays patient dashboard 814. From dashboard 814, the patient can view his or her device program at screen 816 the patient's at-home inventory at screen 818. Prescription screen 816 shows the treatment (or treatment options if multiple prescriptions are available) that machine 100 currently performs for the patient. Inventory screen 818 shows the supplies that the patient should currently have at home. The patient may update inventory screen 818 with information not available to system 110, for example, subtract stock that has been damaged or lost from the patient's at-home inventory. System 110 may log that the patient has made such an adjustment.

Clinicians also use the web portal 150 for information about the home medical device system 110. Clinicians generally have access to more information than do individual patients. In one embodiment, a clinician can view information about each of his or her patients through web portal 150. In one embodiment, the web portal 150 is "clinic-centric," meaning clinicians that belong to one clinic cannot see information about patients or clinicians from other clinics. Nurses and clinicians may be associated with clinics and thus can view all patients for a given clinic. Doctors, however, may be associated with patients, not clinics, and thus system 110 may not allow a doctor to see all the patients associated with a clinic. A web portal administrator, usually a clinician or nurse for a particular clinic, specifies which patients a doctor can see.

Figure 9:
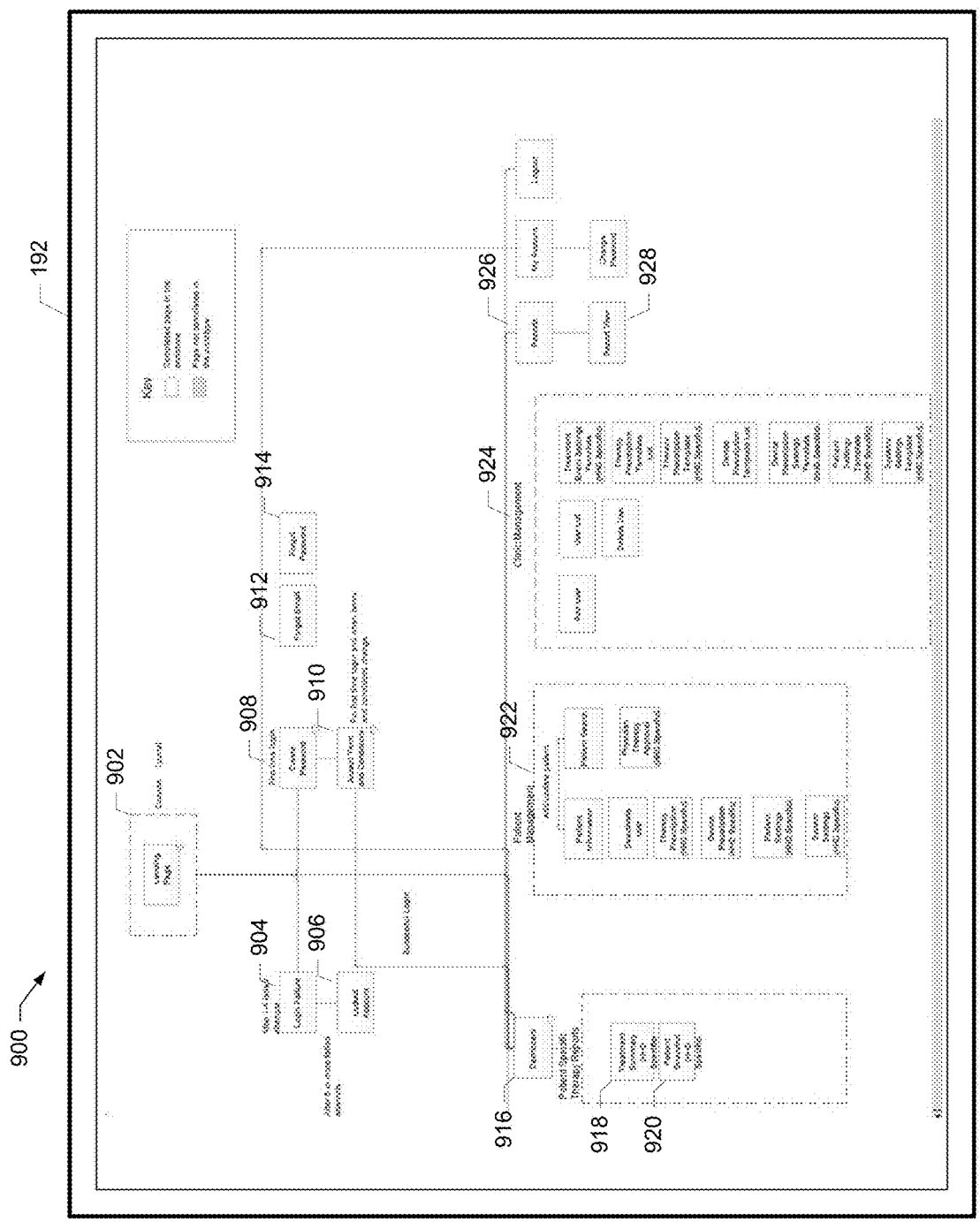
FIG. 9 is a screen shot of an example clinician site map of the present disclosure.

FIG. 9 illustrates an example clinician site map 900 displayed on a clinician's display device 192. Clinician site map 900 includes many more pages that are accessible to the clinician than does patient site map 800 for the patient. The clinician arrives at a landing page 902 and is prompted to log in. If there is a login failure, screen 904 is displayed. System 110 provides locked account screen 906 after several failed attempts. First time users are prompted to create a login and password at screen 908 and accept terms and conditions at screen 910. System 110 also provides help at screens 912 and 914 if the clinician forgets or misplaces his or her login email address or password.

Once logged in, the clinician can view a dashboard 916, which allows for patient-specific reports to be viewed. The patient-specific reports are shown on a treatment summary screen 918 and a patient snapshot screen 920. From the dashboard, system 110 also allows the clinician to set treatment parameters at patient management screens 922. The patient management screens 922 include screens for administrative tasks related to the patient such as obtaining patient information, searching for patients, and deactivating users. The patient management screens 922 include a physician therapy approval screen (not included in the figures), therapy prescription screen (FIG. 10), device program screen (FIGS. 16A to 16G), a patient settings screen (FIGS. 15B, 35A and 35B), and a system settings screen (FIGS. 15C and 36A to 36D). The clinician can also access from the dashboard a clinic management module 924. The clinician can also access account settings (not shown), access reports 926 or a reports view 928.

Figure 10:
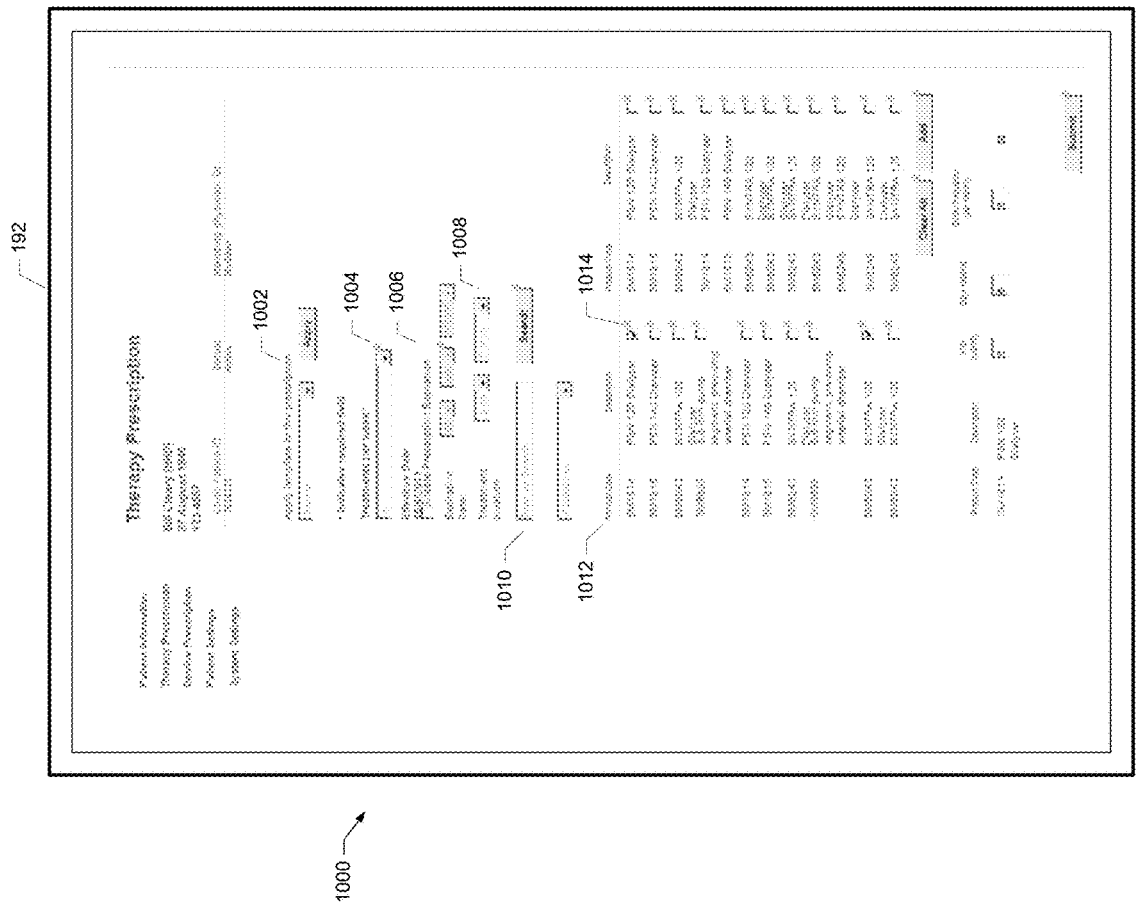
FIG. 10 is a screen shot of an example treatment prescription screen of the present disclosure.

FIG. 10 illustrates an example of a therapy prescription screen 1000 displayed on a clinician's display device 192, which may be referred to herein as a supply order management screen. The upper left corner of therapy prescription or supply order management screen 1000 provides major category selections for the clinicians within web portal 150. Links to each of the major categories include Patient Information, Therapy Prescription, Device Prescription, Patient Settings and System Settings. Device Prescription is referred to herein alternatively and interchangeably as Device Program. Current screen 1000 is a therapy prescription screen, so "Therapy Prescription" is highlighted on the list. To move to any other major category from screen 1000, the clinician selects one of the other links.

Therapy prescription screen 1000 allows the clinician to select the products and supplies that are to be delivered to a patient for treatment. The clinician enters into screen 100 the number of treatments per week 1004, whether the prescription expires 1006 and the duration of the treatment 1008. Screen 1000 also allows the clinician to run a search for products and accessories 1010, which then presents a list of the various products that the clinician searched for 1012. From the various products listed 1012, the clinician, according to the doctor's prescription, selects which products 1014 to send to the patient. The supplies selected at screen 1000 are then delivered to the patient's residence. Again, the therapy prescription screen 1000 is manipulated according to a doctor's prescription, which is stored in the billing and ordering database 142 linked to enterprise resource planning system 140. In other words, the clinician can only order products that conform or are in accordance with a doctor's prescription.

System 110 enables the clinician to apply a template at selection 1002. The templates are created for different kinds of prescriptions, so that selecting a specific prescription from the scroll-down menu at template selection 1002 specifies a list of products and amounts for the clinician without having to check off or select each individual field 1014. Selecting a template allows the clinician to choose from a preexisting set of products, thereby allowing the clinician to quickly place an order for an initial stock of supplies. The templates are extremely convenient because many patients use standard prescriptions needing the same supplies.

Figure 11:
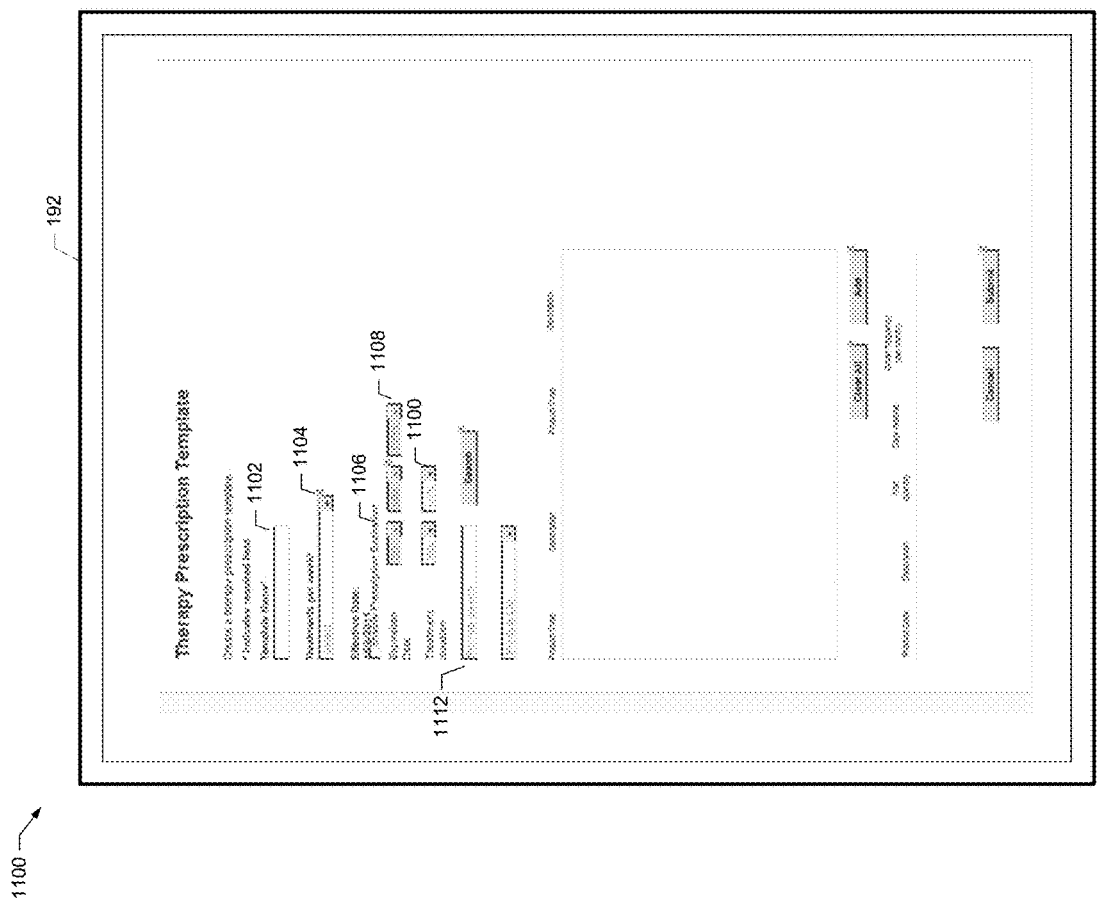
FIG. 11 is a screen shot of an example treatment prescription template of the present disclosure.

FIG. 11 illustrates an example therapy prescription template screen 1100 displayed on a clinician's display device 192, which allows a clinician to create a therapy prescription template. The clinician can enter a template name at box 1102, the number of treatments per week at drop-down menu 1104, whether or not the prescription expires at check box 1106, an expiration date at drop-down menu 1108 and the treatment duration at drop-down menu 1100. The clinician can then also enter a product search 1112 and list and select various different products that the clinician can ship to a patient. All of these selections are then saved for future use and applied when the particular template is selected in field 1002 in the therapy prescription screen illustrated in FIG. 10.

Clinician Dashboard

Figure 12A:
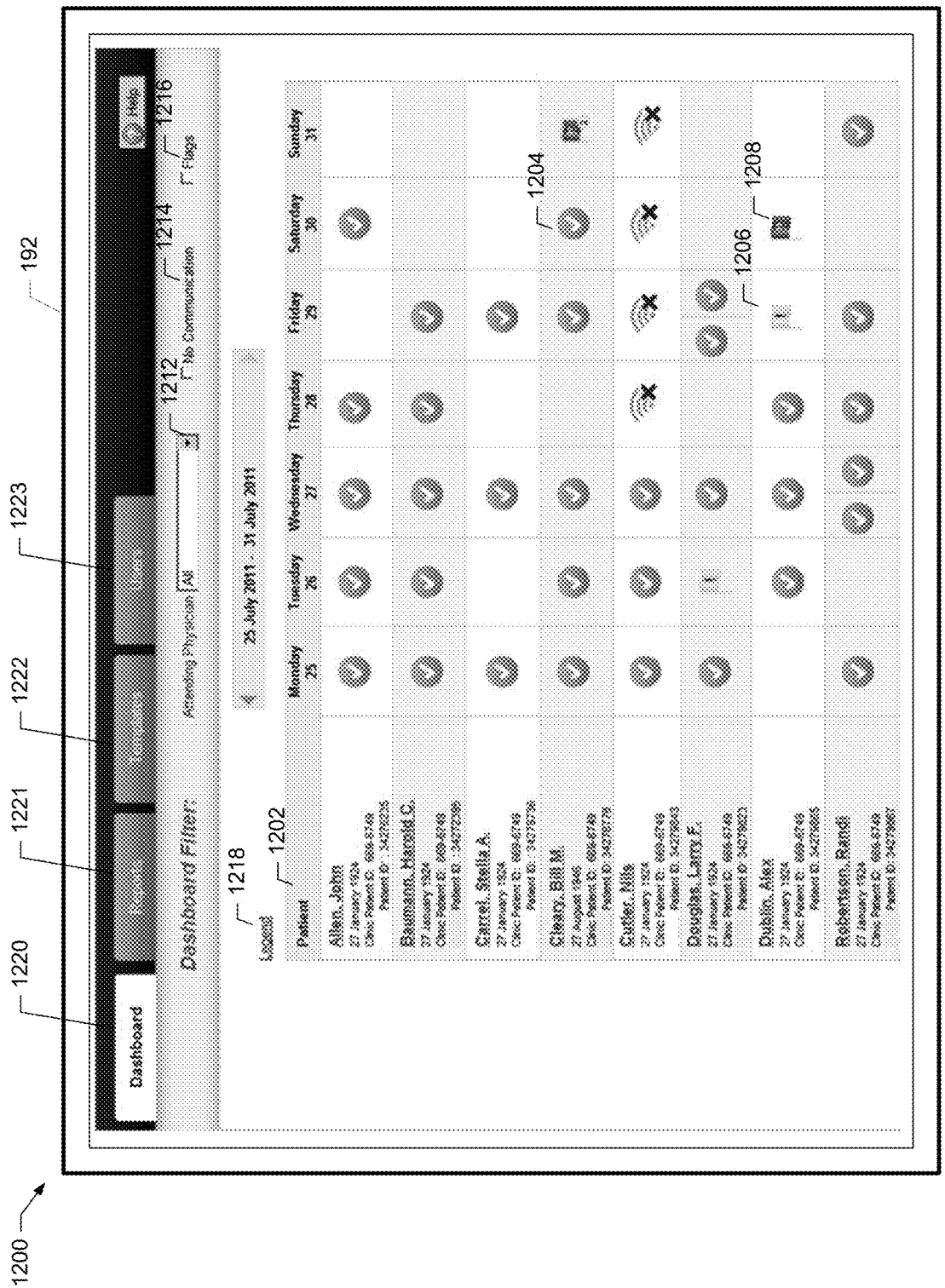
FIG. 12A is a screen shot of an example dashboard screen for a clinic of the present disclosure.

FIG. 12A illustrates an example dashboard screen 1200 for a clinic displayed on a clinician's display device 192. Dashboard screen 1200 is in one implementation the first screen a clinician sees upon logging into the web portal 150. Dashboard screen 1200 provides an overview of information about the patients handled by that clinic. It should be appreciated that information in the dashboard screen is not a clinical assessment of the patient's health or condition and does not provide medical advice, but instead provides an overview of information about patients to a clinician. The patients are listed by name as shown at column 1202. Dashboard 1200 may enable the clinician to apply filters as illustrated by drop down menu 1212. For example, the clinician in the illustrated embodiment can filter information in the dashboard by patient type (not shown), by physician at drop-down menu 1212, or by the status of a patient (not shown). The clinician can also filter information in the dashboard to only show treatments for which there has been no communication using checkbox 1214, or to only show treatments for which a flag has been generated using checkbox 1216. The filters allow the clinician to hone in on particular, desired information.

Various icons 1204, 1206 and 1208 indicate information about a treatment performed by that patient on a specific date. Icons 1204, 1206 and 1208 may indicate different types of events. For example, icon 1204 may be used to indicate that a treatment has been performed successfully. Icon 1206 may be used to notify the clinician about events that are not critical and do not need immediate action, but need to be closely monitored in the future. Icon 1208 for example may be used to notify the clinician of events that need immediate action.

Figure 12B:
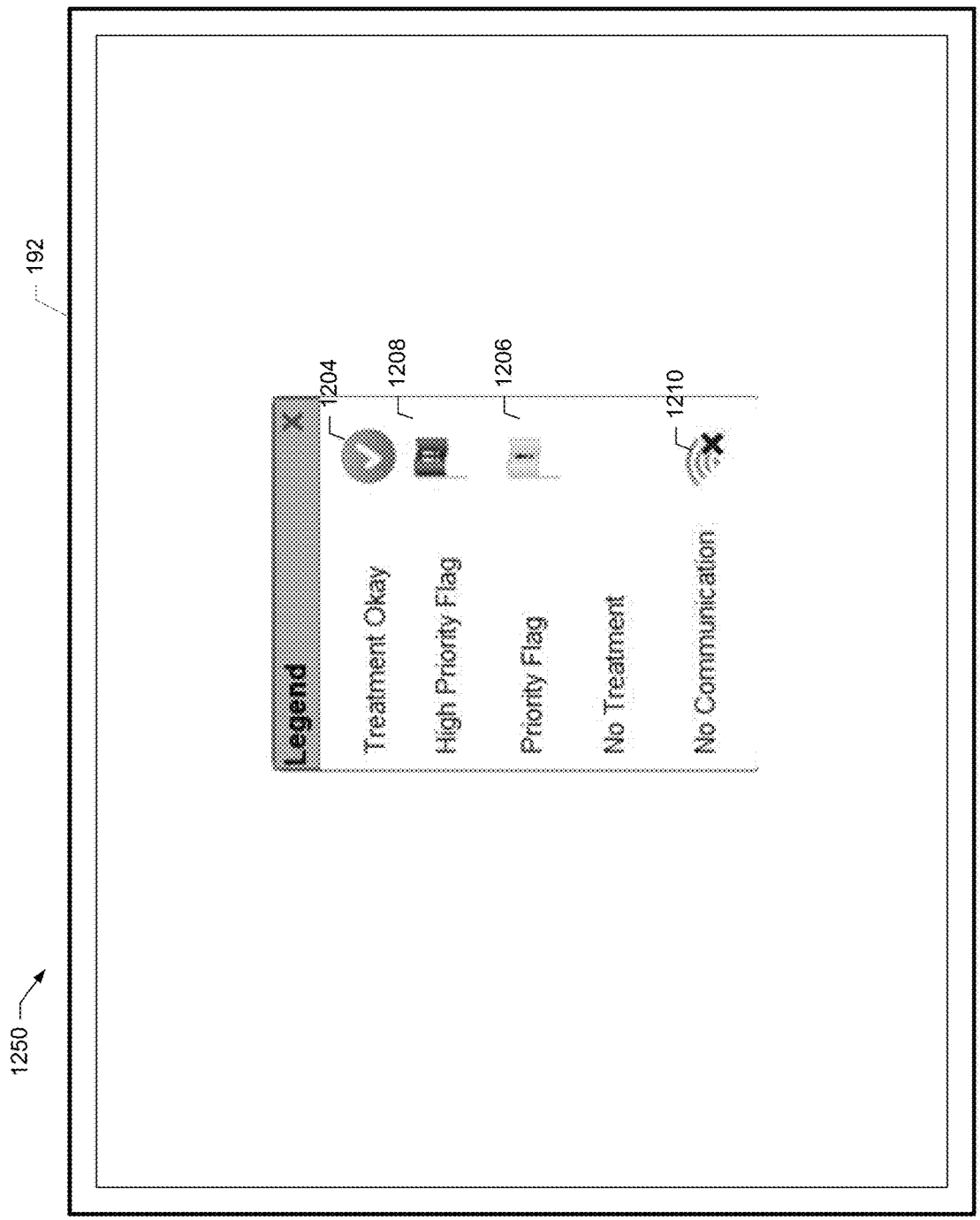
FIG. 12B is a screen shot of an example legend for a dashboard screen of the present disclosure.

A user is able to access a legend using link 1218. When a user selects link 1218, a popup window or new screen 1250 appears. FIG. 12B illustrates an example legend screen 1250 displayed on a clinician's display device 192 that explains the various icons that can appear on dashboard screen 1200. Icon 1204 indicates that the treatment went "Ok." Icon 1208 indicates a high priority flag. Icon 1206 indicates a flag of normal priority. Icon 1210 indicates that there has been no communication with the renal therapy machine 100 associated with that patient for a specific treatment.

Referring again to FIG. 12A, the dashboard screen 1200 may also include navigational tabs to allow the clinician to access various portions of the web portal. For example, navigational tabs include a dashboard tab 1220, a reports tab 1221, a templates tab 1222 and a users tab 1223. A clinician can access different portions of the web portal 150 by selecting an associated navigational tab. The navigational tabs appear on multiple screens at all times in one example embodiment.

Figure 13A:
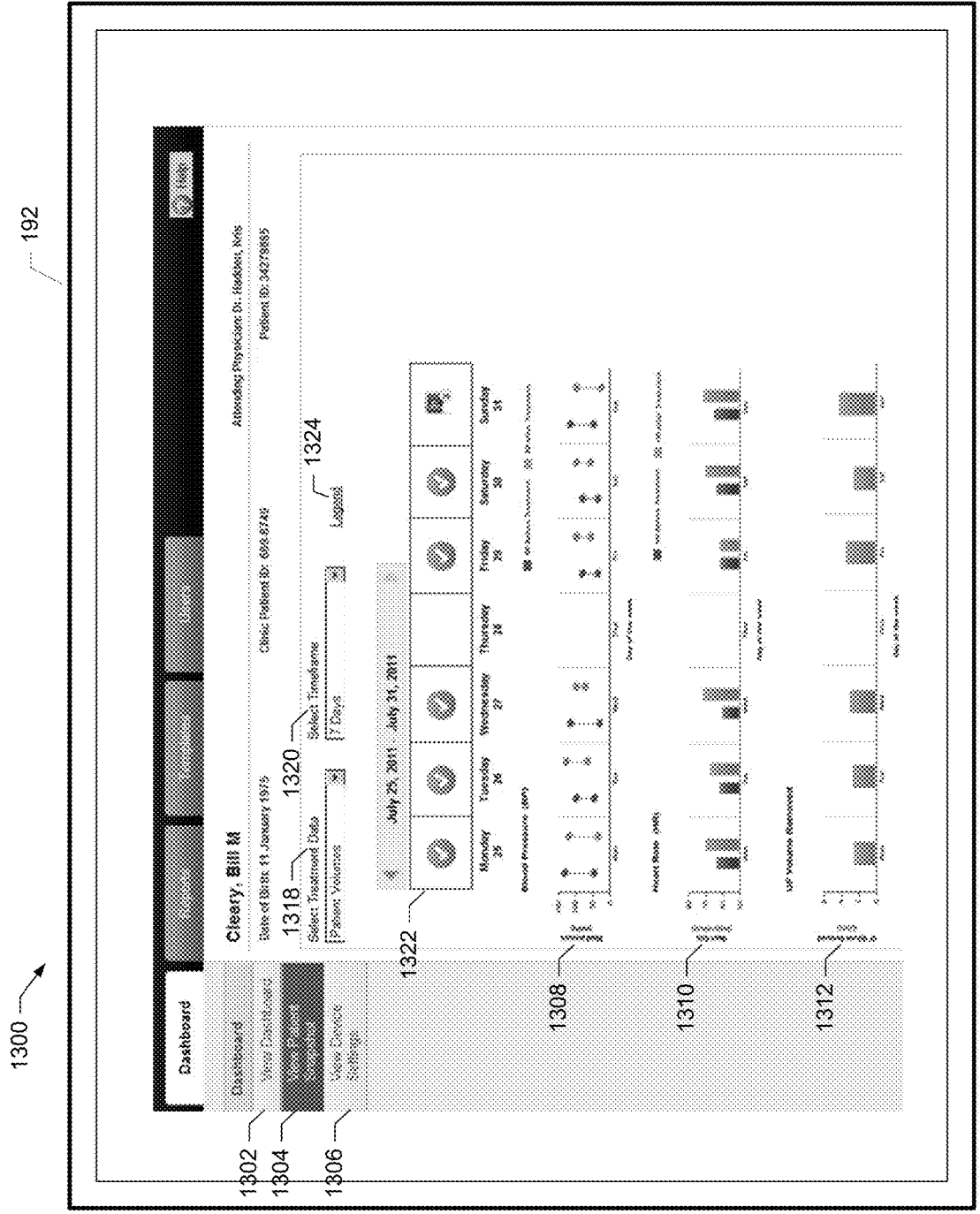
FIG. 13A is a screen shot of an example patient snapshot screen of the present disclosure.

In one example embodiment, selecting a navigational tab such as tab 1220 displays more navigational options. FIG. 13A illustrates an example patient snapshot screen 1300 displayed on a clinician's display device 192 that can be launched from the dashboard screen 1200. As indicated in FIG. 13A, selecting dashboard tab 1220 displays navigational options within the dashboard tab, such as a view dashboard link 1302, a view patient snapshot link 1304 and a view device settings link 1306. The patient snapshot screen 1300 provides detailed information to the clinician about an individual patient. The snapshot screen 1300 provides information such as the blood pressure 1308, heart rate 1310, and the UF volume removed 1312.

The clinician may also be able to filter specific treatment data, for example, using drop-down menu 1318. The clinician can specify which aspect of the treatment data to view in the patient snapshot screen 1300. In the illustrated embodiment, the clinician has selected patient volumes. The clinician can also filter information by selecting a time frame using drop-down menu 1320. In the illustrated embodiment, the clinician has selected to view treatment data over a timeframe of seven days. Selecting seven days using drop-down menu 1320 results in the calendar display 1322, which illustrates seven days of data for a specific patient. A link to a legend 1324 is again provided on patient snapshot screen 1300, which displays the same icons and explanations for the icons as described above in FIG. 12B.

Figure 13B:
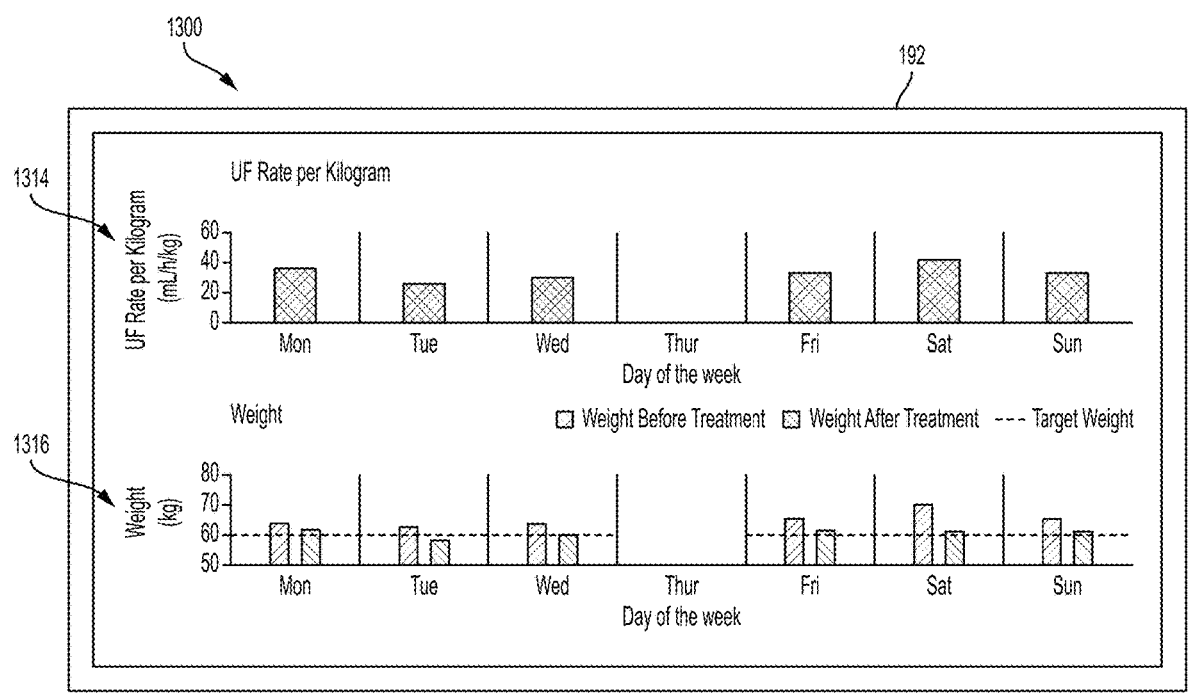
FIG. 13B is another screen shot of an example patient snapshot screen of the present disclosure.

FIG. 13B illustrates additional information that may be displayed on the patient snapshot screen 1300 displayed on a clinician's display device 192. Patient snapshot screen 1300 for example displays an ultrafiltration rate per kilogram 1314 and the patient's weight 1316.

Figure 14A:
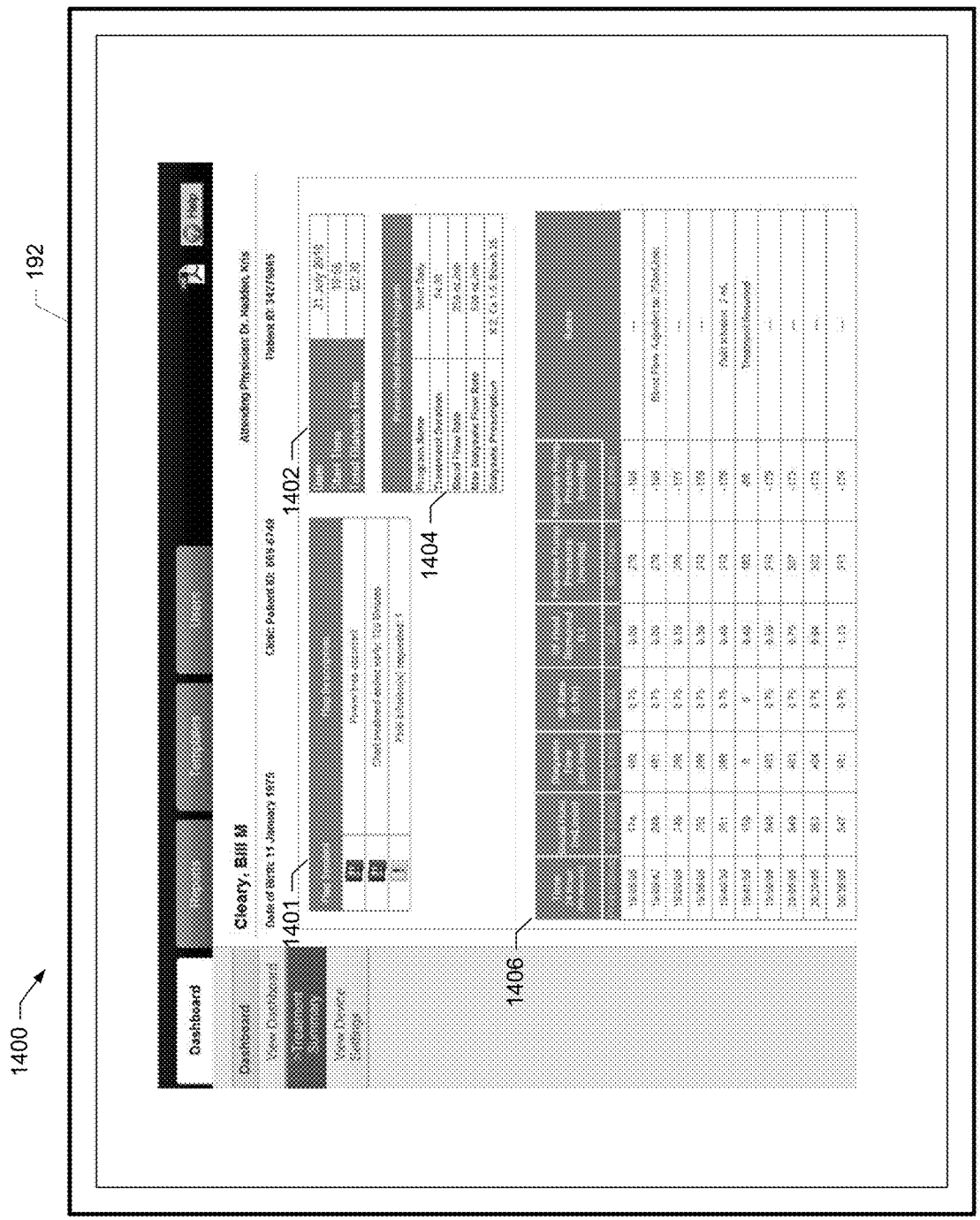
FIG. 14A is a screen shot of an example treatment summary screen of the present disclosure.

FIG. 14A illustrates an example treatment summary screen 1400 displayed on a clinician's display device 192 that provides granulated details about a particular treatment performed on a patient. Treatment summary screen 1400 can be launched by selecting one of the dates in the calendar 1322. In the illustrated embodiment, the user has selected Jul. 31, 2010. FIG. 14A shows information about the treatment for Jul. 31, 2010, as indicated at chart 1402.

Figure 14B:
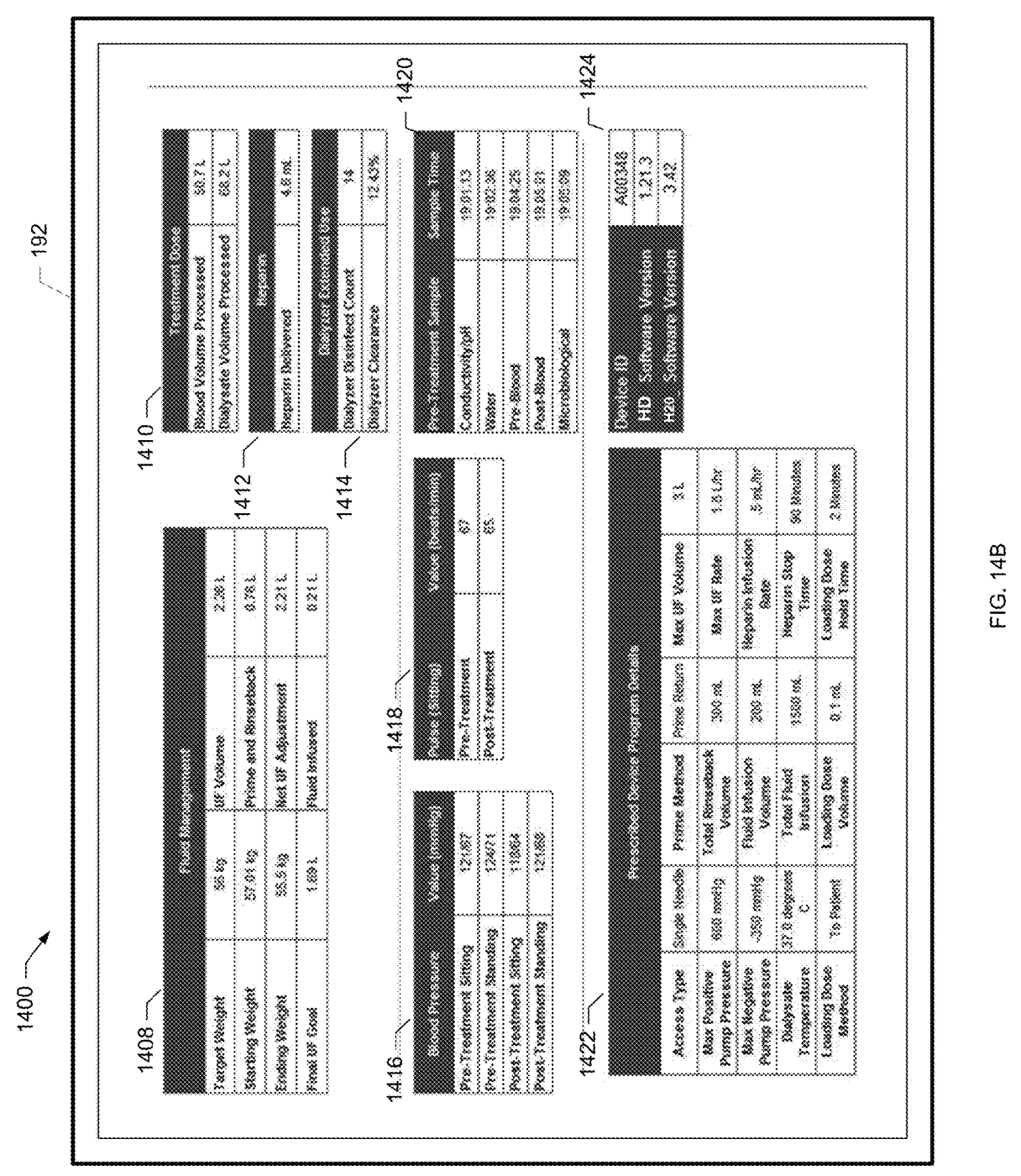

From treatment summary screen 1400, a clinician can see a description of the flag symbols at chart 1401. The clinician can also see the date, start time and total dialysis time at chart 1402, the prescribed device program at chart 1404 and overall treatment summary log in table format showing exact times for various treatment events at chart 1406. The screen 1400, displayed on a clinician's display device 192, is continued on FIG. 14B. As shown in FIG. 14B, a clinician can see fluid management particulars at chart 1408, information about the treatment dose at chart 1410, heparin particulars at chart 1412, dialyzer extended use data at chart 1414, blood pressure at chart 1416, pulse particulars at chart 1418, pretreatment samples taken for comparison purposes at chart 1420 and details about the prescribed device program at chart 1422. The clinician can also see the device ID of the renal therapy machine 100 and the software version of the renal therapy machine 100 as well as the water treatment device 108 at chart 1424.

Figure 15A:
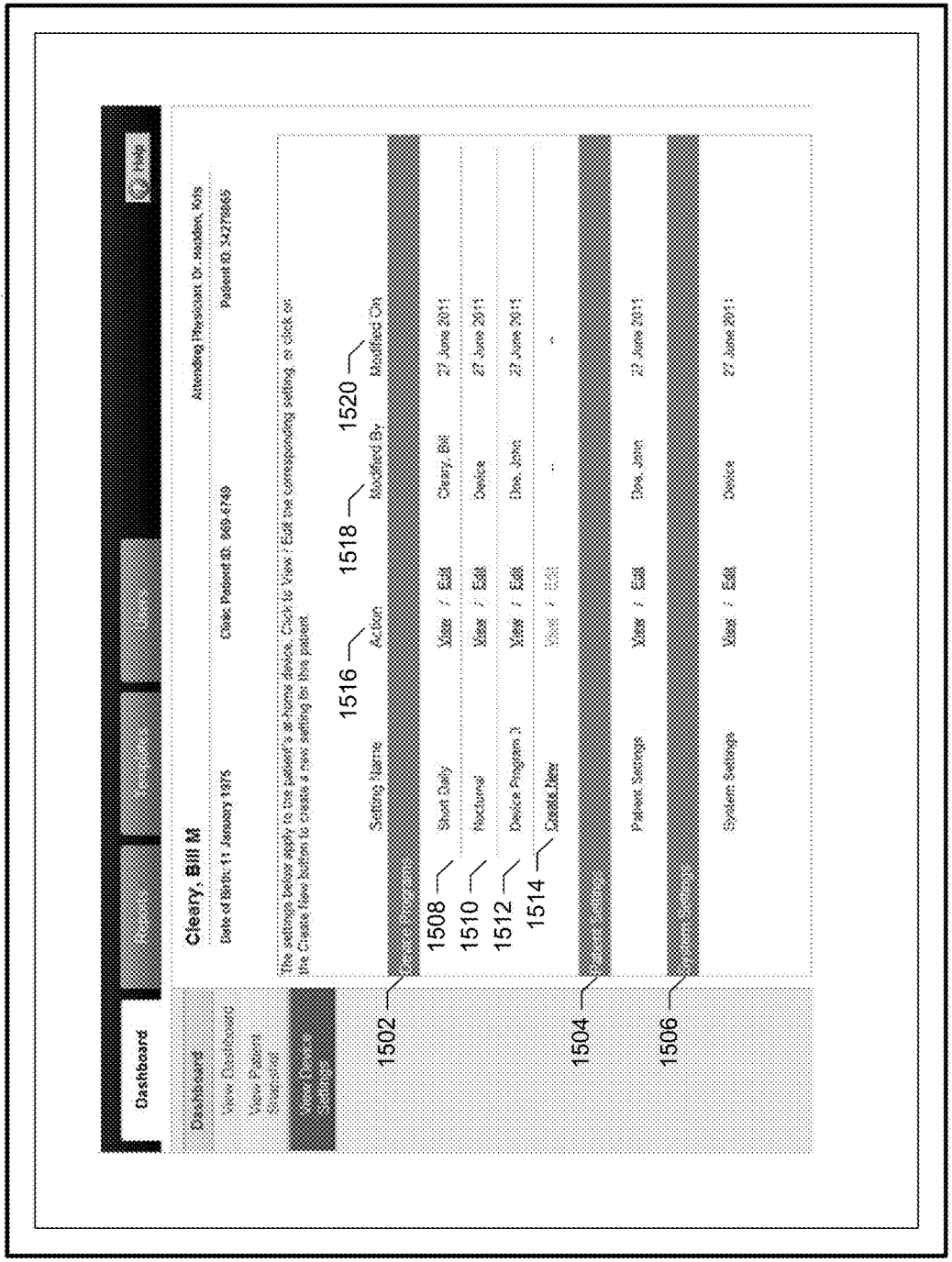
FIG. 15A is a screen shot of an example device settings screen of the present disclosure.

FIG. 15A illustrates an example device settings screen 1500 displayed on a clinician's display device 192, which can be launched from the dashboard screen 1200. The device settings screen 1500 displays relevant consolidated information about the various device programs being used by a patient, patient settings and system settings and also provides a consolidated location or screen for clinicians to be able to access various aspects of the patient care. From the device settings screen 1500, a clinician may be able to access information about device programs 1502, patient settings 1504 or system settings 1506. Under device programs 1502, a clinician can view all of the different device programs stored for that patient. For example, in the illustrated embodiment of FIG. 15A, the patient is using three different device programs: short daily 1508, nocturnal 1510 and a third program titled "device program 3" 1512. The clinician may be able to create a new device program for that patient using link 1514. The clinician can view or edit device programs 1502, patient settings 1504 or system settings 1506 using the links in the action column 1516. The device settings screen also displays the last person to modify any of the device programs, patient settings or system settings using the modified by column 1518. The date of the modification is also shown using the modified on column 1520.

Figure 15B:
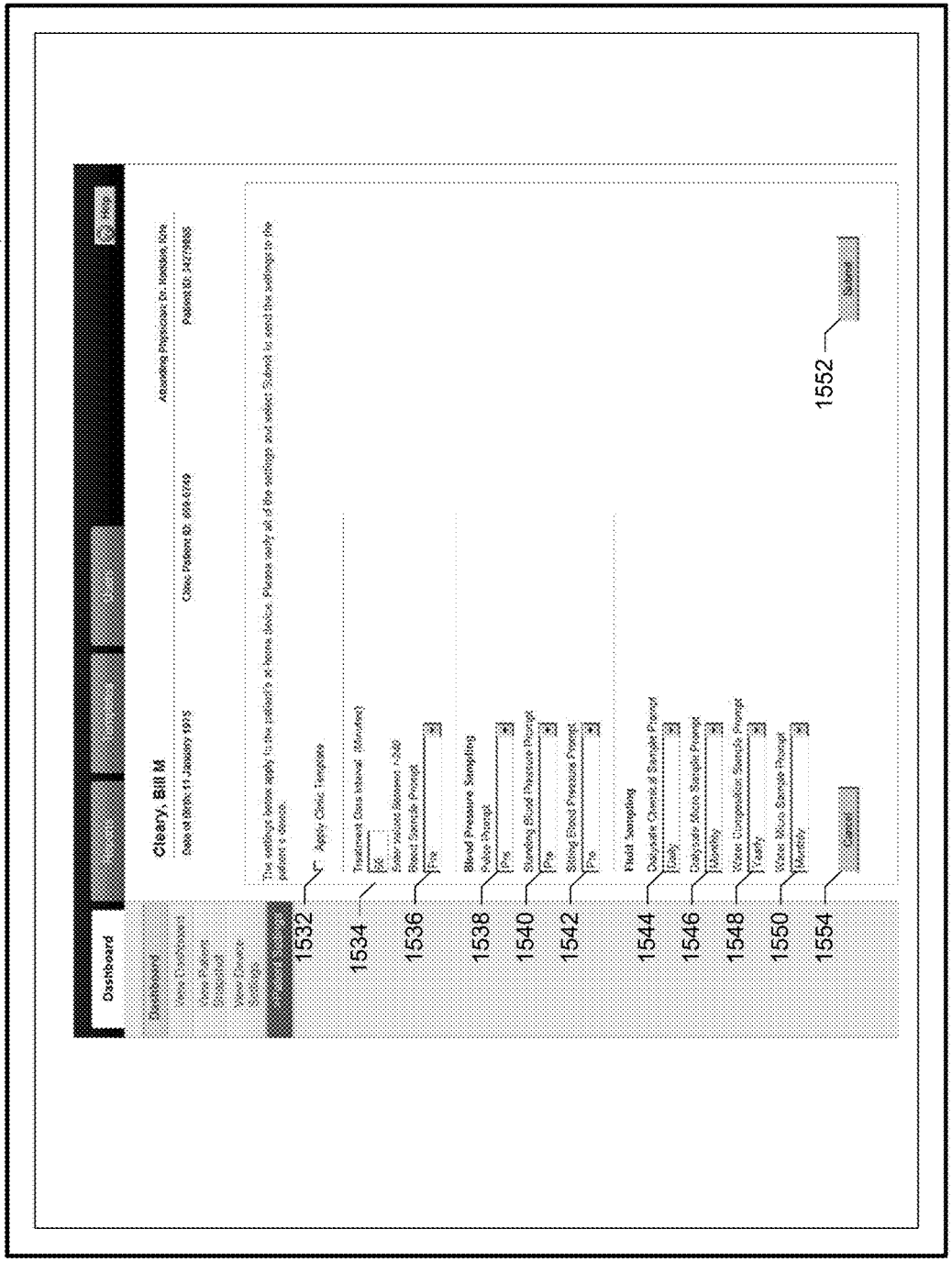
FIG. 15B is a screen shot of an example patient settings screen of the present disclosure.

A clinician may be able to change certain settings for renal therapy using a patient settings screen 1530 displayed on a clinician's display device 192 illustrated in FIG. 15B. The patient settings screen 1530 can be obtained by selecting view or edit under the patient settings section 1504 on FIG. 15A. Changes made in the patient settings screen 1530 modify how the next treatment is performed but are not immediately reported to the system hub 120. Instead, those changes are communicated to the system hub 120 after the next treatment when the log files are sent to the system hub 120. Patient settings in general involve settings that affect how treatment is displayed to the patient and thus do not require a doctor's approval.

In the patient settings screen 1530 displayed on a clinician's display device 192 of FIG. 15B, the clinician can apply a clinic template 1532, which like before enables the clinician to quickly and easily specify and populate a group of preselected settings. On patient settings screen 1530, the clinician can specify a treatment data interval at entry 1534, a blood sample prompt at drop-down menu 1536, a pulse prompt at drop-down menu 1538, a standing blood pressure prompt at drop-down menu 1540, a sitting blood pressure prompt at drop-down menu 1542, a dialysate chemical sample prompt at drop-down menu 1544, a dialysate micro sample prompt at drop-down menu 1546, a water composition sample prompt at drop-down menu 1548, and a water micro sample prompt at drop-down menu 1550. The drop-down menus specify frequency settings for the prompts, e.g., how often does machine 100 prompt the patient for the listed information. The clinician can use the cancel button 1554 and submit button 1552 to respectively cancel or submit the patient settings. In one embodiment, a patient may be able to access the patient settings screen 1530 to modify various settings for the renal treatment.

Figure 15C:
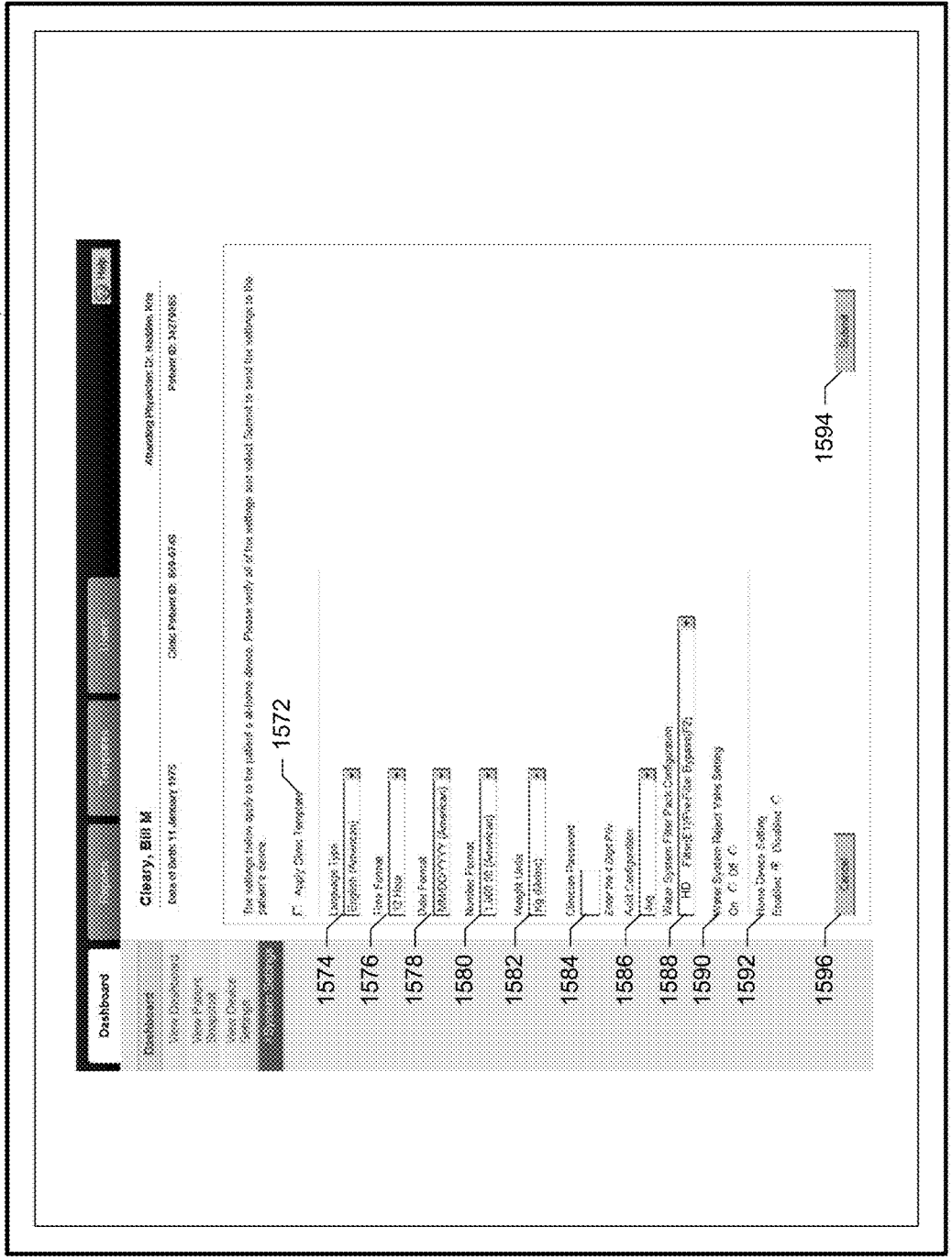
FIG. 15C is a screen shot of an example system settings screen of the present disclosure.

FIG. 15C illustrates an example screen shot of a system settings screen 1570 displayed on a clinician's display device 192. The system settings screen 1570 allows a clinician to specify various settings related to the operation of the system. The clinician can apply a clinic template 1572, which like before enables the clinician to quickly and easily specify and populate a group of preselected settings. The system settings screen 1570 also allows a clinician to select the language type as shown by drop-down menu 1574, specify the time format with drop-down menu 1576, specify the date format with drop-down menu 1578, specify the number format with drop-down menu 1580 and specify the units for weight with drop-down menu 1582.

The system settings screen 1570 also allows the clinician to specify a clinician password 1584. The clinician password is required thereafter for any changes that are to be made to the renal therapy machine 100 from the patient's home. For example, if a patient at his or her home wishes to modify any of the settings for the renal therapy machine 100, the patient must either be given the clinician password 1584, or a clinician who knows the clinician password 1584 must be present at the patient's home to enter in the clinician password 1584 at the renal therapy machine 100. The clinician password thus provides a layer of security to ensure that only authorized users are able to change settings for a renal therapy machine 100 from the patient's home.

The system settings screen 1570 (for online hemodialysis for example) also allows a clinician to specify an acid configuration 1586 (e.g., whether the acid is in a jug), the water system filter pack configuration 1588, the water system reject valve setting 1590 and a home device setting 1592. Different therapies will have different system settings, e.g., dialysate dextrose level for peritoneal dialysis. In one embodiment, many of the screens and options available though web portal 150 are coded to match the screens and options that appear on the renal therapy machine 100. For example, a home device setting accessed through a renal therapy machine 100 allows a user to disable the renal therapy machine 100. Home device setting 1592, accessed through FIG. 15C, allows a clinician to remotely turn a machine off completely. The clinician can submit these settings using submit button 1594 or cancel any changes to settings by using cancel button 1596.

Device Program

FIGS. 16A to 16G illustrate an example device program screen 1600 displayed on a clinician's display device 192, which allows clinicians to set values for parameters that control how the renal therapy machine 100 will perform renal treatment at the patient's home. In FIGS. 16A to 16G, various fields or parameters are specified by the clinician. The fields or parameters are the product of a doctor's prescription for the patient. The fields or parameters as illustrated below may allow for the patient to select a value from a range of values for one or more parameters.

As with the therapy prescription screen, the device program screens 16A to 16G also provide an option for the clinician to apply templates at scroll-down menu 1602. The templates are again convenient because templates allow the clinicians to enter preselected values for multiple parameters at once by selecting a template. For example, the clinician may have many patients that each require the same treatment duration, blood flowrate and heparin dose. The clinician may save the multi-use values under a template, giving the template a recognizable name. When the clinician wants to apply these settings to renal therapy machines 100 for multiple patients, the clinician can select a template instead of having to specify each field on device program screen 1600. Thus when creating or modifying a device program, the template pre-populates the fields with values. From there, the clinician can change the populated fields. If only a few fields are changed, the template has saved the clinician time and effort. The templates simplify settings for renal therapy, but the settings are nonetheless based upon a doctor's prescription. The templates can involve any one or more or all of the treatment device settings discussed below. The templates for the device program screens 16A to 16G are further described in FIGS. 17A and 17B.

Figure 16A:
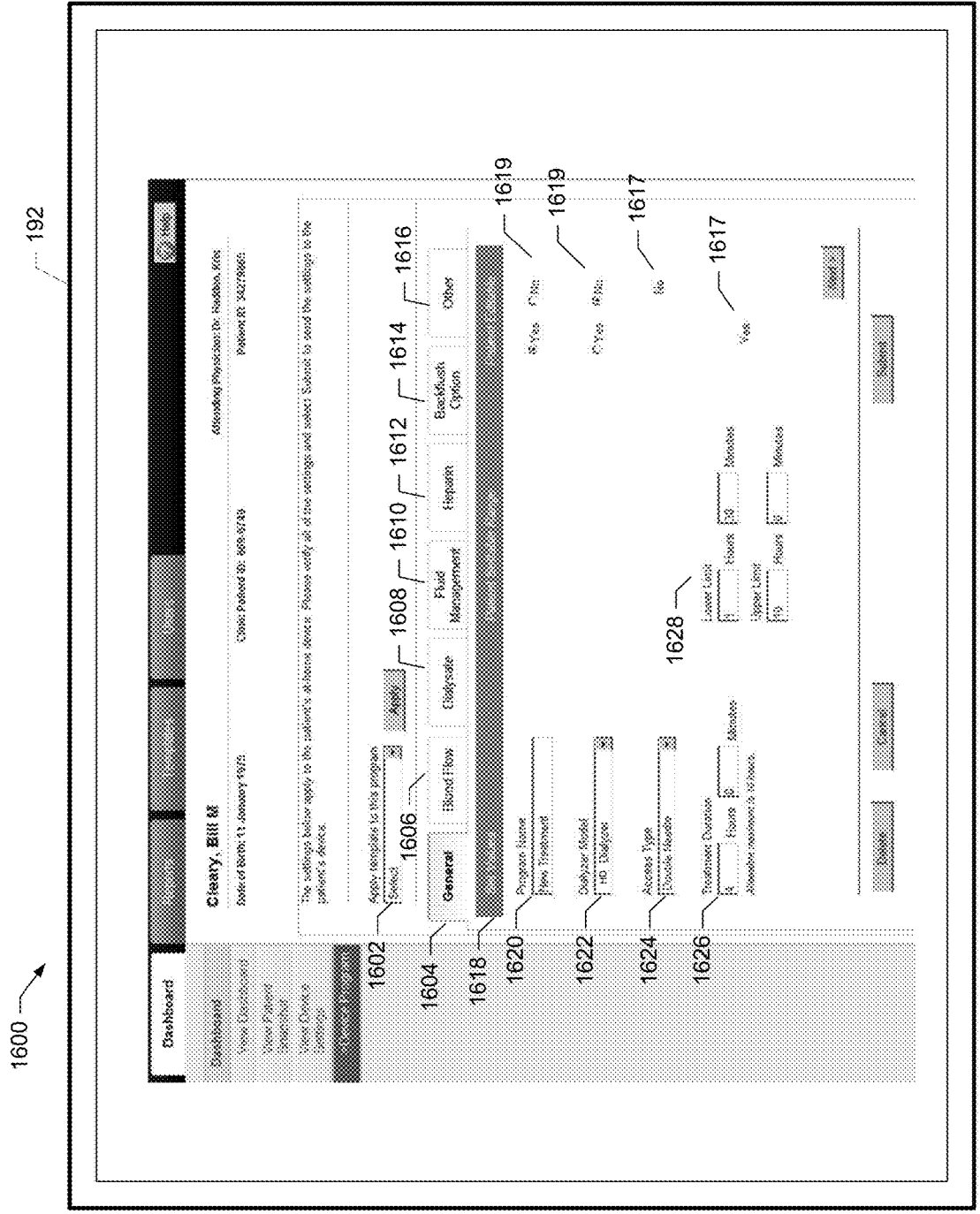
FIG. 16A is a screen shot of an example device program screen of the present disclosure.
Figure 16B:
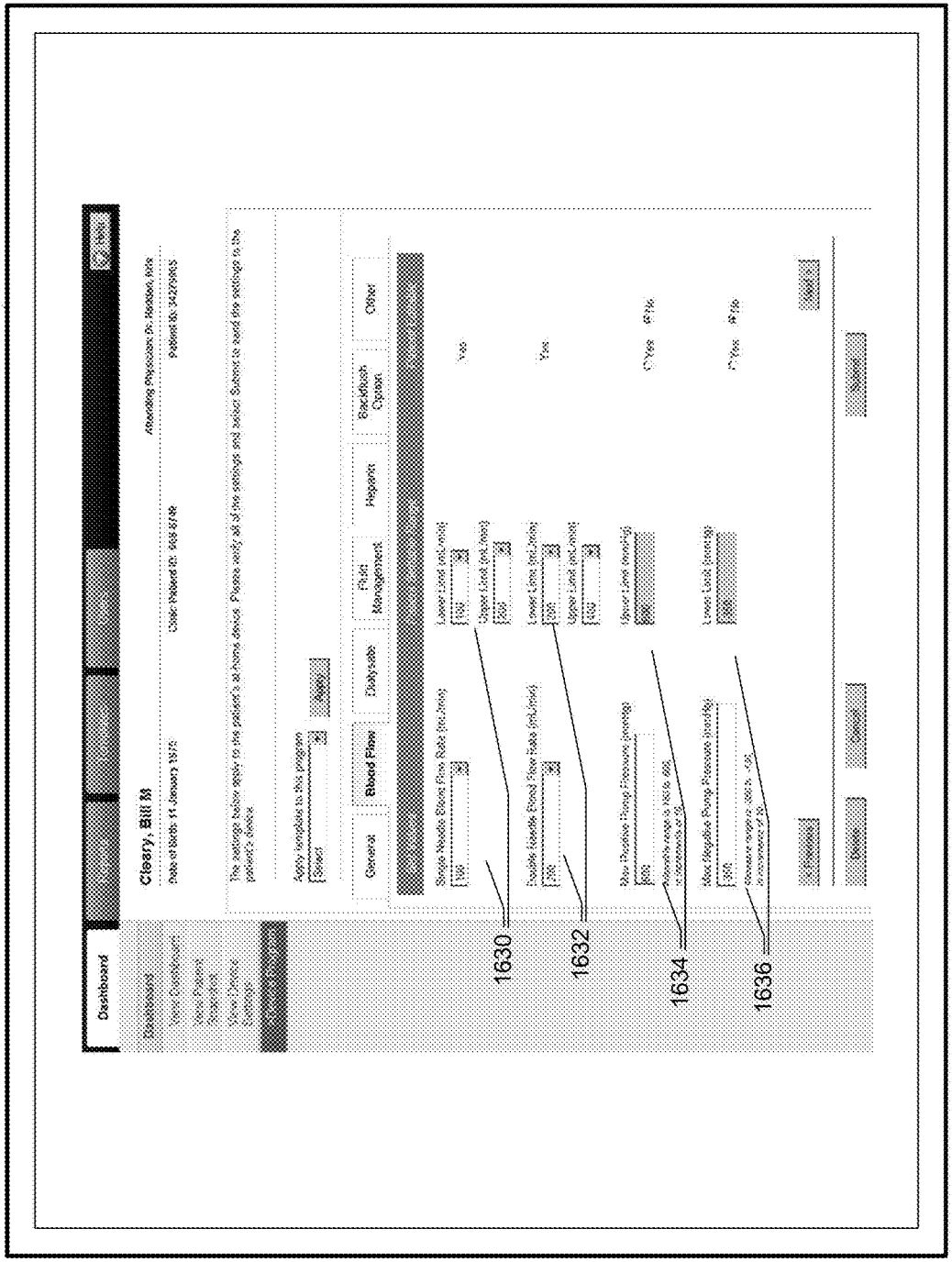
FIG. 16B is another screen shot of an example device program screen of the present disclosure.
Figure 16C:
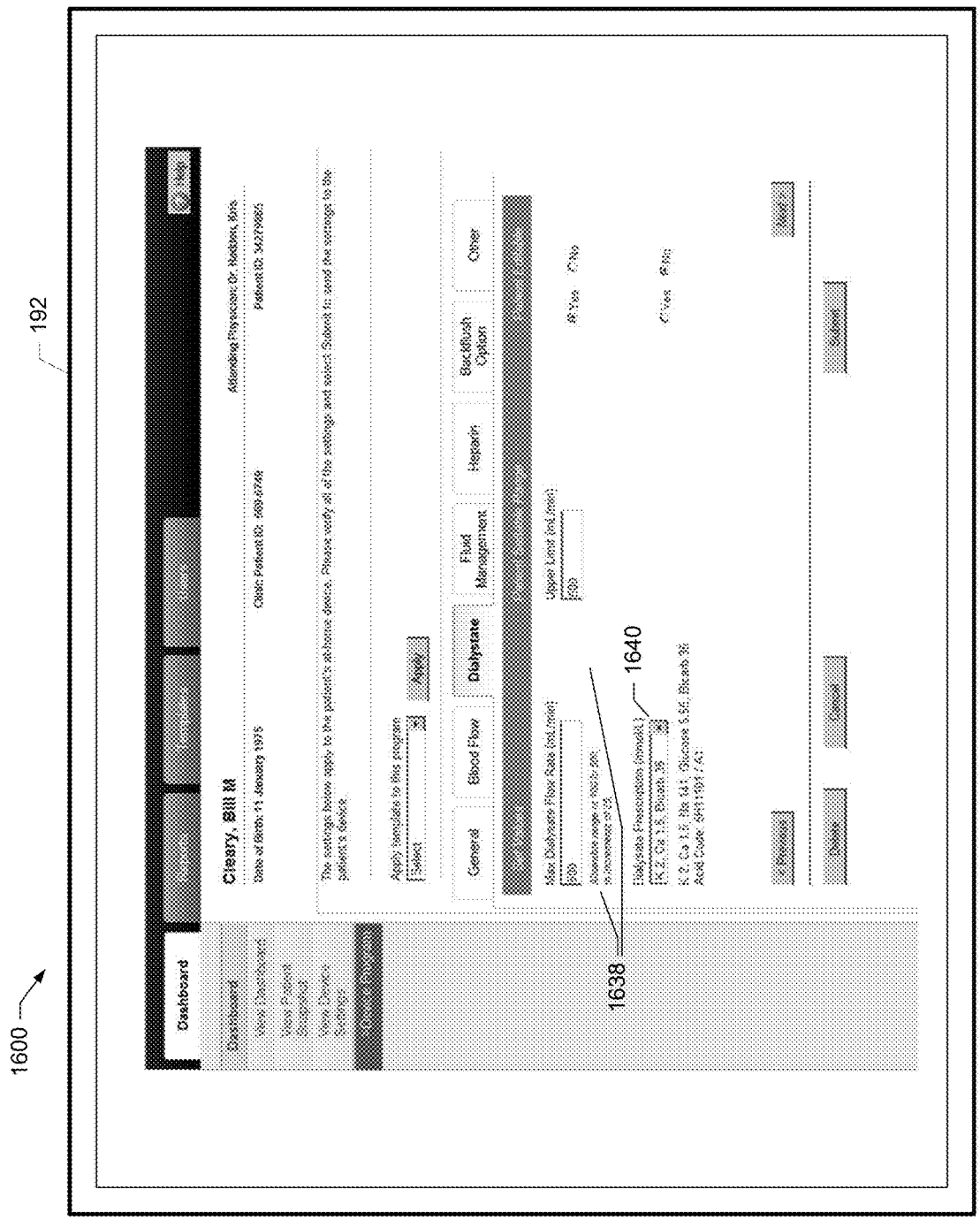
FIG. 16C is a further screen shot of an example device program screen of the present disclosure.
Figure 16D:
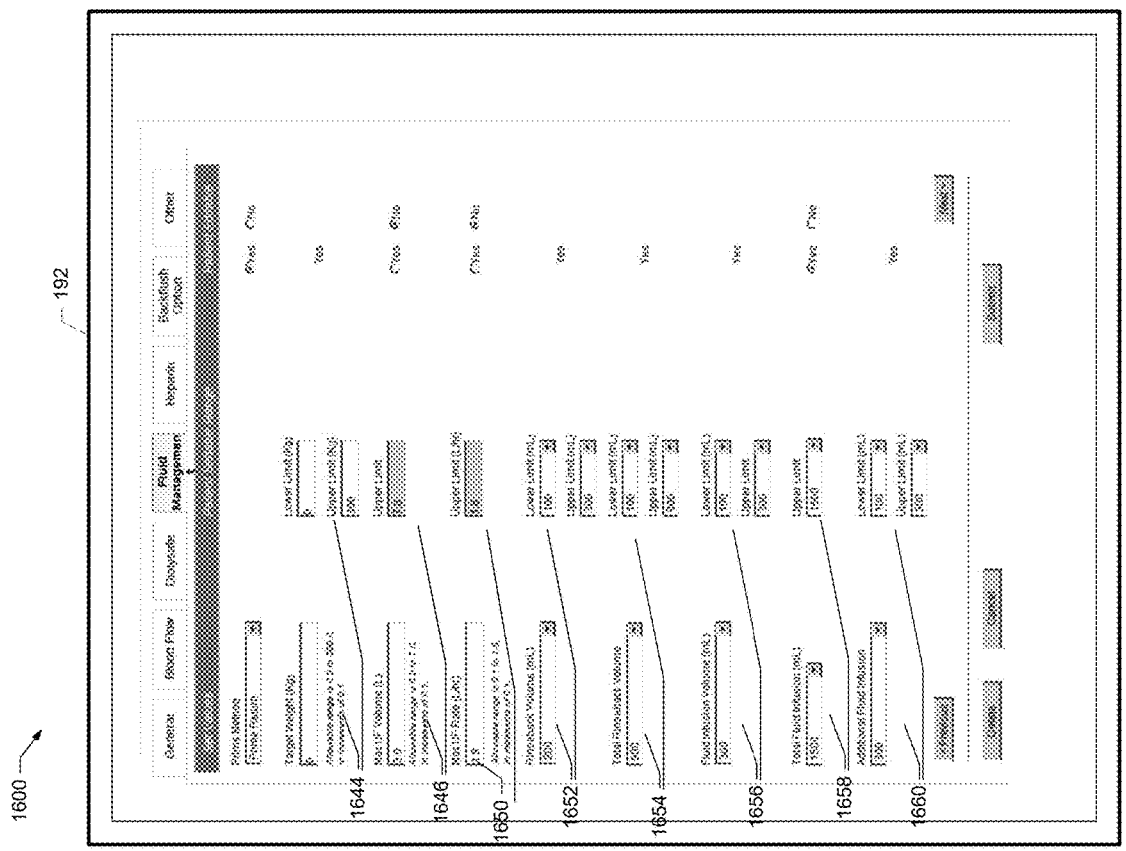
FIG. 16D is yet another screen shot of an example device program screen of the present disclosure.
Figure 16E:
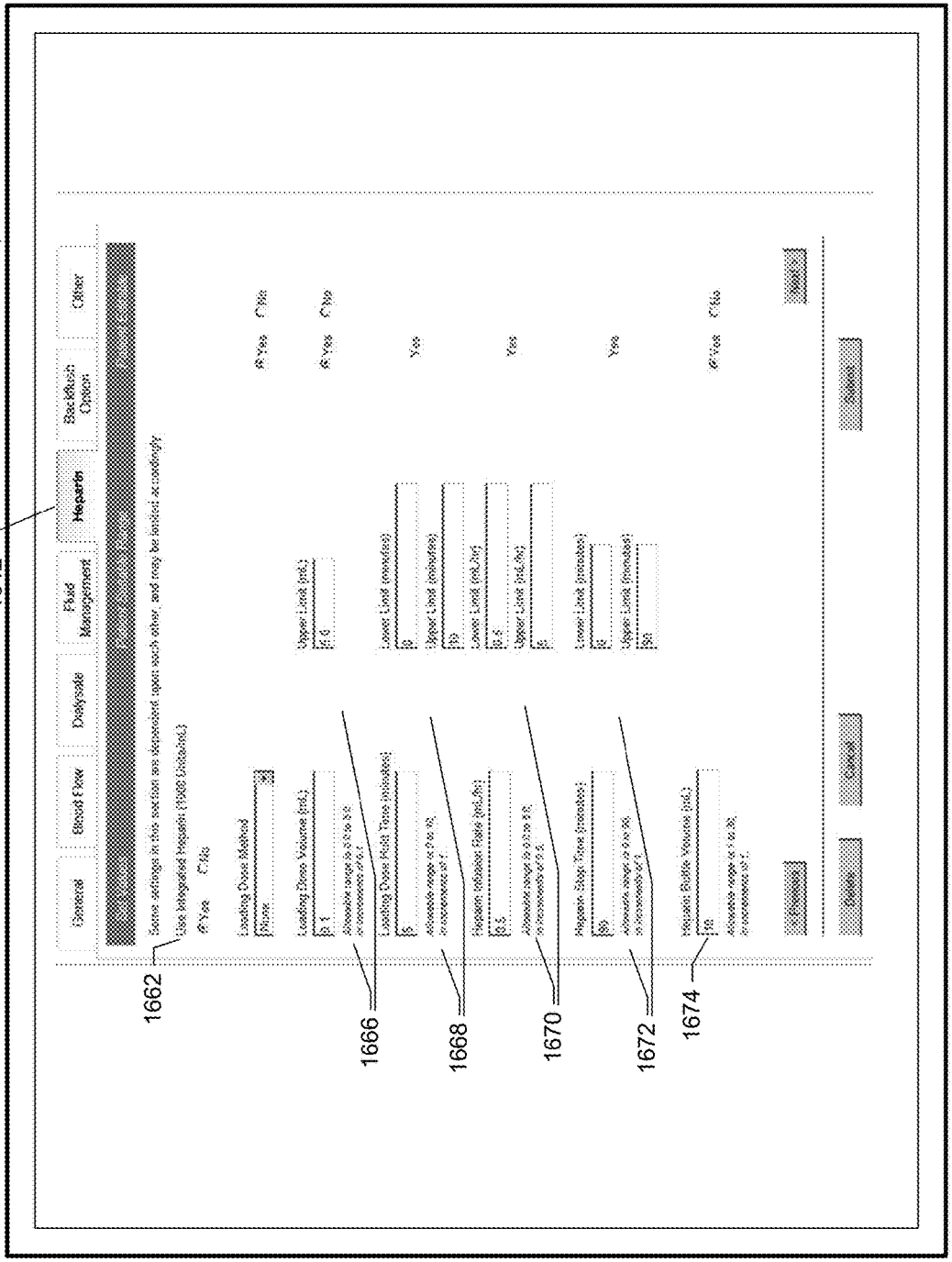
FIG. 16E is yet a further screen shot of an example device program screen of the present disclosure.
Figure 16F:
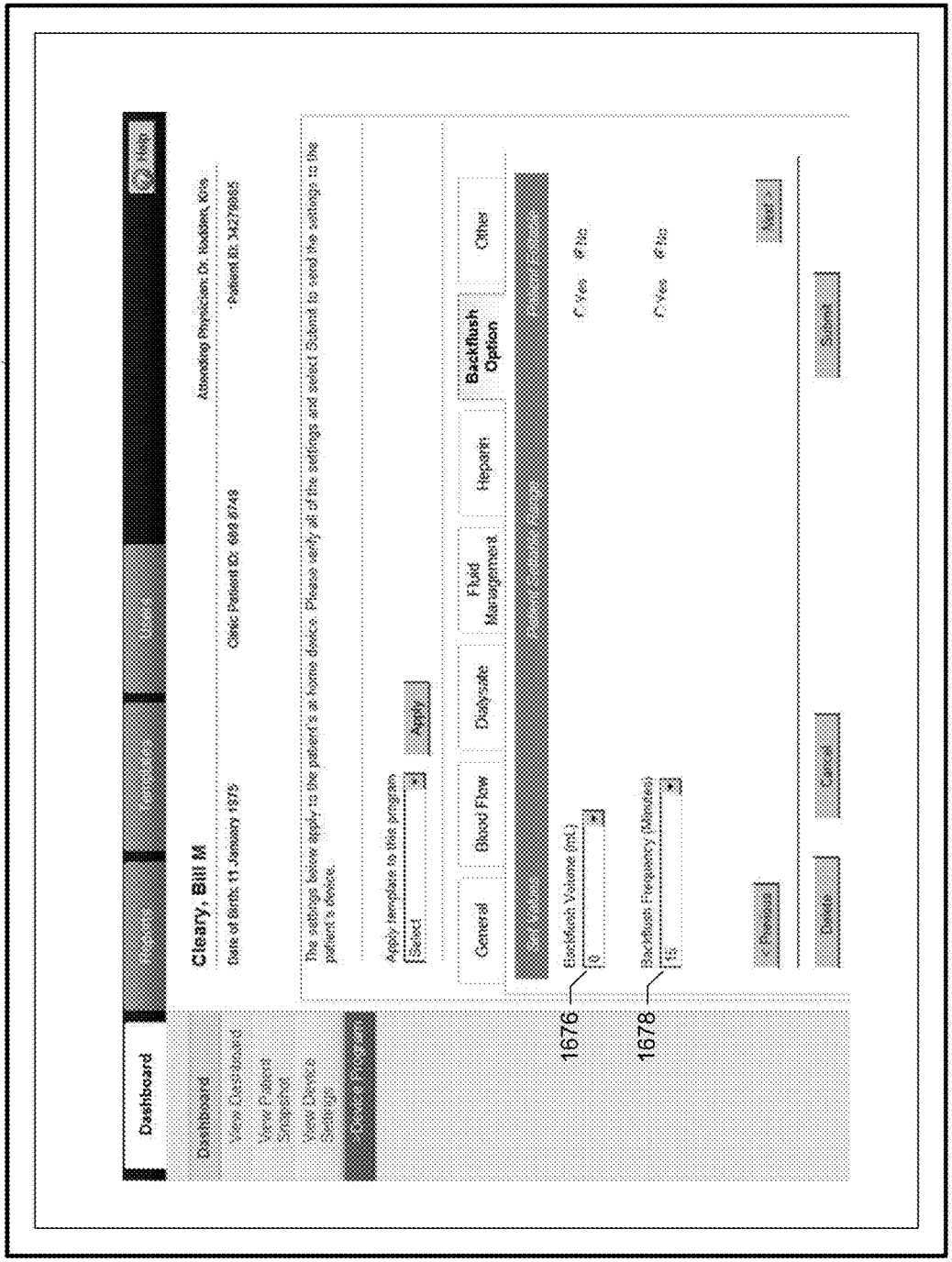
FIG. 16F is still another screen shot of an example device program screen of the present disclosure.
Figure 16G:
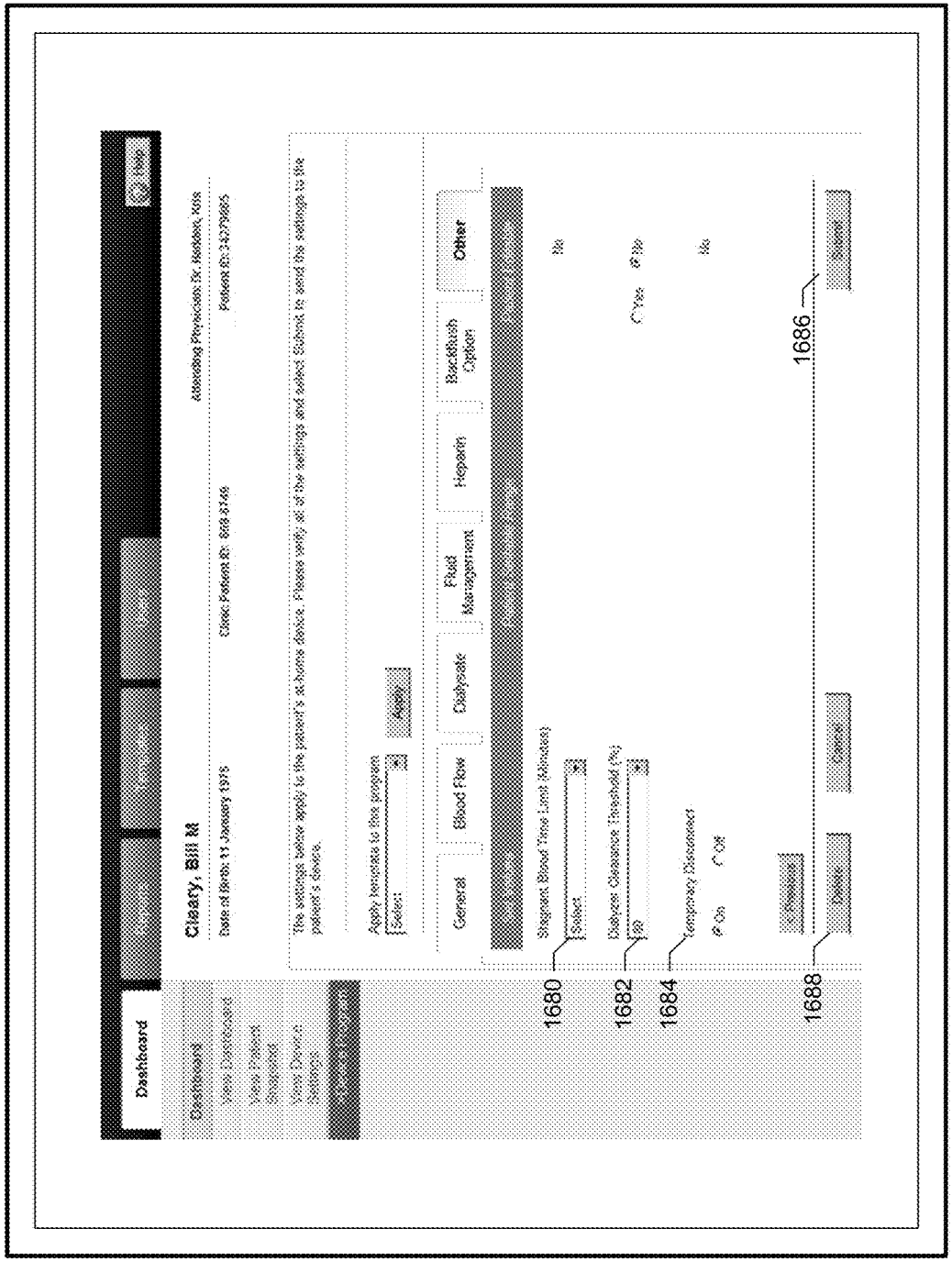
FIG. 16G is still a further screen shot of an example device program screen of the present disclosure.

The device program screen 1600 contains various tabs such as a general tab 1604 (FIG. 16A), a blood flow tab 1606 (FIG. 16B), a dialysate tab 1608 (FIG. 16C), a fluid management tab 1610 (FIG. 16D), a heparin tab 1612 (FIG. 16E), a backflush option tab 1614 (FIG. 16F) and another tab labeled "Other" 1616 (FIG. 16G).

Horizontal bar 1618 explains the various columns listed in each of the various tabs 1604 to 1616. The horizontal bar 1618 lists the same items on tabs 1604 to 1616 and indicates that a clinician can set values, set a patient settable range, and also specify whether those values are patient editable. Treatment features that are marked as not being patient editable in horizontal bar 1618 cannot be changed by a patient. For example, a clinician may be able to specify that a category or a portion thereof is not editable by a patient so that a patient would not be able to change any settings for those values. Or, the clinician can specify, using buttons 1619, that a patient may edit a certain value. In certain instances, the clinician may also allow a patient the flexibility to edit values within a range as described in further detail below. There can be certain items that a clinician has no control over, as indicated by the "Yes" and "No" 1617 that are hard coded into the system, with no ability for the clinician to change those values. Here, a clinician can only change the settings as far as the renal therapy machine 100 allows. Thus the renal therapy machine 100 may have machine limits or ranges that the clinician must stay within.

Device program screen 1600 displayed on a clinician's display device 192 in FIG. 16A illustrates that access type 1624 (discussed below) is not patient editable. Access type, e.g., single needle (usually nightly), dual needle short daily, dual needle nocturnal, dual needle every other day ("EOO"), and dual needle every other night ("EON"), is an overarching parameter or feature that affects many other parameters or features. It is also a, if not the, fundamental piece of the doctor's prescription. The feature is accordingly locked as may other features be if for example changing such features would require the ranges of other features to be changed. A clinician may be also able to lock a category or a portion thereof so that another clinician cannot change the setting. Or, an administrator for a clinic may lock a certain category or portion thereof so that no clinician can change the setting once it is set.

At device program screen 1600, the clinician can specify the device program name at entry box 1620, the dialyzer model that the patient is using at drop-down menu 1622, the treatment or access type at drop- or scroll-down menu 1624 and the treatment duration at fields 1626, which have fields for both hours and minutes. Device program screen 1600 also allows a clinician to specify a setting range 1628.

It is advantageous to allow patients to tailor the renal treatment when appropriate to their schedules and moods but do so within an allowed range. For example, a patient may not be feeling well enough to run a long treatment, may have a prior commitment, or in any case may want to run a shorter treatment. Allowing clinicians to specify acceptable ranges and then letting patients choose the actual values run by machine 100 allows patients to have some control and autonomy over the treatment. Patient choice is important. In no case however, can a patient change a parameter setting outside of a range set by the clinician (per doctor's prescription), or change the range that the clinician has set. System 110 also forces the clinicians to stay within the machine limits described above. In other words, a clinician sets a specific value and a range. The range specified by the clinician is limited by the machine. The patient can then alter the value within the range specified by the clinician.

FIG. 16B illustrates the blood flow tab 1606 of device program screen 1600 displayed on a clinician's display device 192, which allows the clinician to specify single needle blood flowrate at selections 1630, double needle blood flowrate at selections 1632, positive pump pressure at entries 1634, and negative pump pressure at entries 1636. In the illustrated embodiment, blood flowrate allows the minimum and maximum rate to be set by the clinician, and the patient to pick a value in between.

Pump pressure is the pressure by which the blood and dialysate pumps (for hemodialysis), dialysate pumps (for peritoneal dialysis, substitution pups (for hemofiltration and hemodiafiltration), drug pumps (for drug delivery, and so on, are operated. If the pumps are pneumatic pumps, for example, the pressure is set by setting the pump's pneumatic operating pressure.

FIG. 16C illustrates the dialysate tab 1608 of device program screen 1600 displayed on a clinician's display device 192. Tab 1608 allows the clinician to specify dialysate flowrate at entries 1638 and the dialysate prescription at drop-down menu 1640. Dialysate flowrate is the flowrate at which dialysate is pumped to and from a dialyzer (for hemodialysis) or the patient (for peritoneal dialysis). Dialysate prescription relates to the chemical makeup of the dialysate used for treatment, which is generally measured by measuring the conductivity of the dialysate.

FIG. 16D illustrates the fluid management tab 1610 of device program screen 1600 displayed on a clinician's display device 192, which allows the clinician to specify the priming method at drop-down menu 1642, the target weight at entries 1644, maximum UF volume at entries 1646, maximum UF rate at entries 1650, rinseback volume at entries 1652, total rinseback volume at entries 1654, fluid infusion volume at entries 1656, total fluid infusion at entries 1658 and additional fluid infusion at entries 1660.

The priming method can include whether or not the patient wishes to replace priming fluid in the blood set with dialysate before treatment is started. Target weight is the weight the patient wants to be at the end of treatment. Ultrafiltration is the amount of blood plasma or water that has to be removed from the patient over treatment for the patient to reach his or her target weight. UF rate is the rate at any given time during treatment that UF is being removed from the patient. Rinseback volume refers to the volume of fluid that is given at the end of the treatment as part of the process to return the patients blood. Fluid infusion volume to the volume of dialysate that can be given to the patient in response to a hypotensive event.

FIG. 16E illustrates the heparin tab 1612 of device program screen 1600 displayed on a clinician's display device 192. Heparin tab 1612 allows the clinician to specify whether to use integrated heparin via button 1662, loading dose method at drop-down menu 1664, the loading dose volume at entries 1666, the loading dose hold time at selections 1668, the heparin infusion rate at selections 1670, the heparin stop time at entries 1672 and the heparin bottle volume at entry 1674.

Loading dose hold time refers to the amount of time that the system waits after a heparin bolus is given to a patient prior to starting treatment. Heparin rate is the rate at which heparin is delivered to the blood circuit during treatment. Heparin time refers to the time before the end of treatment that heparin delivery is stopped to allow the patients blood to return to normal coagulation. Bottle volume sets how much heparin is available to be delivered over treatment.

FIG. 16F illustrates the backflush option tab 1614 of device program screen 1600 displayed on a clinician's display device 192, which allows the clinician to specify the backflush volume at drop-down menus 1676 and the backflush frequency at drop-down menu 1678. Backflush volume at drop-down menu 1676 is the volume of dialysate that is sent to the dialyzer to prevent clotting of the dialyzer. This volume is also given to the patient. The renal therapy machine automatically compensates its UF rate to remove this fluid, so from the fluid management standpoint there is a net zero fluid transfer. Backflush frequency at drop-down menu 1678 is how often (in minutes) a backflush bolus is given, which allows automating the delivery of the programmed backflush volume at the backflush frequency rate throughout the treatment.

FIG. 16G illustrates the "Other" tab 1616 of device program screen 1600 displayed on a clinician's display device 192, which allows the clinician to specify the stagnant blood time limit at drop-down menu 1680, and the dialyzer clearance threshold 1682. The clinician can also set whether the patient can use a temporary disconnect 1684. Stagnant blood time at drop-down menu 1680 sets how long the blood pump can be paused during treatment before treatment is stopped and rinseback begins. Dialyzer clearance threshold at drop-down menu 1682 sets a minimum clearance value for the dialyzer, which is reused in one embodiment. Once the actual clearance of the dialyzer falls below a certain threshold, the dialyzer has to be replaced. Lowering the threshold value thus increases the life of the dialyzer potentially, but allows for less clearance at the end of the life of the dialyzer.

At the temporary disconnect selection 1684, the clinician can decide whether the patient can get off of the machine during treatment. For example, the patient may have to use the bathroom or attend to some task during treatment. If temporary disconnect is allowed, the patient can pause treatment, disconnect from the blood needles, and attend to whatever needs attention. Blood in the blood tubes is typically rinsed back to the patient before the patient can get off of the machine. The clinician may not be comfortable yet with the patient rinsing back, disconnecting, and then reconnecting, and may therefore opt not to allow temporary disconnect at selection 1250.

Once all the fields have been filled, the clinician selects a Submit button 1686 in FIG. 16G, which sends the settings entered on the device program screen 1600 displayed on a clinician's display device 192 to the renal therapy machine 100. In one embodiment, the clinician may be required to identify himself or herself when the Submit button 1686 is selected to ensure that only an authorized clinician is making changes to the renal therapy machine 100's settings. Indeed, the clinician may be required to enter an identification number to even begin making changes to an existing device program or making a new device program. Selecting the Submit button 1686 in one embodiment leads to a Confirm Screen (not illustrated) that provides a summary of the device programs in a condensed, e.g., one page format. The clinician then confirms that each setting for the device program is correct.

In one embodiment, Submit button 1686 does not send the device program to therapy machine 100. Instead, the Submit button 1686 sends the new device program to the device programs listed at device settings screen 1500 (FIG. 15A) only. In this manner, the clinician can create multiple device programs, each meeting a doctor's prescription, without necessarily sending the device programs to machine 100. This allows an opportunity for afterthought and consultation by the clinician if desired. It is also expressly contemplated for the clinician to send multiple device programs to machine 100 for the same patient. The patient could thus have a device program for short, e.g., short daily, nocturnal, EON, EOD, to allow the patient to have flexibility, e.g., from week to week.

The delete button 1688 allows a clinician to delete a specific device or treatment program. In one embodiment, the clinician must confirm that he or she would like to delete the program before the program is actually deleted or removed from the patient's arsenal of treatment or device programs. In one embodiment, the submit button 1686 and the delete button 1688 appear on each of tabs 1604 to 1616, so that the clinician can submit a program or delete a program from any one of tabs 1604 to 1616.

As discussed above, while machine 100 will not run a treatment until the new device program is approved by the patient, the patient still has to review and accept the new device program before it is finally download for operation via ACPU 112. Thus the patient can see if a new device program is questionable, e.g., if new settings depart radically from the old settings or if the patient is not comfortable with the new settings. The patient can contact the clinic and review the new device programs.

In one embodiment, once the settings are submitted and sent to the renal therapy machine 100, the settings can only be changed with a clinician password (FIG. 15C). The clinician specifies the clinician password at the web portal 150 when selecting values for the parameters on device program screen 1200. If changes to the settings are to be made at the renal therapy machine 100 in the patient's home, the clinician first enters the password. The settings may thereafter be changed.

Figure 17A:
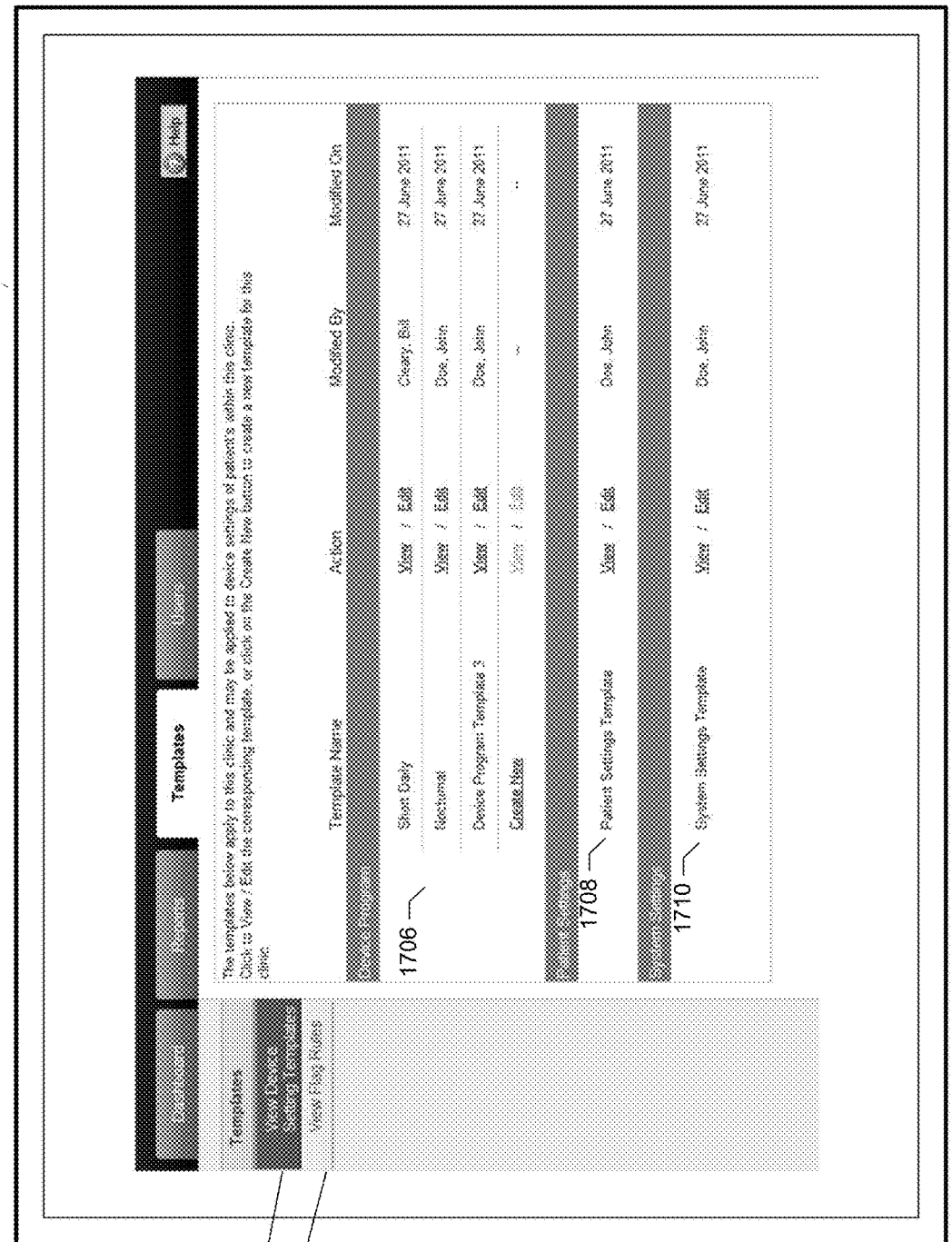
FIG. 17A is a screen shot of an example device setting templates screen of the present disclosure.

As discussed above, templates are provided for convenient entry of preselected values. The template values may be changed to refine the device program. FIG. 17A illustrates an example device setting templates screen 1700 displayed on a clinician's display device 192 that can be used to prepare templates for various portions of the web portal 150. The device setting template screen 1700 allows a clinician to create, view and edit device program templates 1706 to be used to populate settings when creating device programs, a patient settings template 1708 to be used to populate patient settings, and a system settings template 1710 to be used to populate system settings. Device setting template screen 1700 contains many of the same elements of device settings screen 1500 (FIG. 15A) because the templates created using device setting templates screen 1700 can be used to populate values in the device settings screen 1500. The clinician can select links 1702 and 1704 to navigate to device setting templates screen (FIG. 17A) and flag rules screens (FIGS. 17C to 17E).

Figure 17B:
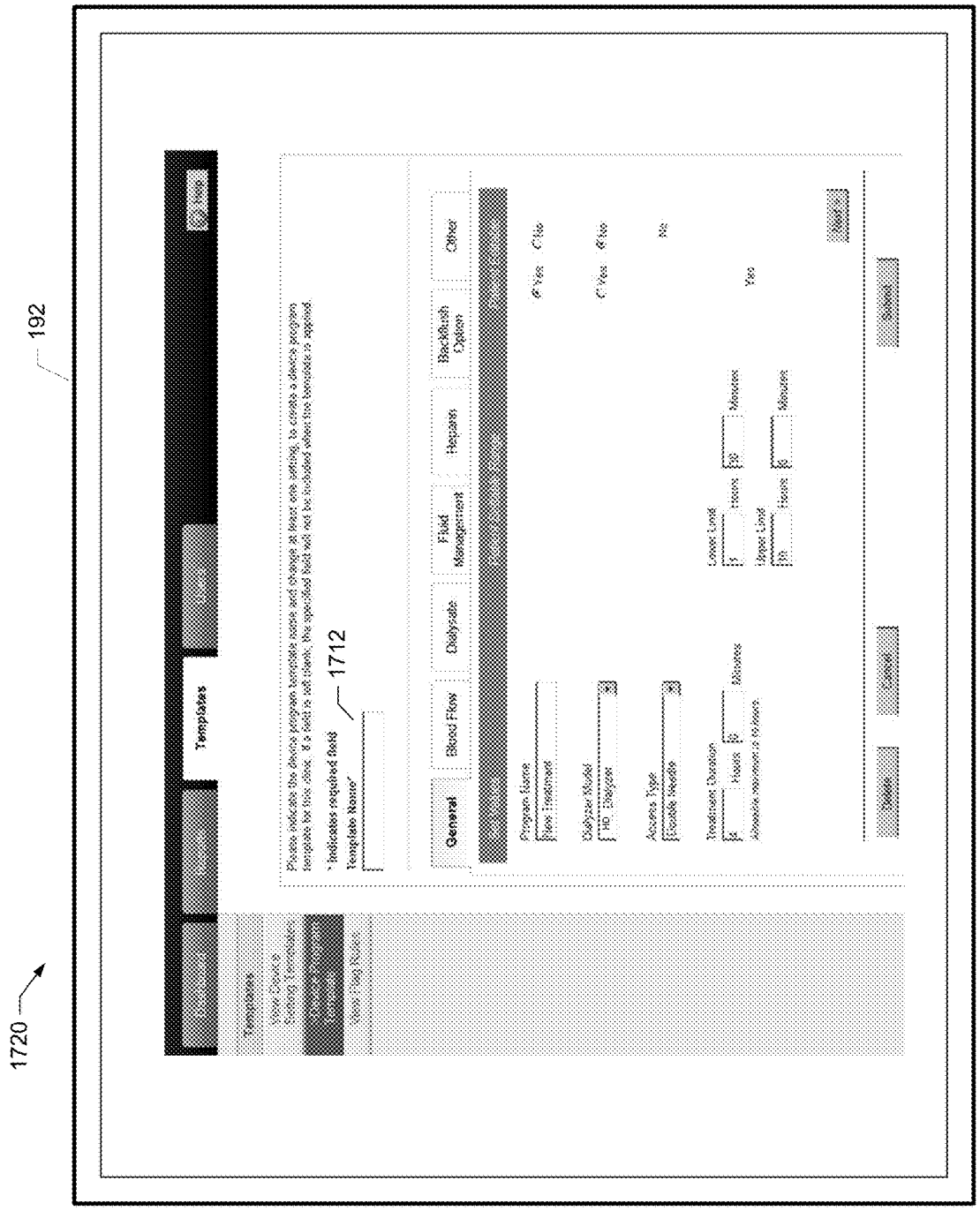
FIG. 17B is a screen shot of an example device program template screen of the present disclosure.

FIG. 17B illustrates a template 1720 displayed on a clinician's display device 192 that a clinician can use to specify values for the parameters and setting ranges described above in the general tab under device program screen 1600 (FIG. 16A). The clinician can specify the template name in field 1712. Additional template screens (not shown) are available for each tab described in FIGS. 16B through 16G.

During a renal treatment, a large number of events take place, which machine 100 stores in its log files. Home medical device system 110 provides a proficient way to notify clinicians regarding pertinent treatment events and conditions. The clinicians can specify the events or conditions that are of most concern. When these events occur or when the conditions are met or not met, system 110 triggers and displays relevant notifications to the clinician who reviews the patient's treatment data.

Figure 17C:
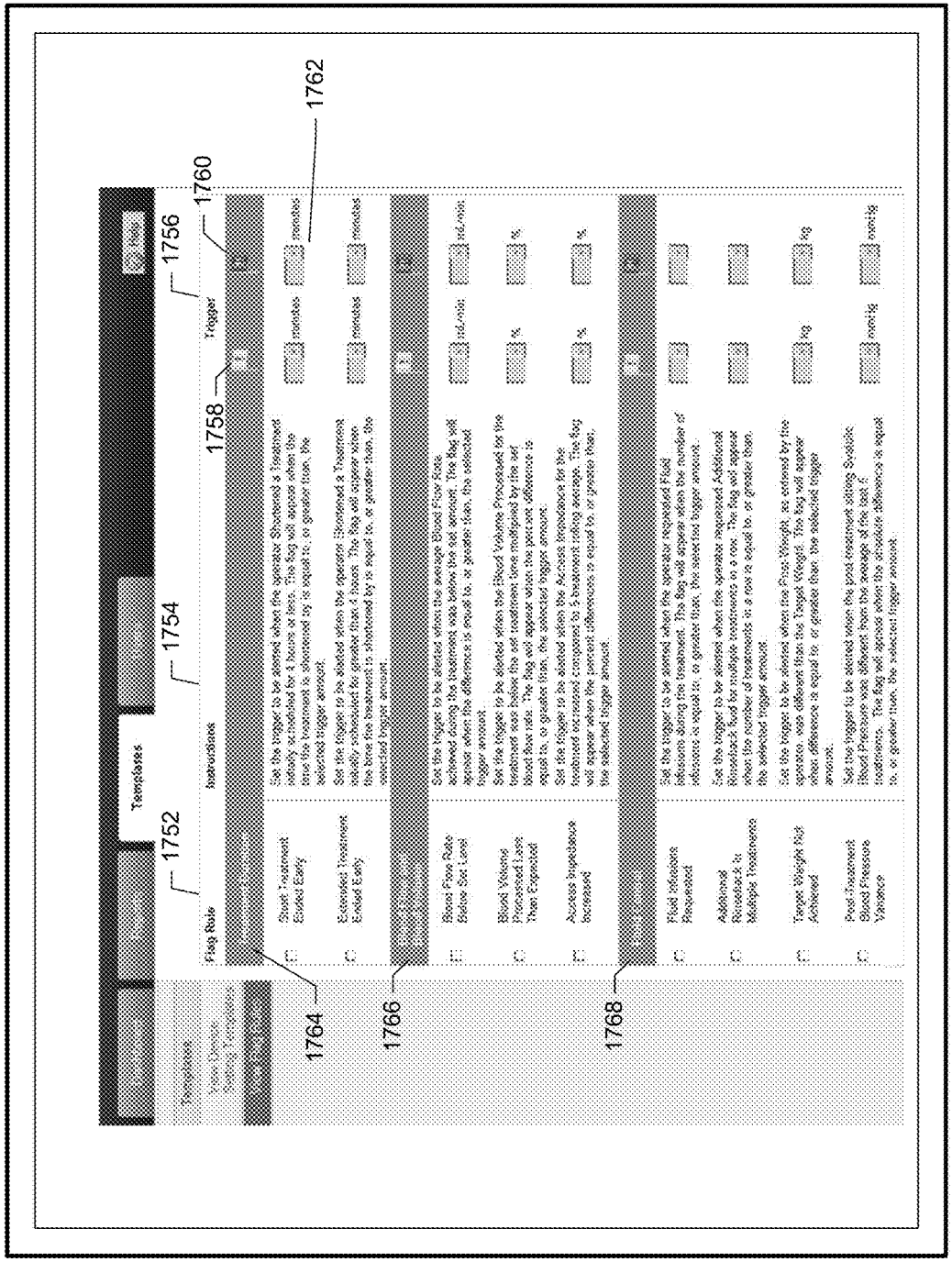
FIG. 17C is a screen shot of an example flag rules screen of the present disclosure.
Figure 17D:
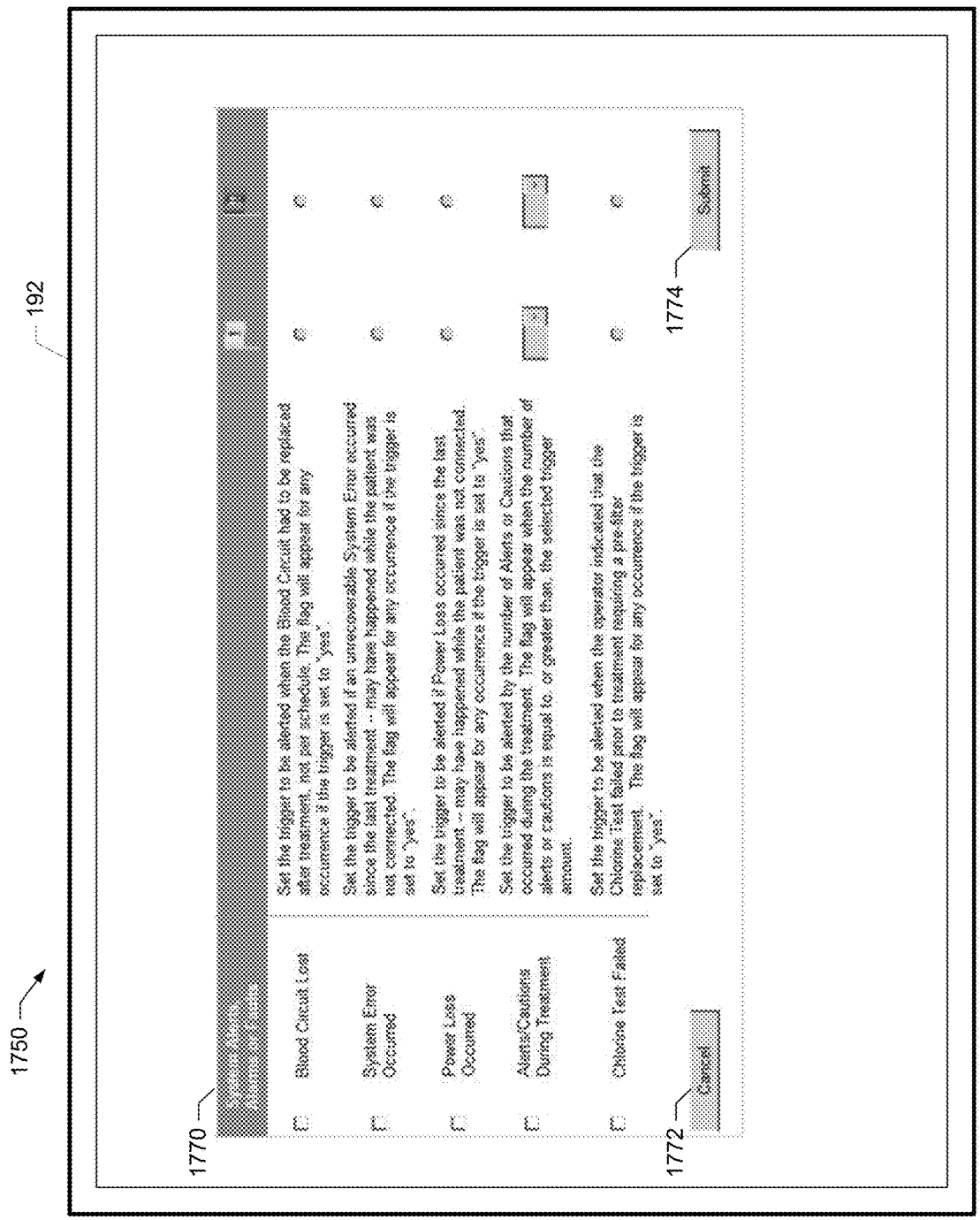
FIG. 17D is another screen shot of an example flag rules screen of the present disclosure.
Figure 17E:
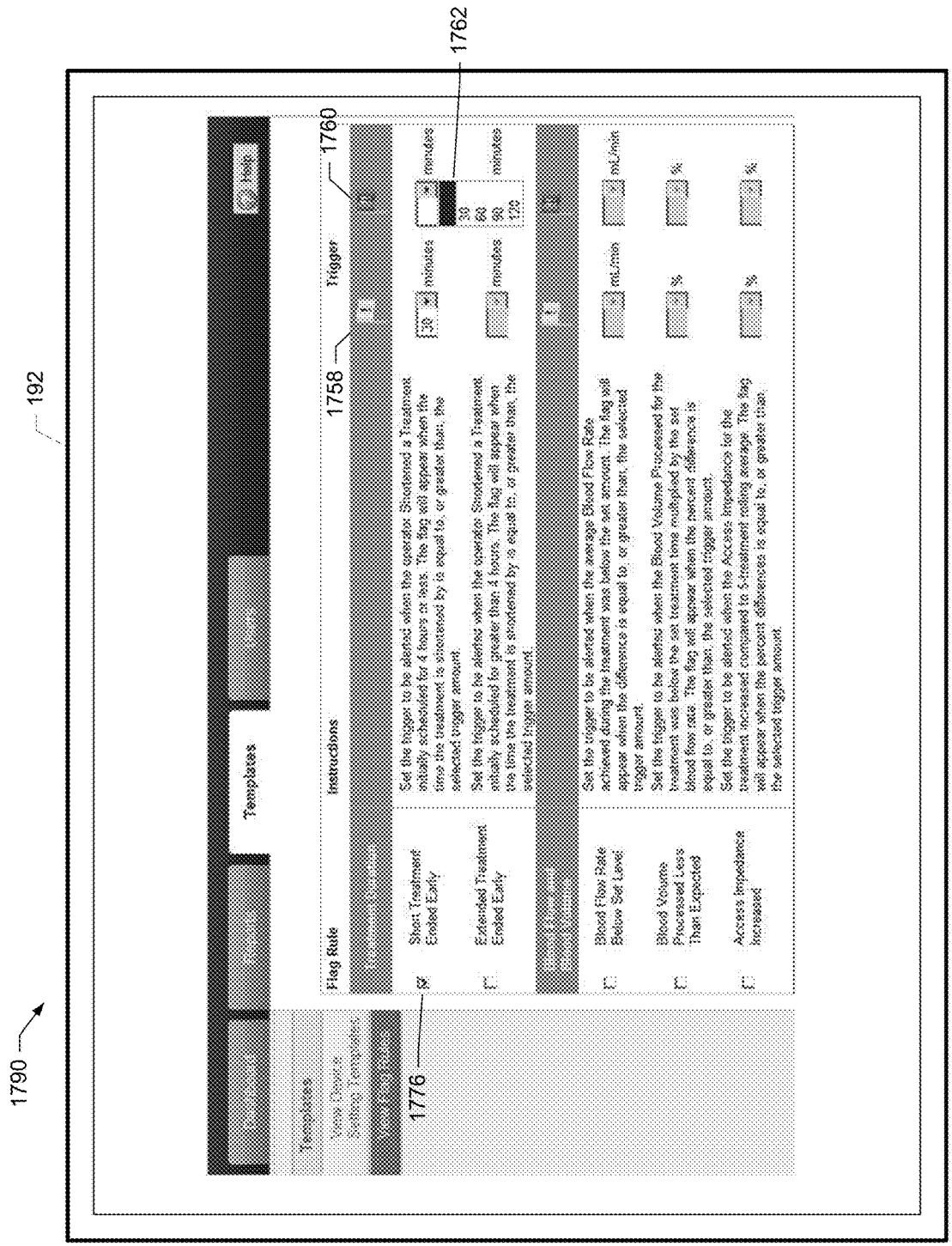
FIG. 17E is a further screen shot of an example flag rules screen of the present disclosure.

FIG. 17C illustrates an example flag rules screen 1750 displayed on a clinician's display device 192 that allows the clinician to select different treatment events shown in column 1752 that will trigger a notification. The flag rules screen is illustrated as being organized under the templates portion of web portal 150, but may be organized under a different portion of the web portal 150. For each treatment event in column 1752, the flag rules screen displays instructions about that event in column 1754 and the trigger for that event in column 1756. As illustrated in FIG. 17C, a clinician can set flag rules relating to treatment duration 1764, blood flow and blood volumes 1766, and fluid control 1768.

Flag rules screen 1750 also allows the clinician to specify the parameters 1762 that either generate a first notification icon 1758 or a second notification icon 1760. Flag rules screen 1750 enables the clinician to quickly specify or check off the different events or conditions that the clinician desires to trigger a flag or a notification on dashboard 1200 described in FIG. 12A. The clinician can check off or specify different values, related to the events in column 1752, which trigger an alert. The different notification icons 1758 and 1760 indicate the different alerts can be triggered. Notification icons 1758 and 1760 are icons that will appear in the dashboard 1200. The notification icons 1758 and 1760 are explained in the legend screen 1250 (FIG. 12B).

FIG. 17D illustrates that events related to system alerts, alarms or faults 1770 can also trigger flag rules on flag rules screen 1750 displayed on a clinician's display device 192. The clinician can submit or cancel the settings using submit button 1774 or cancel button 1772, respectively.

FIG. 17E illustrates an example of the setting of flag rules 1790 displayed on a clinician's display device 192. In the illustrated embodiment, the clinician would like to be alerted on the dashboard screen 1200, via the notification icons, when a short treatment has ended early 1776. The clinician sets parameters 1762 so that notification icon 1758 appears on the dashboard screen 1200 when a treatment is shortened by thirty minutes or more. The clinician can also set parameters 1762 so that notification icon 1760 appears on the dashboard screen 1200 when a treatment is shortened by, e.g., sixty, ninety, or one-hundred-twenty minutes or more.

User Management

Figure 18A:
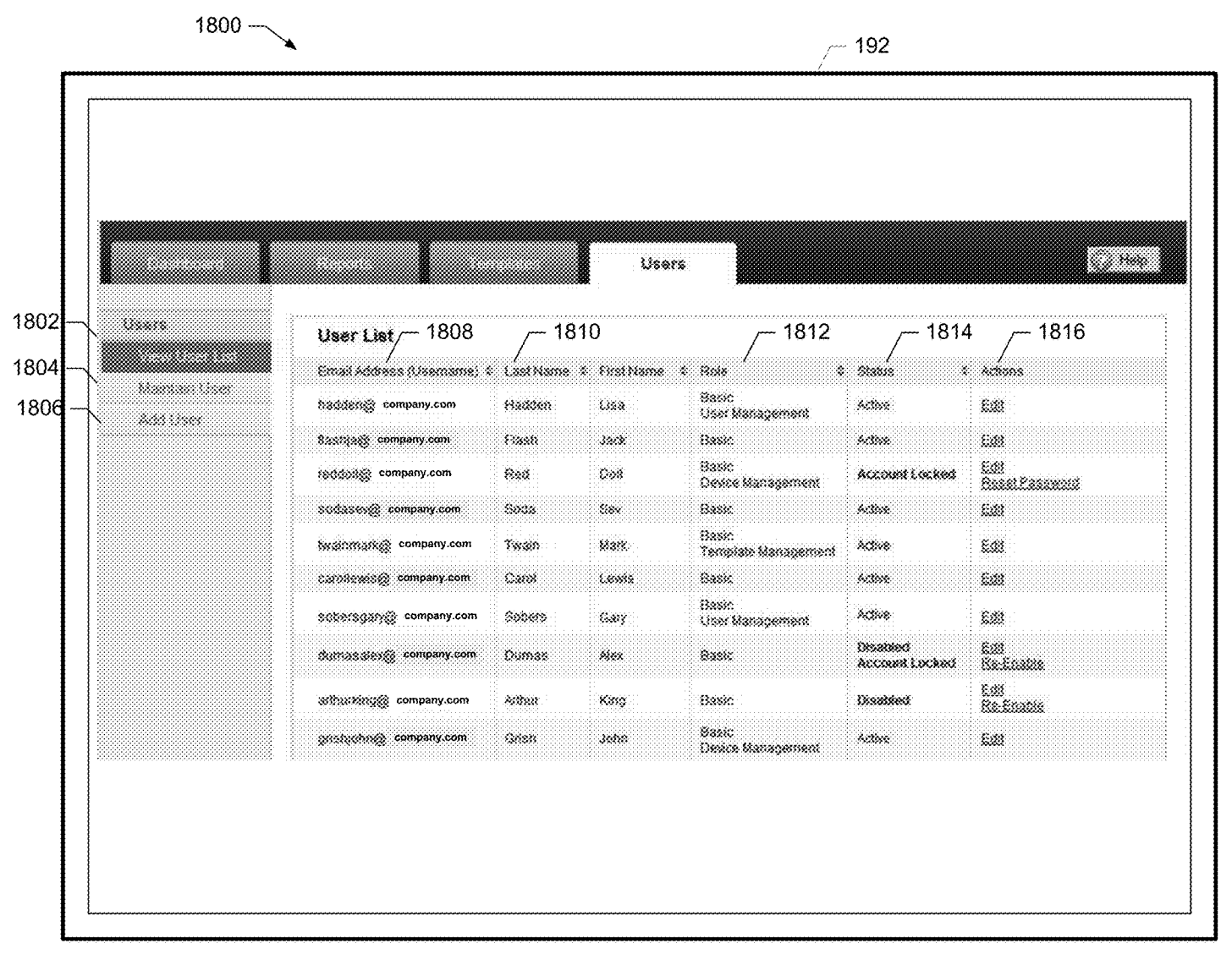

FIG. 18A is an example screen shot of a users screen 1800 displayed on a clinician's display device 192. In one embodiment, only a clinic administrator can access the users tab 1223. Upon selecting the users tab 1223, a clinic administrator is able to view a user list 1802, maintain a user 1804 and add a user 1806 on the left hand side of the screen as illustrated in FIG. 18A. In the illustrated embodiment, the clinic administrator has selected view user list 1802, which appears as being high-lighted. In the user list, a clinic administrator can view an email address or user name 1808, the name of the user 1810, the role of the user 1812, the status of the user 1814 and various actions 1816 that may be performed on that user entry in the user list.

Figure 18B:
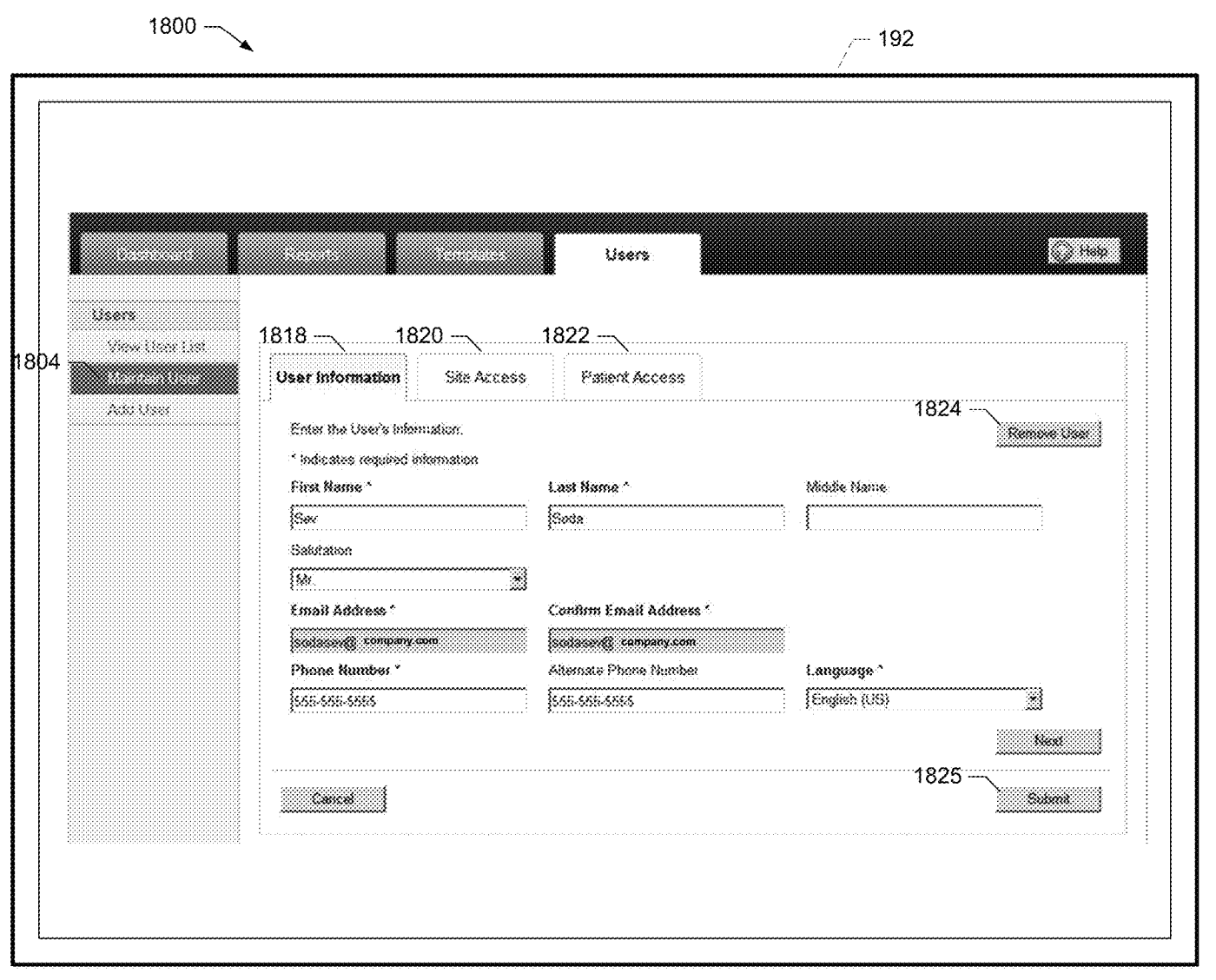

A clinic administrator may select maintain user 1804 to maintain information about a specific user that has been selected. As illustrated in FIG. 18B illustrating a users screen 1800 displayed on a clinician's display device 192, when the maintain user link 1804 is selected, it is highlighted to indicate it is currently selected. Selecting maintain user 1804 displays three more tabs to the clinic administrator: user information 1818, site access 1820 and patient access 1822. On the screen illustrated in FIG. 18B, the clinic administrator also may be able to remove a user using remove user button 1824. Once the clinic administrator fills out or updates information about the user, the clinic administrator can submit the information using submit button 1825.

The clinic administrator may also select site access tab 1820 to specify the role of a user. A user may have more than one of the roles at the same time. Each role unlocks or opens up certain features and abilities for a user. The clinic administrator can specify how much control is given to a user based upon the role or roles selected for that user. For example, as illustrated in users screen 1800 displayed on a clinician's display device 192 in FIG. 18C, a user may be given or take on one or more of four roles: a basic role 1826, a device management role 1828, a device template management role 1830, and a user management role 1832. A basic role 1826 gives a user the ability to view patient information including treatment information, device settings and reports, including the dashboard screen 1200. A device management role 1828 gives a user the ability to create and edit device settings. A device template management role 1830 gives a user the ability to create and edit clinic device templates and clinic flag rules. A user management role 1832 gives a user the ability to create and edit clinic staff users. Multiple roles may be given to a single user to allow for progressive access to system 110. In the illustrated embodiment, the user Dr. John Parker has been given the basic role, as indicated by the check box at selection 1826.

Figure 18C:
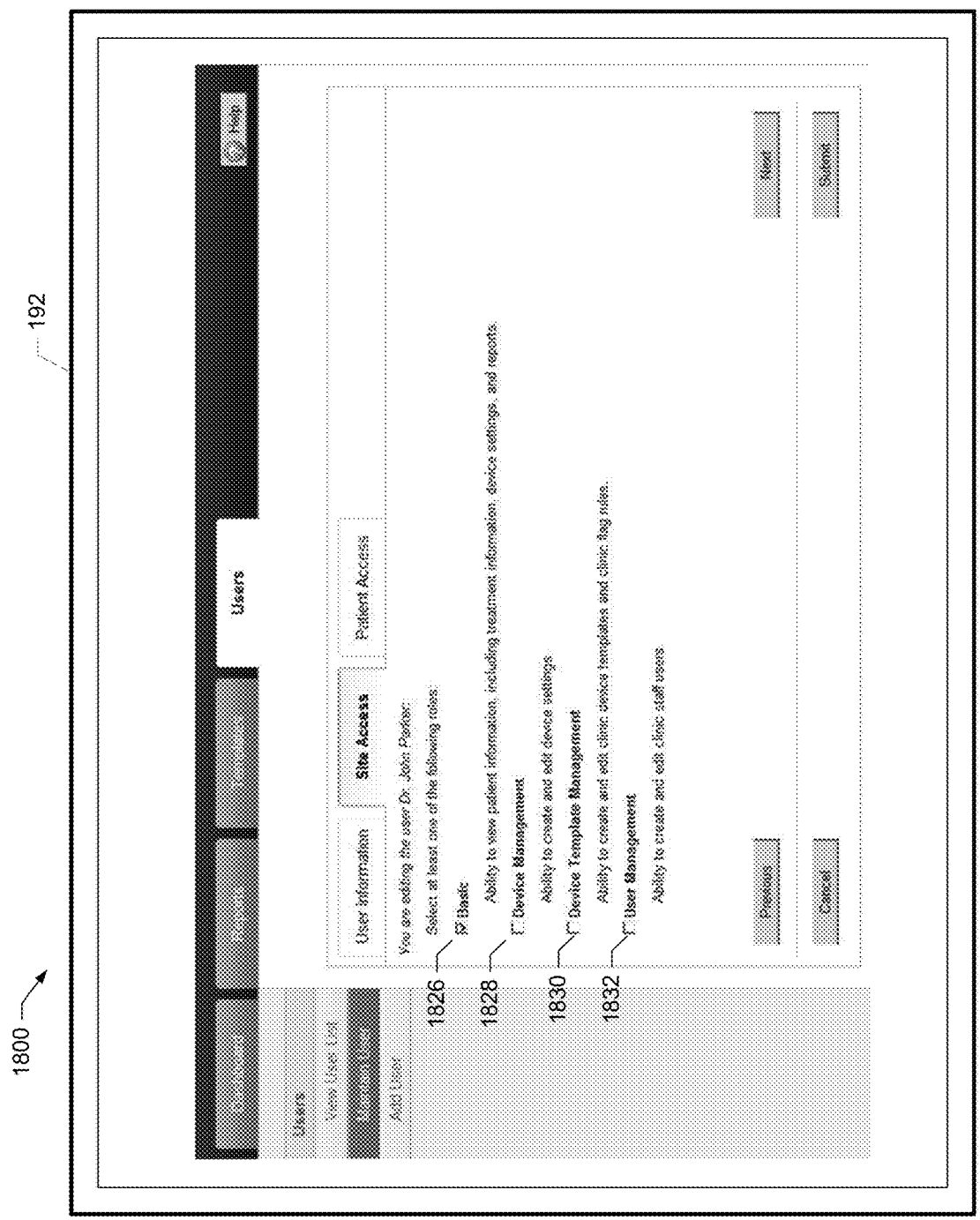
FIG. 18C is a further screen shot of a users screen of the present disclosure.
Figure 18D:
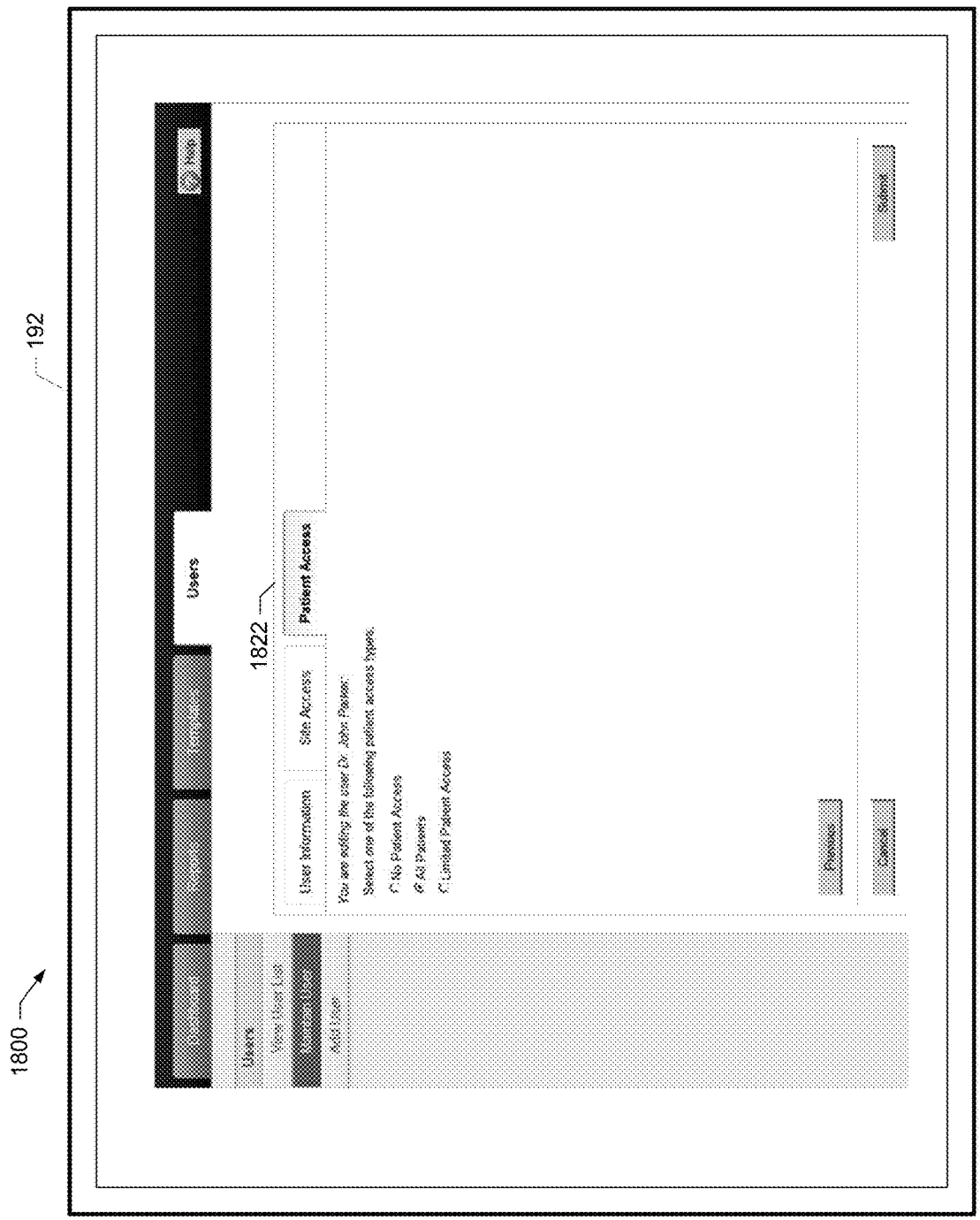
FIG. 18D is yet another screen shot of a users screen of the present disclosure.
Figure 18E:
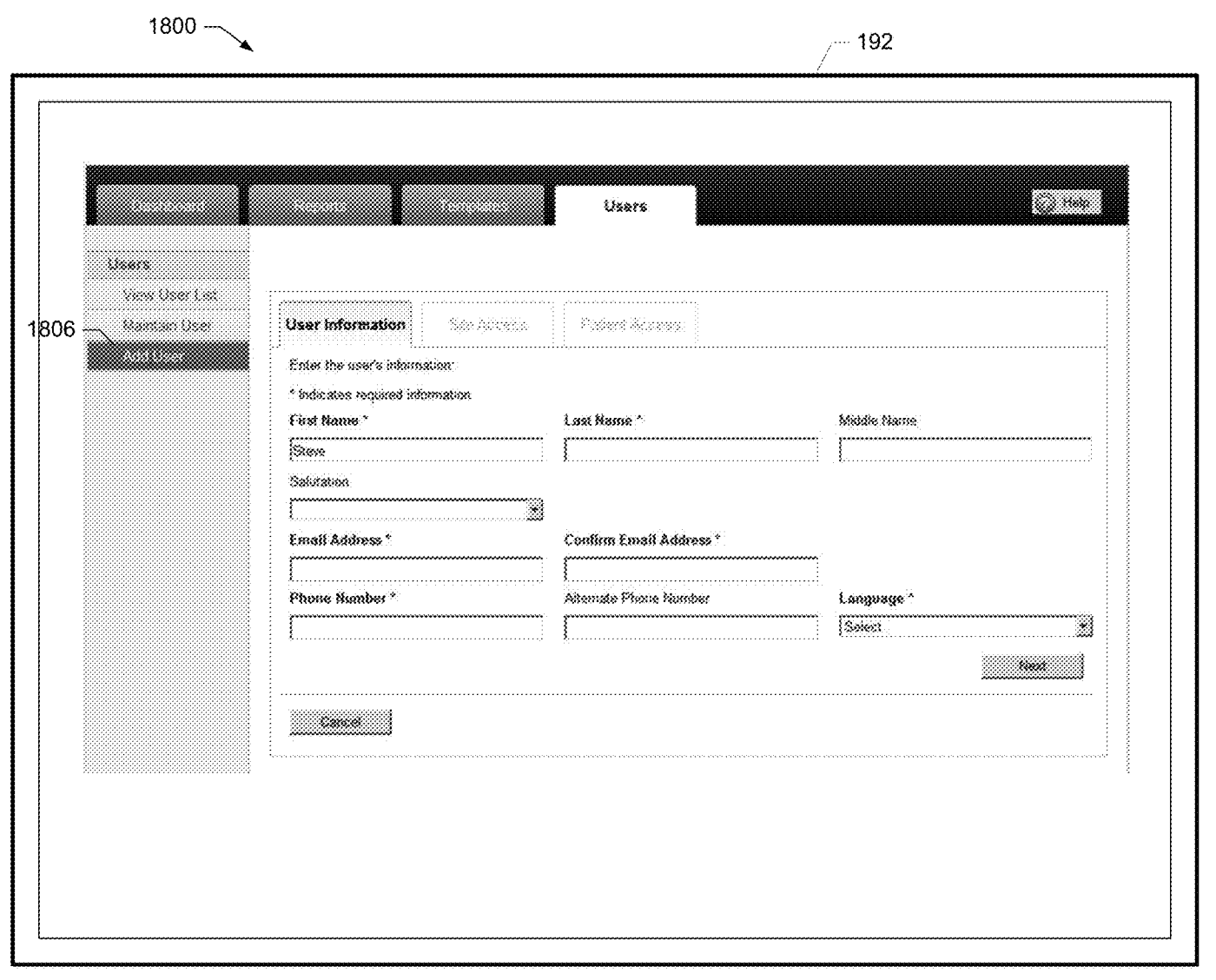

The clinic user may also select patient access tab 1822 displayed on a clinician's display device 192 as illustrated in FIG. 18D. Patient access tab 1822 allows a clinic administrator to specify what type of patient access a user can have. A user may have no patient access, may have access to all patients, or may have limited patient access. When a user has limited patient access, that user can only access information about certain specified patients (not shown). For example, limited patient access may be used to give a doctor access to only his or her patients. Clinic administrator may also be able to add a user using link 1806 as illustrated in a users screen 1800 displayed on a clinician's display device 192 in FIG. 18E.

Reports

Figure 19:
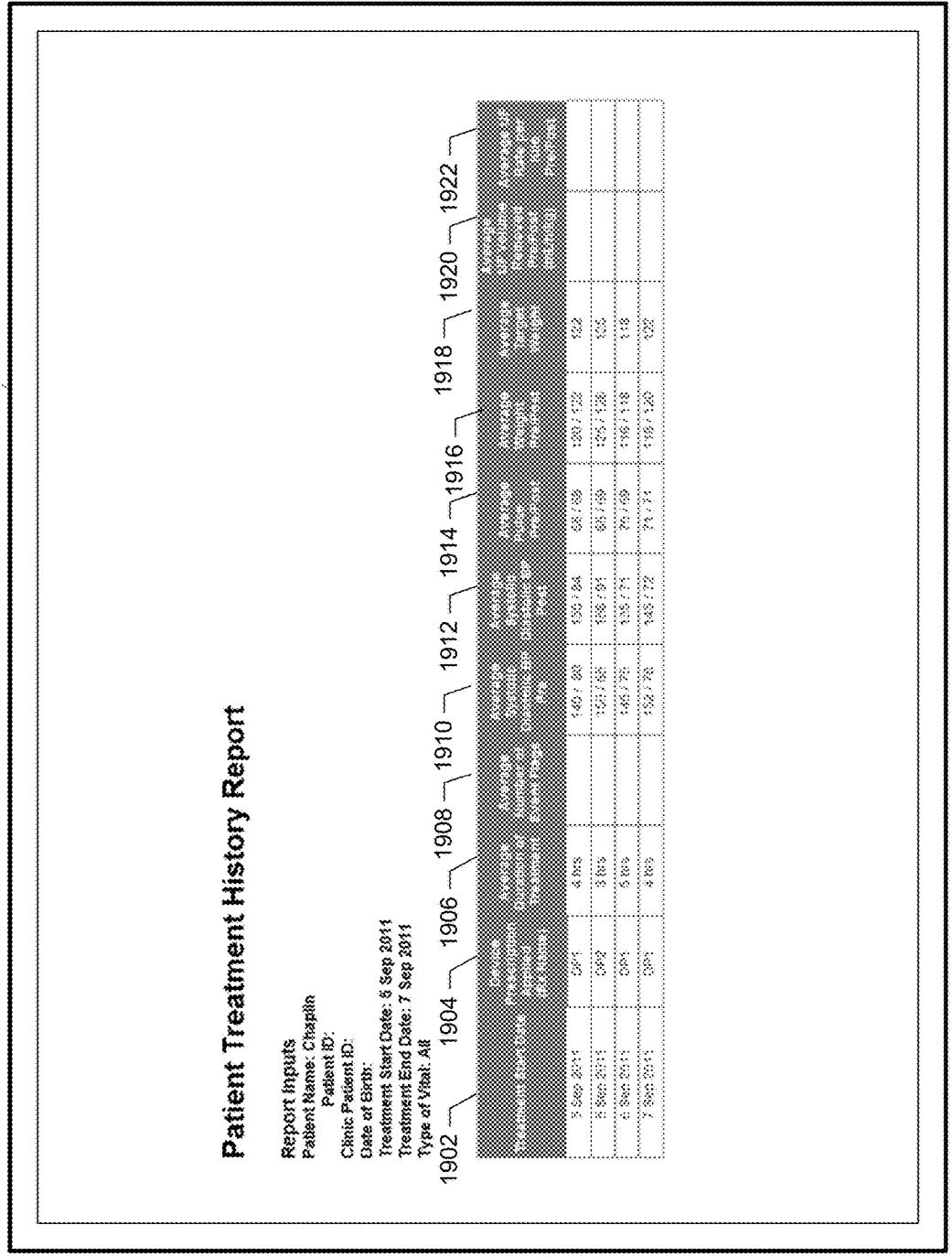
FIG. 19 is a screen shot of an example patient treatment history report of the present disclosure.

FIGS. 19 through 29 illustrate example reports that are presented to a clinician at web portal 150 displayed on a clinician's display device 192. The reports can be accessed from the reports tab 1221 (FIG. 12A). FIG. 19 illustrates an example patient treatment history report 1900 displayed on a clinician's display device 192 that allows the clinician to view the history of the treatment for a patient in tabular format including the treatment date 1902, the name of the device prescription (or device program) that was applied 1904, the average duration of the treatment 1906, the average number of event flags 1908, the average systolic diastolic blood pressure before treatment 1910, the average systolic diastolic blood pressure after treatment 1912, the average pulse before and after treatment 1914, the average weight before and after treatment 1916, the average target weight 1918, the average UF volume removed before and after treatment 1920 and the average UF rate per kilo before and after treatment 1922.

Figure 20:
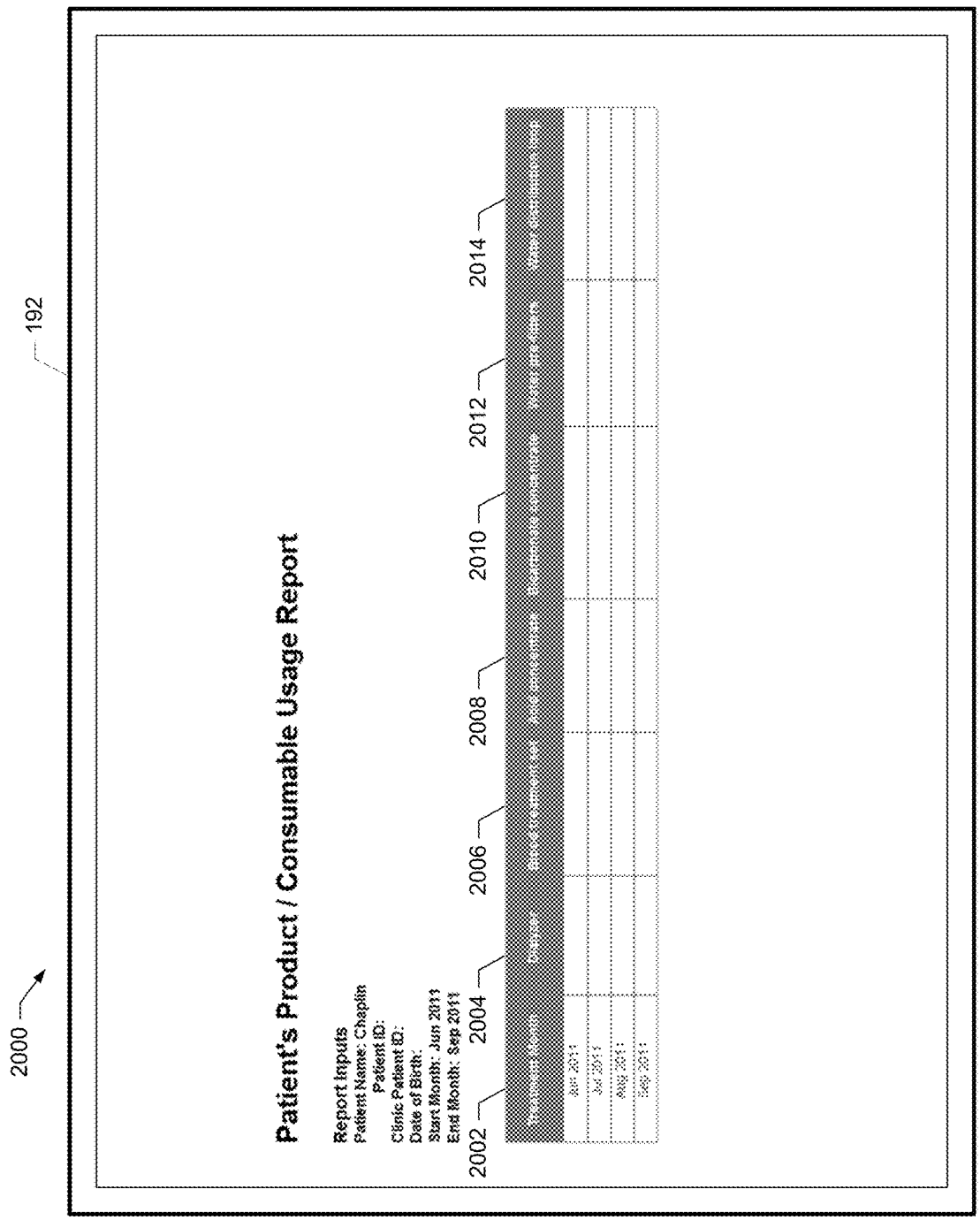
FIG. 20 is a screen shot of an example patient usage report of the present disclosure.

FIG. 20 illustrates an example patient usage report 2000 displayed on a clinician's display device 192 that allows a clinician to see the amount of product or consumables used by a specific patient over a specified time frame. In the patient usage report 2000, the clinician can view the treatment month 2002, the dialyzer used 2004, the blood treatment set used 2006, the acid concentrate used 2008, the bicarbonate concentrate used 2010, the water pre-filters used 2012 and the water distribution loop used 2014.

Figure 21:
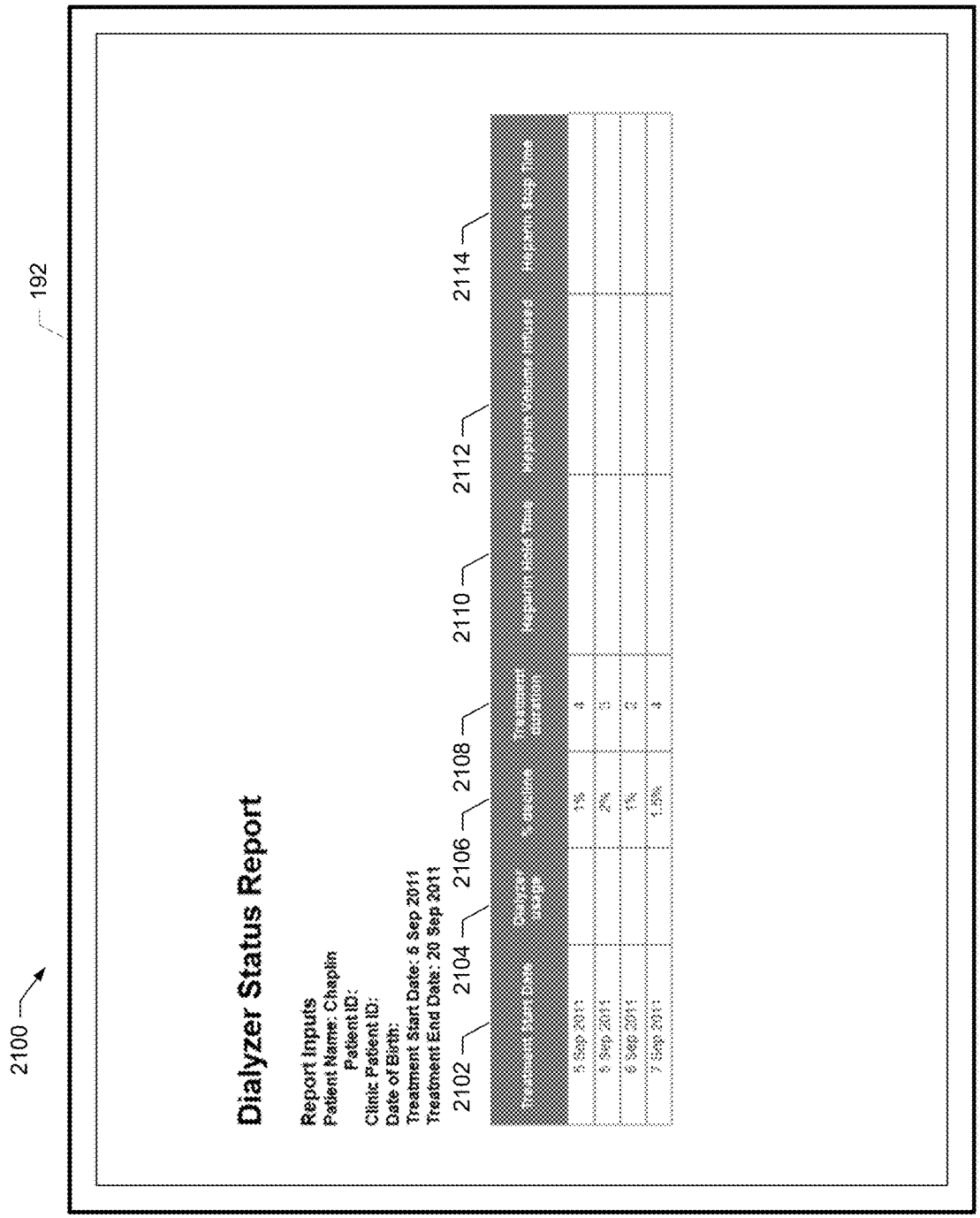
FIG. 21 is a screen shot of an example dialyzer status report of the present disclosure.

FIG. 21 illustrates an example dialyzer status report 2100 displayed on a clinician's display device 192 that allows the clinician to view information about the dialyzer. The dialyzer status report 2100 allows a clinician to view the treatment date 2102, the dialyzer usage 2104, the percentage decline for each treatment 2106, the duration of the treatment 2108, the heparin hold time 2110, the heparin volume infused 2100 and the heparin stop time 2114.

Figure 22:
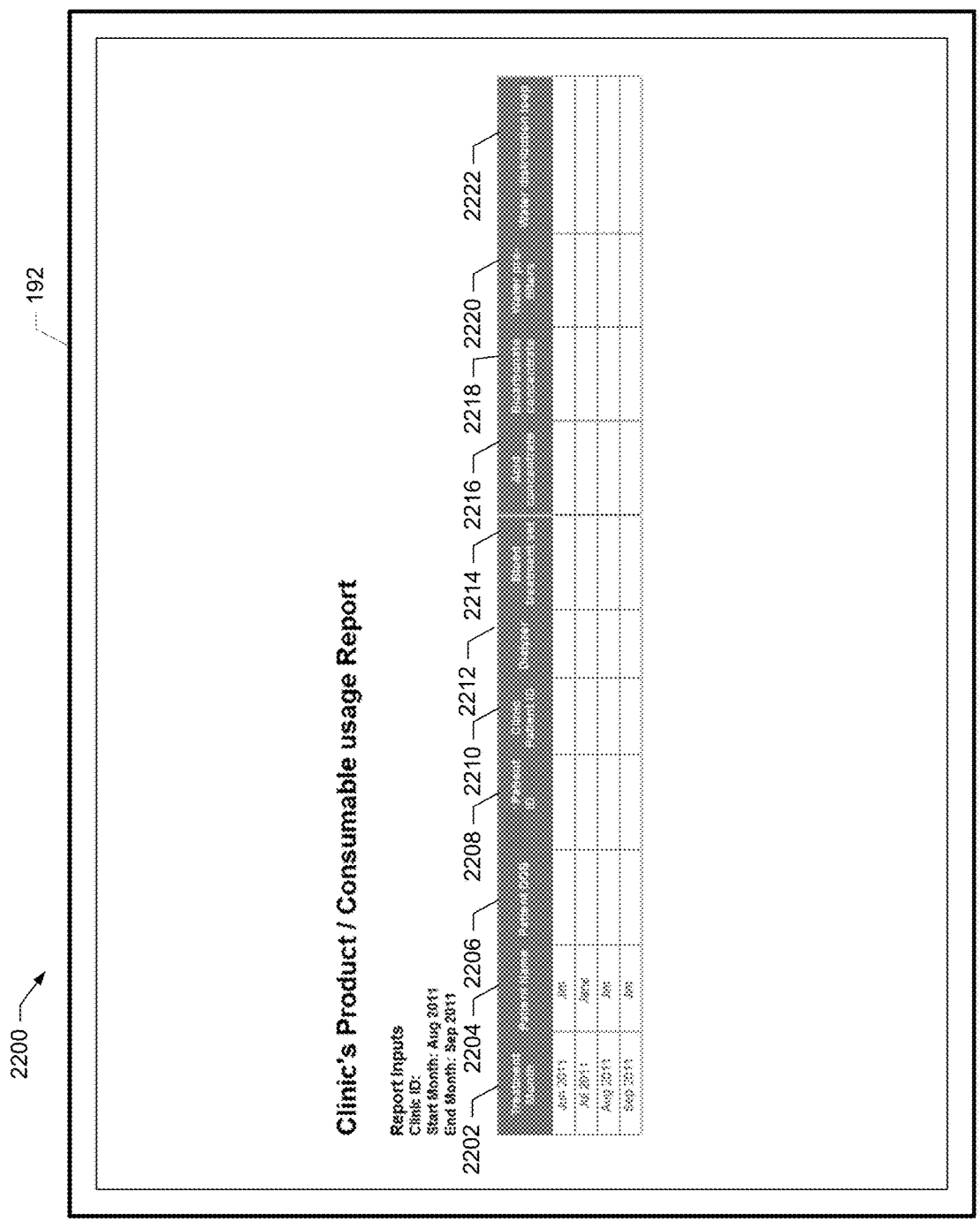
FIG. 22 is a screen shot of an example clinic usage report of the present disclosure.

FIG. 22 illustrates an example clinic usage report 2100 displayed on a clinician's display device 192 that allows the clinician to view the various products or consumables used in a clinic. In the clinic's usage report 2100, the clinician can view the treatment month 2202, the patient name 2204, the patient's date of birth 2206, the therapy provider patient ID 2208, the clinic patient ID 2210, the dialyzer 2212, the blood treatment set 2214, the acid concentrate 2216, the bicarbonate concentrate 2218, the water pre-filters 2220 and the water distribution loop 2222.

Figure 23:
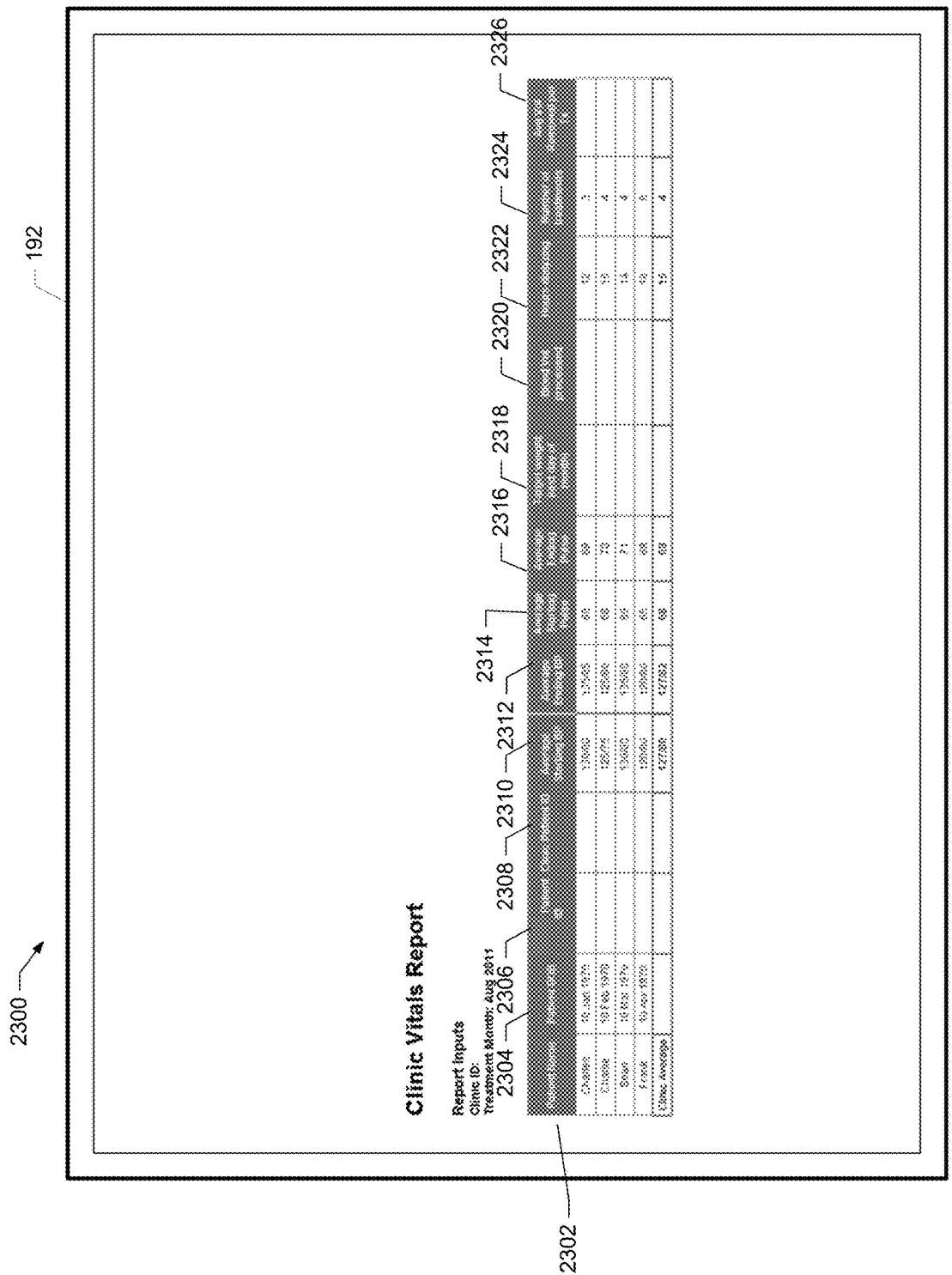
FIG. 23 is a screen shot of an example clinic vitals report of the present disclosure.

FIG. 23 illustrates an example clinic vitals report 2300 displayed on a clinician's display device 192 that allows the clinician to view vital statistics about the clinic, including averages for the entire clinic, as well as per individual patient. The clinic vitals report 2300 allows the clinic to view the patient name 2302, date of birth for each patient 2304, the therapy provider ID 2306, the clinic patient ID 2308, the average starting blood pressure 2310, the average ending blood pressure 2312, the averaging starting pulse 2314, the average ending pulse 2316, the target weight for the last day of the month 2318, the blood volume processed 2320, the amount of hours dialyzing 2322, the number of treatments 2323 and the average volume removed per treatment 2326.

Figure 24:
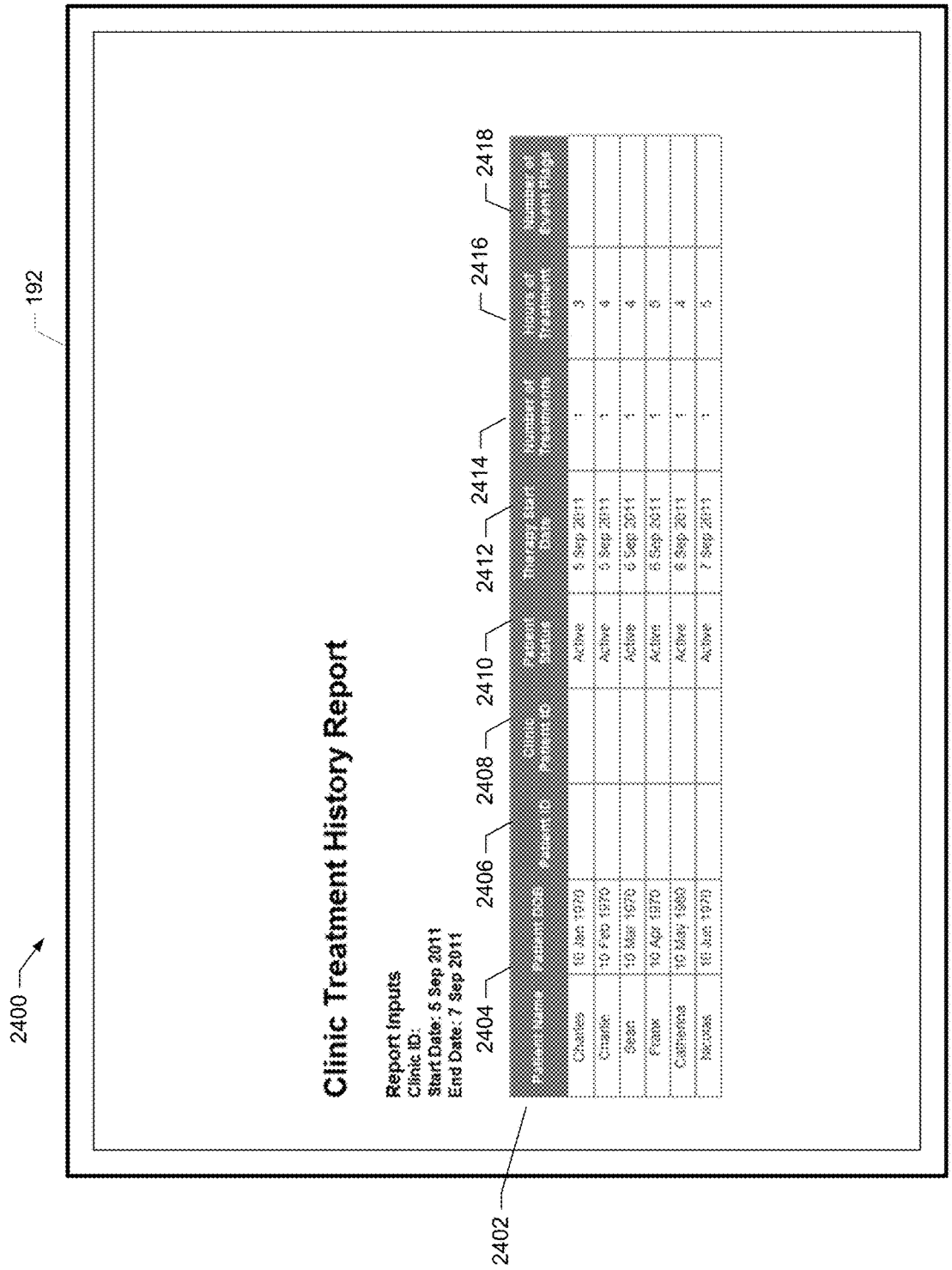
FIG. 24 is a screen shot of an example clinic treatment history report of the present disclosure.

FIG. 24 illustrates an example clinic treatment history report 2400 displayed on a clinician's display device 192 which displays to the clinician a patient name 2402, date of birth of the patients 2404, therapy provider patient ID 2406, the clinic patient ID 2408, the patient status 2410, the therapy start date 2412, the number of treatments 2414, the hours of treatment 2416 and the number of event flags 2418.

Figure 25:
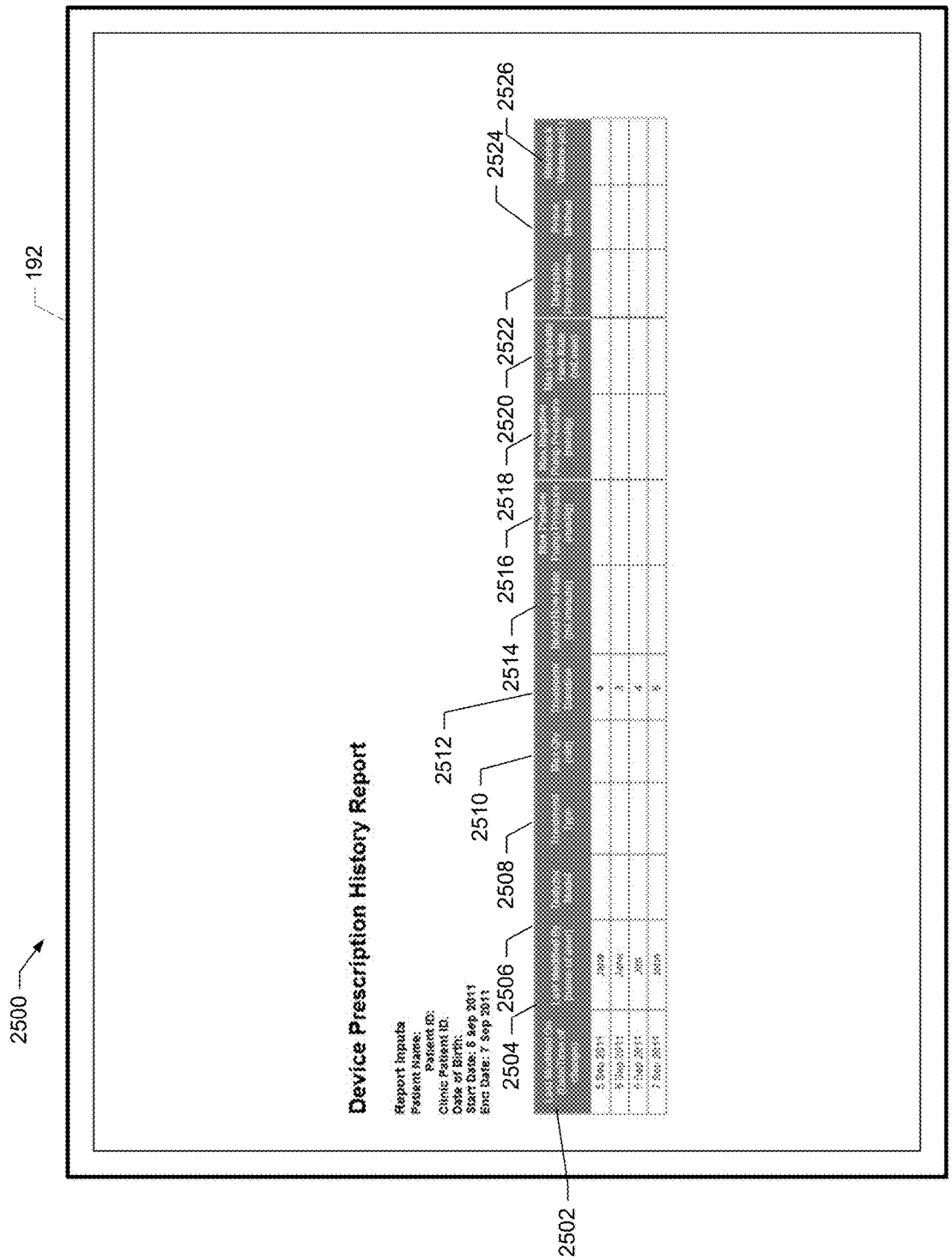
FIG. 25 is a screen shot of an example device program history report of the present disclosure.

FIG. 25 illustrates an example device prescription history report 2500 displayed on a clinician's display device 192. The device prescription history report allows the clinicians to view when the settings for a renal therapy machine 100 were last modified 2502, who made the modification 2504. The device prescription history report 2500 then lists the history of the various settings on different dates. The device prescription history report lists, for each date under 2502, the dialyzer model 2506, the treatment type 2508, the treatment duration 2512, blood flowrate 2514, maximum positive and negative pump pressures 2516 and 2518, maximum dialysate flowrate 2520, dialysate prescription 2522, prime method 2524 and rinseback volume 2526.

Figure 26:
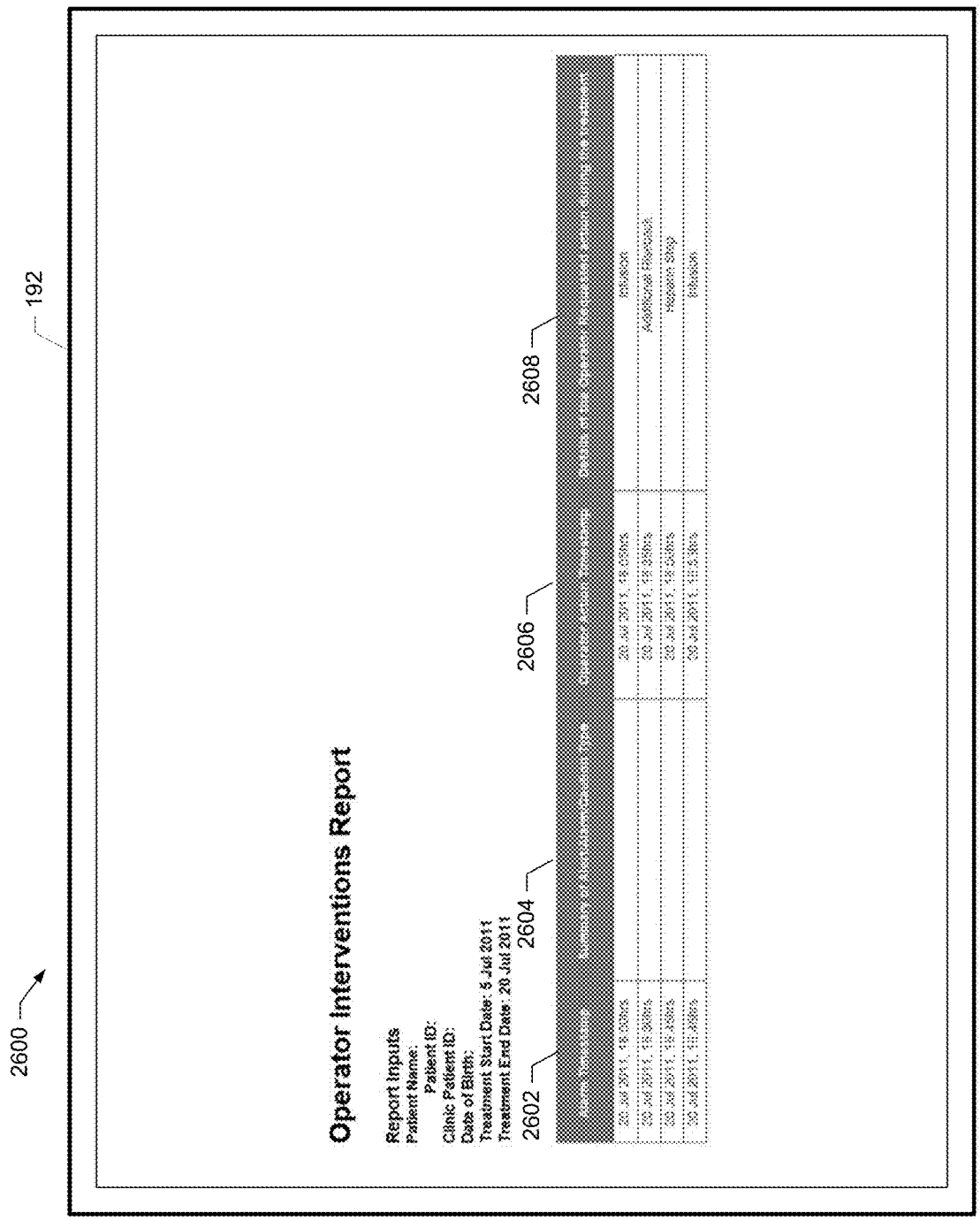
FIG. 26 is a screen shot of an example operator interventions report of the present disclosure.

FIG. 26 illustrates an example operator interventions report 2600 displayed on a clinician's display device 192 that allows a clinician to view when and why alarms were raised during renal treatment, such as alarm timestamps 2602, the type of alert that was raised 2604, when an operator acted 2606 and what the operator requested 2608.

Figure 27:
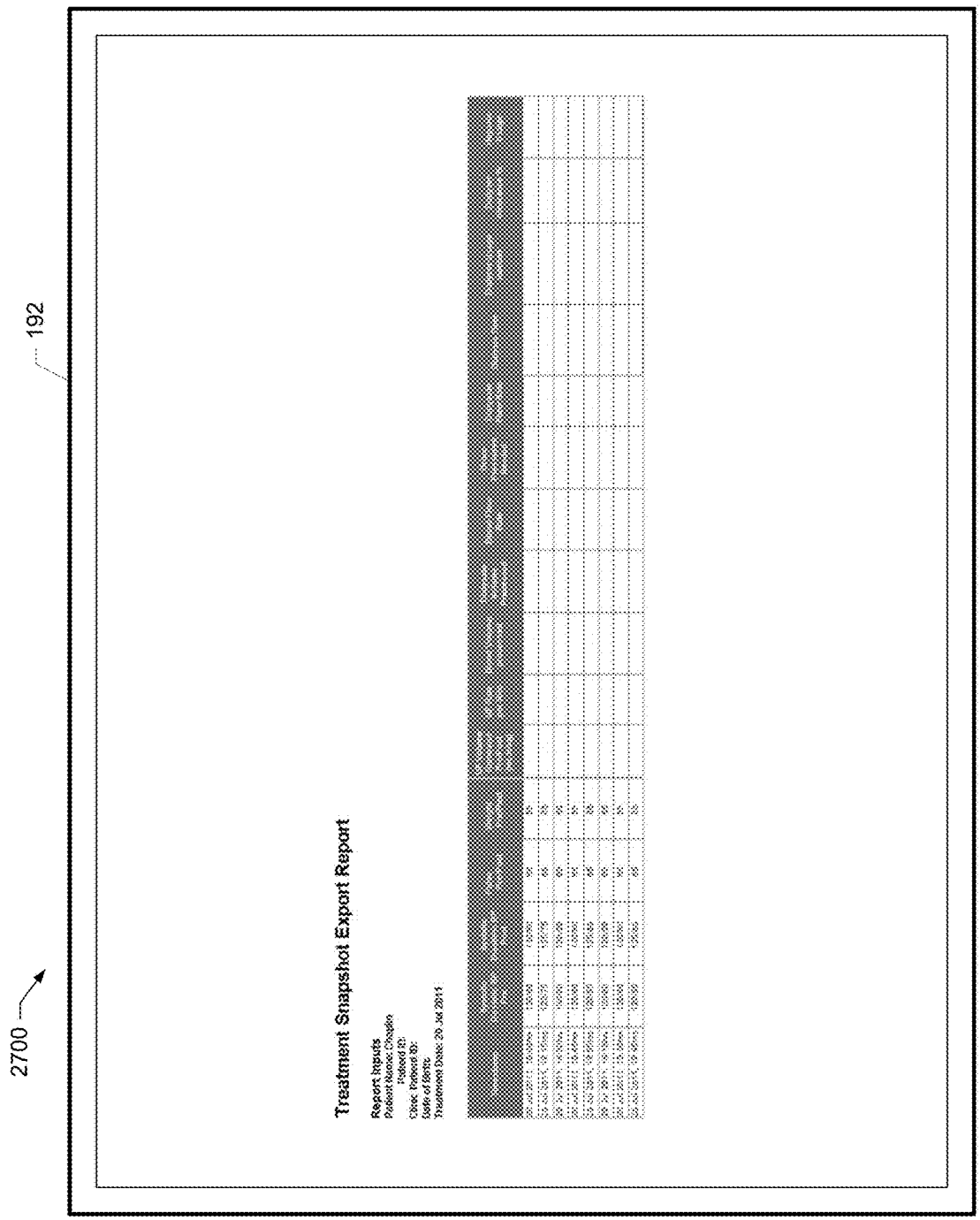
FIG. 27 is a screen shot of an example treatment snapshot export report of the present disclosure.

FIG. 27 illustrates an example treatment snapshot export report 2700 displayed on a clinician's display device 192 that displays, for various times 2702, the systolic diastolic blood pressures before and after treatment 2704 and 2706, the pulses before and after treatment 2708 and the weight before and after treatment 2710.

Figure 28:
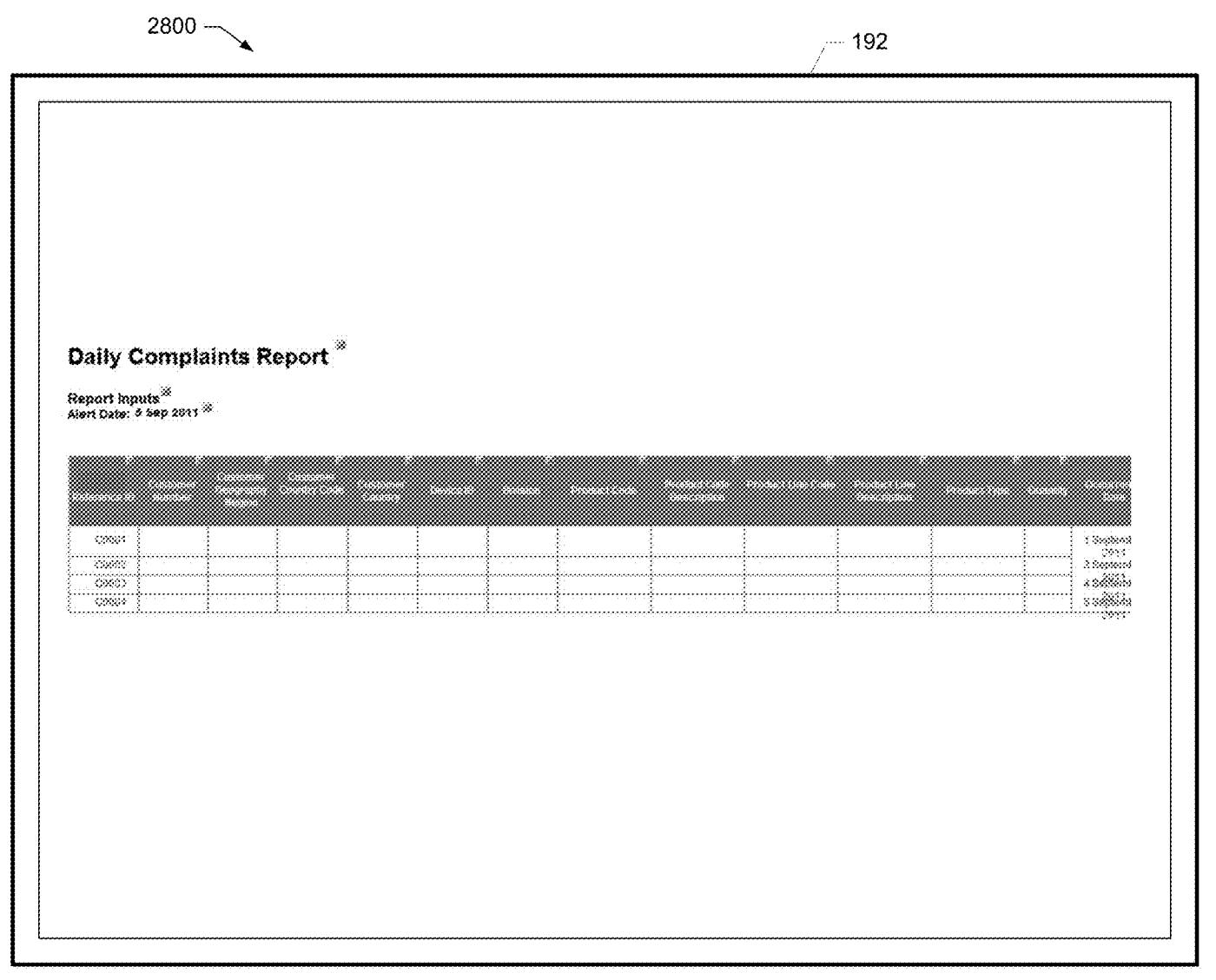
Figure 29:
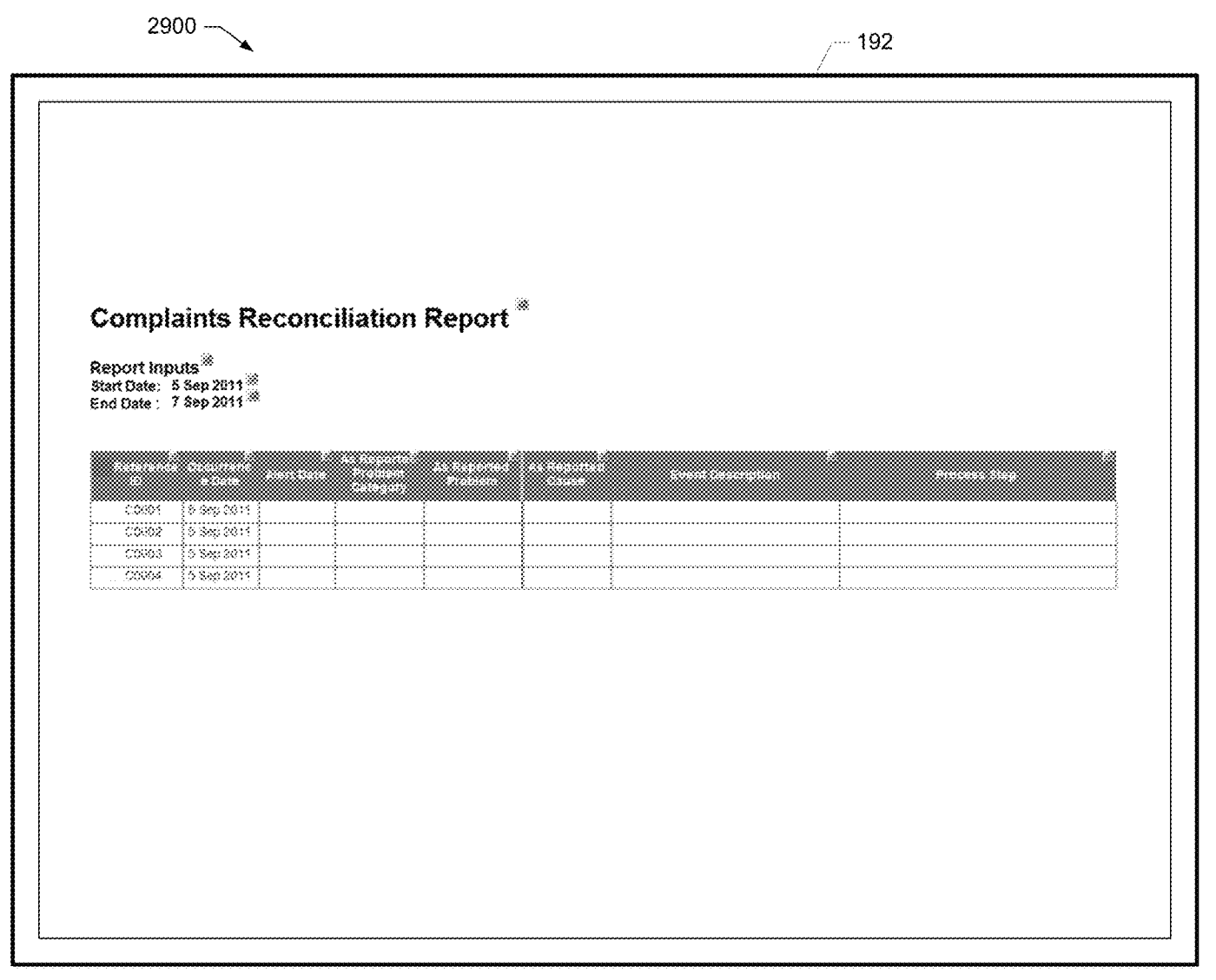

FIG. 28 illustrates an example daily complaints report 2800 displayed on a clinician's display device 192 that lists complaints entered in by patients and FIG. 29 illustrates an example complaints reconciliation report 2900 displayed on a clinician's display device 192 that lists the steps taken to respond to complaints.

Barcode Reader

As illustrated in FIG. 1A, in one embodiment, tablet 122 includes a camera 136. Camera 136 may be used to read barcodes or other identifying symbols on or associated with supplies used with renal therapy machine 100 or components of renal therapy machine 100. Camera 136 may be of any of the following types: barcode, infrared, laser, thermal and thermographic.

Camera 136 is used in one embodiment to scan consumables. For example, a patient may receive a delivery of supplies or consumables to perform treatment with renal therapy machine 100. The consumables may be in a container, e.g., a bottle of heparin or a blood set in a bag, each having a barcode or identifier containing information about the consumable, e.g., the amount and concentration of the heparin, or the type of dialyzer provided with the blood set. The patient can point camera 136 of tablet 122 at the barcode or identifier to photograph or scan the barcode or identifier and identify the concentration, amount, etc., of the heparin or the type, e.g., flex capacity, of the dialyzer. The software to identify the barcode or identifier is in one embodiment provided by machine 100 to tablet 122 along with the tablet's operating software and user information software. The tablet 122 passes the heparin, dialyzer or other information to the renal therapy machine 100. ACPU 112 processes the information received concerning the heparin and verifies that the heparin concentration, amount, etc., is correct according to the prescription or device program downloaded onto the renal therapy machine 100. The same check can be made for the dialyzer, acid concentrate, bicarbonate concentrate or other disposable item as desired. In one embodiment, the ACPU 112 accesses a lookup table stored in renal therapy machine 100, or alternatively accesses a device program stored in renal therapy machine 100, to ensure that the consumable associated with the scanned or photographed barcode is the correct consumable. It is contemplated for ACPU 112 to send to tablet 122, or to cause tablet 122 to recall, an animated picture of the consumables for display on tablet 122 for visual verification.

In this manner, the ACPU 112 can verify that the consumable, e.g., the heparin bottle, that the patient intends to use with renal therapy machine 100 is the correct bottle according to the prescription data contained in the device program. It should be appreciated that the tablet's camera 136 operating as an identifier or barcode reader can perform verification of consumables, so that the patient does not have to manually inspect and verify that the correct consumables have been shipped and selected. It is likely the case that multiple patients across home medical device system 110 use different concentrations or amounts of a consumable according to their different prescriptions and device programs. Thus there may be a possibility that the wrong type or amount of a consumable is shipped to a patient. Or, the patient may be prescribed multiple device programs that call for different types and/or amounts of the same consumable. The tablet 122's camera 136 operating as a barcode reader allows a patient using home medical device system 110 to easily and reliably verify that the correct consumable is used for a particular device program.

If consumable identification information sent from tablet 122 to machine 100 does not match that of the patient's prescription, machine 100 alarms in one embodiment and logs the event to be sent to the clinician. This mismatch is also displayed on tablet 122. The mismatch may be of a type that can be overridden and accepted by the patient if the patient wishes to continue with the current consumables. The patient may be given the opportunity to select and scan a substitute consumable to clear the mismatch. In doing so, tablet 122 instructs the patient to use the tablet camera 136 to take a photograph of the barcode or identifier of the substitute consumable. If the subsequent photograph produces a prescription match, treatment is allowed to continue and a consumable mismatch error corrected message is logged for delivery to a server.

Alternative Clinician Dashboard

Referring now to FIGS. 30A to 43D, various embodiments and aspects of the screens that the clinician sees are illustrated. Various features tie the screens together in a way that is beneficial for the particular tasks that the clinician performs, such as therapy prescription and optimization and patient treatment monitoring. The various features include remotely ordering supplies and setting prescriptions, reusability of templates, interdependency of values entered in different screens, the prevention of the entry of inconsistent values for renal therapy parameters and controlling the flow of data, including, for example, prescription settings, log files documenting treatments and firmware upgrades, between therapy machines at patients' homes and a system hub via a connectivity agent that turns communication on and off. At least some of these features described in FIGS. 30A to 43D may be used in connection with FIGS. 10 to 18E.

Figure 30A:
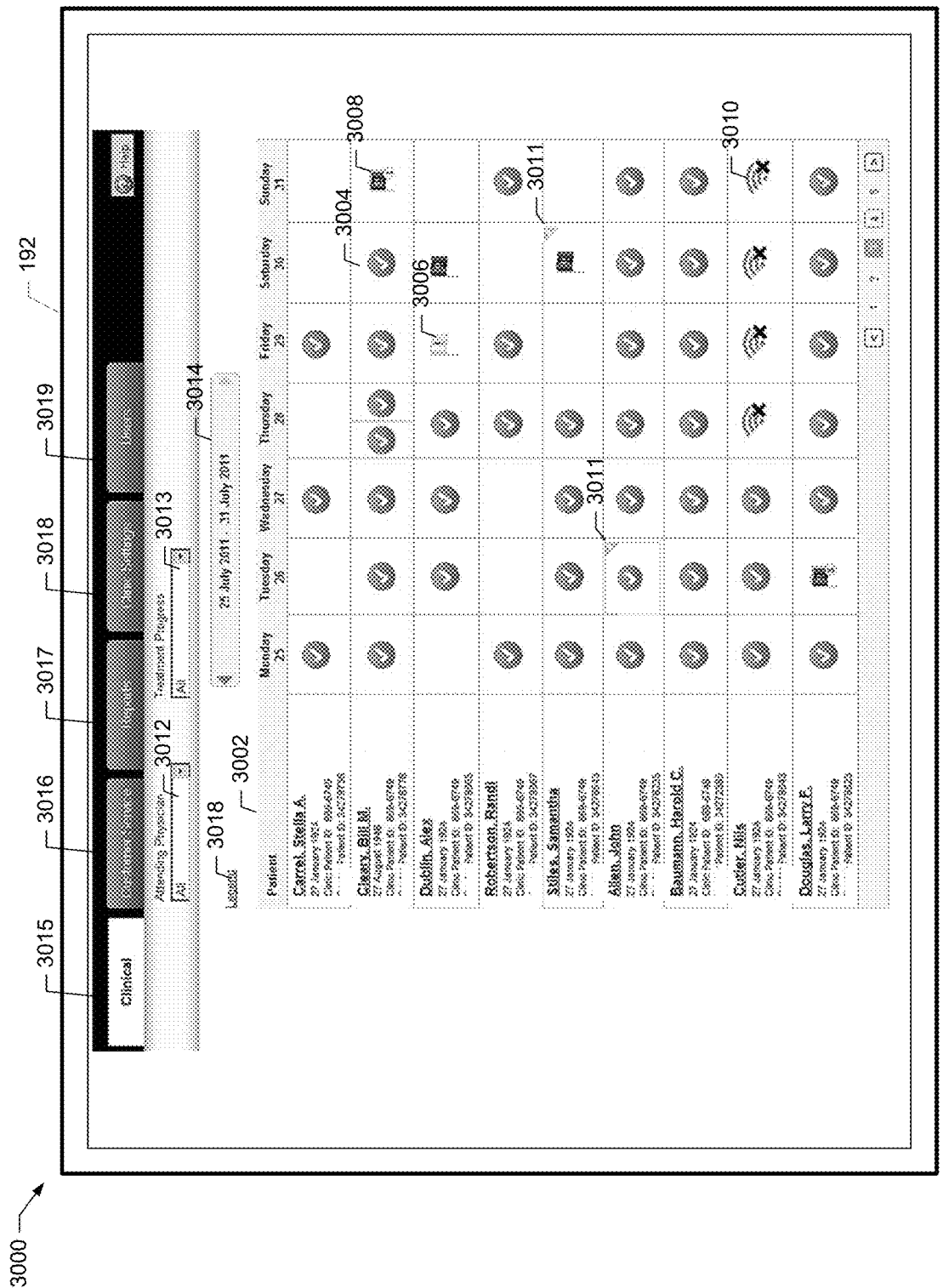
FIG. 30A is a screen shot of an example dashboard screen for a clinic of the present disclosure.

FIG. 30A is an example dashboard screen 3000 for a clinic displayed on a clinician's display device 192 (FIG. 1B). Dashboard screen 3000 is in one implementation a screen that a clinician sees upon logging into the web portal 150. Similar to dashboard screen 1200 (FIG. 12A), dashboard screen 3000 provides an overview of information about the patients handled by a particular clinic. The dashboard presented to a clinician can differ depending upon the type of renal therapy provided to a patient. For example, dashboard screen 1200 is presented to a clinician to display information about patients receiving home hemodialysis via renal therapy machine 100, while dashboard screen 3000 is presented to the same or different clinician to display information about the patients receiving peritoneal dialysis via renal therapy machine 100. It is contemplated for dashboard 1200 (FIG. 12A) and 3000 (FIG. 30A) to have a button or input device that allows the clinician to switch from one type of dashboard (e.g., hemodialysis) to another type of dashboard (e.g., peritoneal dialysis). This would be used on a machine that could run either treatment on a given day, for example, as set forth in U.S. patent application Ser. No. 13/828,731, filed Mar. 14, 2013, entitled "System and Method for Performing Alternative and Sequential Blood and Peritoneal Dialysis Modalities", the entire contents of which are incorporated herein by reference and relied upon.

The clinician's display device 192 may alternatively display a unified dashboard that includes hemodialysis patients and peritoneal dialysis patients. It is contemplated for the unified dashboard to indicate whether a patient is a hemodialysis patient or a peritoneal dialysis patient, and to allow the clinician to filter patients by therapy type, for example, based on whether patients receive hemodialysis or peritoneal dialysis therapy. Dashboard screen 3000 may also allow the clinician to sort by therapy sub-category, such as by an automated peritoneal dialysis patient versus a continuous ambulatory peritoneal dialysis patient. In another example, the clinician can sort by single needle nighttime versus dual needle daily hemodialysis.

In FIG. 30A, the patients are listed by name as shown at column 3002. Similar to dashboard screen 1200 (FIG. 12A), dashboard screen 3000 may enable the clinician to apply filters as illustrated by drop-down menus 3012 and 3013. For example, the clinician in the illustrated embodiment can filter information in the dashboard by patient type (not illustrated, but type may be male or female, age, solute transport type, receiving hemodialysis or peritoneal dialysis, etc.), by attending physician at drop-down menu 3012, or by a treatment progress at drop-down menu 3013. As indicated by item 3014, the dashboard screen 3000 can report information about the treatments occurring in a specified date range, e.g., Jul. 25, 2011 to Jul. 31, 2011 in the illustrated embodiment.

Various icons 3004, 3006, 3008 and 3010 indicate information about a treatment performed by that patient on a specific date. The icons may indicate different types of events similar to the icons on dashboard screen 1200 (FIG. 12A). In the illustrated embodiment, a check-mark icon 3004 means treatment proceeded as planned that day. A flag with one exclamation point icon 3006 indicates events that are not critical and do not need immediate action, but need to be closely monitored in the future. A flag with two exclamation points icon 3008 may indicate events that need immediate action. The X icon 3010 indicates that there has been no communication with the machine 100 associated with that patient for a specific treatment.

Dashboard screen 3000 may also include navigational tabs to allow the clinician to access various portions of the web portal 150. For example, navigational tabs in dashboard 3000 may include a clinical tab 3015, a customer service tab 3016, a reports tab 3017, a clinic settings tab 3018 and a users tab 3019. A clinician can access different portions of the web portal 150 by selecting an associated navigational tab. The navigational tabs appear on multiple screens at all times in one example embodiment and thus serve to tie the different dashboard screens together. Certain tabs of screen 3000 may only appear if the current user has been given access to those tabs, based for example upon whether the user is a patient, clinician or a clinic administrator.

Tab 3015 is used to access patient snapshots and treatment summary screens and view and edit device settings for the patients handled by a particular clinic, as well as to return to dashboard 3000 if the user has navigated away from dashboard 3000. Tab 3016 is used to view and edit information such as contact and delivery information, therapy, solution and disposables information, and order information about an individual patient, and to add additional patients to the list of patients handled by a particular clinic. Tab 3017 is used to view various reports relating to patients, clinics, components of therapy machines and events that occur during treatments. Tab 3018 is used to view and edit device settings templates and flag rules that generate flags on the dashboard 3000. Tab 3019 is used to view, maintain and add authorized users that can access some or all of the various screens described below.

Figure 30B:
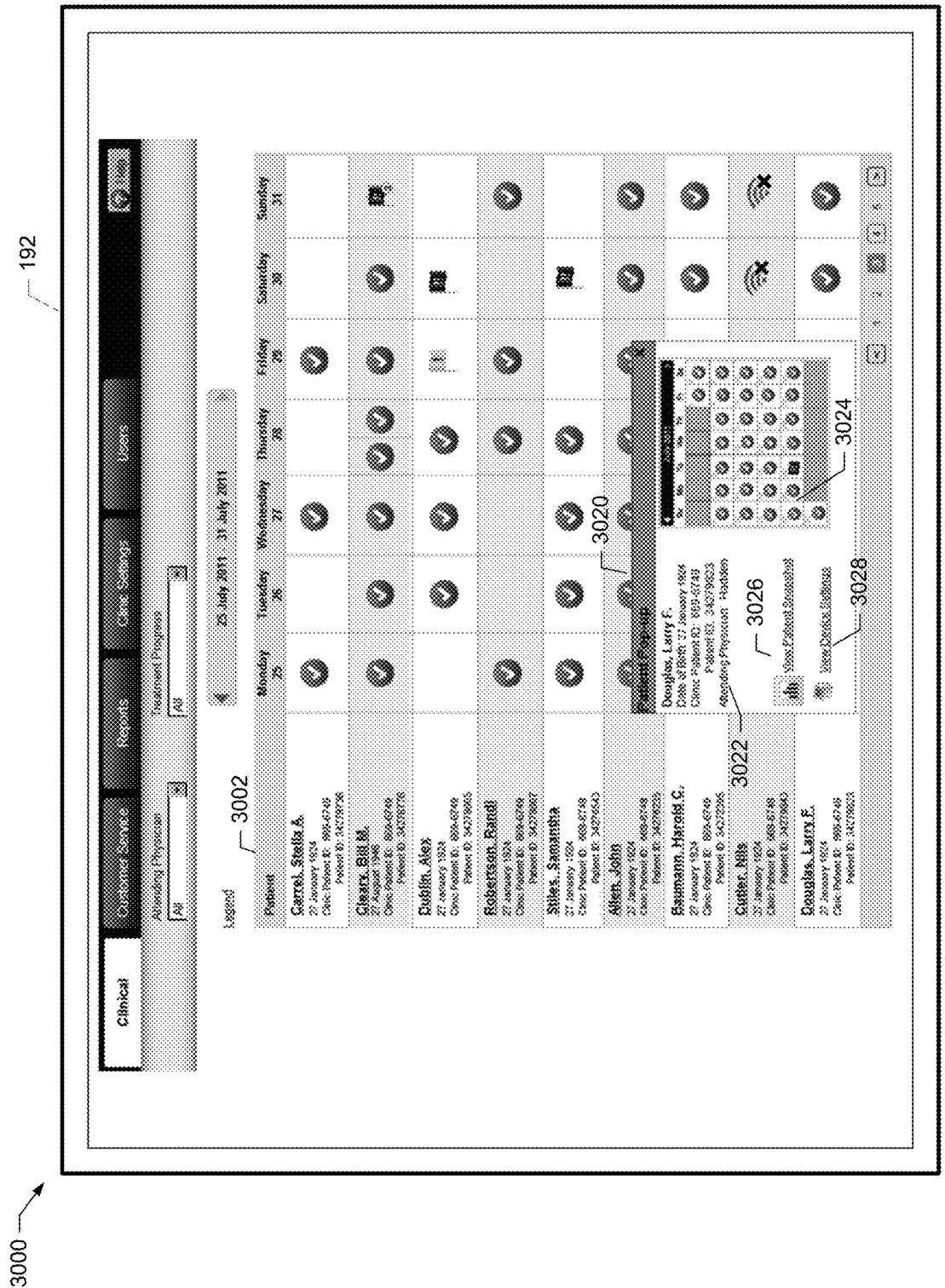
FIG. 30B is a screen shot of another example dashboard screen for a clinic of the present disclosure.

As illustrated in FIG. 30B, patient popup 3020 appears on dashboard screen 3000 when the clinician clicks on one of the patients listed in column 3002. Patient popup 3020 provides additional information 3022 about the selected patient as well as a calendar view 3024 that provides icons and thus treatment outcome information for an entire month of treatment for the selected patient. Patient popup 3020 may also allow a user, e.g., a clinician, to access a patient snapshot via link 3026 or view device settings via link 3028. Patient snapshot 3026 and the device settings via link 3028 are described in detail below.

Figure 30C:
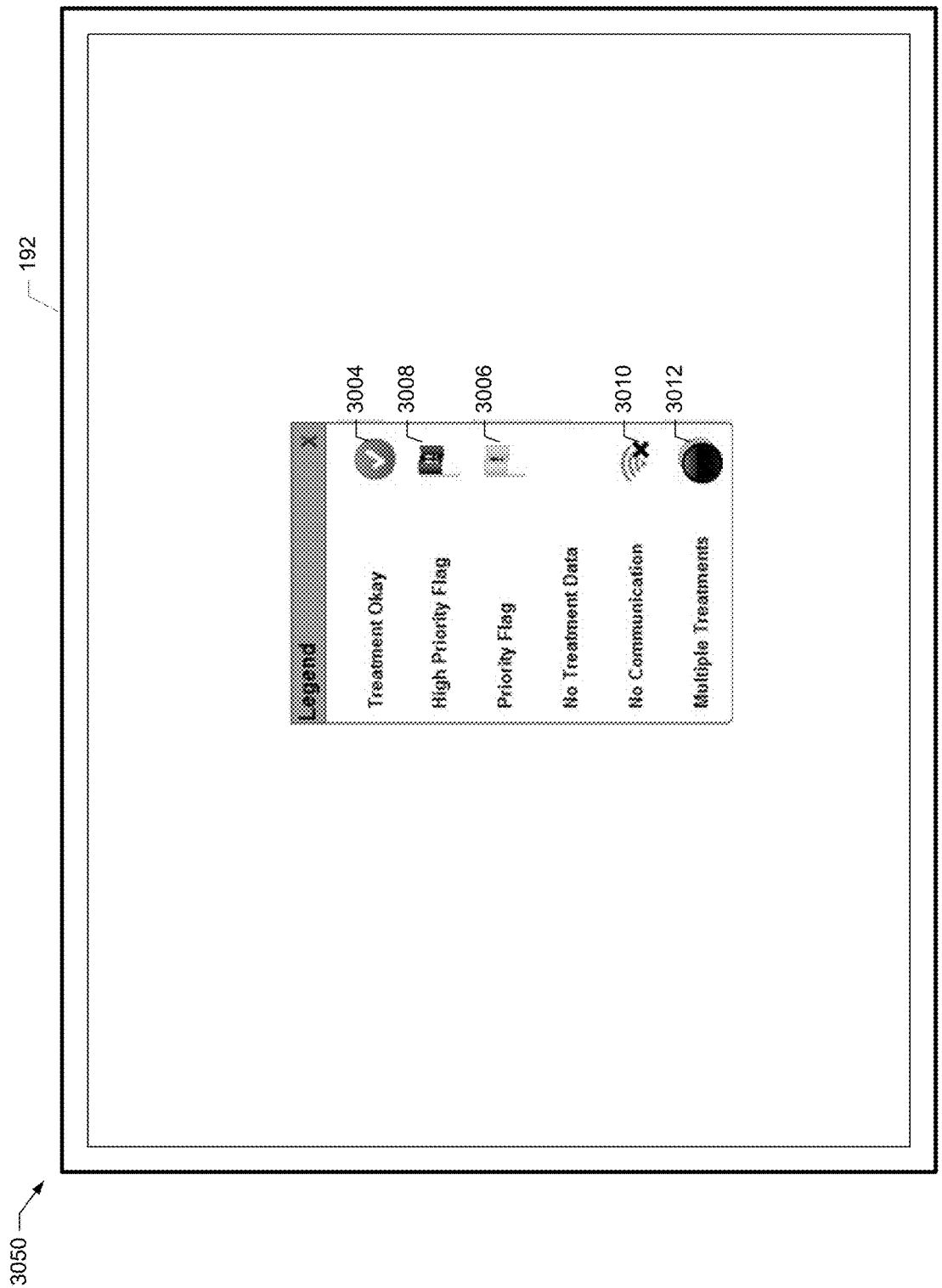
FIG. 30C is a screen shot of an example legend for a dashboard screen of the present disclosure.

Referring again to FIG. 30A, a user is able to access a legend using link 3018 similar to link 1218 in dashboard screen 1200 (FIG. 12A). When a user selects legend link 3018, a popup window or new screen 3050 appears. FIG. 30C illustrates an example legend screen 3050, which is provided on a clinician's display device 192 to explain the meaning of the various icons that can appear on dashboard screen 3000. As discussed above, icon 3004 indicates that the treatment went "Ok." Icon 3006 indicates a flag of normal priority. Icon 3008 indicates a high priority flag. Icon 3010 indicates that there was no communication with the renal therapy machine 100 associated with that patient for a particular day.

Icon 3011 is a treatment review indicator that indicates whether a clinician has reviewed the treatment associated with the treatment review indicator. For example, in the illustrated embodiment, the treatment review indicator 3011 indicates to a clinician that the Jul. 30, 2011 treatment has already been reviewed by a clinician. Thus, a clinician viewing the dashboard is informed that the Jul. 30, 2011 treatment marked with a high priority flag 3008 has already been reviewed. Treatment review indicator 3011 also serves as a record that high priority flags 3008 has been reviewed. Without the treatment review indicator 3011, each time a clinician logs in and views the dashboard, the clinician may see various flags, some of them requiring immediate attention, but would not know whether the flags have already been reviewed.

Icon 3012 indicates that the patient performed multiple treatments on a certain day. One or more of the icons, including flag icons 3006 and 3008, can be selected to view more detailed information concerning the icon. Selecting the flag, for example, causes the reason for the flag occurring during a particular treatment to be displayed to the clinician.

Figure 31A:
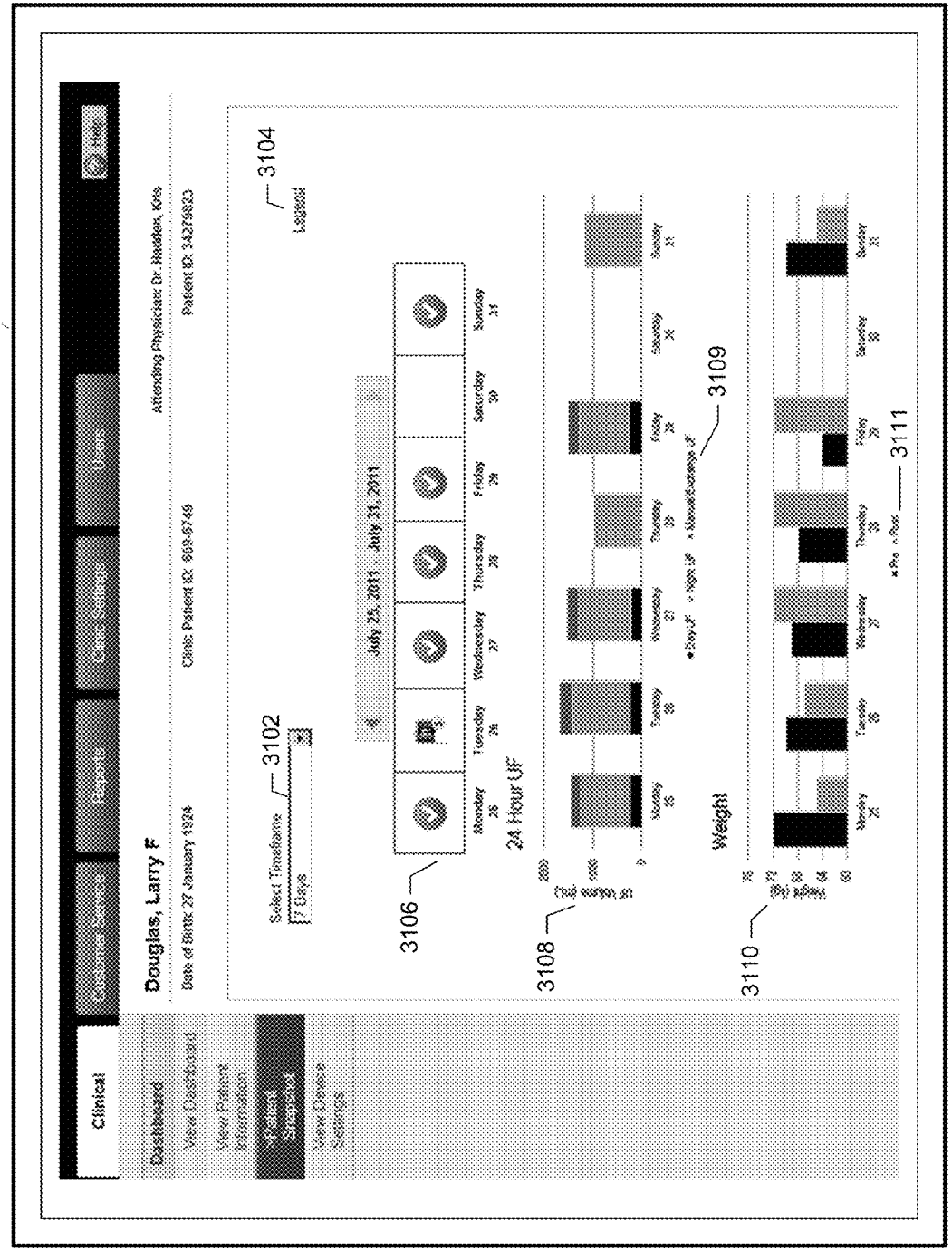
FIG. 31A is a screen shot of an example patient snapshot screen of the present disclosure.

Referring again to FIG. 30B, and as described above, the patient popup 3020 may include a view patient snapshot link 3026 and a view device settings link 3028. FIG. 31A illustrates an example patient snapshot screen 3100 displayed on a clinician's display device 192 that can be launched from link 3026. The patient snapshot screen 3100 provides detailed information to the clinician about an individual patient, e.g., about peritoneal dialysis treatments that were performed by renal therapy machine 100 on the patient. The clinician may filter information by selecting a timeframe using drop-down menu 3102. In the illustrated embodiment, the clinician has selected to view treatment data over a timeframe of seven days. Calendar 3106 displays a calendar view of the icons discussed above for the seven days in which data is viewed. A link to a legend 3104 is again provided on patient snapshot screen 3100, which displays the same icons and explanations for icons as described above in FIG. 30C.

The patient snapshot screen 3100 provides information such as the 24 hour ultrafiltrate volume 3108 and the patient weight before and after therapy 3110. The information displayed on snapshot screen 3100 may provide multiple items of information in the same graph. For example, chart 3108 provides a bar indicating how much ultrafiltrate was removed over the course of twenty-four hours. The bar is made up of three different colors or shades. As indicated by key 3109, each shade represents a different way in which the ultrafiltrate was removed, e.g., how much ultrafiltrate was removed by renal therapy machine 100 during the day and during the night, as well as how much ultrafiltrate was removed via manual peritoneal dialysis exchanges.

Similarly, in chart 3110, each graph indicating the patient's weight for a day indicates the patient's weight before and after treatment. As illustrated in key 3111, the darker bar graph for a day indicates the patient's weight before treatment and a lighter or different colored bar graph indicates the patient's weight after treatment. Chart 3110 could also display blood pressure and/or glucose level data for the patient on the highlighted days, for example.

Figure 31B:
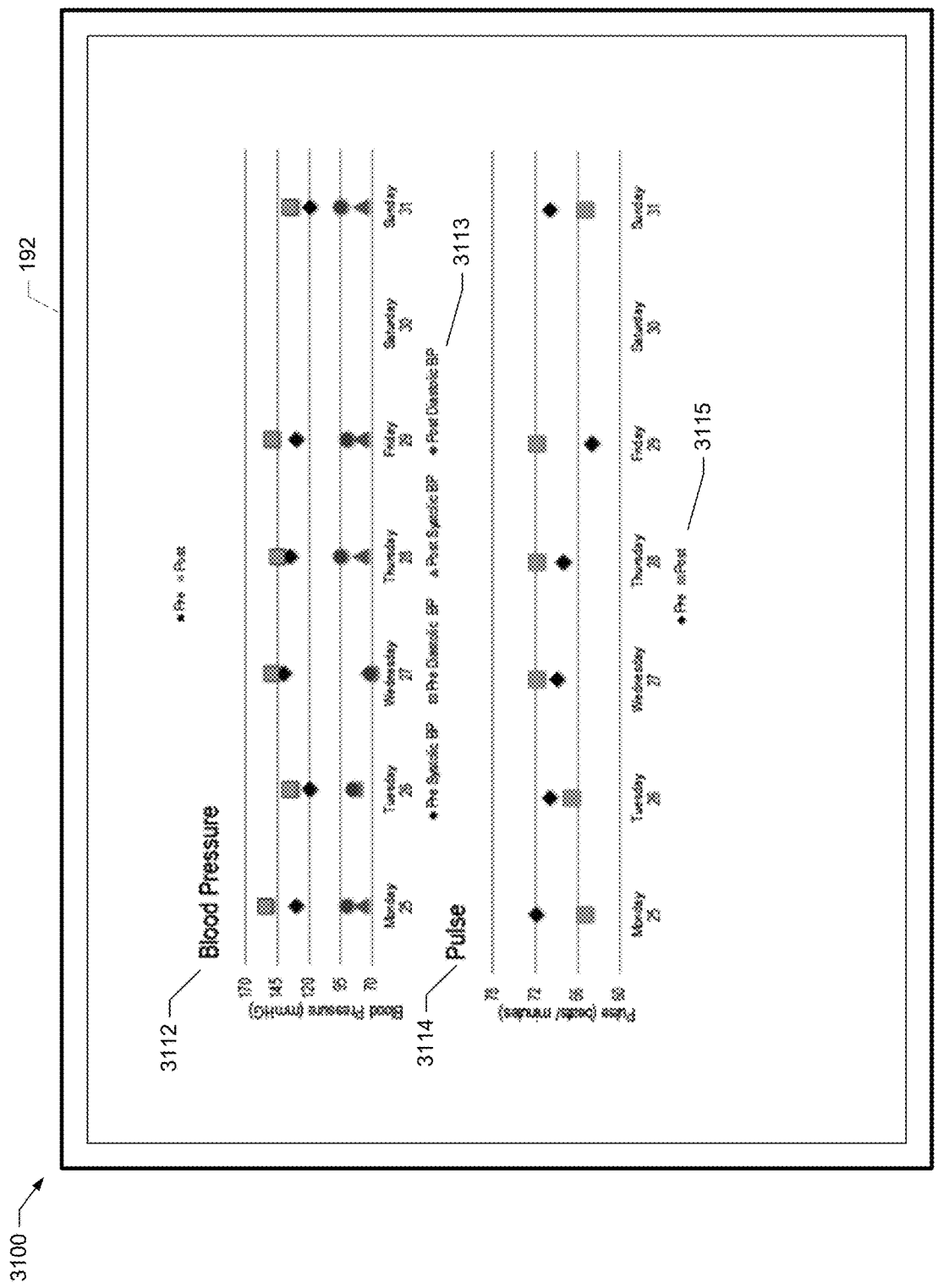
FIG. 31B is a screen shot of another example patient snapshot screen of the present disclosure.

FIG. 31B illustrates additional information that may be displayed on the patient snapshot screen 3100 displayed on a clinician's display device 192. Patient snapshot screen 3100 for example displays a blood pressure chart 3112 and a pulse or beats per minute chart 3114. The blood pressure information chart 3112 contains four types of blood pressure readings for each displayed day. As indicated by key 3113, for example, each graph for a day indicates a pre-systolic blood pressure indicated by the diamond-shaped icon, a pre-diastolic blood pressure information as indicated by the square icon, a post-systolic blood pressure as indicated by the triangle icon and a post-diastolic blood pressure as indicated by the circle icon. Pulse chart 3114 also indicates different information related to a patient's pulse before and after peritoneal dialysis treatment as indicated by key 3115. For example, the graph for each day indicates a pre-treatment pulse indicated by a diamond-shaped icon and a post-treatment pulse as indicated by the square icon. The blood pressure and pulse readouts may be instantaneous readouts indicating a single sample taken at a single point in time or be an average readout taken and averaged over multiple points in time.

It should be appreciated that the patient snapshot screen 3100 therefore allows a clinician to quickly view and visually assess how treatments have been performed for a specific patient over a defined period of time. The clinician can easily view data regarding the various parameters related to therapy, e.g., peritoneal dialysis. For example, the clinician can see a breakdown of the how the ultrafiltrate removal has progressed and can also visually assess the patient's weight, blood pressure, and pulse both before and after treatment. Although patient snapshot screen 3100 is displayed across FIGS. 31A and 31B, in one embodiment, all of patient snapshot screen 3100 is displayed to the clinician at the same time on clinician's display device 192. Other screens described elsewhere that may be divided across multiple figures for convenience may also likewise be presented to the clinician as one continuous scrollable screen on clinician's display device 192.

Figure 32A:
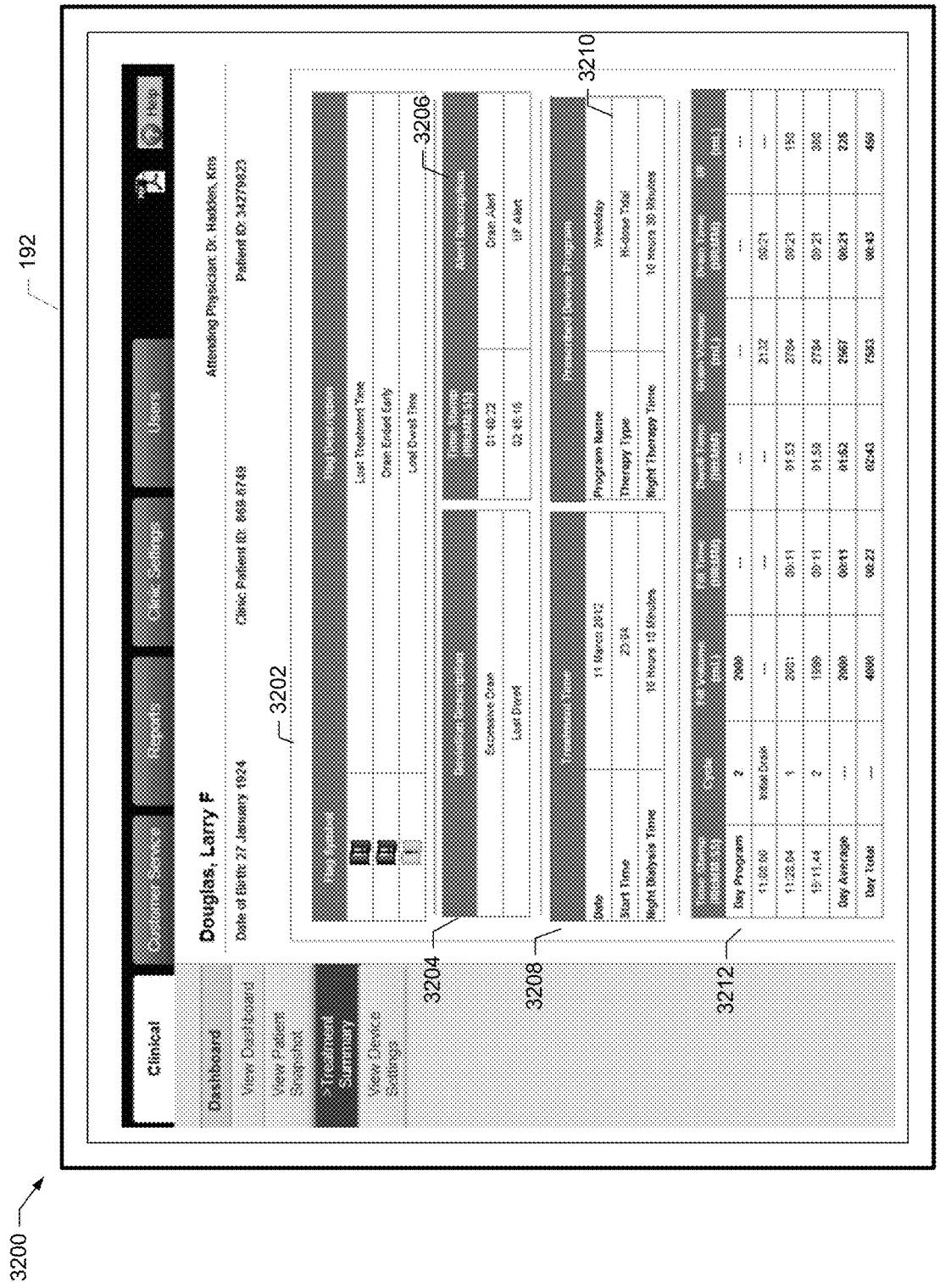
FIG. 32A is a screen shot of an example treatment summary screen of the present disclosure.

FIG. 32A illustrates an example treatment summary screen 3200 on clinician's display device 192. Summary screen 3200 provides granulated details about a particular treatment. Treatment summary screen 3200 can be launched by selecting one of the dates on calendar 3106 of FIG. 31A. In the illustrated embodiment, the user has selected Mar. 11, 2012, as indicated in chart 3208. From treatment summary screen 3200, a clinician can see a description of the flag symbols at chart 3202. The clinician can also see a description of any deviation from planned treatment at chart 3204 and alerts that occurred during a treatment, e.g., a peritoneal dialysis treatment, at chart 3206. The clinician can also see the date and time of treatment as indicated at chart 3208, the prescribed device program at chart 3210, and an overall treatment summary log in table format showing exact times for various treatment events at chart 3212. Chart 3212 along with its treatment summary log may be printed and added to a patient's file. In the illustrated embodiment, information about the cycles that make up a peritoneal dialysis treatment are displayed in chart 3212. Chart 3212 displays a beginning time of each cycle as a well as a fill volume, fill time, dwell time, drain volume, drain time and UF removed for each cycle.

Figure 32B:
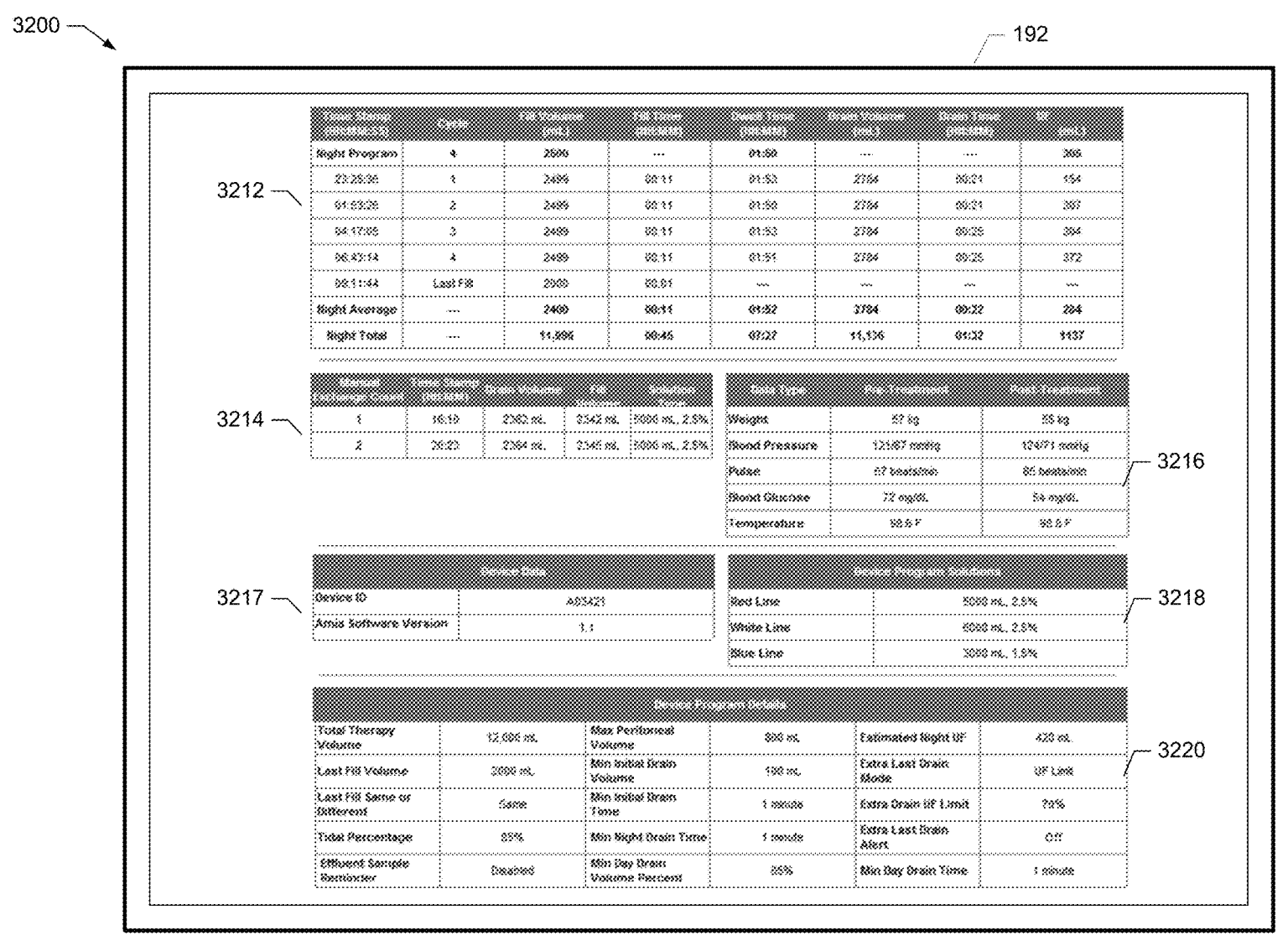

The screen 3200 displayed on a clinician's display device 192, including chart 3212, is continued in FIG. 32B. As shown in FIG. 32B, a clinician can also see manual peritoneal dialysis exchange particulars in chart 3214, and a summary of physical parameters before and after treatment in chart 3216. The clinician can also see the device ID of the renal therapy machine 100 and the software version of the renal therapy machine 100 at chart 3217. The clinician can likewise see device program solutions at chart 3218 and device program details at chart 3220. The solution data, e.g., for peritoneal dialysis, includes volume and dextrose levels. The device program data includes how machine 100 has been programmed to operate for the particular day or treatment, and may include multiple treatments per day for peritoneal dialysis.

Figure 33:
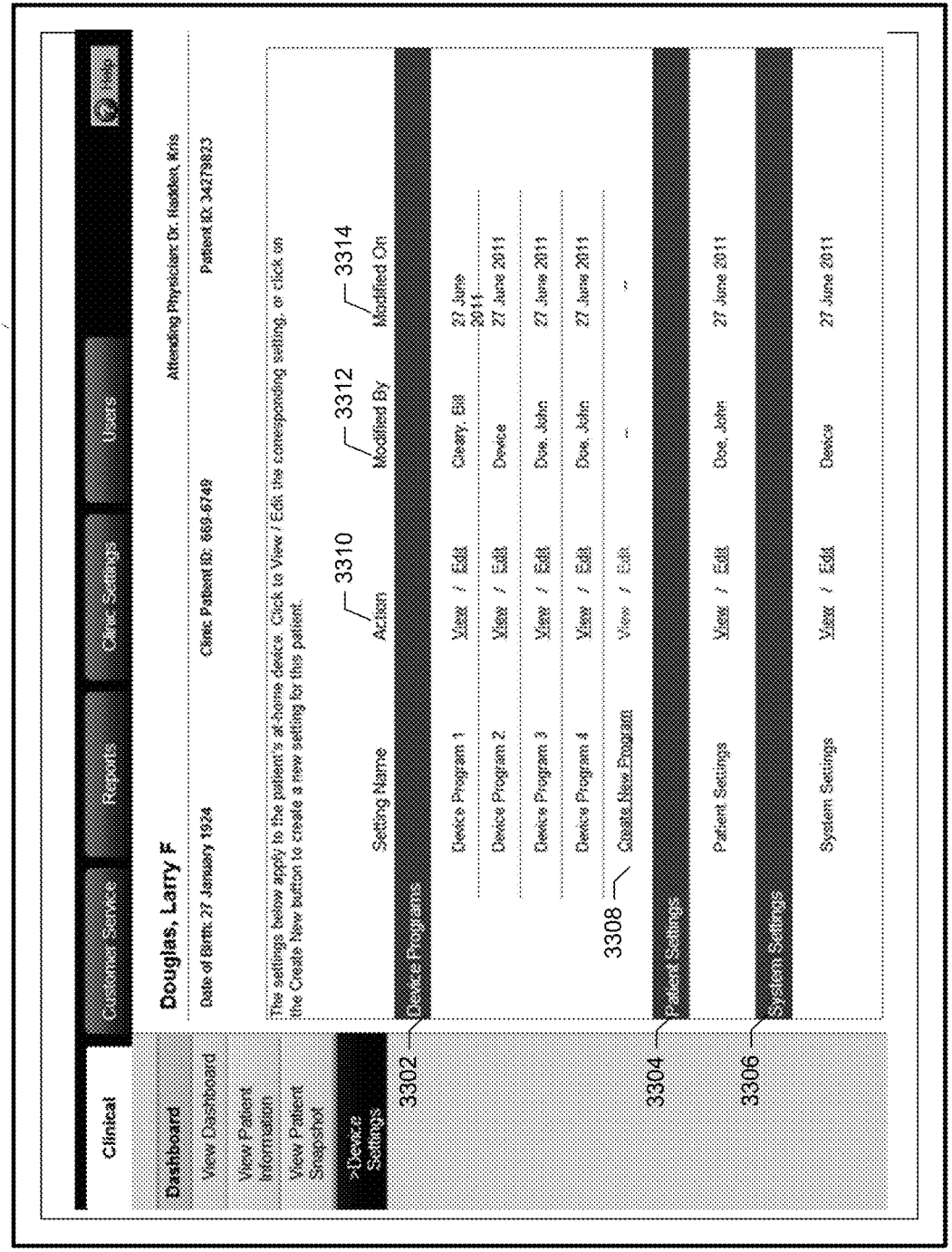
FIG. 33 is a screen shot of an example device settings screen of the present disclosure.

FIG. 33 illustrates an example device settings screen 3300 displayed on a clinician's display device 192, which can be launched from the dashboard screen 3000 (FIG. 30B). Similar to device settings screen 1500 of FIG. 15A, device settings screen 3300 displays relevant consolidated information about the various device programs, patient settings and system settings being used to run a peritoneal dialysis machine 100, and also provides a consolidated location or screen for clinicians to access various aspects of the patient care. From the device settings screen 3300, a clinician may be able to access information about device programs 3302, patient settings 3304 or system settings 3306. Under device programs 3302, a clinician can view all of the different device or machine operation programs stored for that patient, e.g., for peritoneal dialysis. A clinician may be able to create a new device program for that patient using link 3308. The clinician can also edit existing device programs 3302, patient settings 3304 and system settings 3306 using the links in the action column 3310. Similar to the device settings screen 1500 of FIG. 15A, device settings screen 3300 also indicates the last person to modify any of the device programs, patient settings or system settings as shown in the modified by column 3312. The date of the modification is shown in the modified on column 3314.

FIGS. 34A to 34F illustrate an example device program screen 3400 displayed on a clinician's display device 192, which allows clinicians to set values for parameters that control how a dialysis treatment such as a peritoneal dialysis treatment will be performed at the patient's home. Similar to device program screen 1600 illustrated in FIGS. 16A to 16G, device program screen 3400 illustrates fields or parameters that are specified by a clinician that are the product of a doctor's prescription for the patient. A clinician can name the device program using field 3402. As with device program screen 1600, the device program screen 3400 also provides an option for the clinician to apply templates at scroll-down menu 3404. As before, the templates are convenient because templates allow the clinicians to enter preselected values for multiple parameters at once by selecting a template.

Figure 34A:
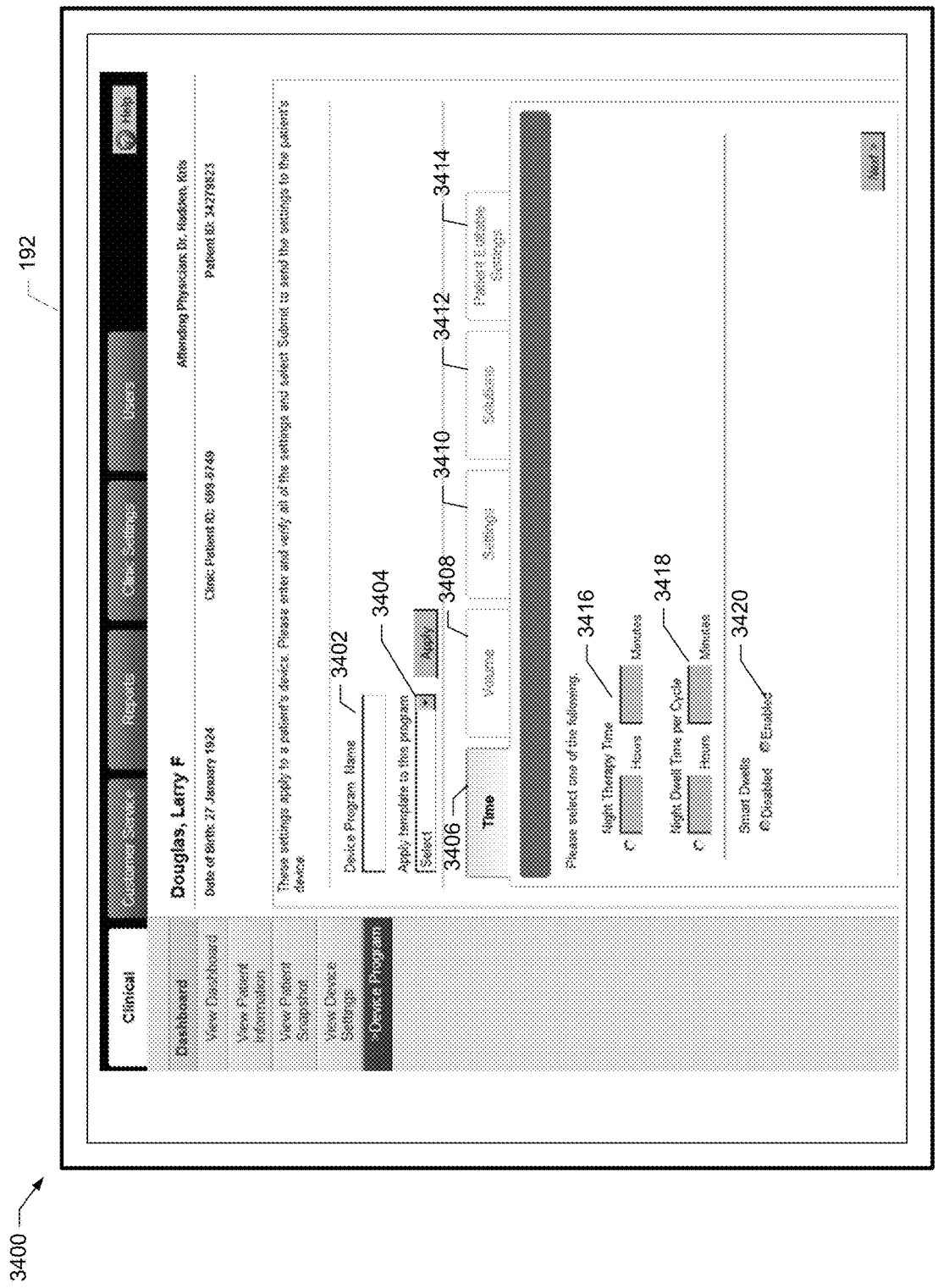
FIG. 34A is a screen shot of an example device program screen of the present disclosure.
Figure 34B:
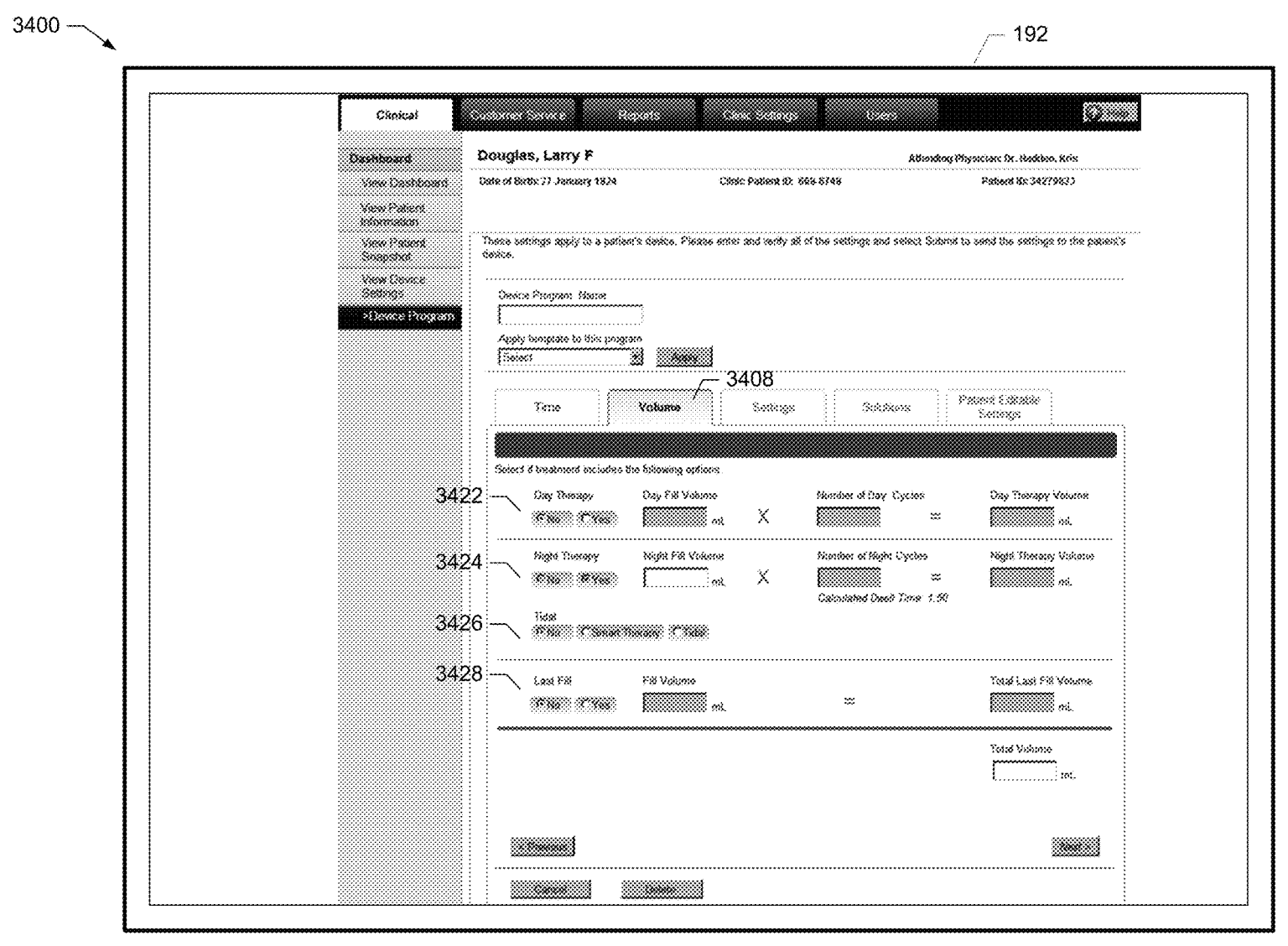
Figure 34C:
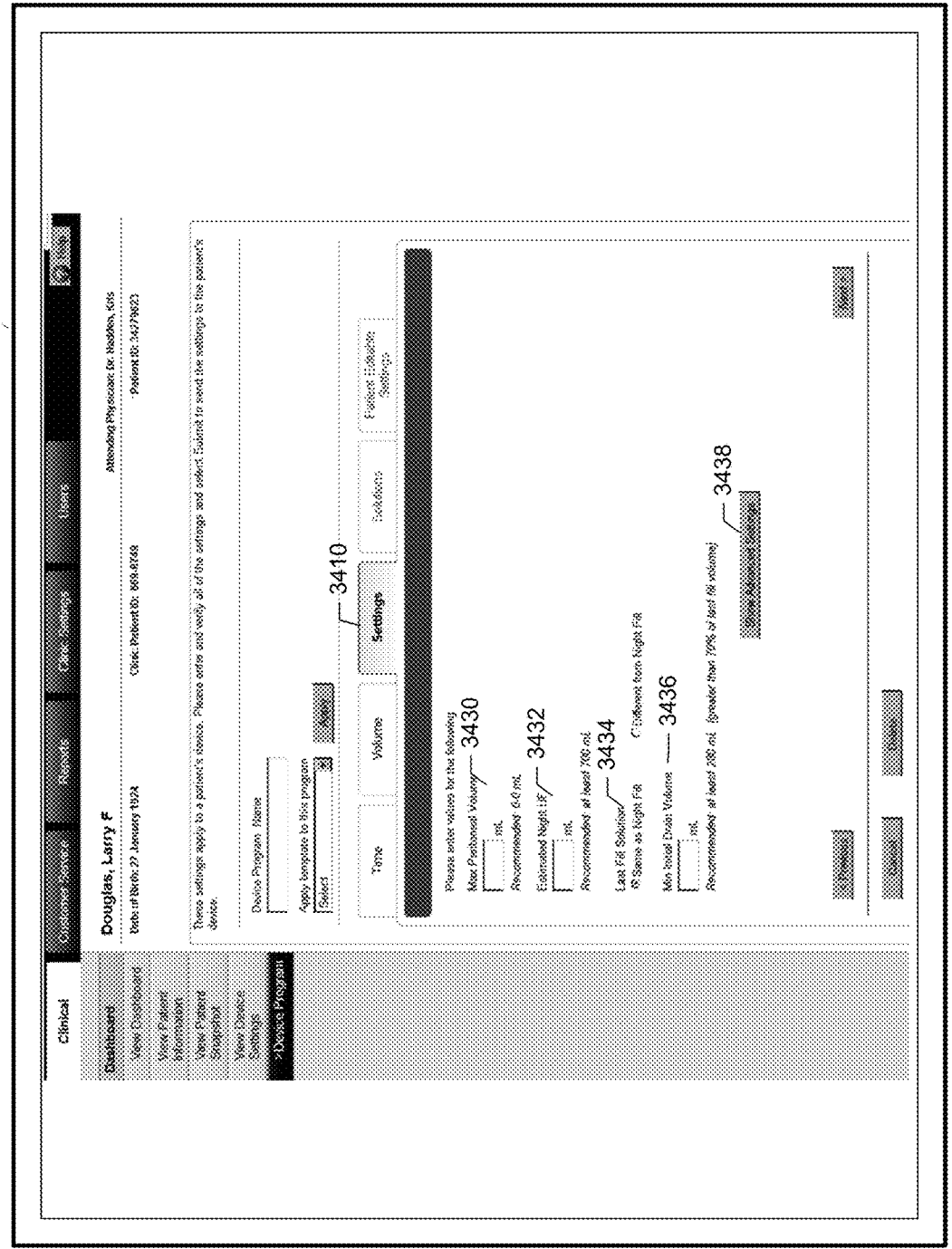
FIG. 34C is a screen shot of a further example device program screen of the present disclosure.
Figure 34D:
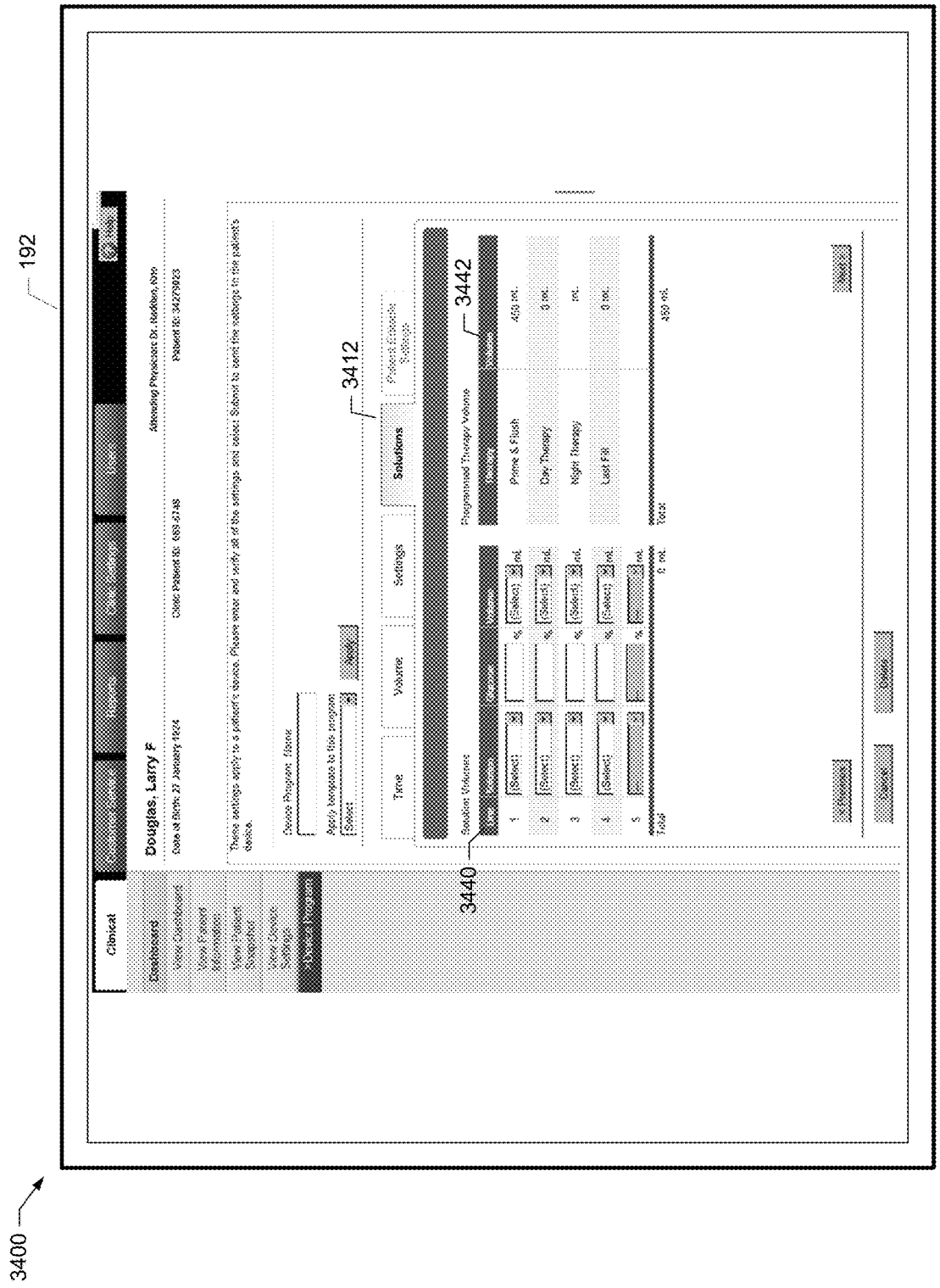
FIG. 34D is a screen shot of yet another example device program screen of the present disclosure.
Figure 34E:
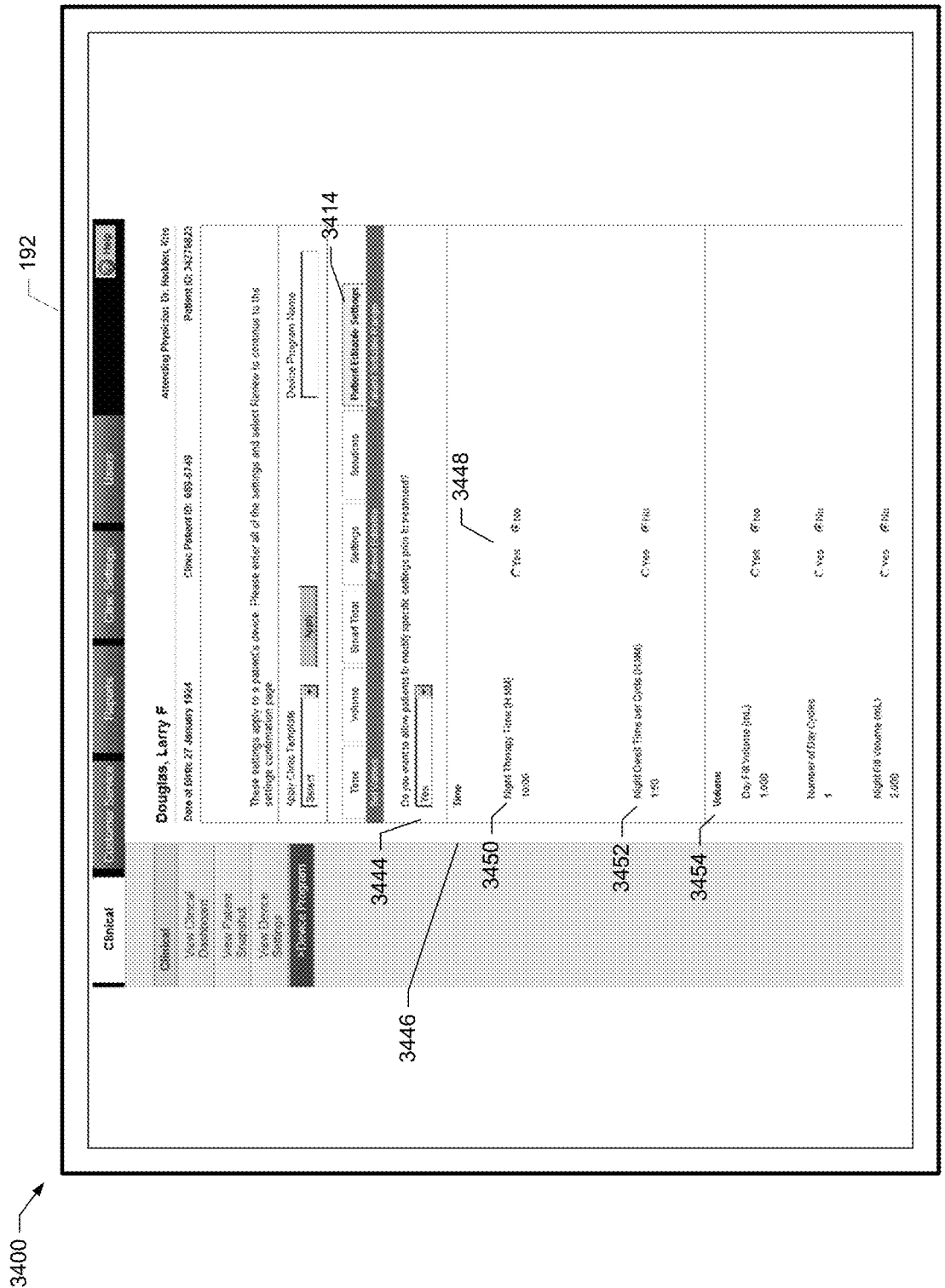
FIG. 34E is a screen shot of yet a further example device program screen of the present disclosure.
Figure 34F:
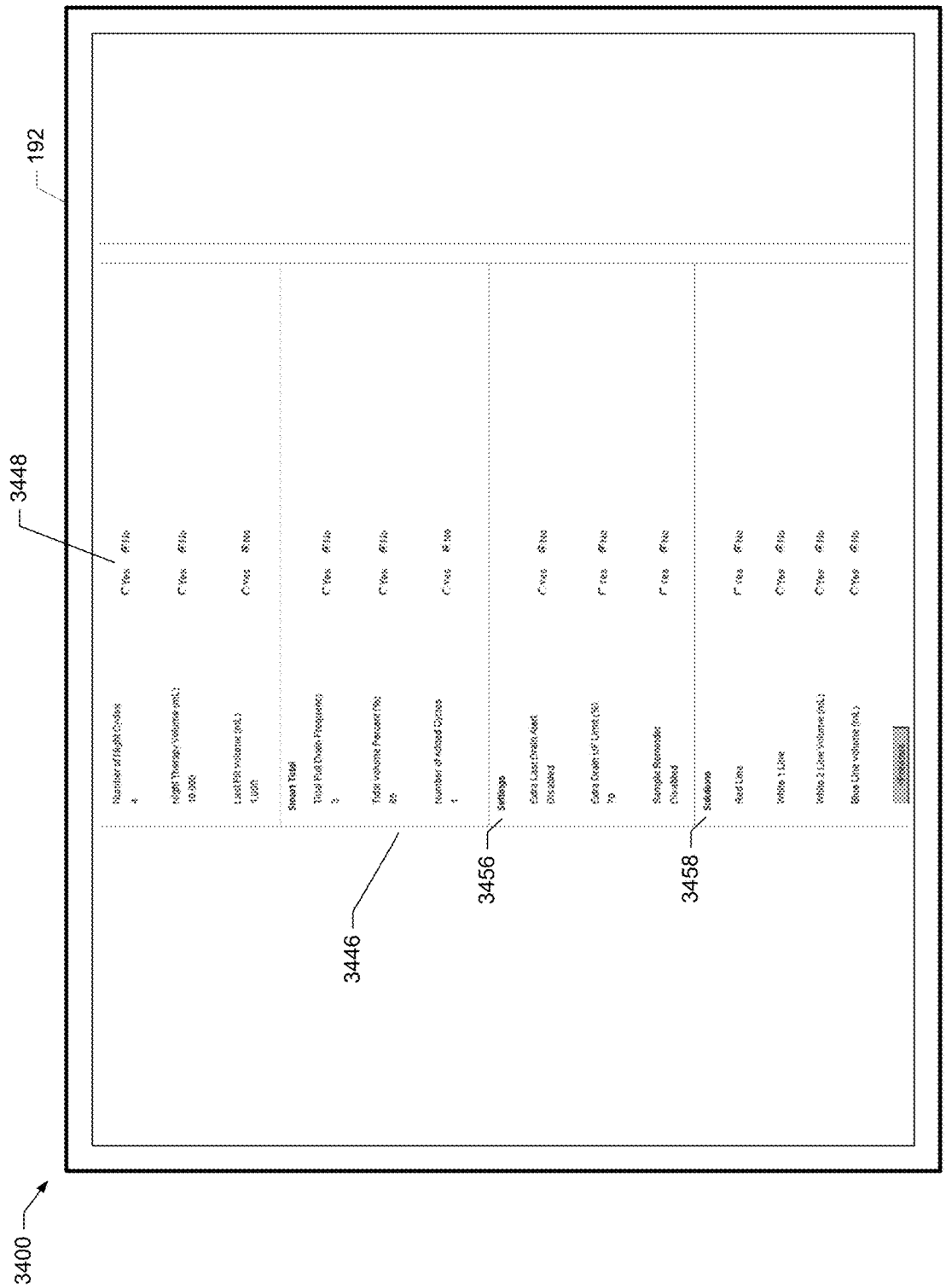
FIG. 34F is a screen shot of still another example device program screen of the present disclosure.
Figure 34G:
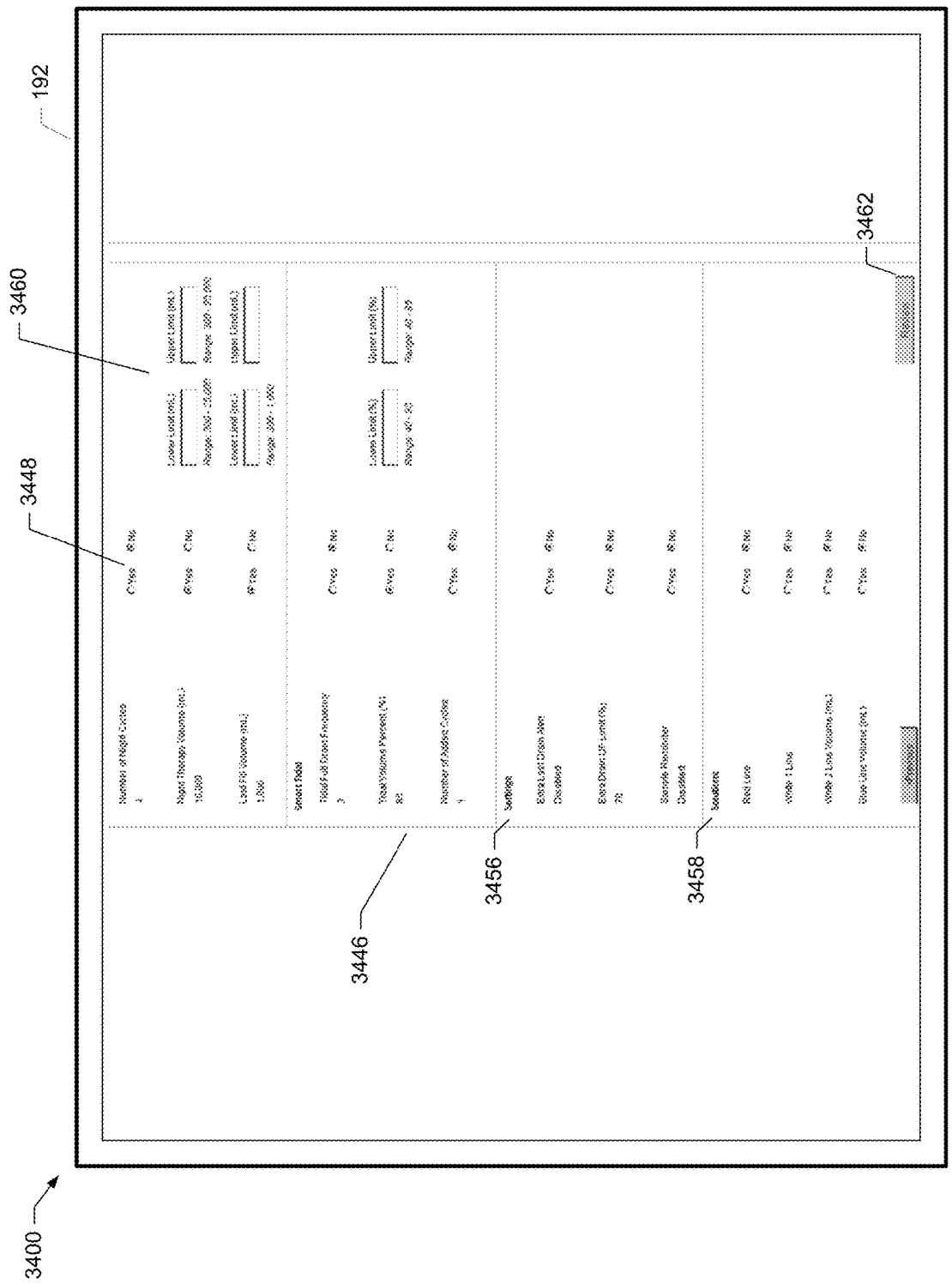
FIG. 34G is a screen shot of yet another example device program screen of the present disclosure.

The device program screen 3400 contains various tabs, such as a time tab 3406 (FIG. 34A), a volume tab 3408 (FIG. 34B), a settings tab 3410 (FIG. 34C), a solutions tab 3412 (FIG. 34D), and a patient editable settings tab 3414 (FIGS. 34E to 34G). In one embodiment, the fields displayed across the various tabs are inter-related. For example, the values entered into the time tab 3406, volume tab 3408, settings tab 3410, solutions tab 3412 and patient editable settings tab 3414 all work together, depend on and influence each other. It is contemplated for a second one of tabs 3406 to 3414 to display values that are acceptable based upon what the clinician entered under a first one of the tabs 3406 to 3414. The user accordingly need not be concerned with calculating or determining what values may be available for entry based upon what the user has already entered and selected in other previous tabs. The clinician's computer in operation with home medical device system 110 performs the calculations for this use and only allows entry and selection of valid values under the tabs. For example, only values available for selection may be displayed under the tabs. The clinician therefore need not be concerned with verifying whether the values entered and selected are consistent with each other.

In FIG. 34A, the clinician has selected and may enter values into fields in the time tab 3406. Here, the clinician can select and enter values for either a night therapy time 3416 or a night dwell time per cycle 3418. The clinician enters values for the displayed hours and minutes fields. The clinician also has the ability to enable a treatment option, such as smart dwells option 3420, which provides more control over the dwell time during the night portion of peritoneal dialysis therapy. Enabling smart dwells 3420 allows a clinician to select parameters that comport with the patient's lifestyle. When smart dwells is set to "Enabled", the renal therapy machine 100 adjusts the dwell time to accommodate changes in the fill and drain times, so that the treatment ends as scheduled. When smart dwells is set to "Disabled", the therapy dwell times are not changeable, therefore, the treatment may end at a different time then scheduled.

FIG. 34B illustrates that the clinician has scheduled the volume tab 3408 of device program screen 3400 displayed on a clinician's display device 192 which allows the clinician to specify if the treatment includes a day therapy 3422, a night therapy 3424, a tidal therapy 3426 or a last fill 3428. If any one of items 3422, 3424, 3426 or 3428 is selected as "Yes", the clinician enters a volume and a number of cycles for the selected item. The clinician's computer in operation with system 110 in one embodiment then multiplies the volume times the number of cycles to determine and display an aggregate volume for that option. The device program screen 3400 uses programmed logic stored in the clinician's computer to determine what values may be entered under volume tab 3408 based upon the values entered into the time tab 3406. The clinician may for example not be able to enter a particular volume or a number of cycles if that particular volume and/or number of cycles cannot be safely used or performed in the amount of time specified in previous tab time tab 3406.

It should therefore be appreciated that the dashboard 3400 on clinician's display device 192 allows a clinician to safely specify the parameters that will actually work for a given patient by only presenting fields that can be filled and only allowing the entry of values that can work or be performed with other selected values and/or the patient's prescription. Home medical device system 110 accordingly removes the burden from the clinician of having to ensure that the selected values are all consistent.

To accomplish the goal of relieving the clinician of having to verify all settings against one another, it is contemplated to make one or more tabs 3406 to 3416 sequentially dependent on one or more other tabs. In one example, the clinician can only proceed from the time tab 3406 to the volume tab 3408 after values have been specified in the time tab 3406, e.g., at least one of night therapy time 3416 and night dwell time 3418 have been selected by clinician and the associated amount of time in hours and minutes has been entered by the clinician. The values entered into the time tab 3406 limit the values that may be entered into subsequent tabs. The clinician then specifies information in the volume tab 3408, which may further limit or inform the values that can be entered in the settings tab 3410 and the solutions tab 3412. In this manner, the clinician is presented with a smart system in which the screens and fields that are presented to the user depend upon values entered in previous screens. It should therefore be appreciated that dashboard 3400 allows the clinician to specify one aspect of treatment at a time, which then influences the parameters that can be entered for other aspects of the treatment.

The smart system can use machine limitations and/or therapy limitations to help filter the values available in subsequent tabs. For example, once time is entered, available volume can be limited by knowing a safe maximum flow rate for machine 100, e.g., how fast can machine 100 fill or empty the patient in a peritoneal dialysis therapy. In another example, a particular type of solution may require a minimum dwell time to ensure that the benefit provided by the solution is used effectively. These types of rules are implemented on the clinician's software, which may be stored thereon by downloading the software via system hub 120 and web portal 150 to the clinician's computer.

Referring back to FIG. 34B of device program screen 3400, the clinician enters the needed information in the volume tab 3408 and presses next. FIG. 34C displays an example settings tab 3410. The clinician is asked to enter values for an estimated maximum peritoneal volume 3430, an estimated night ultrafiltrate 3432, whether the last fill solution is the same as or different from the night fill solution 3434 and a minimum initial drain volume 3436. The maximum peritoneal volume 3430 may be an estimated volume that a patient's peritoneal cavity can accept for peritoneal dialysis. This volume is used to determine when partial drains are not adequate. The settings tab 3410 may recommend an amount to enter for the maximum peritoneal volume 3430 field based upon the body mass of the patient. As described above, the values that can be entered in the fields in settings tab 3410 can alternatively depend upon the time and volume amounts previously specified by the clinician in time tab 3406 and volume tab 3408, respectively. For example, estimated UF depends on solution volume, solution type and dwell time.

The clinician may also be able to access advanced settings by pressing button 3438. Advanced settings may include additional settings for tailoring treatment for a particular patient, thereby increasing convenience and satisfaction for the patient. Advanced settings may include an option for enabling an effluent sample reminder, which pauses therapy before emptying solution bags at the end of treatment to allow a patient to collect an effluent sample before the unused solutions dilute the sample (assuming unused solution is collected with drained effluent). Advanced settings may also include an option for enabling an extra last drain mode, which is designed to ensure that a patient is completely drained before his or her last fill volume is delivered, and an extra drain UF limit, which is a percentage setting indicating the percentage of expected night UF needed before the patient receives the extra last drain mode option. Advanced settings may also include an option for enabling an extra last drain alert, which occurs at the end of the last drain and prompts the patient to press a confirm button on renal therapy machine 100 before receiving the last fill volume.

Advanced settings may further include an option for (i) modifying a minimum initial drain time, which is the minimum length of time allowed to complete an initial drain, (ii) modifying a minimum night drain time, which is the minimum length of time allowed to complete a night drain, (iii) modifying a minimum day drain time, which is the minimum length of time allowed to complete a day drain, and (iv) modifying a minimum day drain volume percentage, which is the percentage of day fill volume that needs to be drained before moving to next phase of therapy.

FIG. 34D of device program screen 3400 illustrates that the user has pressed a solutions tab 3412 (FIG. 34A) which allows a clinician to specify solution bag volumes 3440 and view a programmed therapy volume 3442. The clinician can specify the solution bag type (e.g., Dianeal, Extraneal, etc.), the glucose percentage or concentration (e.g., 1.5%, 2.5%, 4.25%, etc.) and the bag volume (e.g., 1000 mL, 2000 mL, 5000 mL, 6000 mL, etc) in solution volumes 3440 that should be used by the patient for treatment. Again, the values that can be entered by the clinician depend upon the values that have been previously entered into time tab 3406, volume tab 3408 and settings tab 3410. The programmed therapy volume 3442 in one embodiment displays for convenience the amount of the solution volume the clinician has programmed, e.g., in other tabs.

The solution volumes 3440 is the volume of solution for one days' worth of treatment. Thus the clinician must select a solution volume, the total programmed solution volume of all the lines set by the clinician in solution volumes 3440 (FIG. 34D), that is greater than or equal to the programmed therapy volume, which is made up of the sum of the volume used during day therapy (specified in field 3422 of FIG. 34B), during night therapy (specified in field 3424 of FIG. 34B), and in a last fill (specified in field 3428 of FIG. 34B). In one embodiment, the clinician's display device displays an error message if the solution volume is not greater than or equal to the programmed therapy volume 3442.

FIG. 34E illustrates an example screen shot under patient editable settings tab 3414 (FIG. 34A) displayed on a clinician's display device 192. The clinician uses patient editable settings tab 3414 to specify whether or not a patient can modify certain values. Similar to the ranges described in connection with device program screen 1600 of FIG. 16A, patient editable settings tab 3414 allows the clinician to specify whether a patient can edit or modify certain parameters of the treatment. The clinician specifies in drop-down menu 3444 which patients can modify which parameters. If the clinician selects "Yes" in drop-down menu 3444, a list 3446 of parameters that may be edited by the patient is displayed. For each parameter in list 3446, the clinician can select in column 3448 whether or not the patient can edit that parameter. In the illustrated example, a clinician can decide whether or not a patient can edit the duration of night therapy 3450, the night dwell time per cycle 3452 or aspects about the volume 3454 such as day fill volume, number of day cycles and night fill volume.

The screen 3400 displayed on a clinician's display device 192, including list 3446, is continued in FIG. 34F. As shown in FIG. 34F, the clinician may also decide that a patient can edit additional aspects about the volume such as the number of night cycles, night therapy volume, last fill volume, tidal full drain frequency, tidal volume percentage and the number of added cycles. The clinician may also decide that a patient can edit settings 3456, such as whether to apply an extra last drain alert, whether to apply an extra drain UF limit and whether a fluid sample reminder is enabled or disabled. The clinician may also decide that a patient can edit information about solutions 3458, such as for example, the solution volume.

If the clinician allows the patient to edit values for a parameter, the clinician selects "Yes" next to that parameter in column 3448. As shown in FIG. 34G, system 110 displays additional fields next to a parameter when "Yes" in column 3448 is selected for that parameter. In the illustrated example, the clinician has decided to allow the patient to edit the night therapy volume, last fill volume, and tidal volume percent. The clinician then sets a range in column 3460 between which the patient can choose for each parameter. System 110 may preclude a clinician from entering certain values into column 3460 if those values are inconsistent with values previously entered into other fields in other tabs. The patient can only choose a value for a parameter at or within the limits entered by the clinician. System 110 advantageously allows patients to tailor therapy under the system, such as peritoneal dialysis, depending upon patient schedules and desires, but to do so within a safe, allowed range.

Figure 34H:
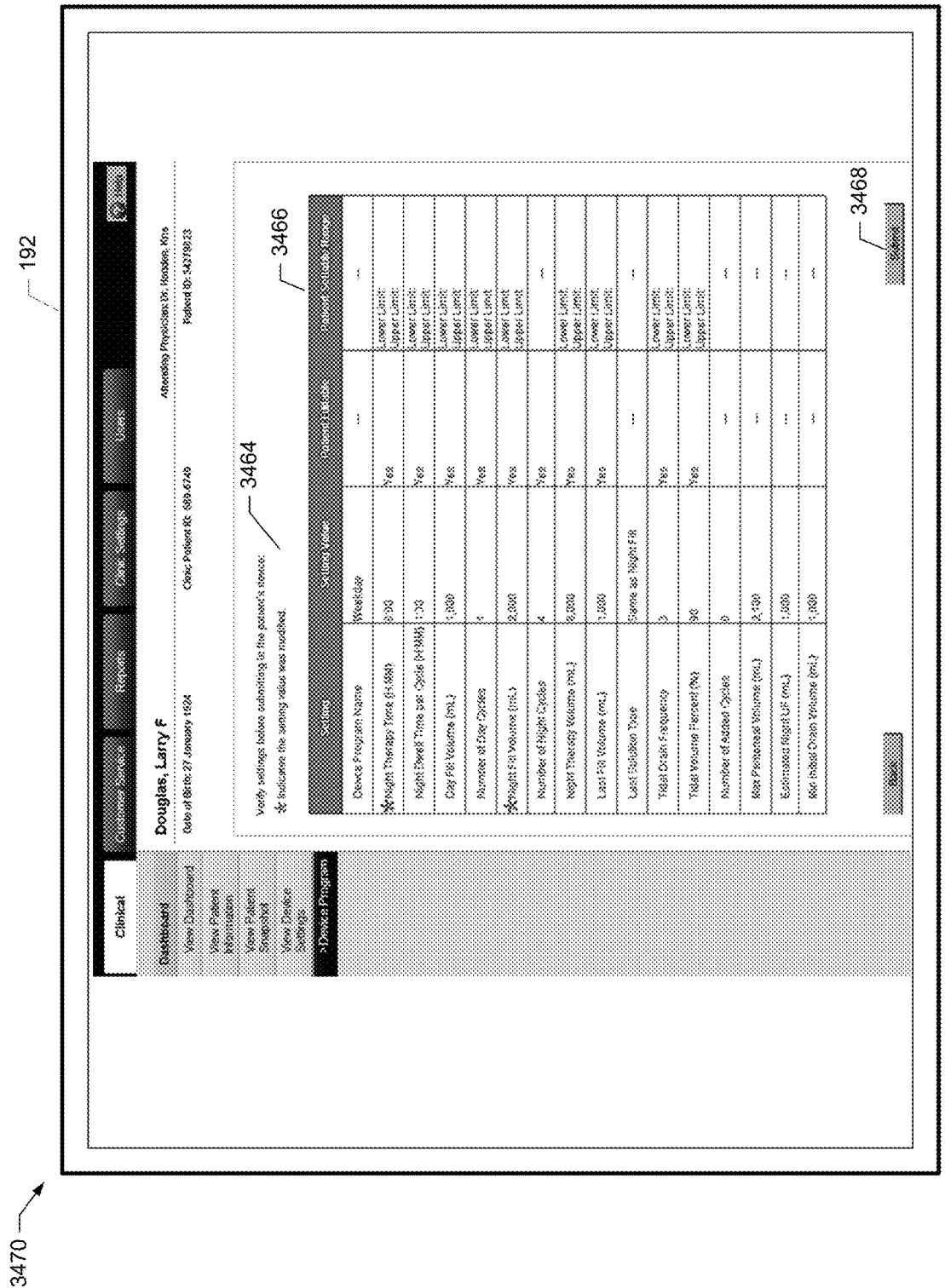
FIG. 34H is a screen shot of an example device program confirmation screen of the present disclosure.

FIG. 34H illustrates a device program confirmation screen 3470 that allows a clinician on one screen to view and confirm the values specified using the tabs in the device program screen 3400 (FIGS. 34A to 34G). The device program confirmation screen 3470 may be accessed by pressing the review button on the patient editable settings tab 3414 (FIGS. 34E to 34G) in the device program screen 3400. FIG. 34H allows the clinician to verify the settings all together before actually submitting the settings to renal therapy machine 100 at the patient's home via the connectivity server 118. As indicated at message 3464, an asterisk indicates that a setting value has been modified by the clinician as opposed to using a default value. The device program confirmation screen 3460 displays a settings summary table 3466 that lists all the values for the parameters, a patient settable range and whether or not the clinician will allow the patient to edit those values. Device confirmation screen 3470 allows the clinician to view at a high level and in summary format all of the different settings that have been selected via device program screen 3400 (FIGS. 34A to 34G). After reviewing table 3466 for accuracy and correctness, the clinician can submit the settings to the patient's device via connectivity server 118 by pressing submit button 3468. Once submit button 3452 is selected, the values and parameters are forwarded to renal therapy machine 100 via connectivity service 118 as described above.

As described above, the device program screen 3400 allows a clinician to control the treatment provided by machine 100. Patient settings screen 3500 described below in connection with FIG. 35A allows a clinician to specify whether the patient is to perform a task such as check his or her weight, pulse, blood pressure, glucose and temperature or whether a manual exchange is performed. The patient settings screen 3500, illustrated in FIG. 35A, may be accessed on a clinician's display device 192 from device settings screen 3300 (FIG. 33). As with patient settings screen 1530 (FIG. 15B), changes made in the patient settings screen 3500 modify how the next treatment is performed but are not immediately reported to the system hub 120. In the patient settings screen 3500, the clinician can apply a clinic template 3502 which again allows the clinician to quickly and easily populate a group of pre-selected settings on patient settings screen 3500. In any case, patient settings screen 3500 enables the clinician to specify a setting for the weight 3504, the pulse 3506, blood pressure 3508, glucose 3510, temperature 3512 and manual exchanges 3514. The clinician can use the cancel button 3516 and submit button 3518 to cancel or submit respectively the patient settings selected on patient settings screen 3500. In an embodiment, a patient may be able to access the patient settings screen 3500 to modify various settings for peritoneal dialysis treatment.

Figure 35A:
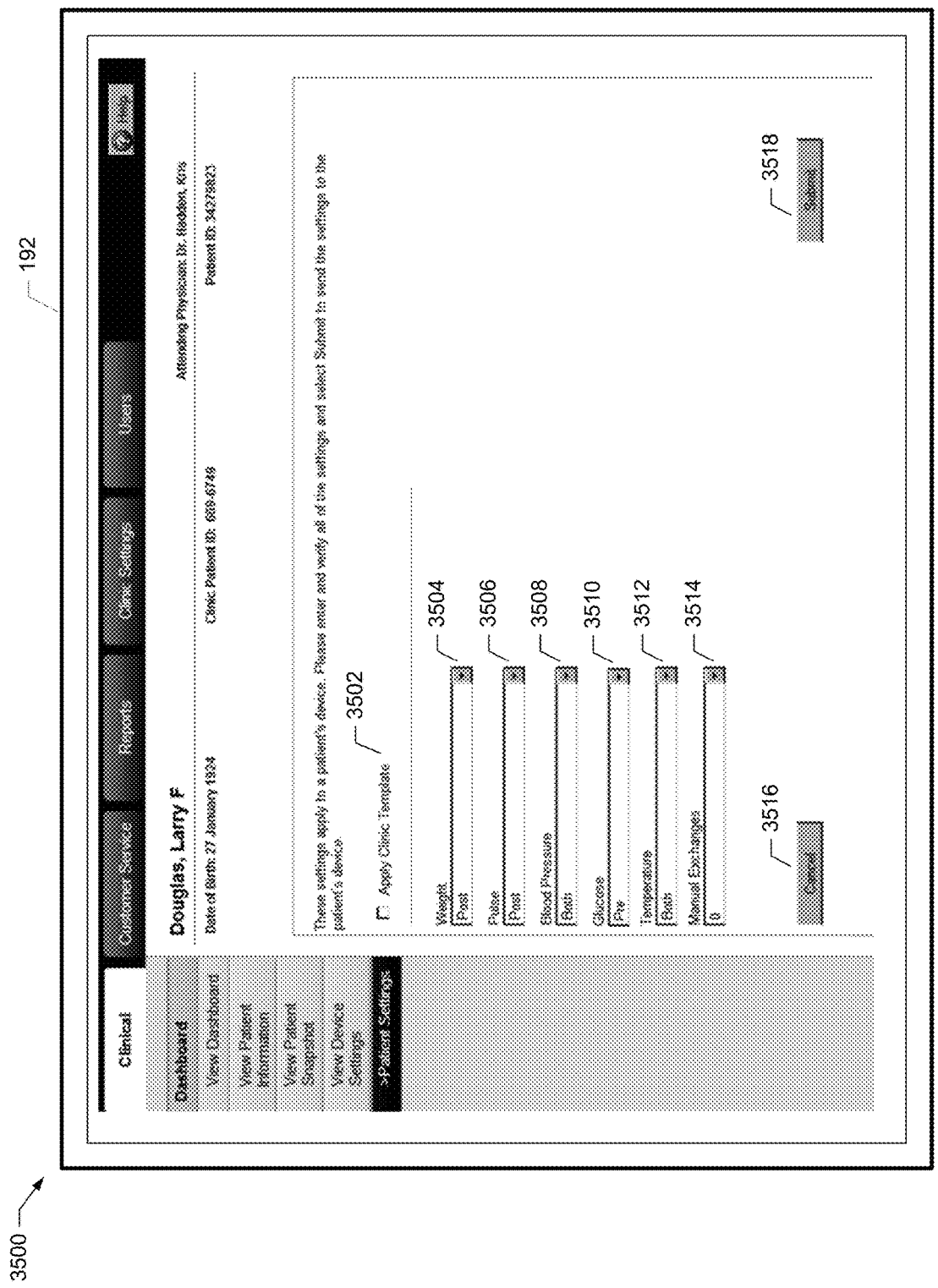
FIG. 35A is a screen shot of an example patient settings screen of the present disclosure.
Figure 35B:
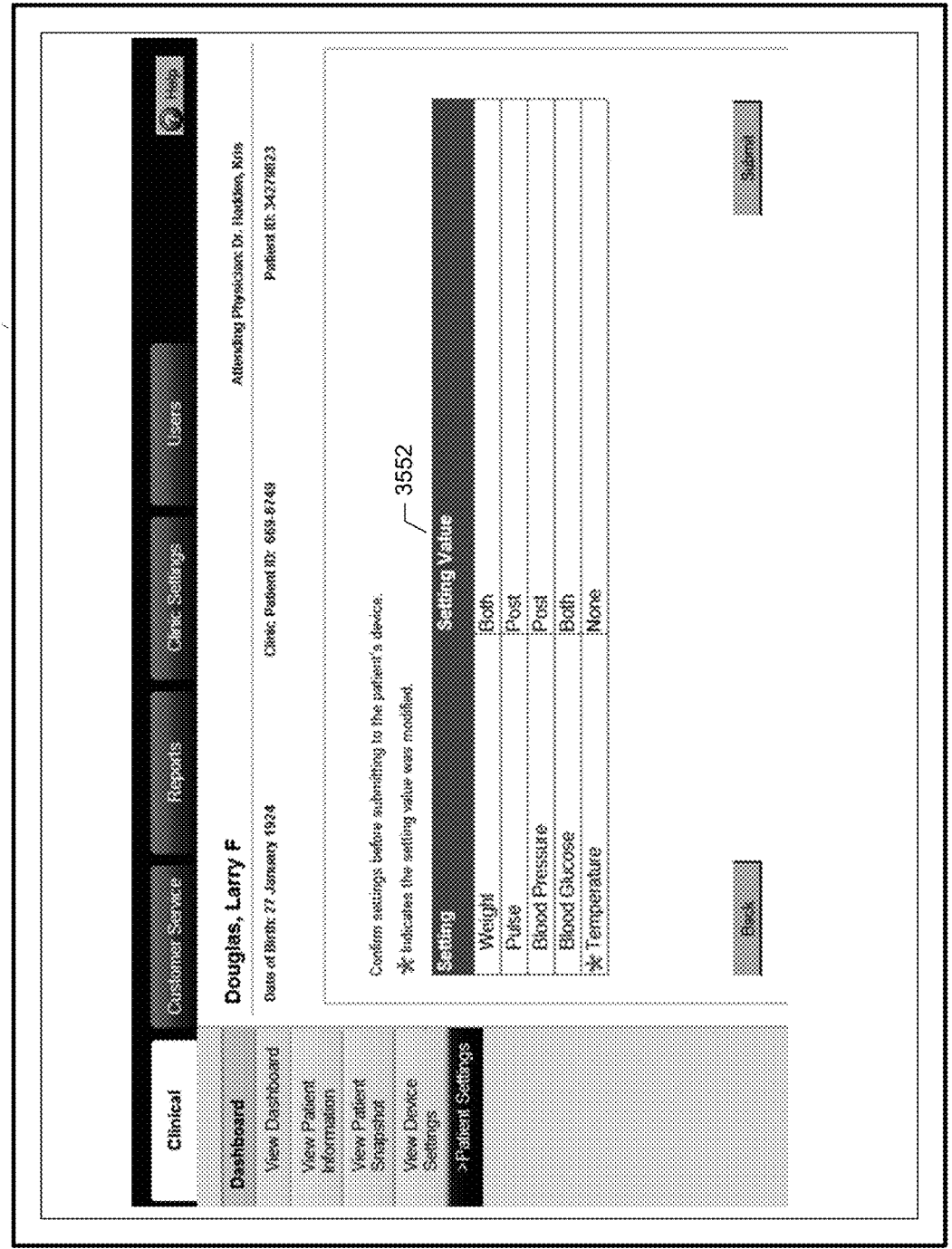
FIG. 35B is a screen shot of an example patient settings confirmation screen of the present disclosure.

FIG. 35B illustrates a patient settings confirmation screen 3550. FIG. 35B also illustrates the type of data that is set by patient settings screen 3500, namely, when the patient is to perform a task. For example, FIG. 35B shows that the patient weighs himself/herself before and after treatment. Blood pressure and heartbeat are measured after treatment. Blood glucose is measured before and after treatment. Patient temperature is not taken in the illustrated embodiment, but can be if desired. These patient settings tell machine 100 when to prompt the patient for such information. Patient settings confirmation screen 3550 may be accessed by pressing the submit button on the patient settings screen 3500 (FIG. 35A). Table 3552 summarizes the values selected at patient settings screen 3500 so that the clinician can review the settings before submitting the settings to the patient's device via connectivity server 118. Patient settings confirmation screen 3550 allows the clinician to view at a high level and in summary format all the different settings that have been selected. After reviewing table 3552 for accuracy and correctness, the clinician can submit the settings to the patient's device via connectivity server 118.

Figure 36A:
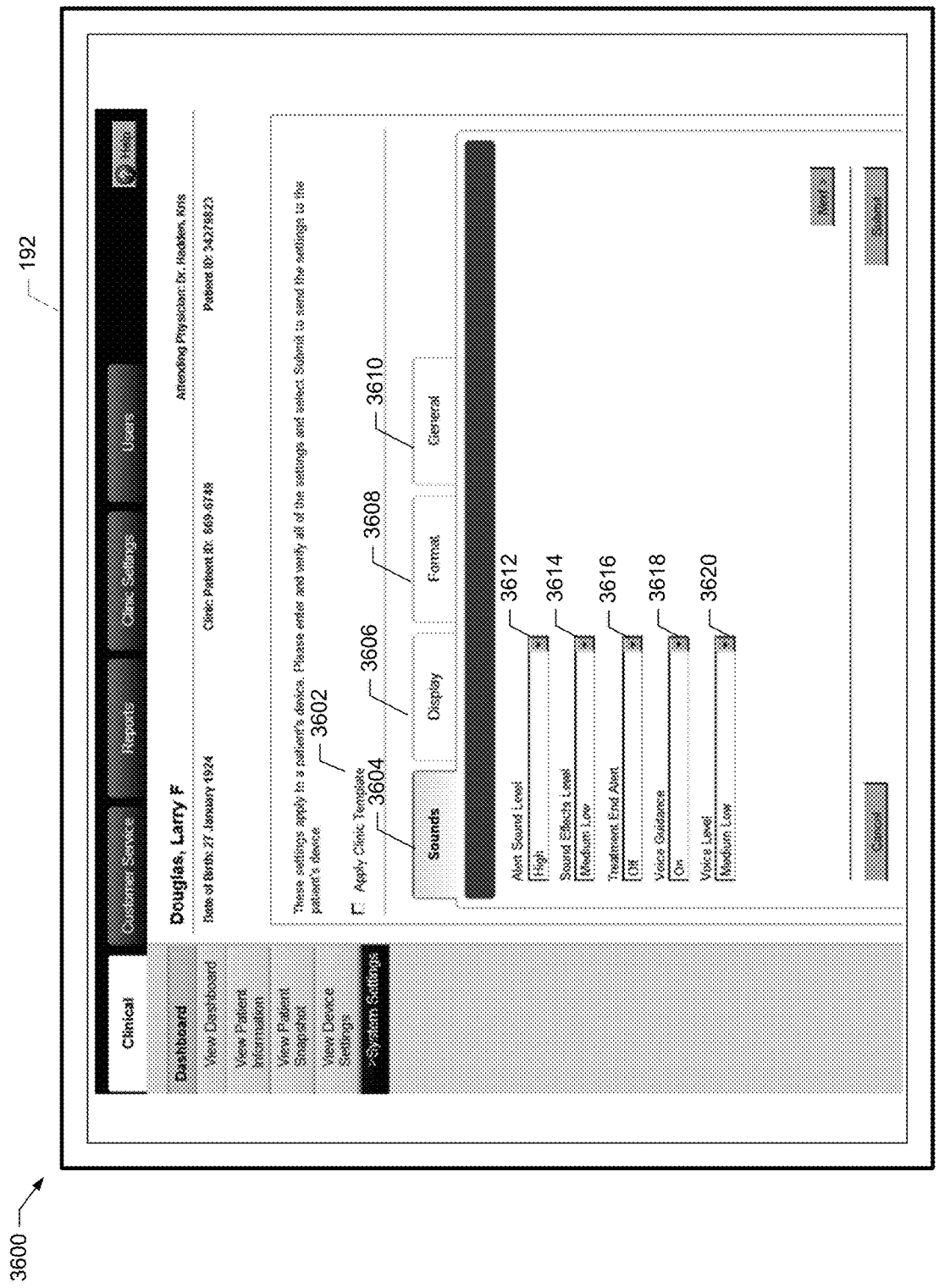
FIG. 36A is a screen shot of an example system settings screen of the present disclosure.

FIG. 36A illustrates an example screen shot of a system settings screen 3600 displayed on a clinician's display device 192. The system settings screen 3600 allows a clinician to specify various settings related to alarms and outputs renal therapy machine 100 makes. Outputted sound can be raised for patients with hearing disabilities. Voice guidance helping the patient with set-up can be activated. The clinician can apply a clinic template 3602 which, like before, enables the clinician to quickly and easily specify and populate a group of pre-selected machine or system settings. The system settings screen 3602 allows a clinician to select system settings for various aspects of the patient's device via sounds tab 3604, display tab 3606, format tab 3608, and general tab 3610. Under the sounds tab 3604 illustrated in FIG. 36A, the clinician can specify an alert sound level 3612, a sound effect level 3614, a treatment end alert 3616, voice guidance 3618, and voice level 3620. Again, the sound may be adjusted based on patient hearing ability. Or, alarm sounds may be set higher than the sound level for standard therapy sounds, e.g., sound effects or voice guidance, to activate the alarm output.

Figure 36B:
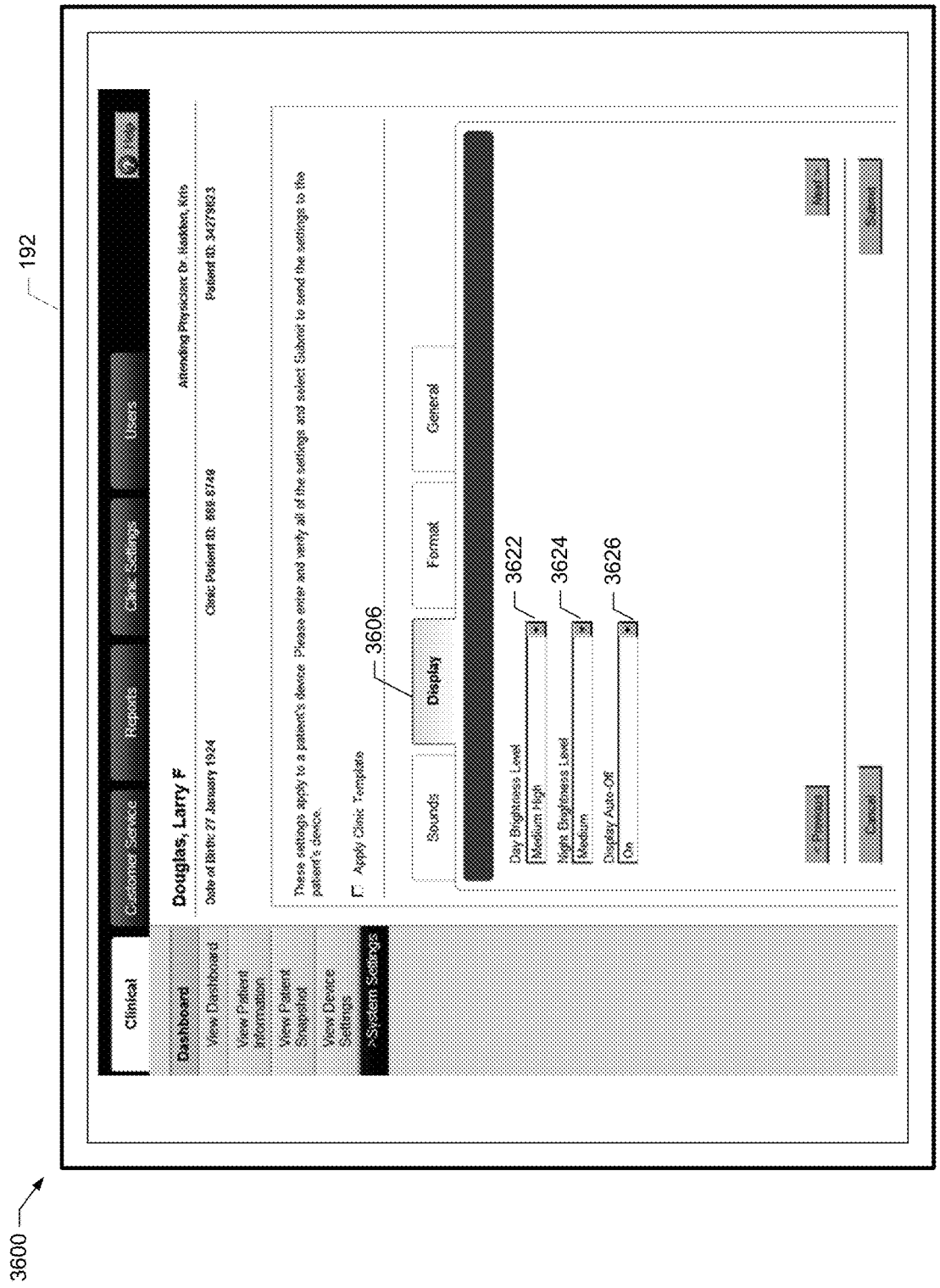
FIG. 36B is a screen shot of another example system settings screen of the present disclosure.
Figure 36C:
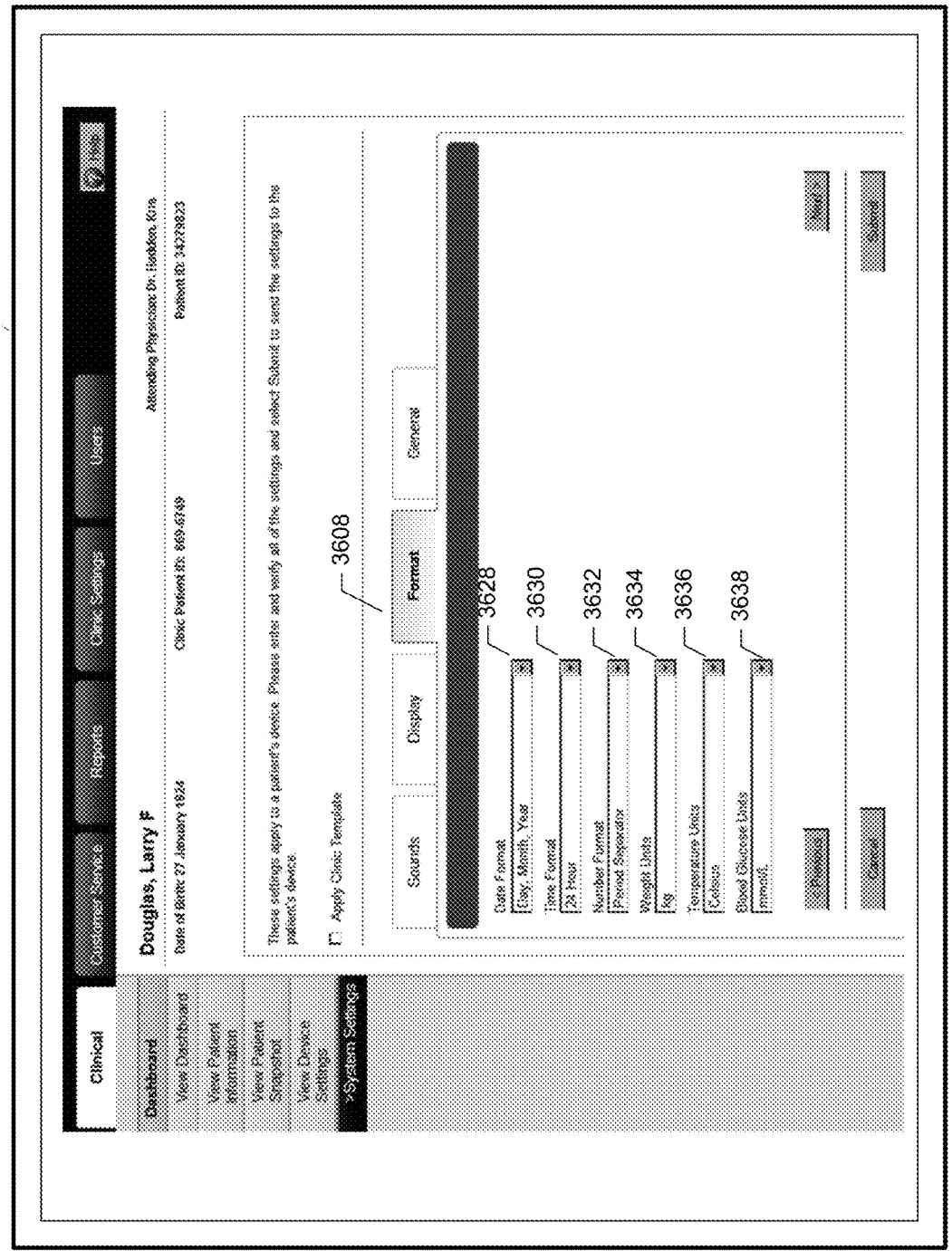
FIG. 36C is a screen shot of a further example system settings screen of the present disclosure.

FIG. 36B illustrates display tab 3606 in system settings screen 3600 displayed on a clinician's display device 192. At the display tab 3606, the clinician can specify a day brightness level 3622, a night brightness level 3624 and display auto-off 3626, which sets whether the display of machine 100 (which may be a dedicated screen for peritoneal dialysis, for example, instead of a tablet 122 for hemodialysis, for example) goes into a hibernate mode after a certain period of time. FIG. 36C illustrates an example screen shot of format tab 3608 in system settings screen 3600 displayed on a clinician's display device 192. At the format tab 3608, the clinician can specify a date format 3628, a time format 3630, a number format 3632, weight units 3634, temperature units 3636 and blood glucose units 3638. Format accordingly generally applies to data format.

Figure 36D:
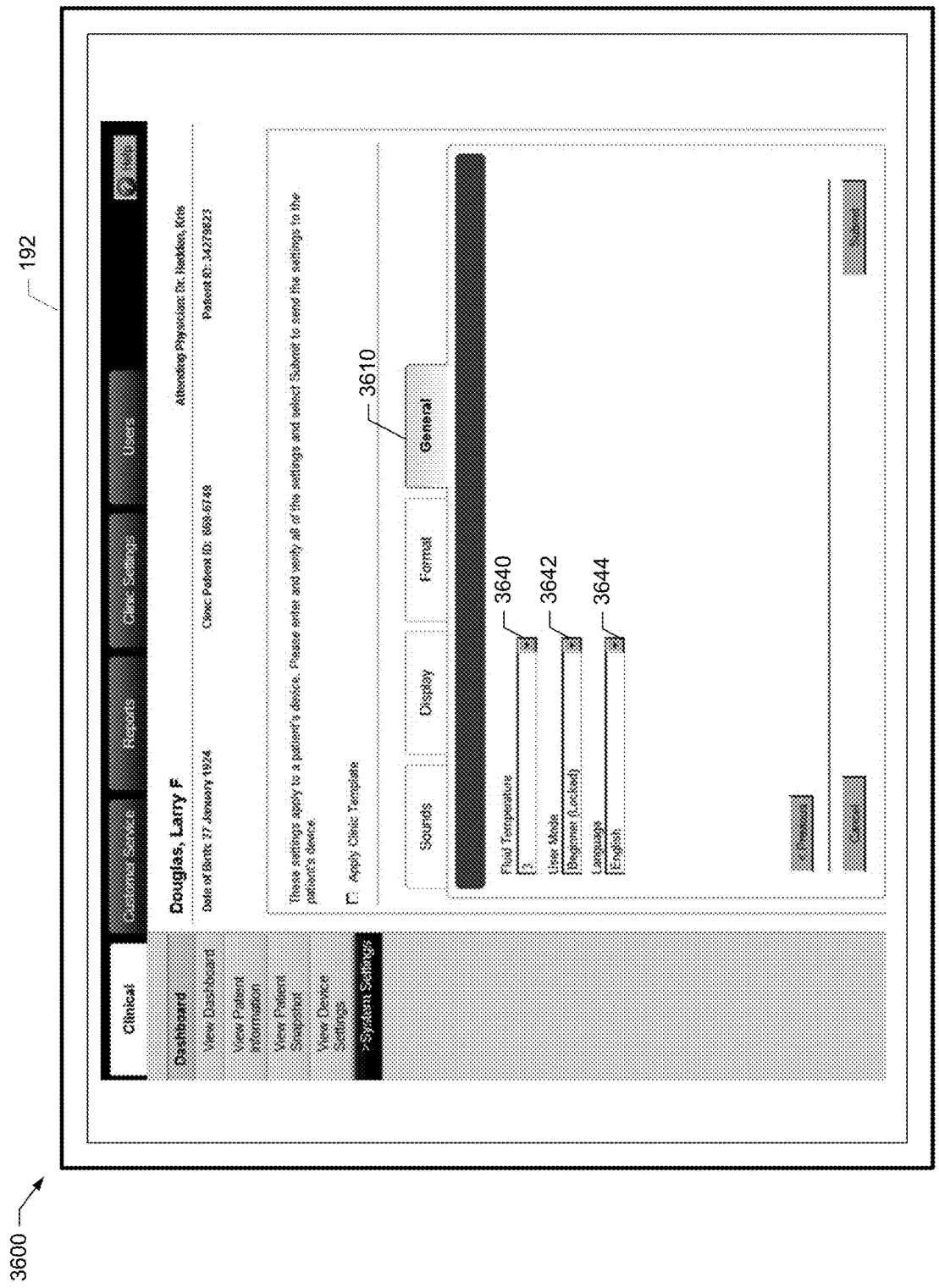
FIG. 36D is a screen shot of yet another example system settings screen of the present disclosure.

FIG. 36D illustrates an example screen shot of a general tab 3610 in system settings screen 3600 displayed on a clinician's display device 192. On the general tab 3610, a clinician can specify fluid temperature 3640, a user mode 3642 and the language 3644. Fluid temperature 3640 controls the temperature of the fluid warmer and the temperature of the fluid that will be infused into the patient. User mode 3642 allows the user to consolidate the treatment screens as the user's expertise grows. Language 3644 sets the language in which text is displayed and words are enunciated. Each of the screens for tabs 3606, 3608 and 3610 is also provided with a clinician's template option to auto-populate the respective settings.

Figure 37A:
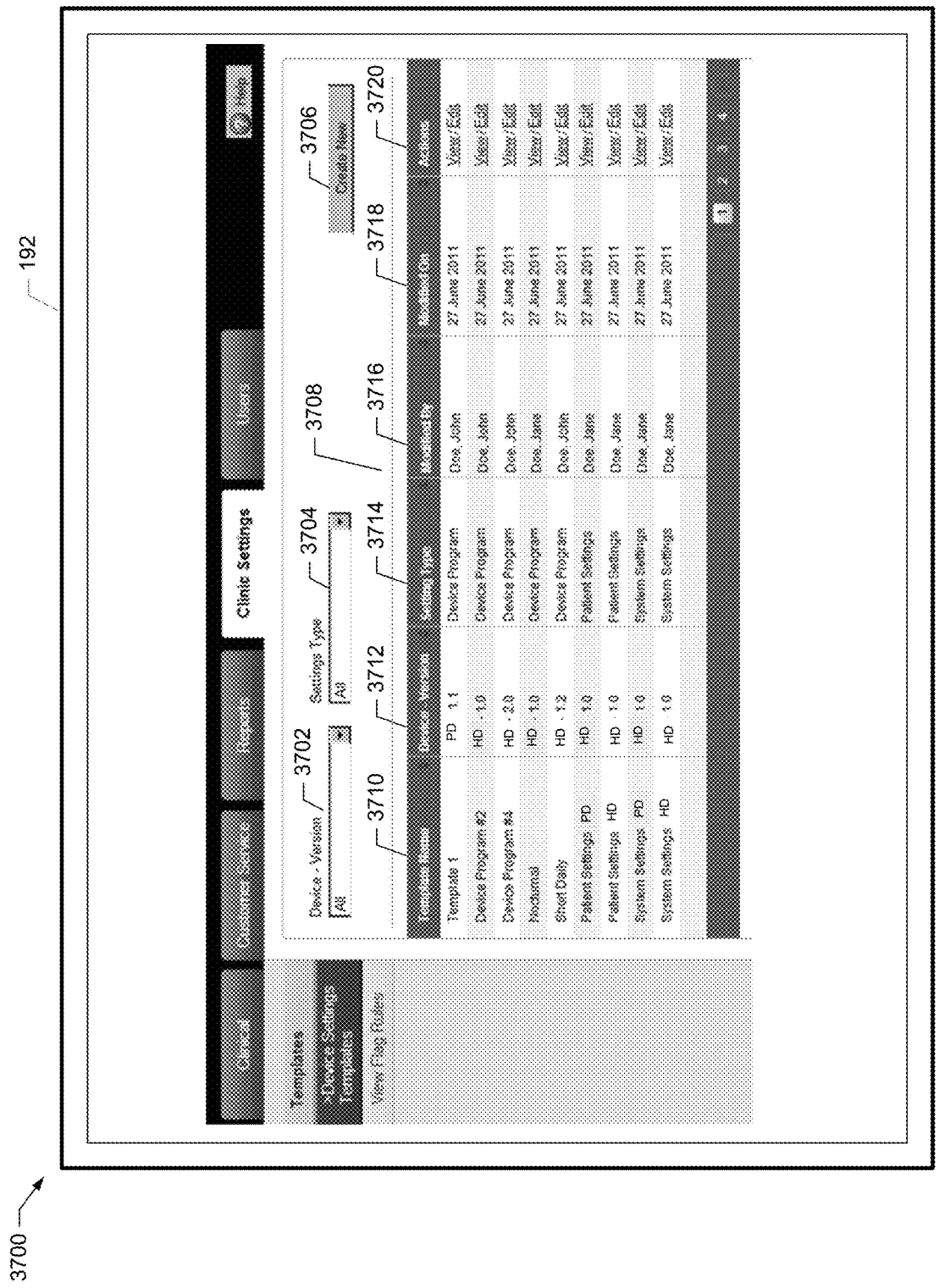
FIG. 37A is a screen shot of an example device setting templates screen of the present disclosure.

FIG. 37A illustrates an example screen shot of a device settings templates screen 3700 displayed on a clinician's display device 192. The device settings template screen 3700 is accessed from clinic settings tab 3018 (FIG. 30A) and allows a clinician to view all the different templates that are accessible to the clinician throughout web portal 150. As explained previously, templates allow a clinician to enter pre-selected values for multiple parameters at once. The clinician can filter the templates that are displayed on device settings templates screen 3700 and thus throughout web portal 150 by using drop-down menu 3702 to filter by device version or drop-down menu 3704 to filter by settings type. The device version 3702 allows a clinician to filter templates according to different software versions or hardware versions that are installed on machine 100. The settings type 3704 allows a clinician to filter the different types of templates, such as, device program templates, patient settings templates or system settings templates. The clinician can also create a new template using create new button 3706.

Once the templates are filtered according to the clinician's selections at drop-down items 3702 and 3704, the device settings templates screen 3700 displays table 3708 which lists the various templates that remain available to the clinician. Table 3708 lists the name of the template in column 3710, device version of the template in column 3712, setting type of the templates in column 3714, last user to modify the template in column 3716, date that the template was modified in column 3718, and actions that a clinician is allowed to perform on a template, such as to view or edit a template, in column 3720.

Figure 37B:
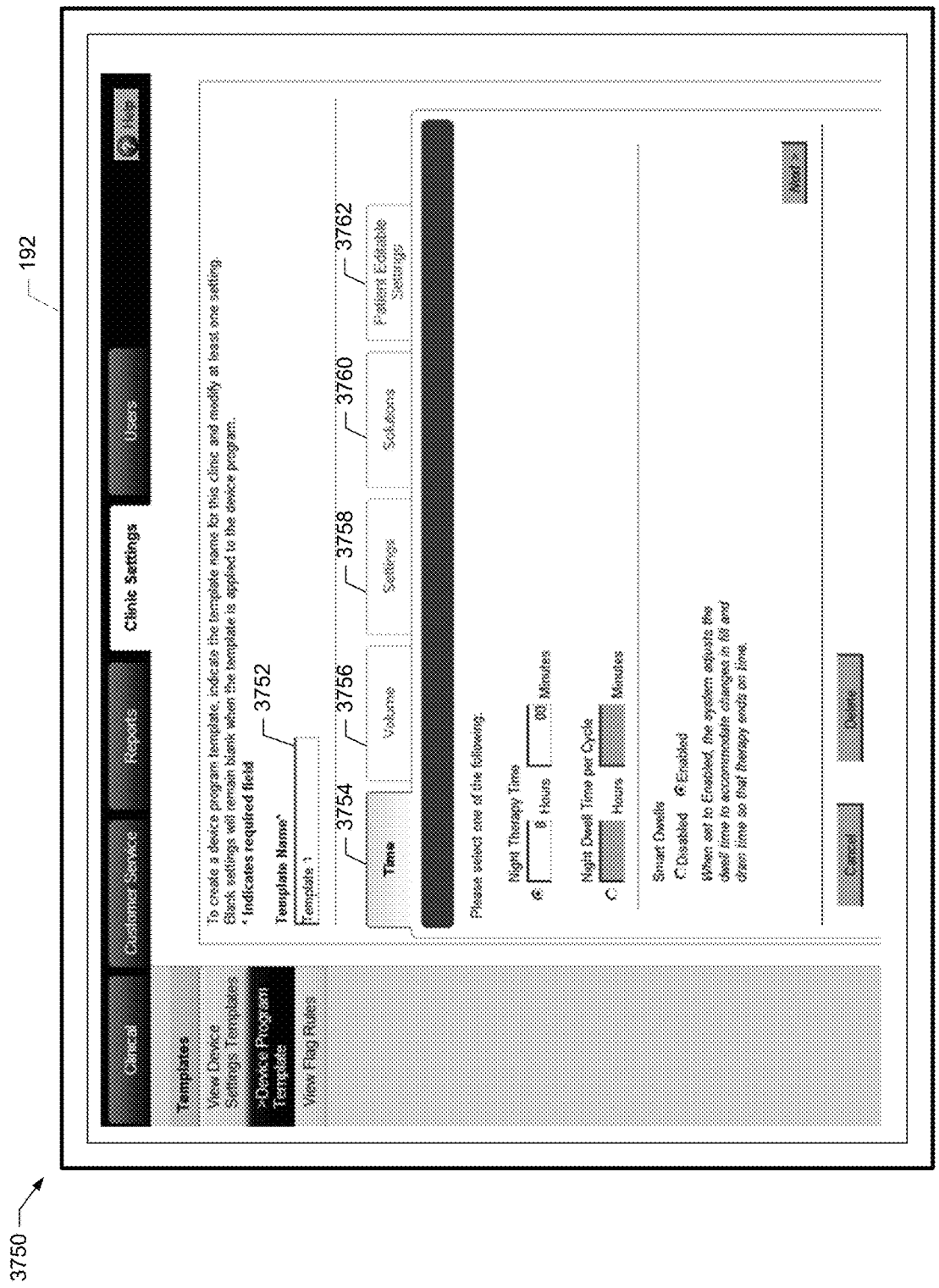
FIG. 37B is a screen shot of an example device program template screen of the present disclosure.

FIG. 37B illustrates an example screen shot of a device program template screen 3750. The clinician arrives at screen shot 3750 by selecting one of the device program templates to view or edit on device settings templates screen 3700 (FIG. 37A). The device program template screen 3750 displays the template name 3752 and different tabs that correspond to the selected template. For example, device program template screen 3750 displays time tab 3754, volume tab 3756, settings tab 3758, solutions tab 3760, and patient editable settings tab 3762. The tabs and fields displayed in FIG. 37B correspond to the tabs and fields displayed in FIGS. 34A to 34G. It should therefore be appreciated that the values stored as part of a template in device program template screen 3750 can be recalled quickly by selecting field 3404 on device program screen 3400 (FIG. 34A). The values set at template screen 3750 can be average values for all or many patients as opposed to values customized for a single patient.

Figure 38A:
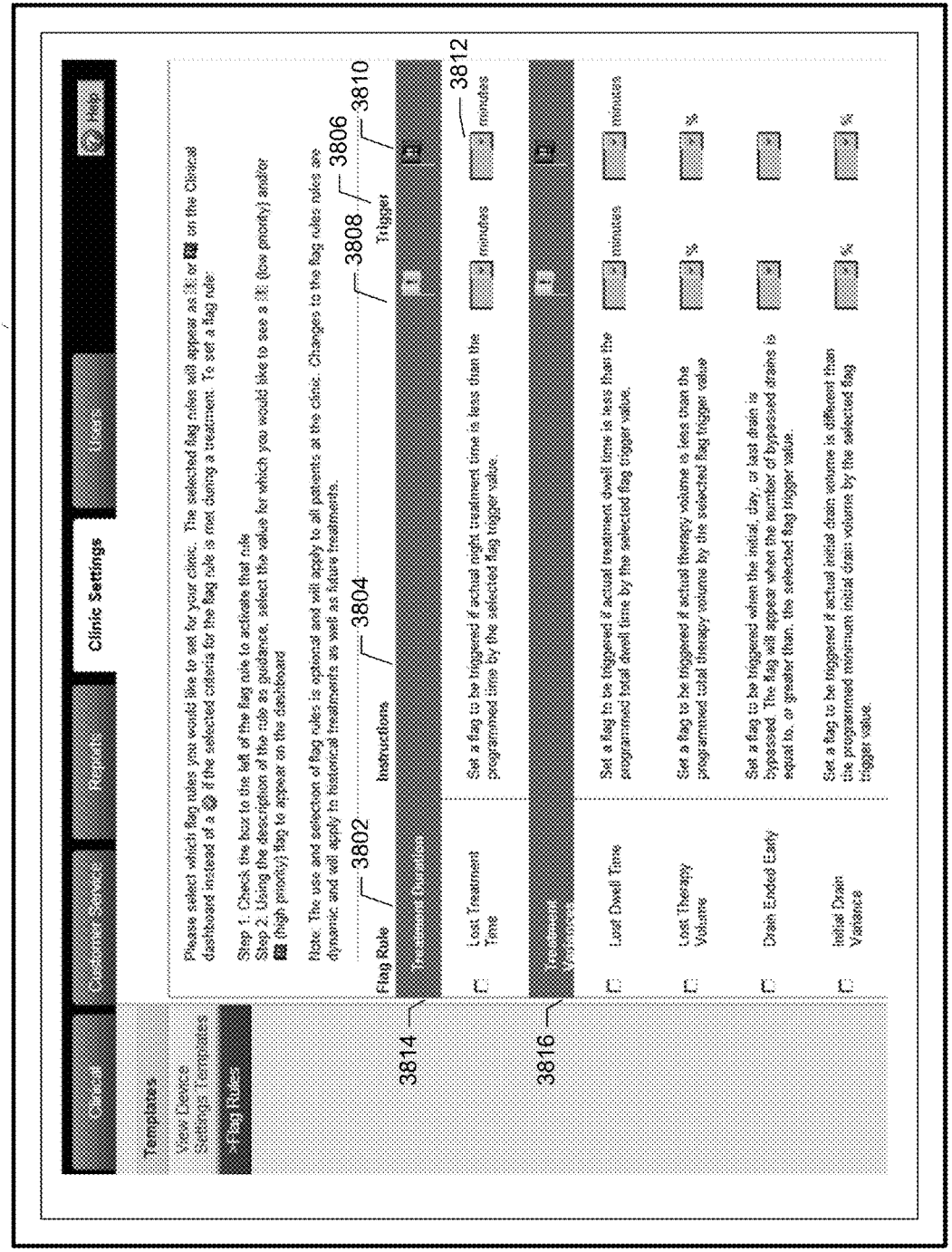
FIG. 38A is a screen shot of an example flag rules screen of the present disclosure.
Figure 38B:
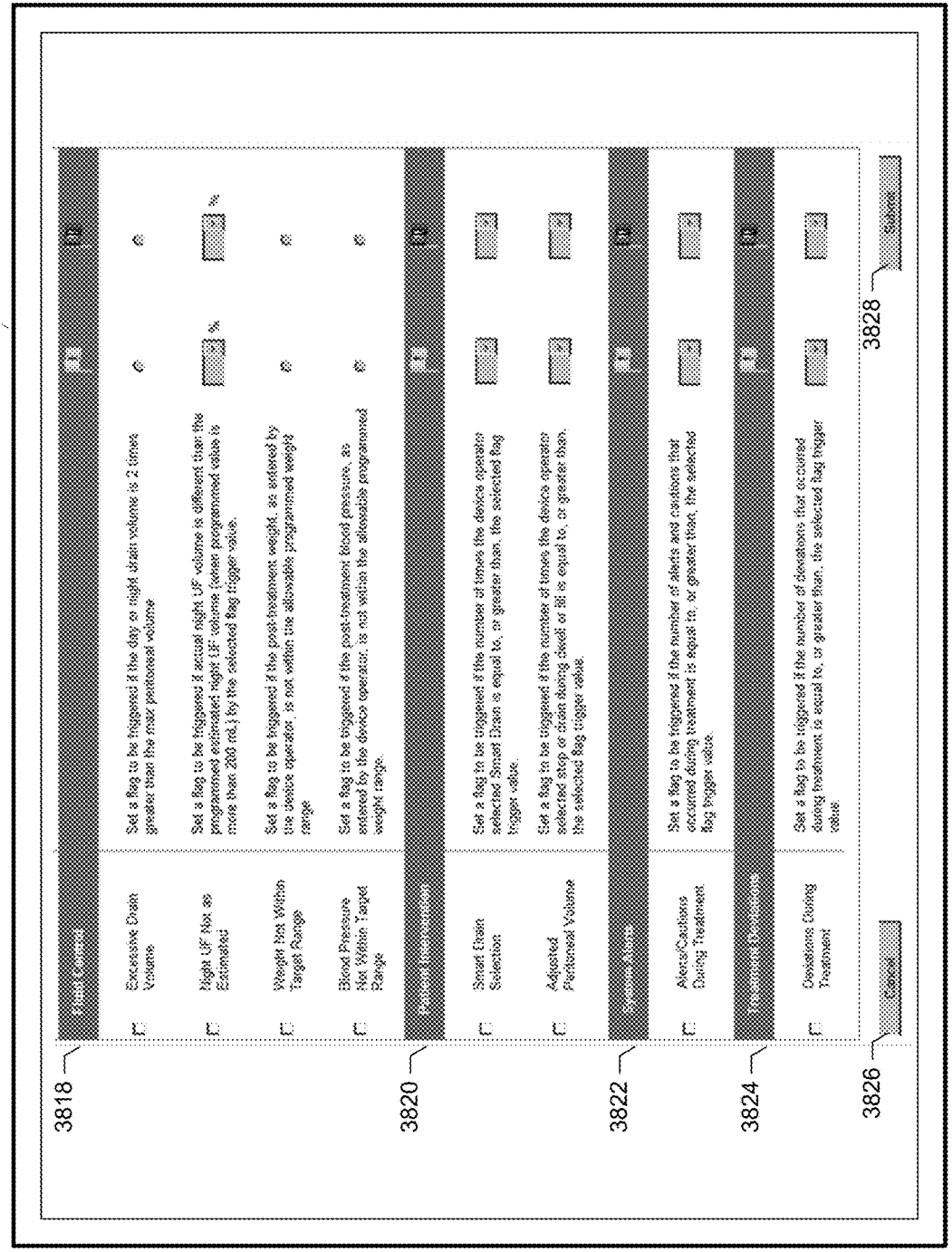
FIG. 38B is a screen shot of another example flag rules screen of the present disclosure.

FIG. 38A illustrates an example flag rules screen 3800 displayed on a clinician's display device 192. Similar to example flag rules screen 1750 (FIGS. 17C and 17D), flag rules screen 3800 allows a clinician to select different treatment events selected from column 3802 that will trigger a flag notification, which will then be displayed on dashboard 3000 (FIG. 30A). For each treatment event in column 3802, the flag rules screen 3800 displays how the flag is set in column 3804 and the trigger for the flag event in column 3806. Flag rules screen 3800 allows the clinician to specify the parameters 3812 that generate a first level notification icon 3808 or a second level notification icon 3810. Similar to flag rules screen 1750 of FIGS. 17C and 17D, flag rules screen 3800 allows the clinician to quickly specify or check off the different events or conditions that the clinician desires to trigger a flag or notification on dashboard 3000 described in FIG. 30A. As illustrated in FIG. 38A, a clinician can set flag rules relating to treatment duration 3814 and treatment variances 3816. Flag rules screen 3800 is continued in FIG. 30B, which illustrates that the clinician can also set flag rules relating to fluid control 3818, patient intervention 3820, system alerts 3822, and treatment deviations 3824. Each of the flag rules is described in sufficient detail in connection with FIGS. 31A and 31B. The clinician can cancel the settings or submit the settings using cancel button 3826 or submit button 3828 respectively.

Figure 39A:
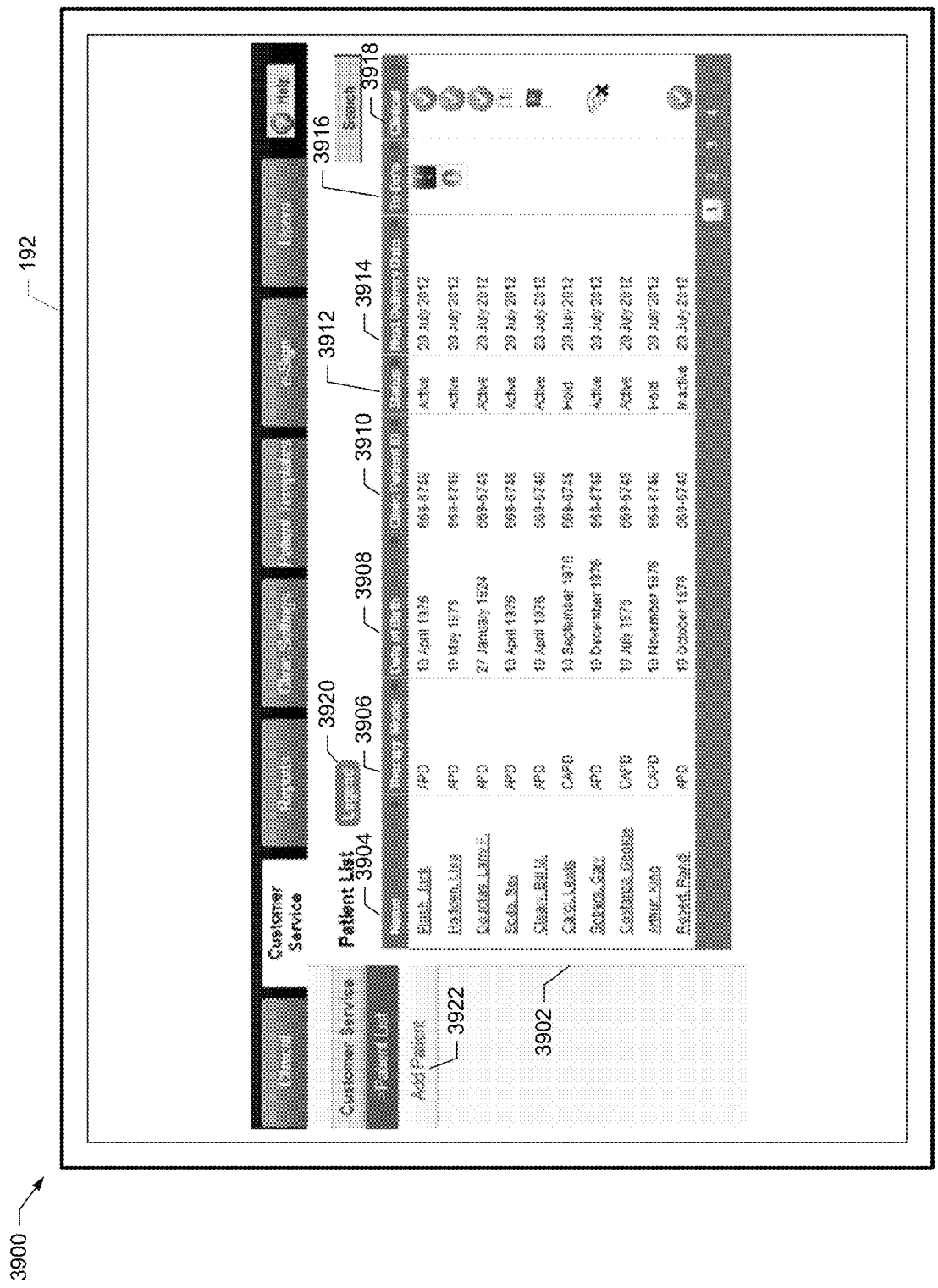
FIG. 39A is an example screen shot of a patient list screen of the present disclosure.

FIG. 39A illustrates an example screen shot of a patient list 3900 displayed on a clinician's display device 192. Patient list 3900 is accessible from tab 3016 (FIG. 30A). The clinician can view a list of patients in table 3902 in FIG.

39A. As illustrated in FIG. 39A, the clinician can view the patient's name 3904, a therapy mode 3906, the patient's date of birth 3908, the clinic patient ID 3910, the status of the patient, such as whether the patient is active, on hold or inactive, in column 3912, the next delivery date that supplies will be delivered to that patient 3914, a list of to-dos for the patient 3916 and clinical status of the patient 3918. A clinician can access legend link 3920 to see the meaning of the icons in to-do column 3916. The clinical status 3918 displays information using icons from the clinician dashboard 3000 (FIG. 30A). A clinician can also navigate to an add patient screen (FIG. 41A) to add a patient by selecting add patient link 3922.

Figure 39B:
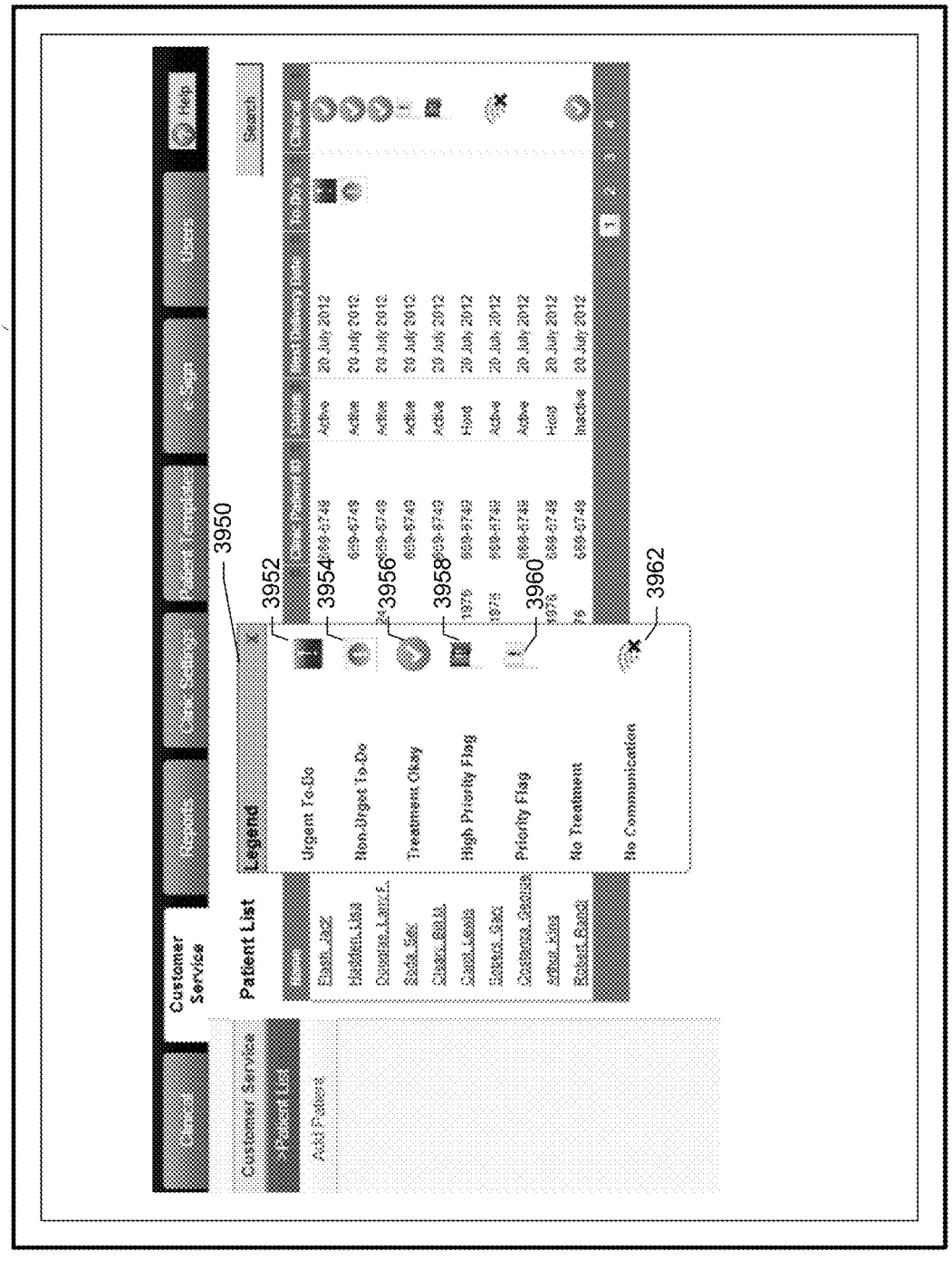
FIG. 39B is a screen shot of an example legend for a patient list screen of the present disclosure.
Figure 39C:
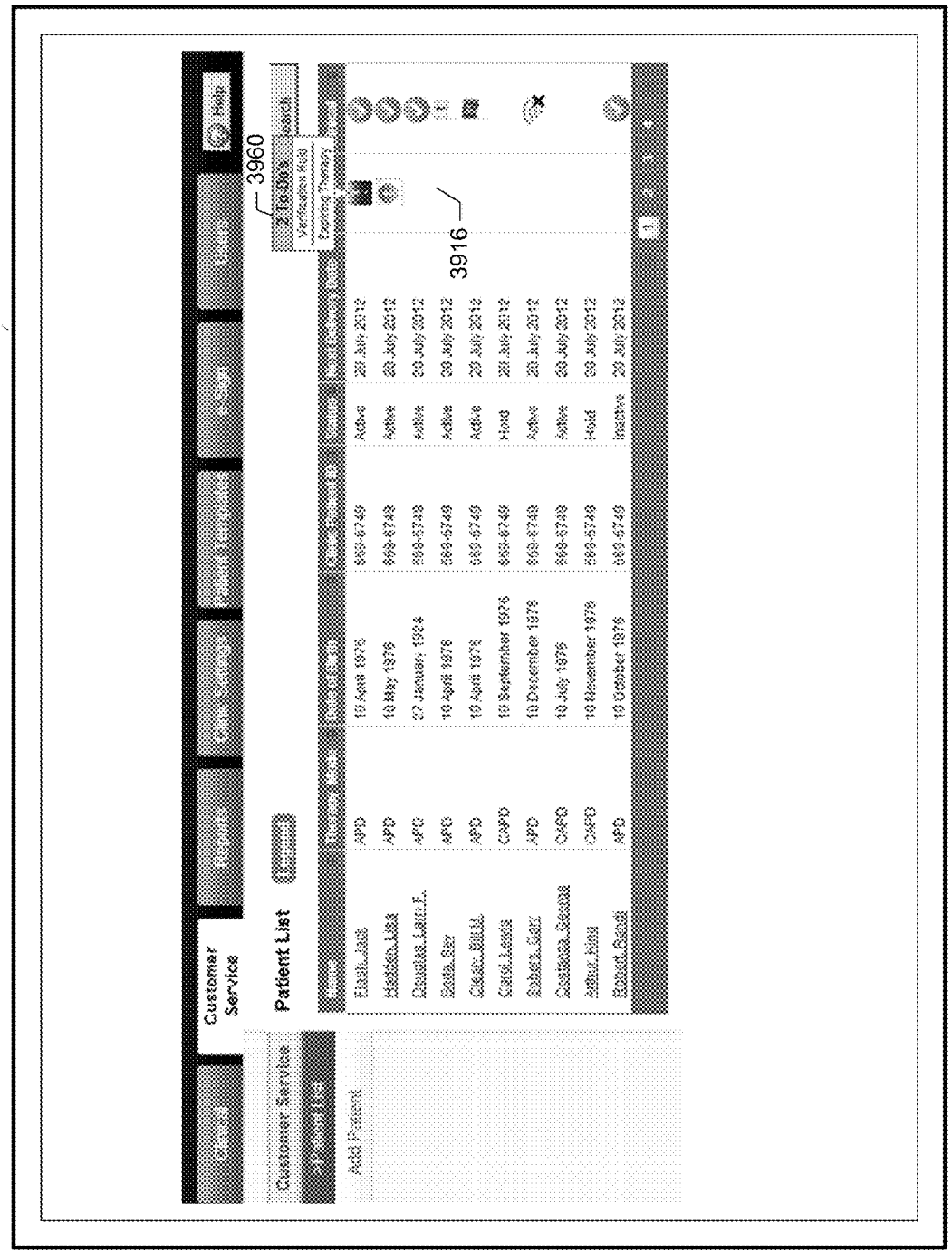
FIG. 39C is a screen shot of another example patient list screen of the present disclosure.

FIG. 39B illustrates an example screen shot of a legend screen pop-up 3950 displayed on a clinician's display device 192. The legend screen pop-up 3950 may display a list of icons and their associated meaning. Pop-up 3950 is obtained by selecting legend link 3920. Icon 3952 indicates an urgent to-do, icon 3954 indicates a non-urgent to-do, icon 3956 indicates that the treatment was "Ok", icon 3958 indicates a high priority flag, icon 3960 indicates a normal priority flag, no icon indicates that no treatment was performed and icon 3962 indicates that there was no communication with the patient's therapy machine 100, such as a peritoneal dialysis machine, on the associated date. A clinician can also hover a mouse cursor or pointer over to-do column 3916 in screen 3900, which leads to pop-up 3960 (FIG. 39C) displayed on a clinician's display device 192. As illustrated in FIG. 39C, the clinician can see in pop-up 3960 that there are two to-dos for the patient Jack Flash.

Figure 40A:
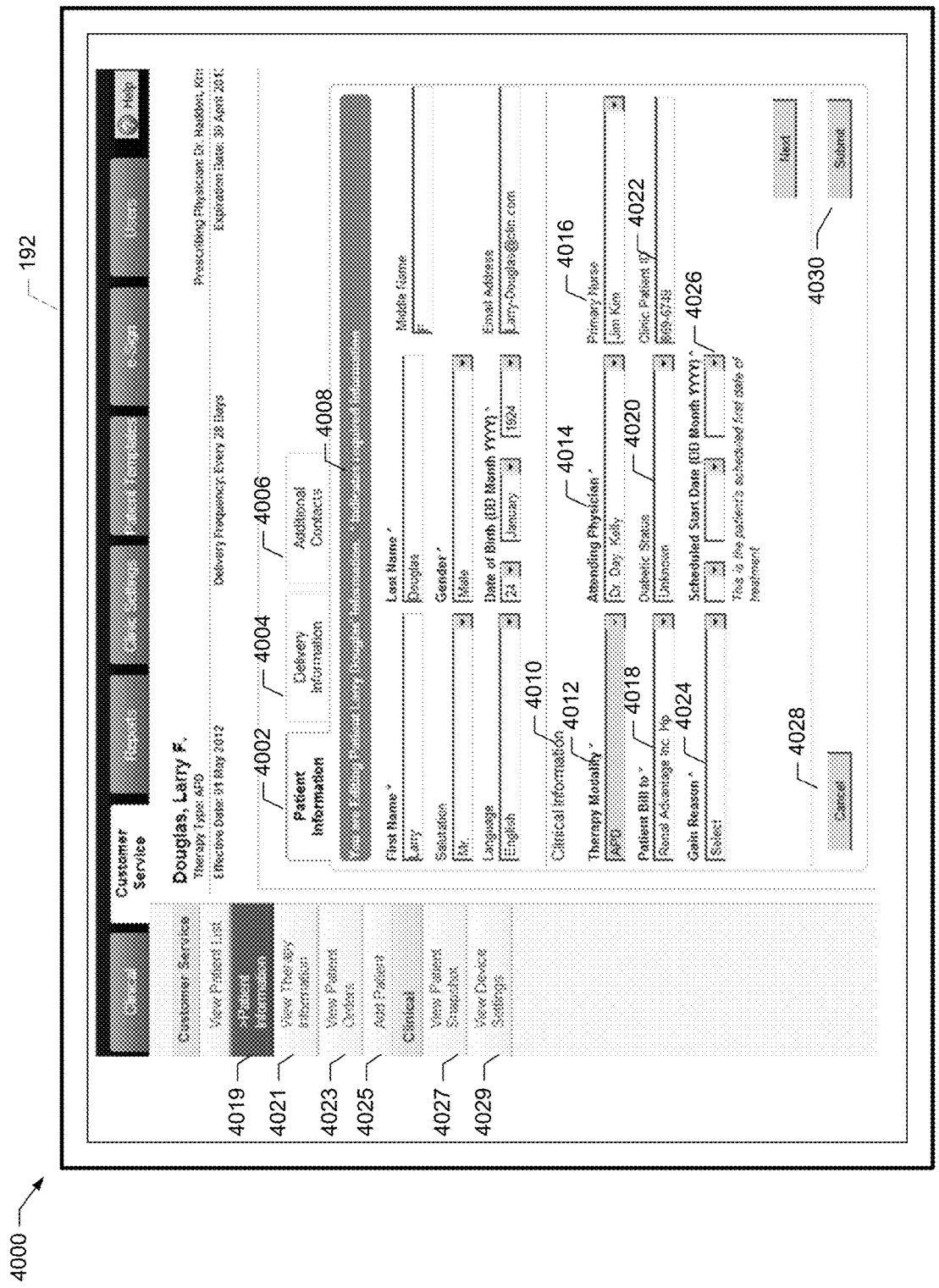
FIG. 40A is an example screen shot of a patient information screen of the present disclosure.

FIG. 40A illustrates an example screen shot of a patient information screen 4000 displayed on a clinician's display device 192. Patient information screen 4000 is accessed by selecting any one of the patients in column 3904 of the patient list 3900 (FIG. 39A). The clinician can view information about the patient in patient information tab 4002, delivery information tab 4004 and additional contacts tab 4006. The clinician can also view message 4008, which indicates that the patient information screen 4000 may be used to edit a patient's information. A clinician can view and edit information about the patient, such as name, gender and birth date, in tab 4002. The clinician can also view and edit clinical information related to the patient such as therapy modality 4012, attending physician 4014, primary nurse 4016, patient billed to 4018, diabetic status 4020, clinic patient ID 4022, gain reason 4024, and scheduled start date 4026, which is the patient's scheduled first date of treatment. The clinician can cancel or submit the information on screen 4000 using cancel or submit buttons 4028 or 4030 respectively. The clinician can also return to patient list 3900 (FIG. 39A) by selecting view patient list link 4019. The clinician can likewise navigate to various screens for viewing and editing data related to a patient by using view therapy information link 4021, view patient orders link 4023 and add patient link 4025. The clinician can also navigate to the patient snapshot (FIGS. 31A and 31B) via view patient snapshot link 4027 and to the device settings (FIG. 33) via view device settings link 4029.

Figure 40B:
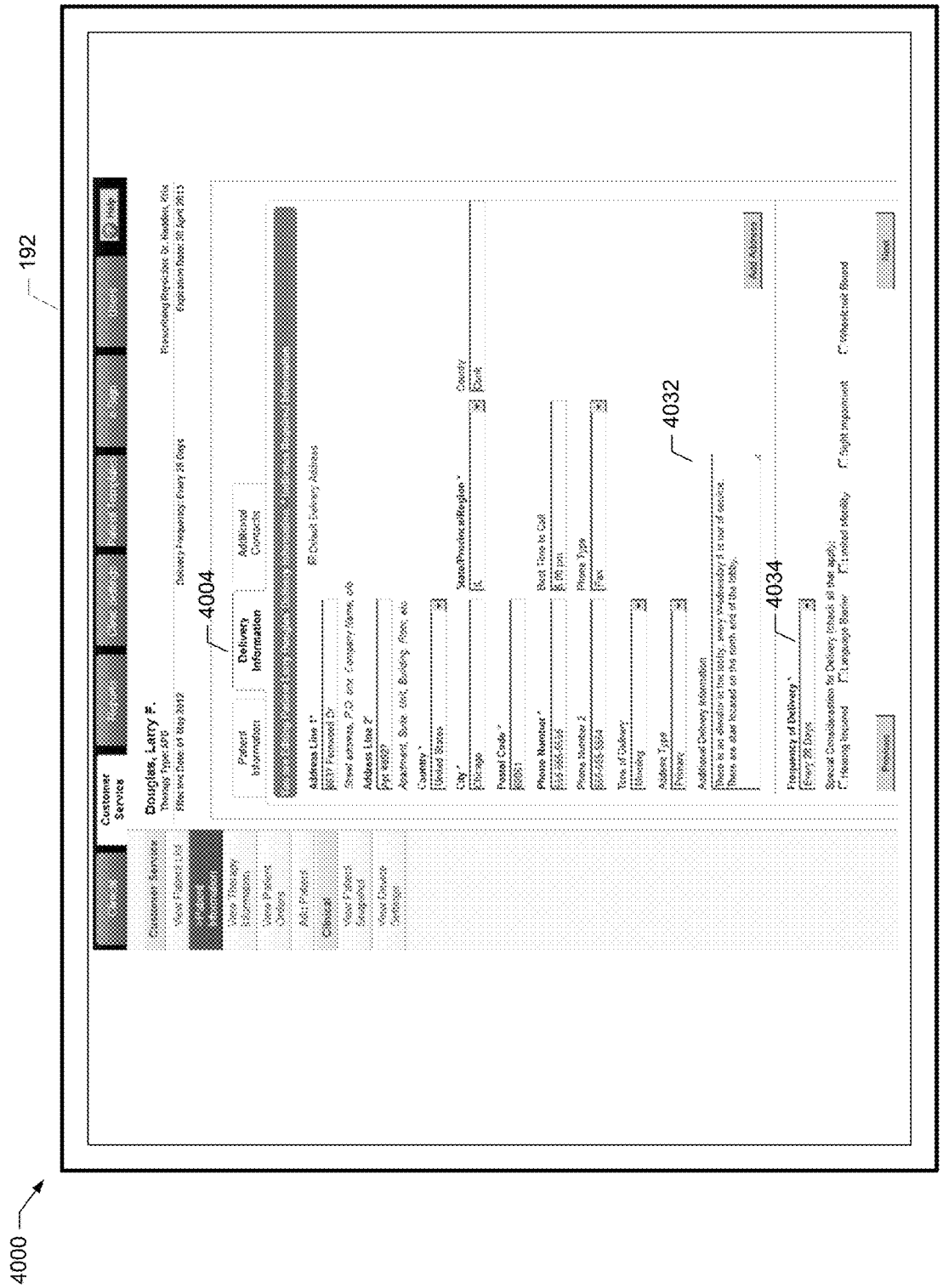
FIG. 40B is a screen shot of another example patient information screen of the present disclosure.

FIG. 40B illustrates an example screen shot of the delivery information tab 4004 of patient information screen 4000 displayed on a clinician's display device. Delivery information tab 4004 allows a clinician to view and/or edit information related to delivery of supplies for a particular patient. The clinician can also view and edit additional delivery information that may make it easier to deliver supplies to a patient as illustrated in field 4032. The clinician can also specify the frequency of delivery for a patient as indicated by drop-down 4034.

Figure 40C:
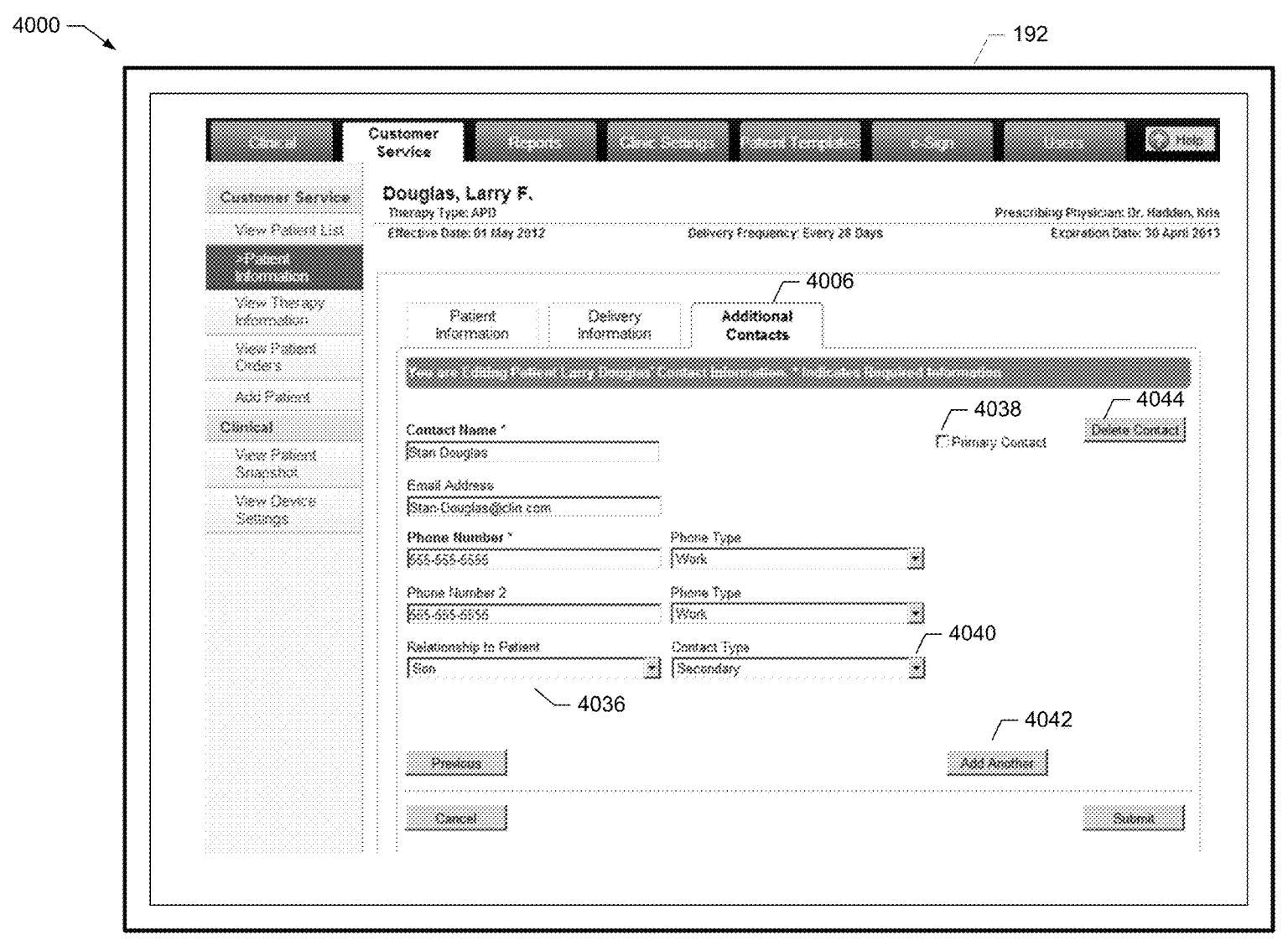

FIG. 40C illustrates an example screen shot of the additional contacts tab 4006 of patient information screen 4000 displayed on a clinician's display device 192. The clinician can view and edit contact information for people related to or who otherwise support the patient in receiving supplies and/or therapy. The clinician can specify an additional contact including the relationship of the contact 4036 and whether the contact is a primary contact using checkbox 4038 or a secondary contact using drop-down 4040. The clinician may also add or delete contacts using buttons 4042 and 4044 respectively.

Figure 41A:
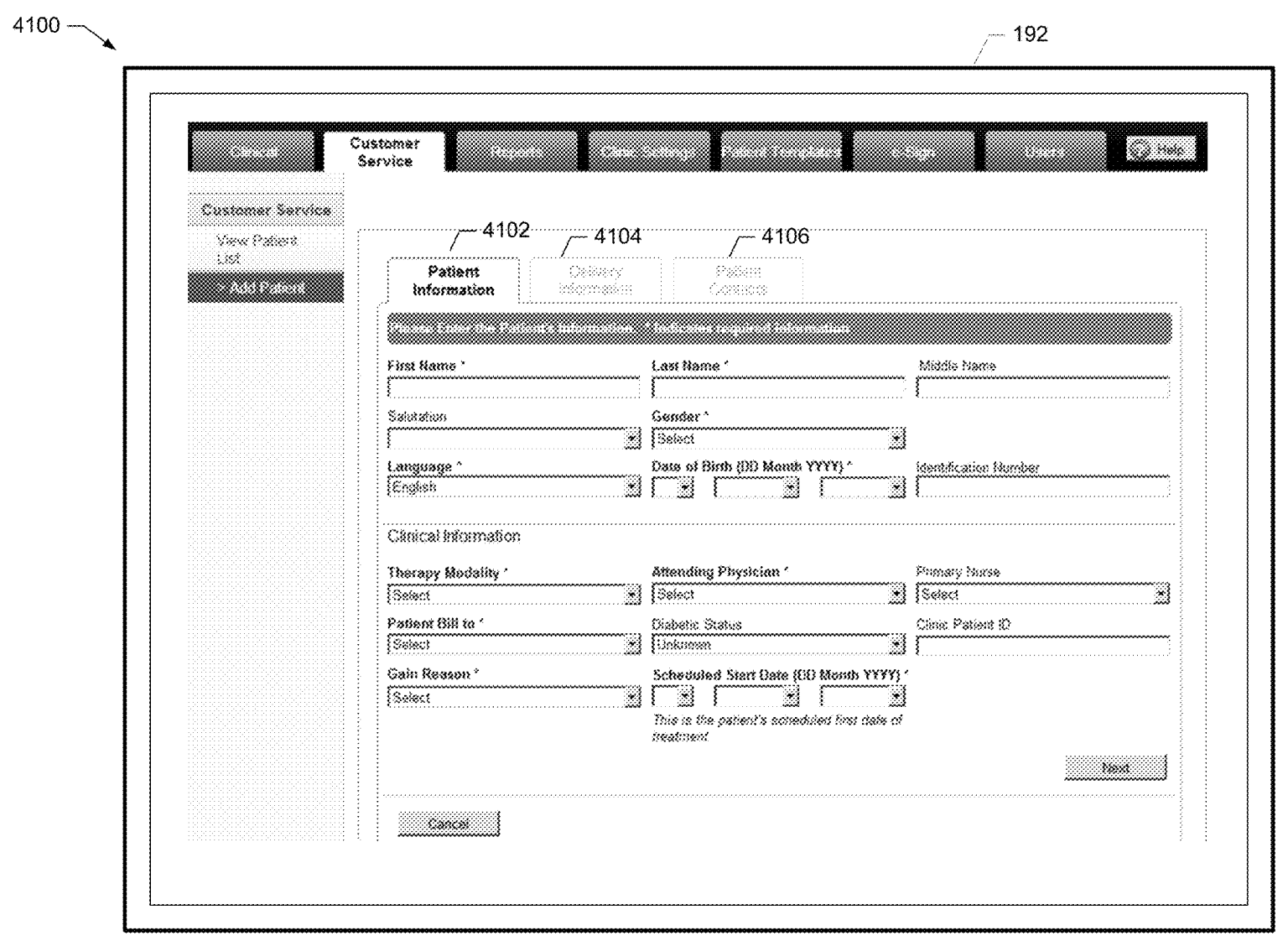
Figure 41B:
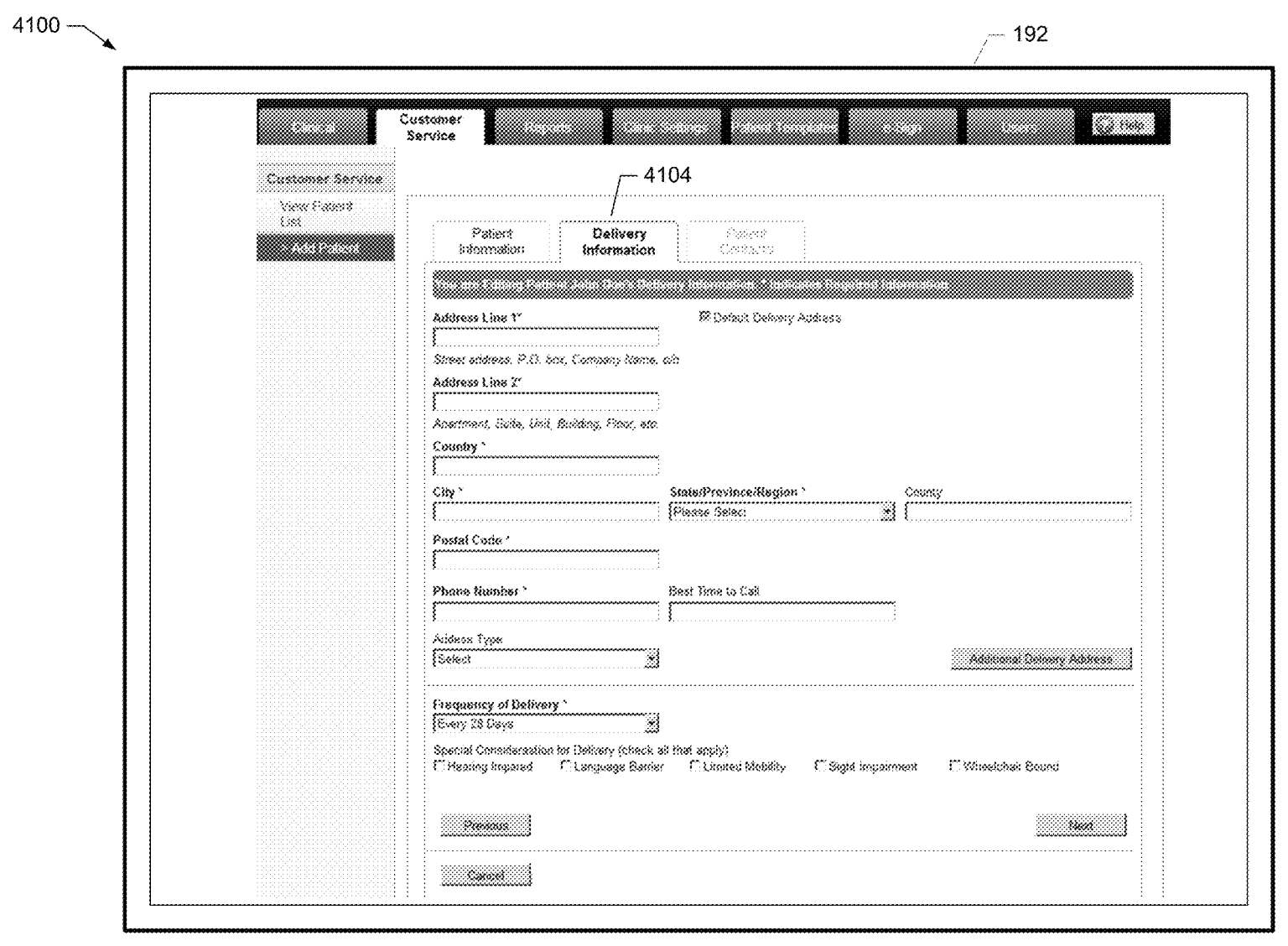
Figure 41C:
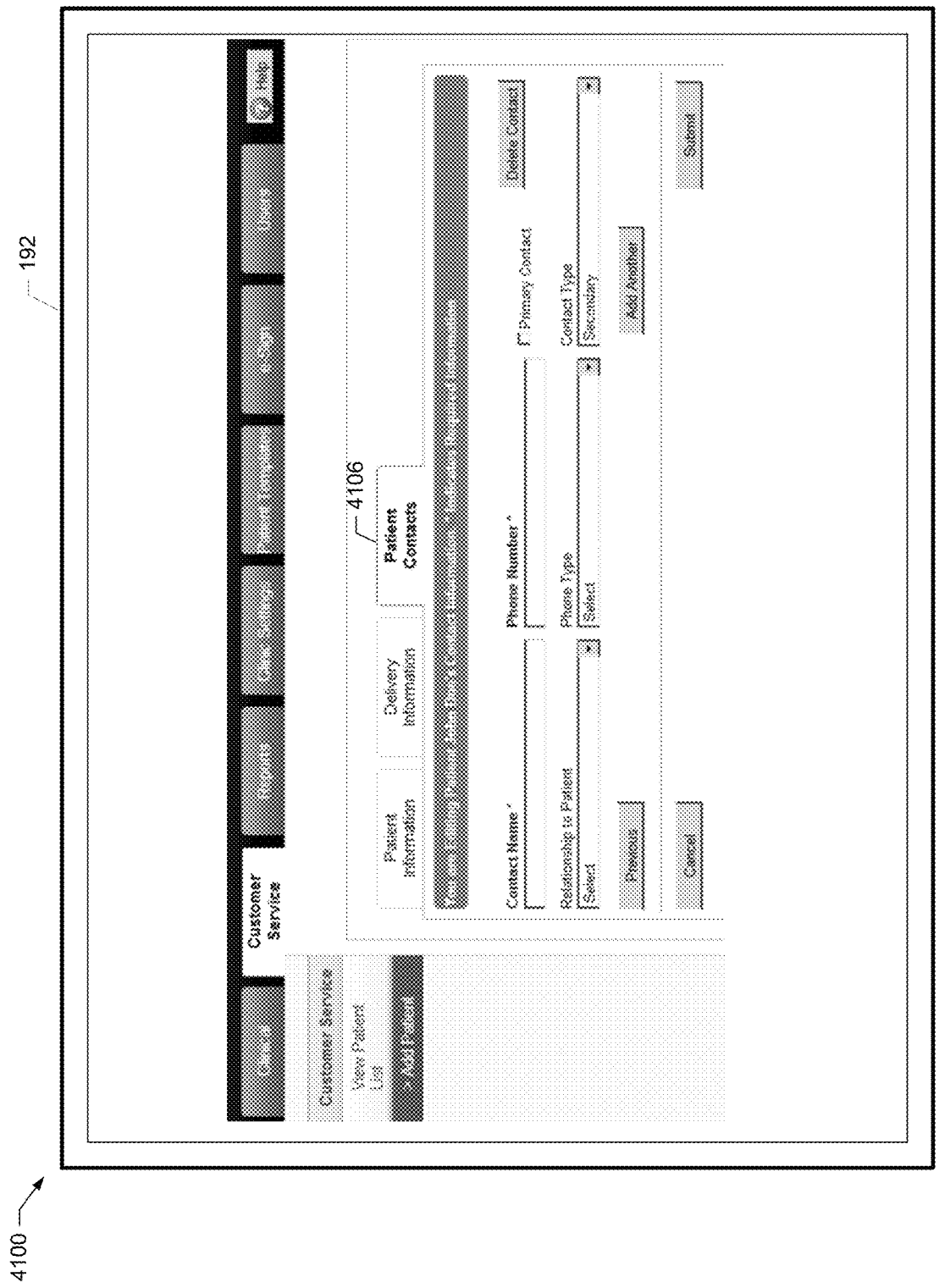
FIG. 41C is a screen shot of a further example add patient screen of the present disclosure.

FIG. 41A illustrates an example screen shot of an add patient screen 4100 displayed on a clinician's display device 192 accessed by selecting add patient link 3922 (FIG. 39A). The add patient screen 4100 displays tabs similar to the tabs in the patient information screen 4000 (FIGS. 40A to 40C), such as patient information tab 4102, delivery information tab 4104 and patient contacts tab 4106. The clinician can specify information about the patient using tab 4102. FIG. 41B illustrates delivery information tab 4104 of add patient screen 4100 displayed on a clinician's display device 192. Delivery information tab 4104 may be used by the clinician to specify the location and frequency of delivering supplies to a patient. FIG. 41C illustrates a patient contacts tab 4106 in an example screen shot of add patient screen 4100 displayed on a clinician's display device 192. Patient contacts tab 4106 may be used by the clinician to specify the patient's contact information.

Figure 42A:
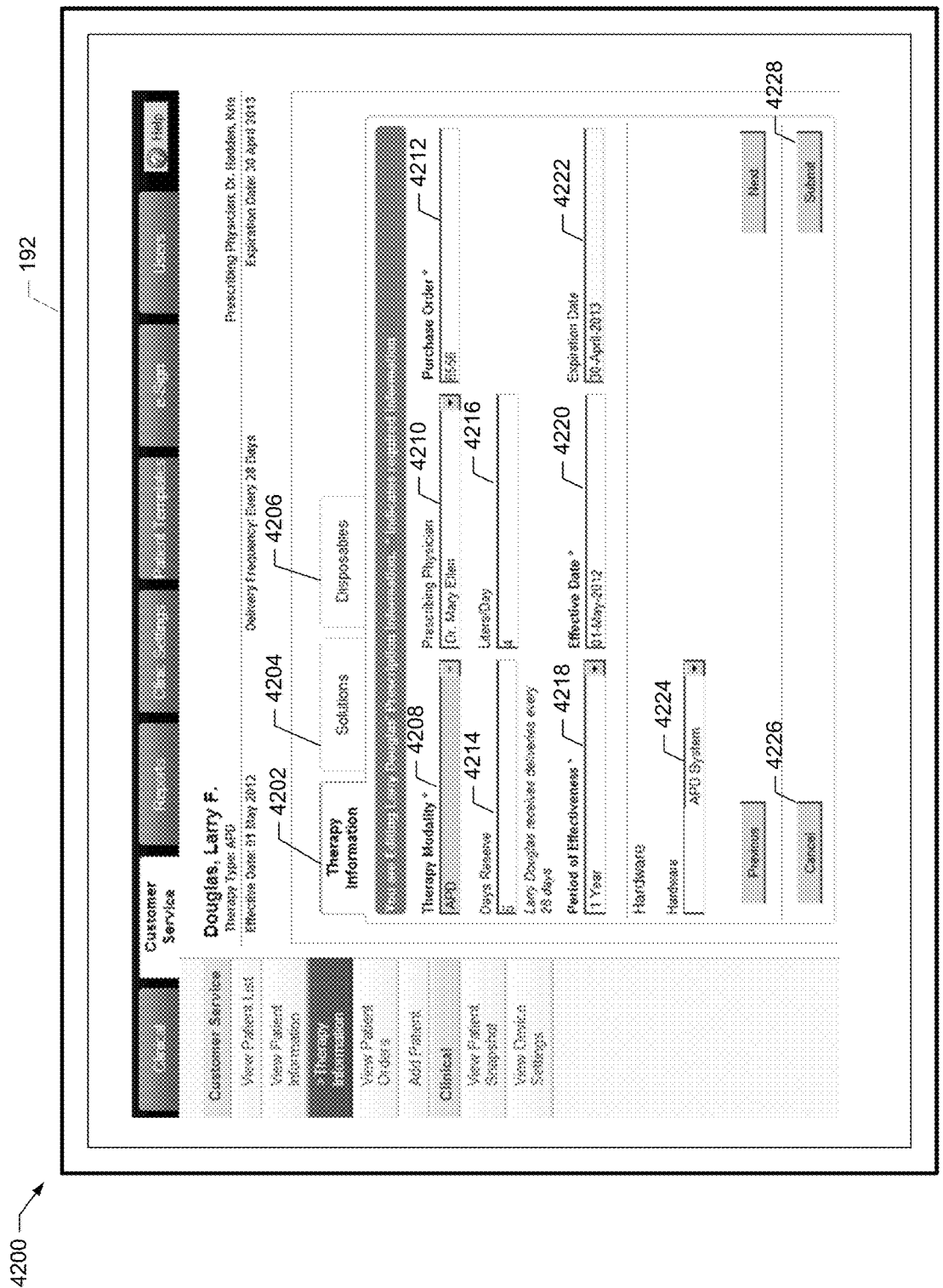
FIG. 42A is a screen shot of an example therapy information screen of the present disclosure.

FIG. 42A illustrates an example screen shot of a therapy information screen 4200 accessible from view therapy information link 4021 (FIG. 40A) and displayed on a clinician's display device 192. Therapy information screen 4200 displays therapy information tab 4202, solutions tab 4204 and disposables tab 4206. As illustrated in FIG. 42A, the clinician can view and/or edit a patient's therapy information in therapy information tab 4202. The clinician can view or edit a therapy modality 4208, the prescribing physician 4210, a purchase order number 4212, a days reserve 4214 (which indicates how many days of reserve supplies the patient should have), a liters per day field 4216, a period of effectiveness drop-down 4218, an effective date 4220 and an expiration date 4222. The clinician can also specify the patient's hardware using drop-down 4224. The clinician can cancel or submit the information on screen 4200 using cancel or submit buttons 4226 or 4228 respectively.

Figure 42B:
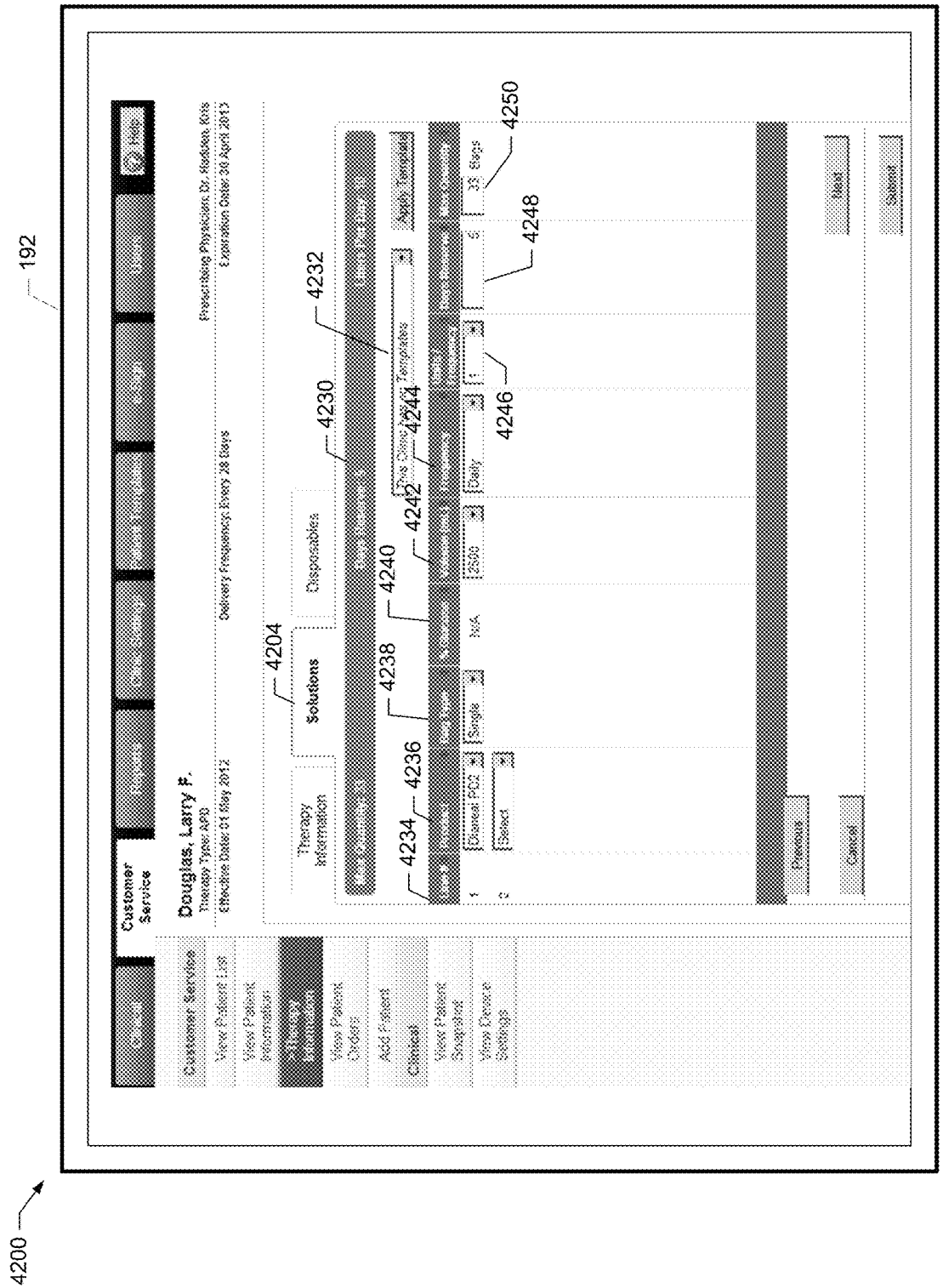
FIG. 42B is a screen shot of an example therapy information screen of the present disclosure.

FIG. 42B illustrates an example screen shot of a solutions tab 4204 in therapy information screen 4200 displayed on a clinician's display device 192. Therapy information screen 4200 is accessible from view therapy information link 4021 (FIG. 40A). The clinician can view information about solutions that will be used by renal therapy machine 100 at the patient's home. As illustrated in FIG. 42B, a clinician can view message 4230 that lists information about the solutions, such as a maximum quantity, days reserve and liters per day. The clinician can apply a template using drop-down 4232, which again allows the clinician to enter preselected values for multiple parameters displayed on a screen at once by selecting a template.

A clinician can also view the solutions that are used per line. In the illustrated embodiment, the clinician can view and edit information about two lines used for peritoneal dialysis, as indicated in column 4234. Column 4236 specifies the solutions that are used in the lines. Column 4238 specifies the bag type for a line. Column 4240 indicates a percentage of glucose, column 4242 indicates a volume, column 4244 indicates a frequency, column 4246 indicates units per frequency, column 4248 indicates the number of days of reserve solution and column 4250 indicates the maximum quantity of bags.

Figure 42C:
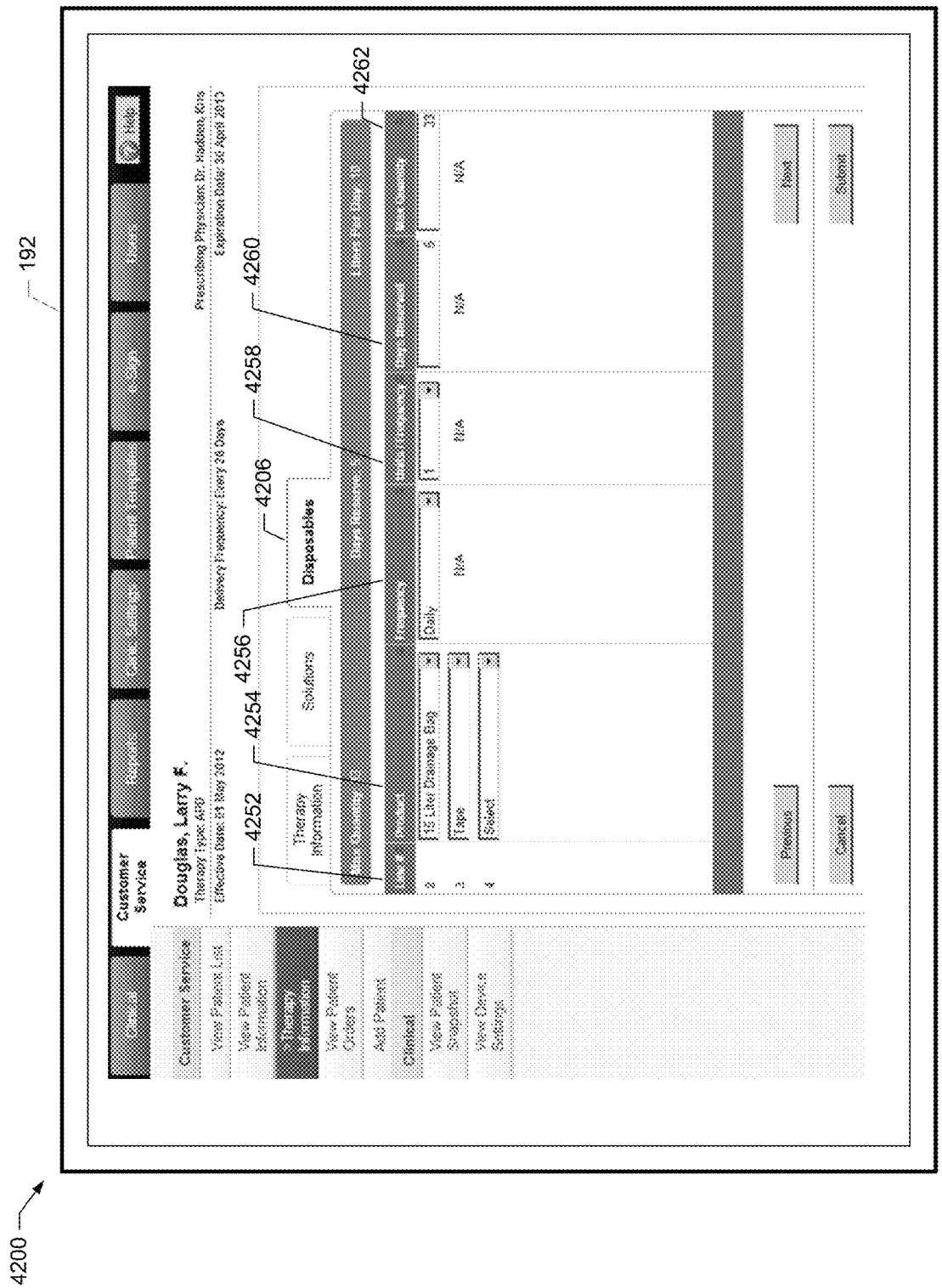
FIG. 42C is an example screen shot of a further example therapy information screen of the present disclosure.

FIG. 42C illustrates an example screen shot of disposables tab 4206 in therapy information screen 4200 displayed on a clinician's display device 192. Therapy information screen 4200 is accessible from view therapy information link 4021 (FIG. 40A). The clinician can view and edit information about disposables per line as indicated at column 4252 and the product for each line at column 4254. Column 4256 indicates a frequency, column 4258 indicates units per frequency, column 4260 indicates the number of days of reserve solution and column 4262 indicates the maximum quantity for the disposable.

Figure 43A:
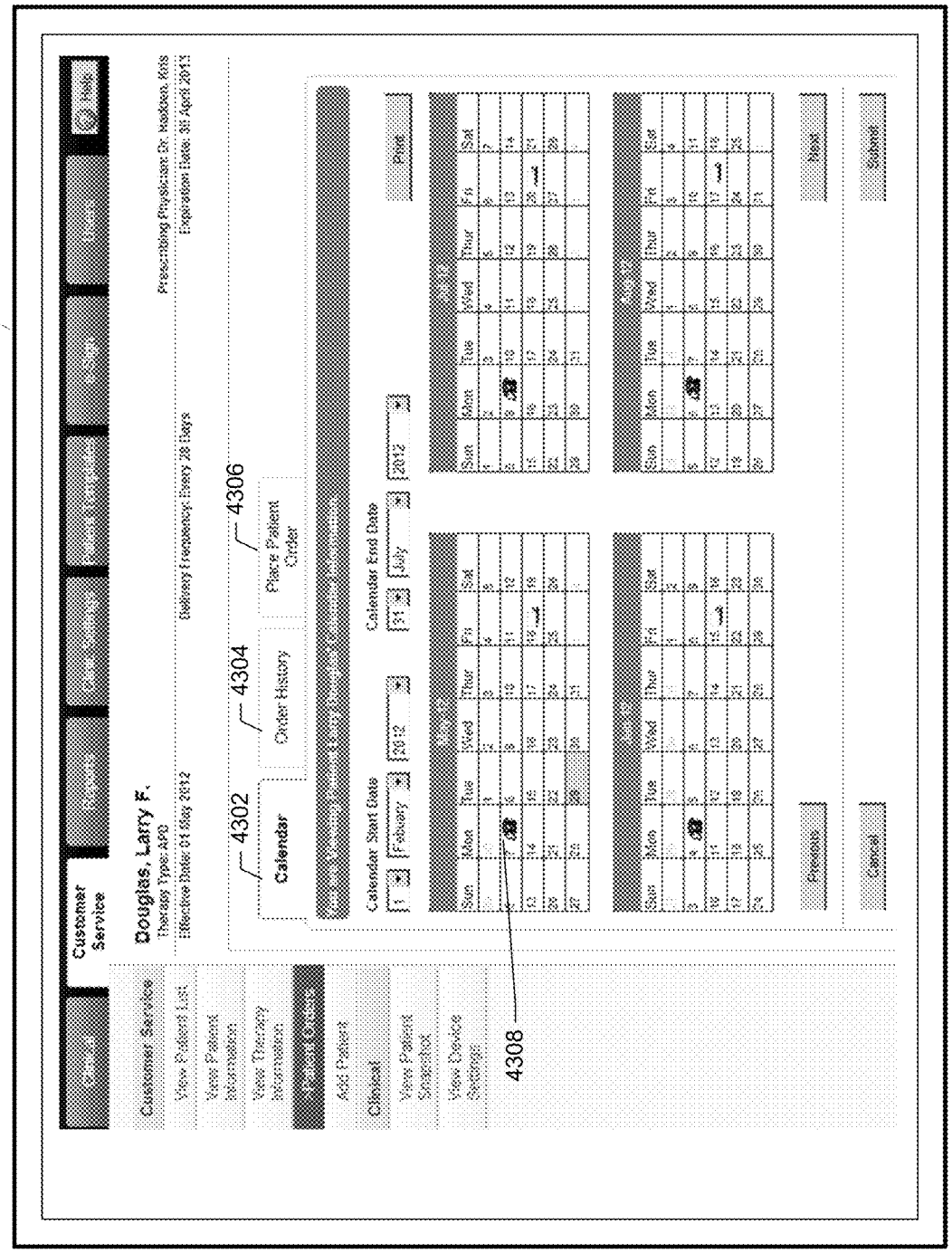
FIG. 43A is a screen shot of an example patient order screen of the present disclosure.

FIG. 43A illustrates an example screen shot of a patient order screen 4300 displayed on a clinician's display device 192. Patient order screen 4300 is accessible from view patient orders link 4023 (FIG. 40A). The patient order screen 4300 illustrates calendar tab 4302, order history tab 4304 and patient order tab 4306. The clinician can view a patient's calendar information at tab 4302. Icons indicate events that occurred on specific dates, such as icon 4308 that indicates that a phone call was placed on May 7, 2012, for example.

Figure 43B:
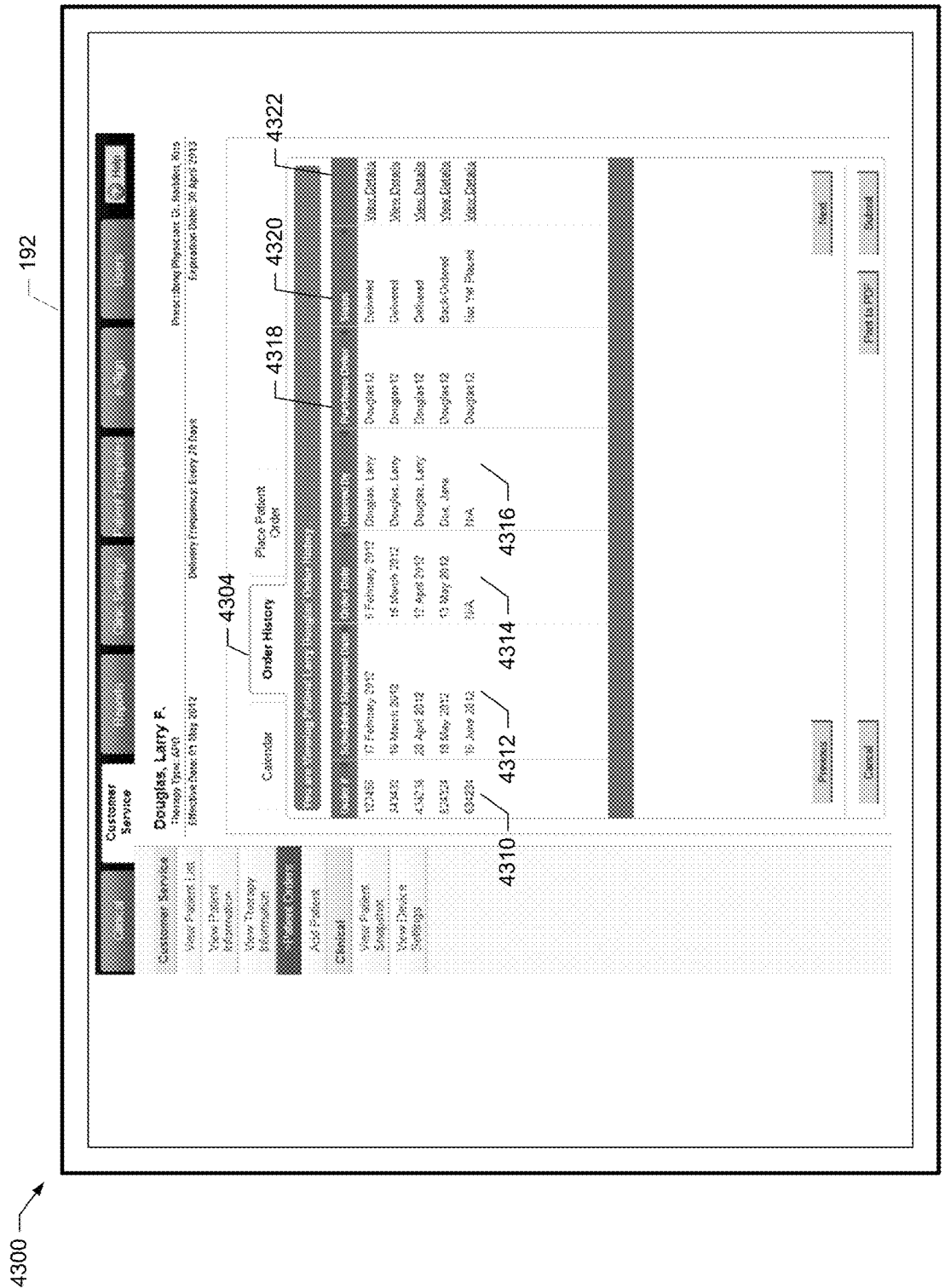
FIG. 43B is a screen shot of another example patient order screen of the present disclosure.

FIG. 43B illustrates an example screen shot of an order history tab 4304 of patient order screen 4300 displayed on a clinician's display device 192. The clinician can view at FIG. 43B the patient's order history, such as an order number in column 4310, scheduled shipment date in column 4312, order date in column 4314, ordered by information in column 4316, purchase order in column 4318 and status in column 4320, such as whether an order has been delivered, backordered, or not yet placed. The clinician can also view additional details about an order using the view details link in column 4322.

Figure 43C:
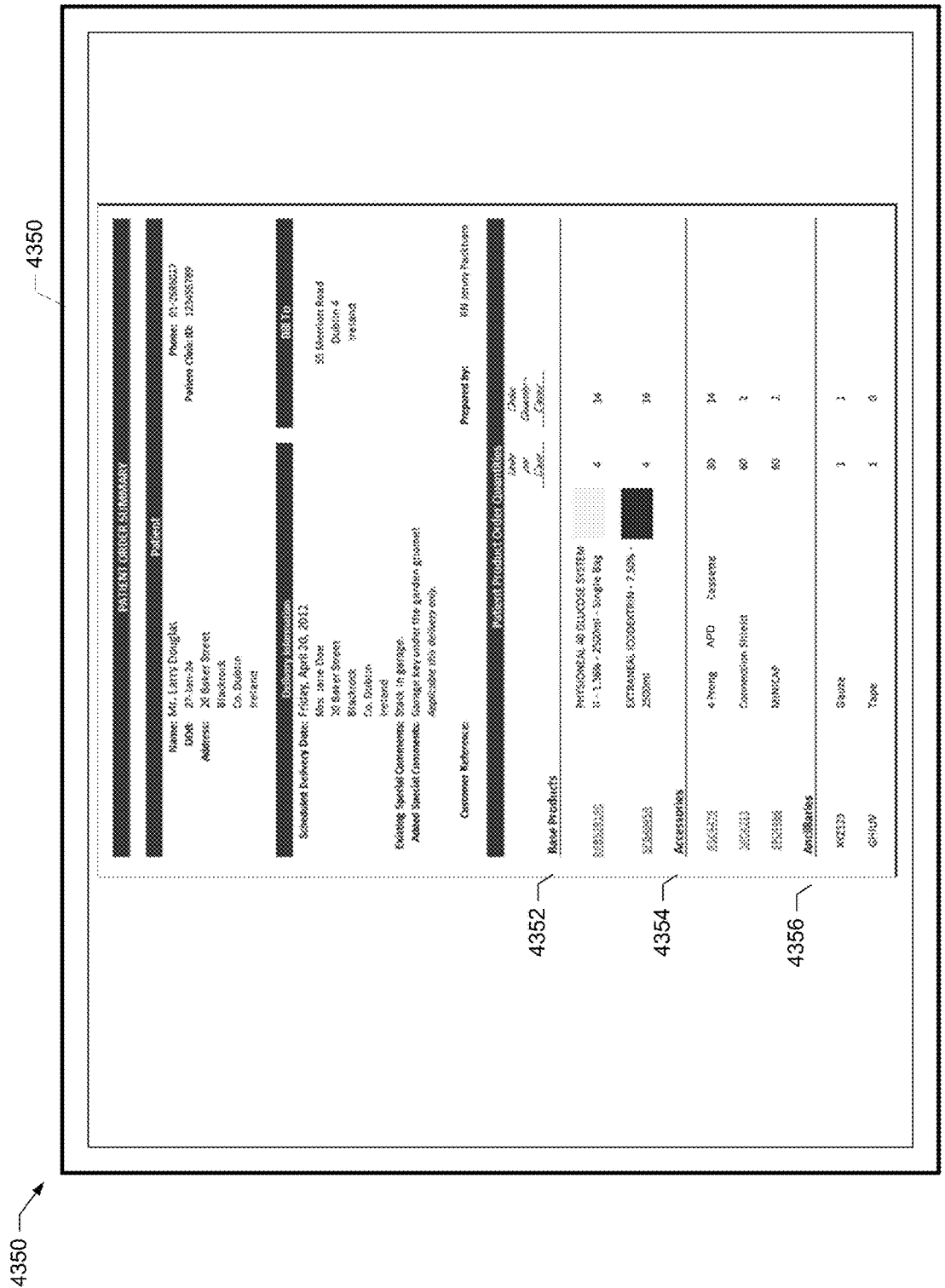
FIG. 43C is a screen shot of a further example patient order screen of the present disclosure.

FIG. 43C illustrates an example screen shot 4350 of the additional details that may be viewed by selecting the view details link in column 4322 (FIG. 43B). As indicated in FIG. 43C, the clinician can view information about the patient, delivery information, billing information and patient product order quantities, such as the base products 4352, accessories that are part of the order 4354 and ancillary supplies that are part of the order 4356.

Figure 43D:
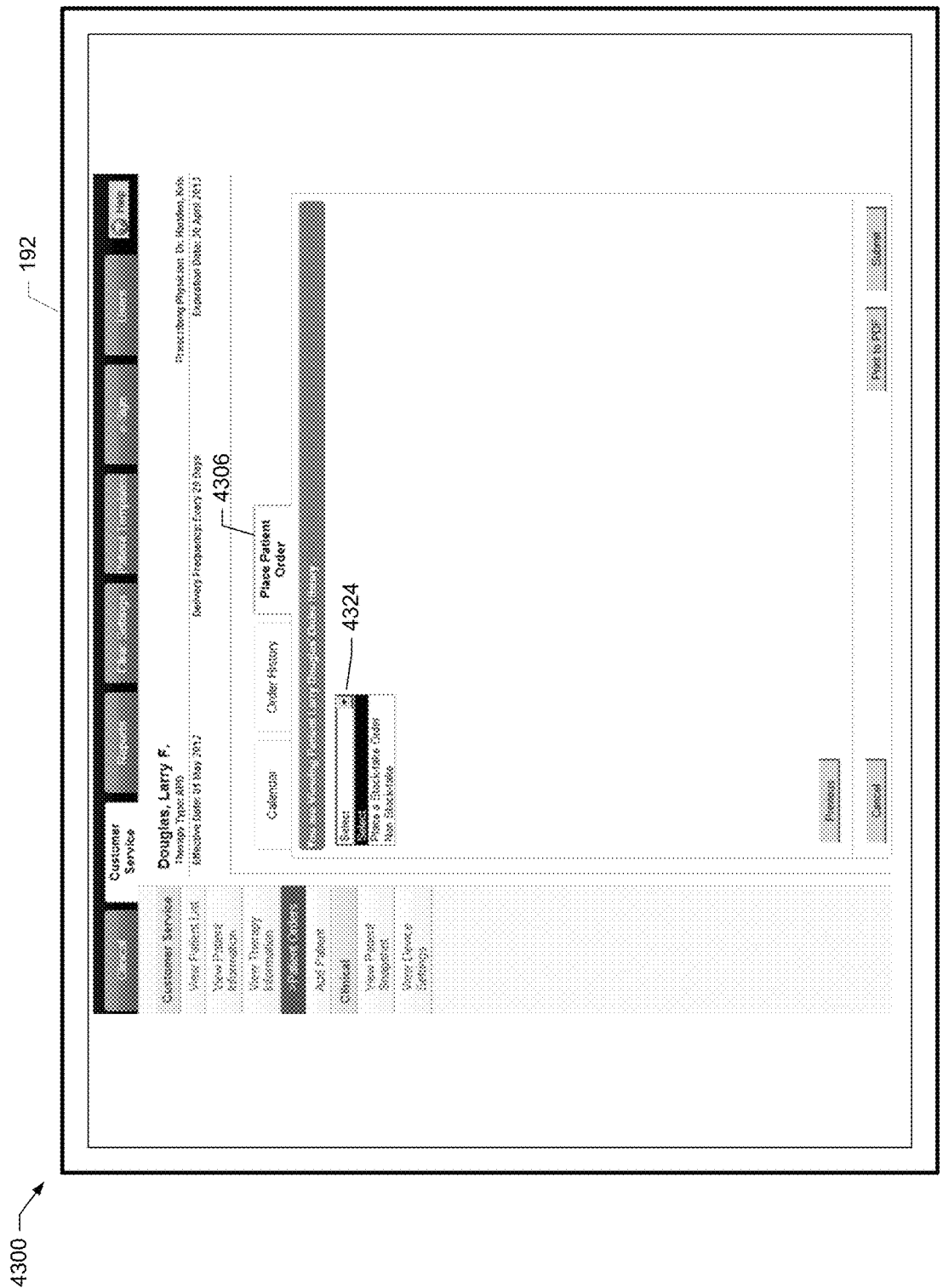
FIG. 43D is a screen shot of yet another example patient order screen of the present disclosure.

FIG. 43D illustrates an example screen shot of a place patient order tab 4306 of patient order screen 4300 displayed on a clinician's display device 192. A clinician can use drop-down 4324 to place either a stock-take order or a non-stock take order.

It should therefore be appreciated that the screens illustrated in FIGS. 30A to 43D enable a clinician to efficiently and remotely manage therapy provided by machine 100. The clinician can remotely order supplies and set prescriptions to remotely control machine 100 for providing treatment to a patient, while still allowing the patient to control certain aspects of therapy. The screens enable the performance of these functions efficiently and conveniently via the use of templates, and make entering values failsafe because the clinician does not have to determine whether values entered and selected are consistent with each other. The clinician can also review logs documenting the treatments and be alerted if certain conditions occur during the treatments. The screens are not limited to peritoneal dialysis and can likewise be implemented in hemodialysis, hemofiltration, hemodiafiltration, CRRT, nutritional therapy or medical delivery of a drug.

Patient Portal

Figure 44:
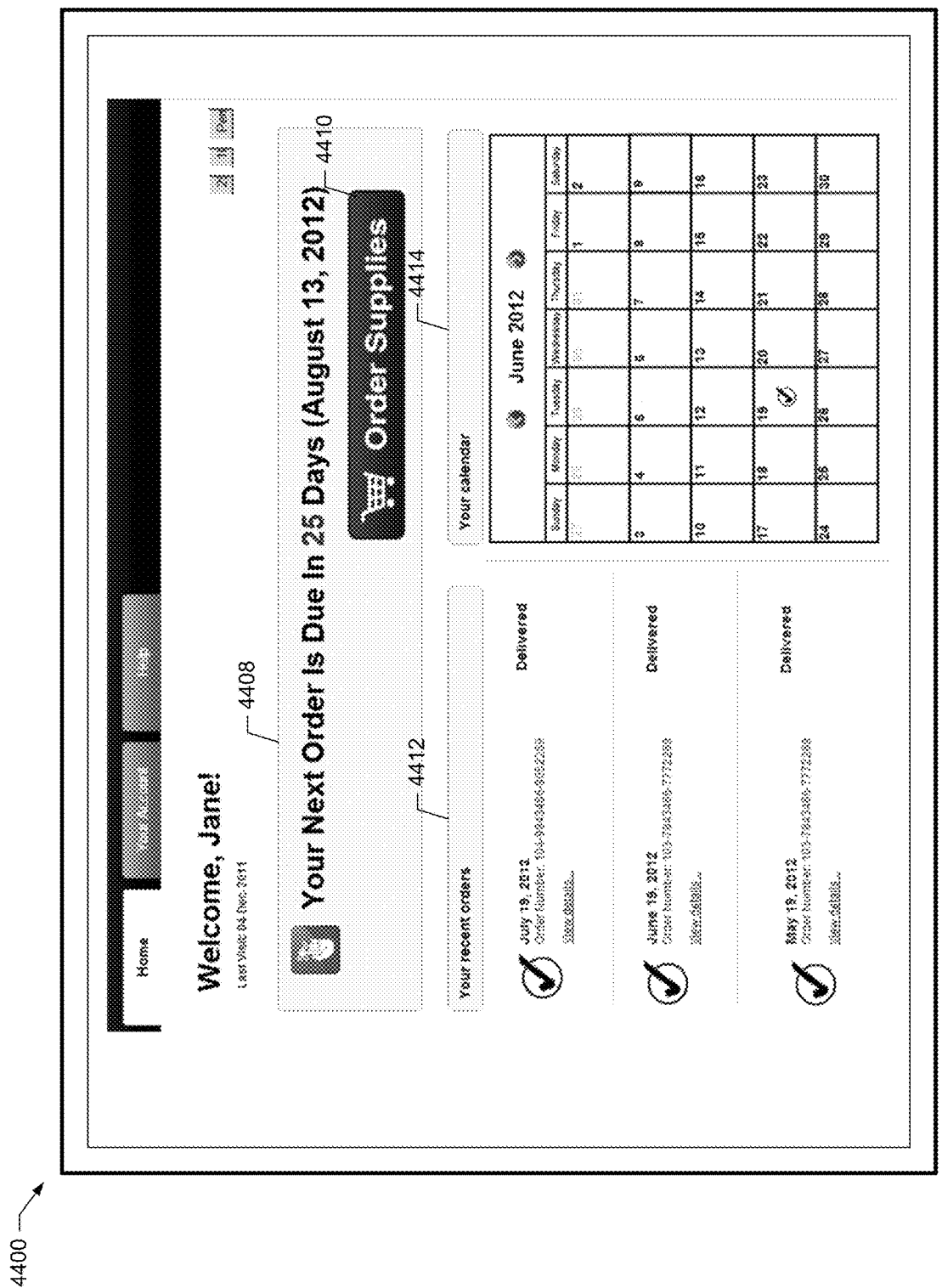
FIG. 44 is a screen shot of an example patient dashboard screen for a patient of the present disclosure.

As described above, web portal 150 may be used by clinicians as well as patients to access system hub 120. In one embodiment, web portal 150 provides a patient dashboard that may be viewed on tablet 122 or on a dedicated display device of therapy machine 100 at the patient's home. FIG. 44 illustrates an example screen shot of a patient dashboard 4400 displayed on tablet 122 or dedicated display device of machine 100. As indicated in FIG. 44, the patient dashboard 4400 displays a home tab 4402, a your account tab 4404 and help tab 4406. In one embodiment, home tab 4402 provides information to the patient about the patient's supply orders. In the illustrated embodiment, message 4408 indicates to the patient that the next order is due from the patient in twenty-five days. A patient may place the supply order via link 4410. The home tab 4402 also displays the patient's recent orders 4412 as well as a calendar view 4414 of the patient's order. The recent orders information 4412 in the illustrated embodiment includes the dates and order numbers for recent orders as well as the status of those orders, e.g., delivered or pending. The calendar of orders 4414 shows an icon on the day that the order is placed, providing order status.

Figure 45A:
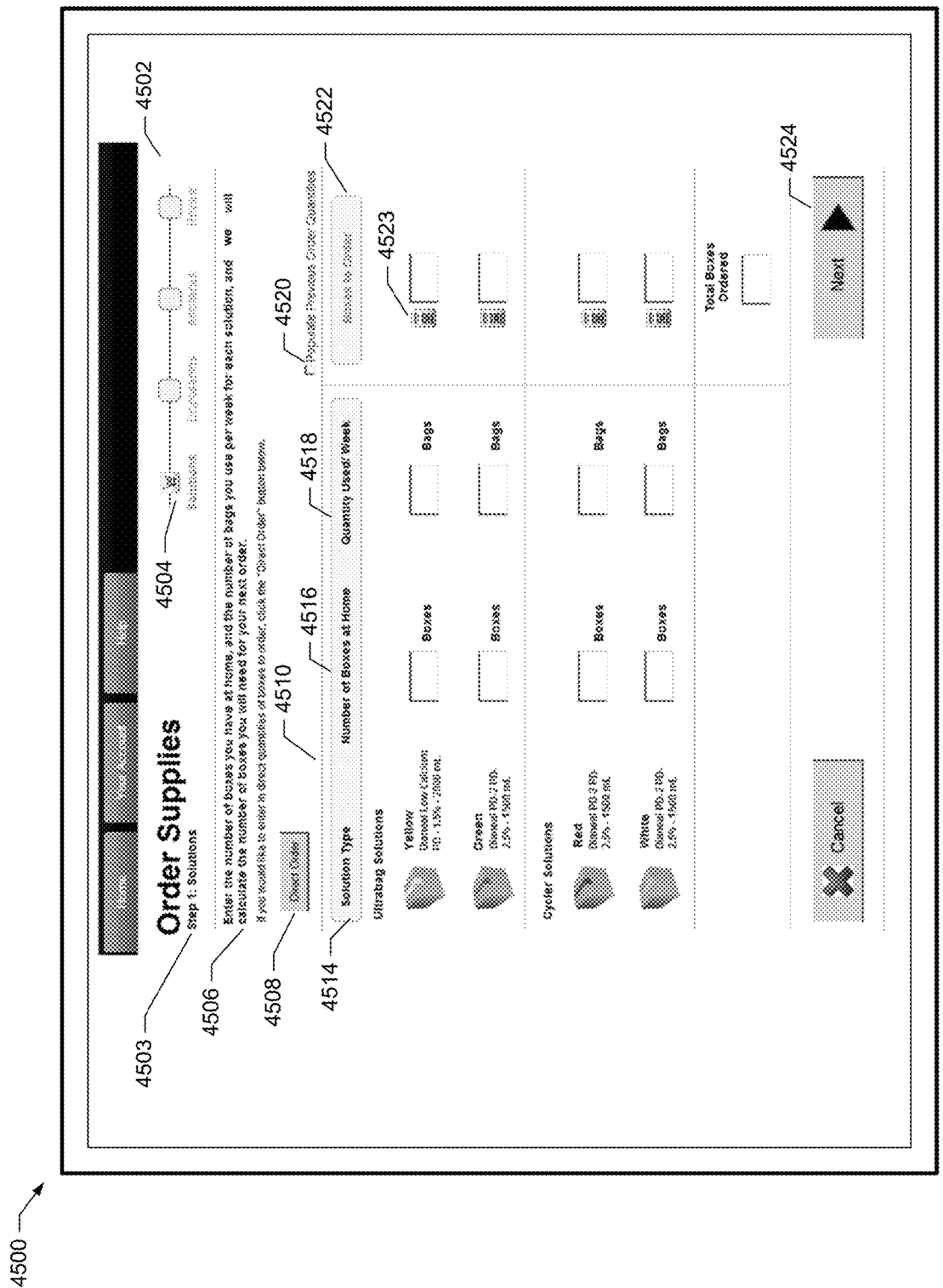
FIG. 45A is a screen shot of an example patient order screen for a patient of the present disclosure.

FIGS. 45A to 45G are example screen shots displayed on order screen 4500 of tablet 122 or dedicated display device of machine 100. In the illustrated embodiment, the patient is currently on step 1, solutions, as indicated at item 4503. As indicated in FIG. 45A displayed on tablet 122 or dedicated display device of machine 100, a patient can view a timeline 4502 listing the steps that the patient needs to complete to order supplies. Cart icon 4504 inside of timeline 4502 indicates how far the patient has proceeded along the order process. The patient is instructed at message 4506 to enter the number of supply boxes remaining at the patient's home and the number of bags the patient uses per week for each solution. The home medical device system 110 then calculates the number of boxes that will be needed for the patient's next order.

Order screen 4500 displayed on tablet 122 or dedicated display device of machine 100 displays a chart 4510 of different types of consumables that can be ordered. A solution type column 4514 lists different types of solutions such as ultra bag solutions or cycler solutions. Column 4516 lists fields for the number of boxes at the patient's home for each solution. Column 4518 allows the patient to enter in the quantity used per week. The patient may use check box 4520 to populate information into the fields from previous orders. The patient can thereby save time and conveniently order the same number of supplies as in a previous order using check box 4520. As values are entered into columns 4516 and 4518 in table 4510, renal therapy machine 100 calculates the number of boxes to order as illustrated in column 4522. Alternatively, the patient can press a calculator icon 4523, which causes renal therapy machine 100 to calculate the number of boxes to order for column 4522. The patient can then press the next link 4524 to proceed to the next step in the timeline 4502, disposables.

Alternatively, the patient may be able to directly enter in the quantities of boxes that need to be ordered as indicated in message 4506. Home medical device system 110 allows the patient to use his or her experience with a renal, nutritional or medical delivery therapy and its corresponding consumable and supply usage to ensure that the patient's home is stocked with a sufficient quantity of consumables and supplies. A patient can thus either provide information about the supplies remaining in the patient's home and let home medical device system 110 calculate the number of boxes that are needed, or the patient can directly order a specific number of boxes. It should therefore be appreciated that the patient dashboard 4400 and order screen 4500 provide flexibility as to how supplies may be ordered.

Figure 45B:
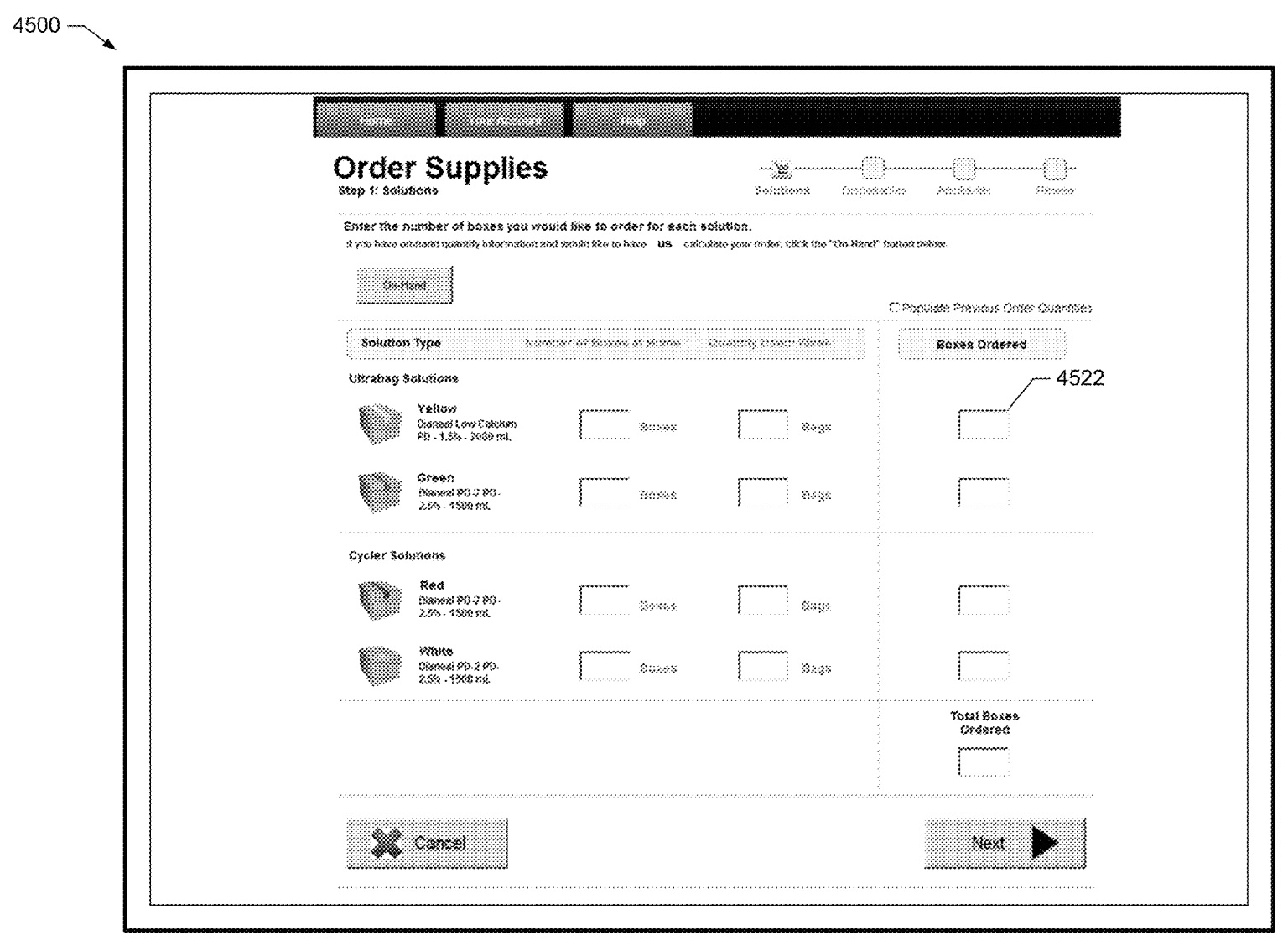

If the patient chooses to enter in direct quantities of boxes to order by pressing link 4508 in FIG. 45A, the patient is then presented with the example order screen 4500 displayed in FIG. 45B. FIG. 45B illustrates an alternative order screen 4500 displayed on a tablet 122 or dedicated user interface for directly entering the number of boxes to order. In contrast to the order screen 4500 displayed in FIG. 45A, which allows a user to enter the number of boxes at the patient's home and the number of bags the patient uses per week for each solution so that home medical device system 110 can calculate the number of boxes needed for the patient's next order, order screen 4500 or FIG. 45B instead allows the patient to enter in the number of boxes to order directly. Thus in FIG. 45A, the patient enters values into columns 4516 and 4518 and in FIG. 45B, the patient enters values into column 4522.

Figure 45C:
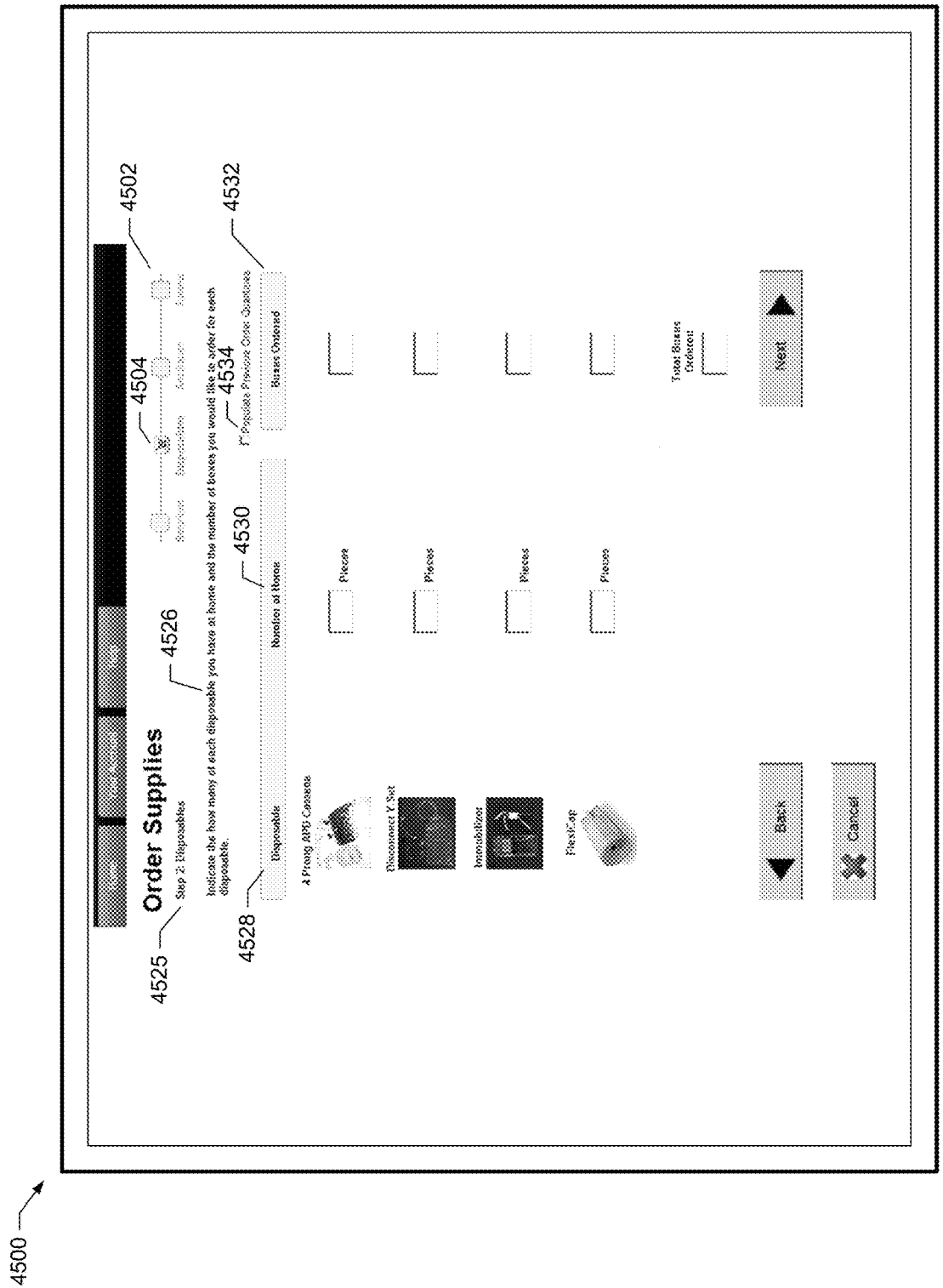
FIG. 45C is a screen shot of a further example patient order screen for a patient of the present disclosure.

FIG. 45C illustrates an example screen shot of order screen 4500 displayed on tablet 122 or dedicated display device of machine 100. Item 4525 indicates that the patient is at step 2, disposables as opposed to the solutions of step 1. Timeline 4502 indicates that cart icon 4504 is in the disposables step inside of timeline 4502. On the screen illustrated in FIG. 45C, the patient can indicate the quantity of disposables he or she has at home and the number of boxes he or she would like order for each disposable as indicated at message 4526. As illustrated in FIG. 45C, column 4528 lists various disposables that may be ordered, column 4530 allows the user to specify how many of the disposables he or she has at home, and column 4532 allows the user to specify the number of boxes he or she would like to order for each disposable. Check box 4534 again allows the patient to populate the fields with the values entered in previous orders, saving the patient time in the event that the patient would like to order the same number of disposables as in the previous order.

Figure 45D:
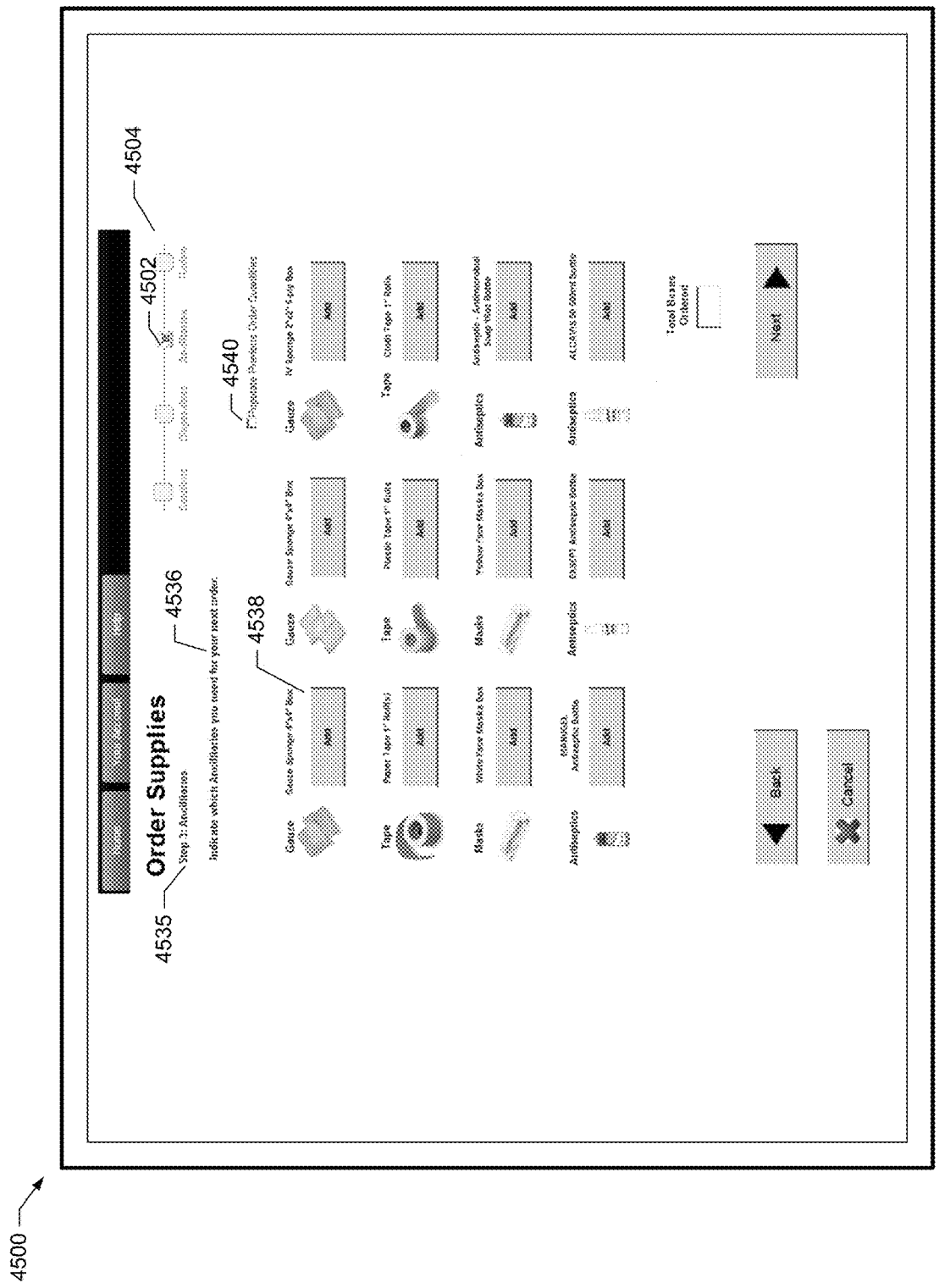
FIG. 45D is a screen shot of yet another example patient order screen for a patient of the present disclosure.

FIG. 45D illustrates another example screen shot of order screen 4500 displayed on tablet 122 or dedicated display device of machine 100. Item 4535 indicates that the patient is at step 3, ancillaries. Timeline 4502 indicates that cart icon 4504 is also in the ancillaries step inside of timeline 4502. Message 4536 asks the patient to indicate which ancillary supplies he or she needs for the next order. As illustrated in FIG. 45D, the patient can specify the ancillary supplies needed by selecting an add button, e.g., 4538, associated with the desired ancillary item. The patient can again populate this screen with previously ordered quantities using check box 4540.

Figure 45E:
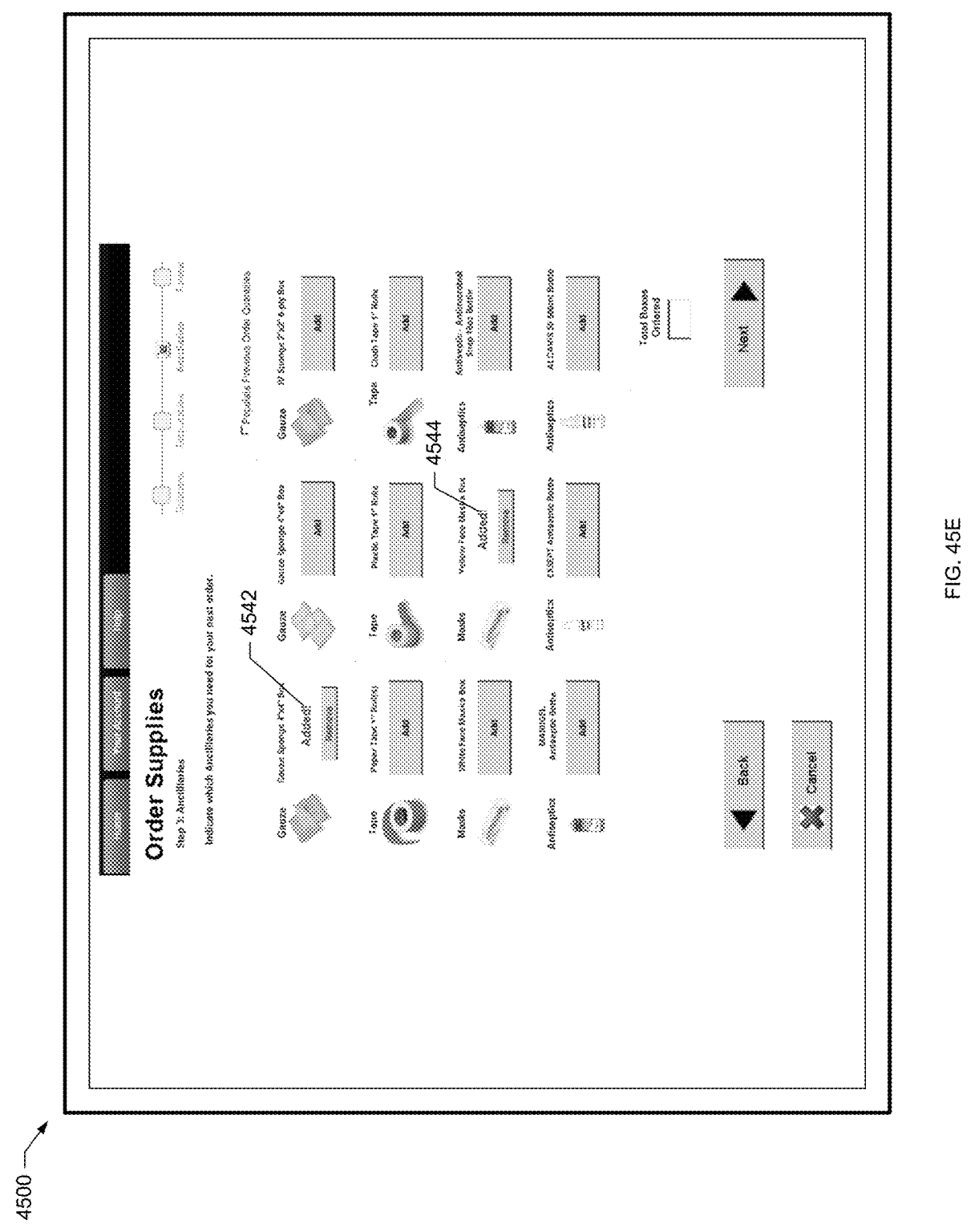

FIG. 45E illustrates an example screen shot of order screen 4500 displayed on tablet 122 or dedicated display device of machine 100 illustrating that the user has selected to add ancillary items gauze and masks as indicated by messages 4542 and 4544.

Figure 45F:
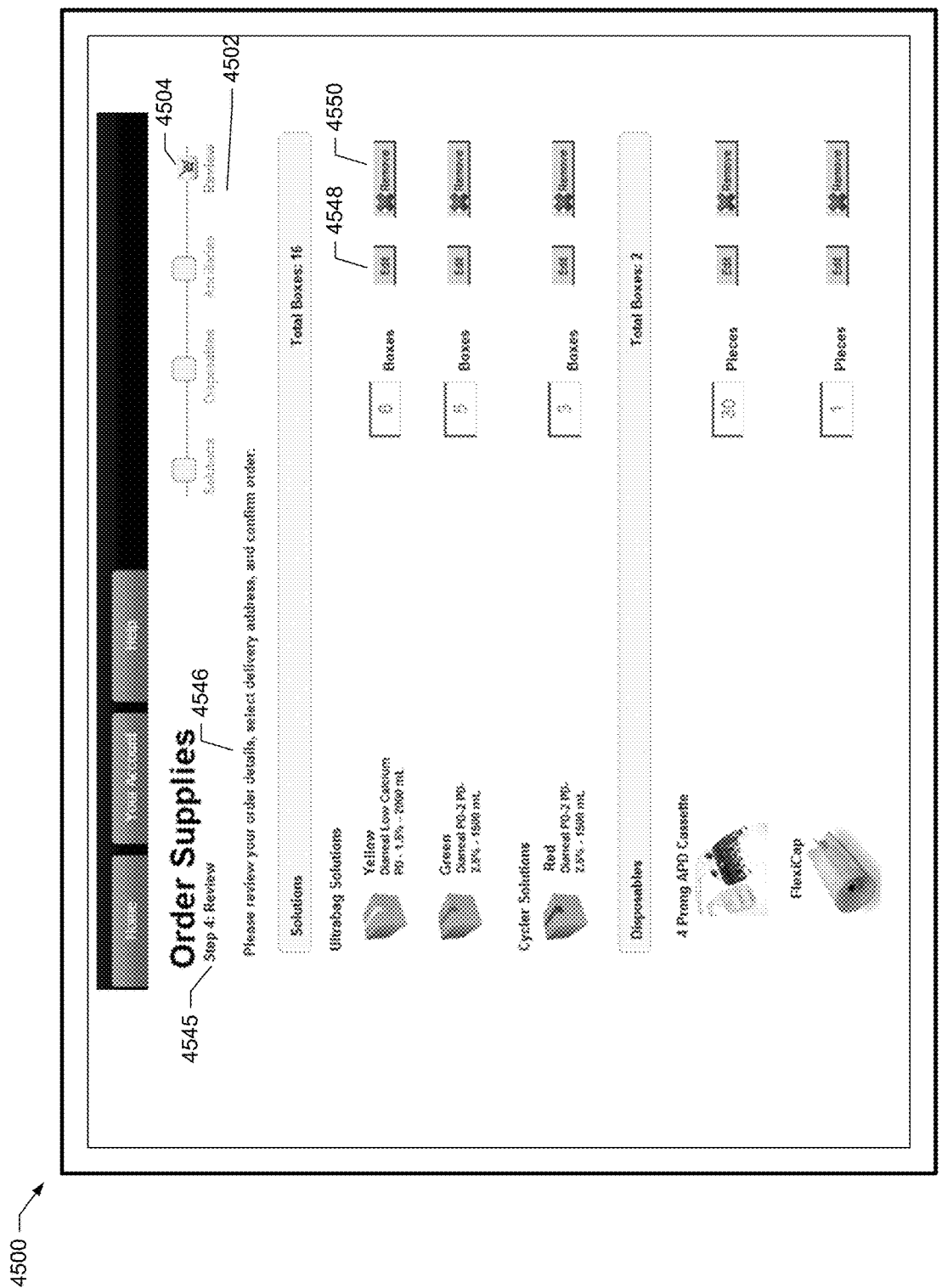
FIG. 45F is a screen shot of still another example patient order screen for a patient of the present disclosure.
Figure 45G:
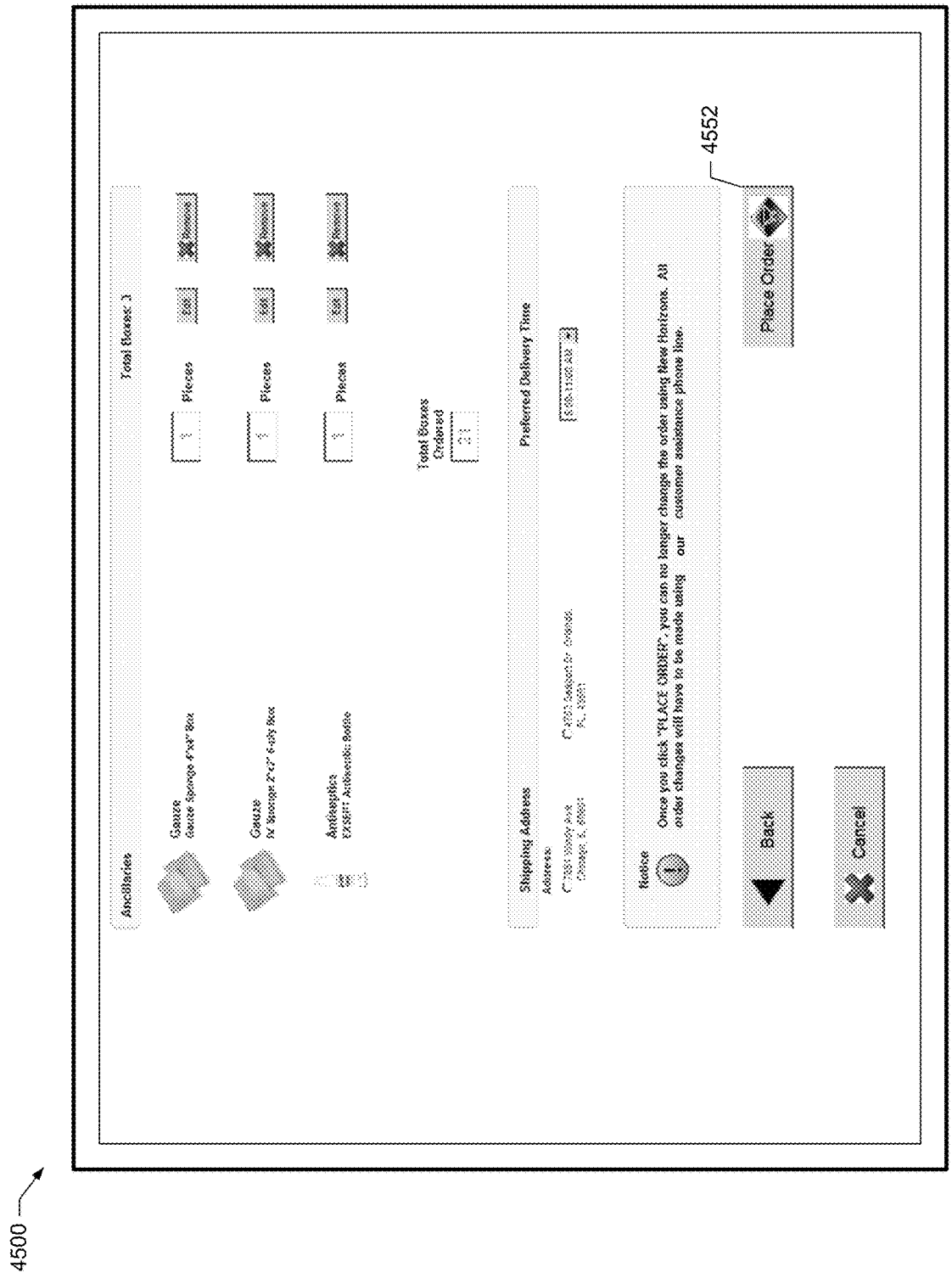
FIG. 45G is a screen shot of still a further example patient order screen for a patient of the present disclosure.

FIG. 45F illustrates a further example screen shot of order screen 4500 displayed on tablet 122 or dedicated display device of machine 100. Item 4545 indicates that the patient is now at step 4, review. Timeline 4502 indicates that cart icon 4504 is in the review step along timeline 4502. On this screen, the user can review order details, select a delivery address and confirm the order as indicated at message 4546. The user can edit an order item using edit button 4548 or remove an order item by using remove button 4550. FIG. 45G continues the example screen shot of FIG. 45F for order screen 4500. Here, the user can press button 4552 to place the order.

Figure 46A:
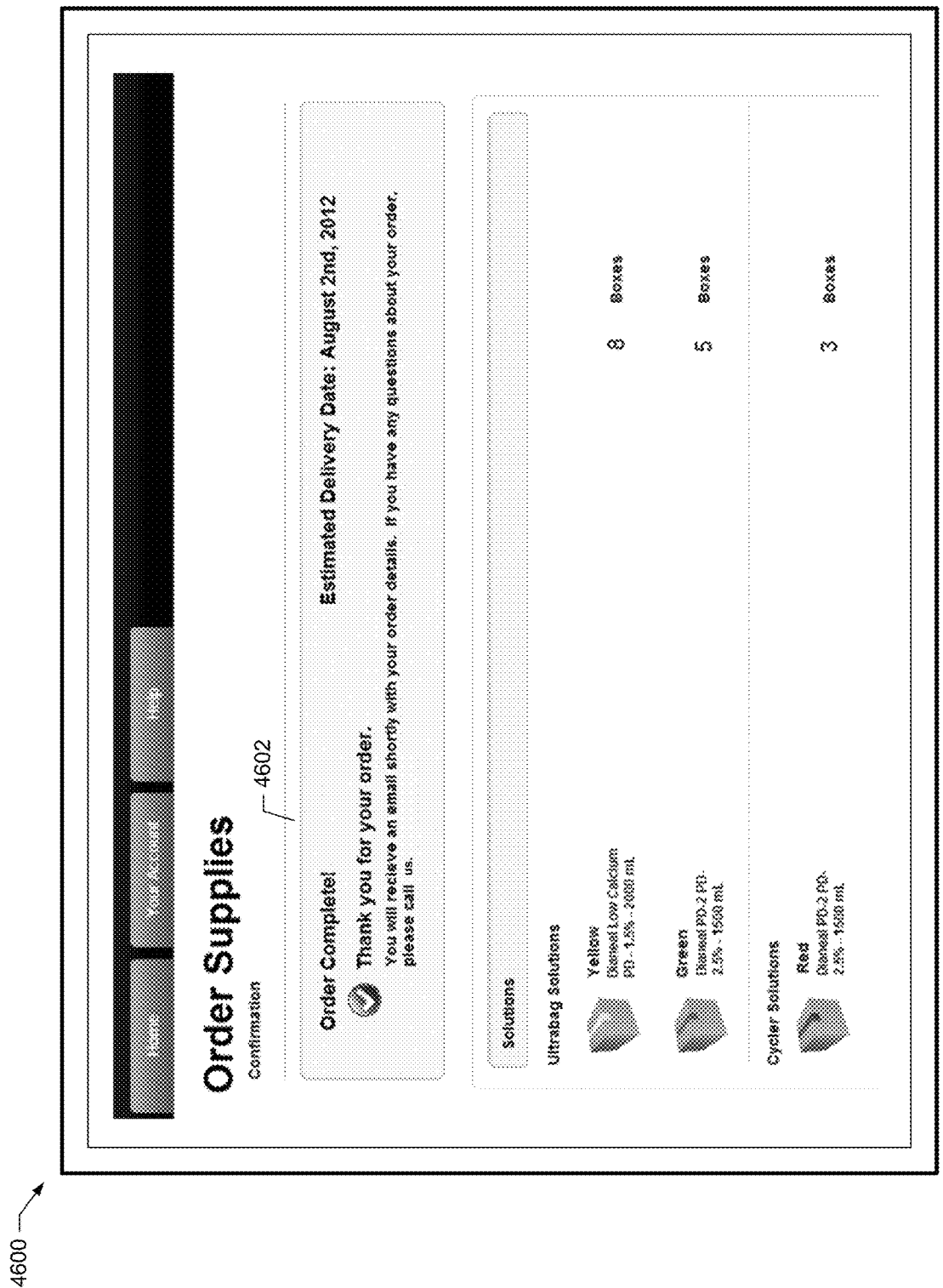
FIG. 46A is a screen shot of an example confirmation screen of the present disclosure.
Figure 46B:
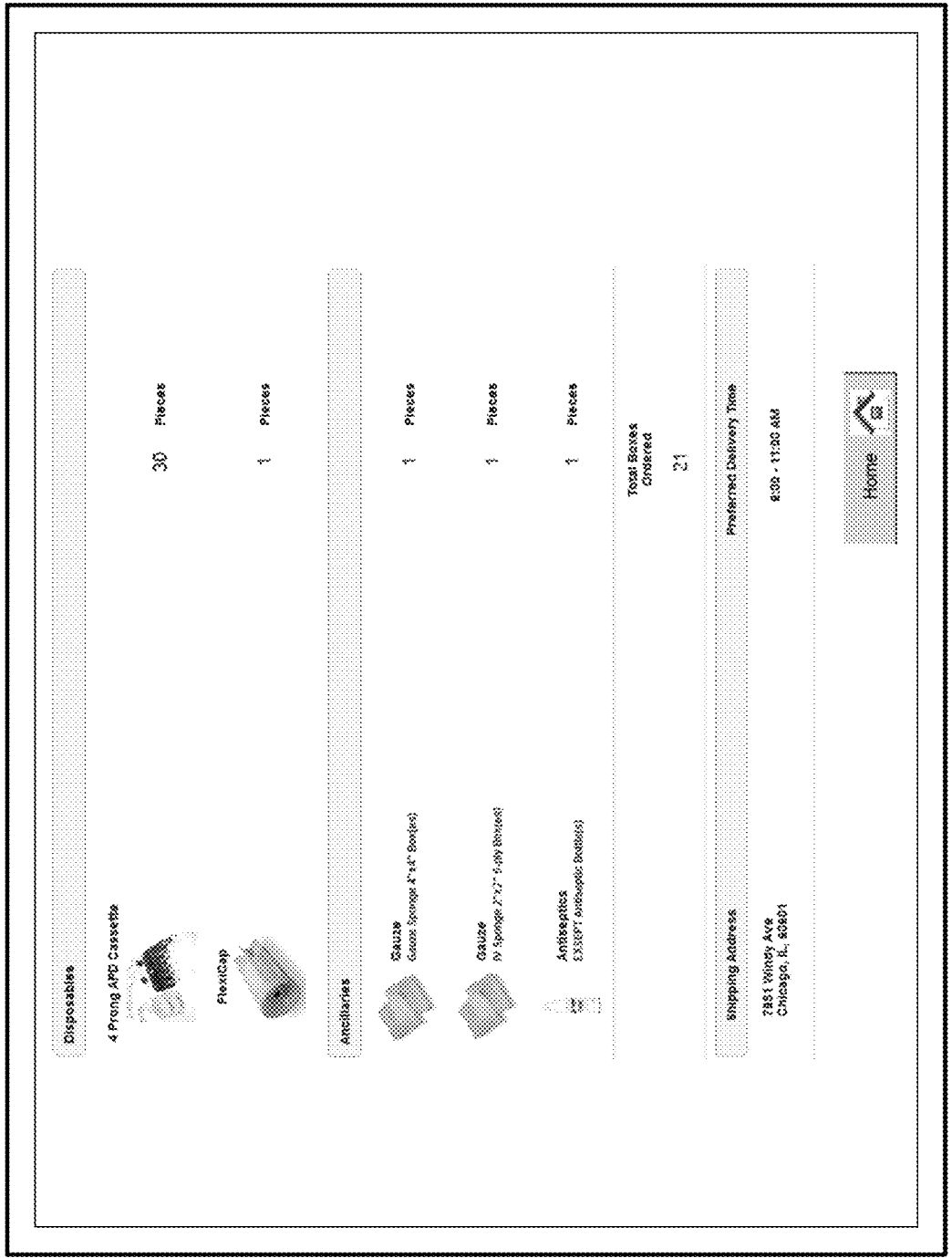
FIG. 46B is a screen shot of another example confirmation screen of the present disclosure.

FIG. 46A illustrates an example screen shot of a supply order confirmation screen 4600 that may be displayed on user tablet 122 or dedicated display device of machine 100. Confirmation screen 4600 provides a message 4602 that the order is complete and recounts all items ordered. FIG. 46B continues the example screen shot of confirmation screen 4600.

Additional Aspects of the Present Disclosure

Aspects of the subject matter described herein may be useful alone or in combination with any one or more of the other aspect described herein. Without limiting the foregoing description, in a first aspect of the present disclosure, a home medical device system comprising: a plurality of home therapy machines that perform a home therapy on a patient; a connectivity server; a system hub coupled to the home therapy machines through the connectivity server; a web portal configured to access the system hub; a plurality of clinics connected to the system hub via the web portal; and a website accessible via the web portal, the website including a patient portion available to patients using the plurality of home therapy machines, the website further including a clinician portion that enables the clinics to manage the home therapy machines.

In a second aspect of the present disclosure, which may be used in combination with any one, or more, or all of the other aspects described herein, the home therapy includes renal therapy.

In a third aspect of the present disclosure, which may be used in combination with any one, or more, or all of the other aspects described herein, the renal therapy includes any one or more of hemodialysis, peritoneal dialysis, hemofiltration, hemodiafiltration, or continuous renal replacement.

In a fourth aspect of the present disclosure, which may be used in combination with any one, or more, or all of the other aspects described herein, the home therapy machine is of at least one type selected from the group consisting of: (i) a hemodialysis machine, (ii) a peritoneal dialysis machine, (iii) a hemofiltration machine, (iv) a hemodiafiltration machine, (v) a continuous renal replacement machine, (vi) a medical delivery machine, or (vii) a machine running a nutritional therapy.

In a fifth aspect of the present disclosure, which may be used in combination with any one, or more, or all of the other aspects described herein, each home therapy machine generates log files documenting treatments performed by the home therapy machine and sends the log files to the system hub through the connectivity server.

In a sixth aspect of the present disclosure, which may be used in combination with any one, or more, or all of the other aspects described herein, the connectivity server receives and stores data from the clinics until corresponding home therapy machines are turned on, after which the data is transferred to the corresponding home therapy machines.

In a seventh aspect of the present disclosure, which may be used in combination with any one, or more, or all of the other aspects described herein, the system is configured such that if the data transferred includes a new device program, the patient for the corresponding home therapy machine must accept the new device program before the new device program is performed by the corresponding home therapy machine.

In an eighth aspect of the present disclosure, which may be used in combination with any one, or more, or all of the other aspects described herein, the clinician portion of the website includes a therapy prescription screen for specifying supplies needed at the patient's home for operating one of the home therapy machines.

In a ninth aspect of the present disclosure, which may be used in combination with any one, or more, or all of the other aspects described herein, the clinician portion of the website includes a device program screen for setting parameters by which one of the home therapy machines operates.

In a tenth aspect of the present disclosure, which may be used in combination with any one, or more, or all of the other aspects described herein, the device program screen allows the parameters to be set differently in different device programs for the same home therapy machine and patient.

In an eleventh aspect of the present disclosure, which may be used in combination with any one, or more, or all of the other aspects described herein, at least one of the parameters is set as a range, and wherein the patient is enabled to choose within the range for operation with the home therapy machine.

In a twelfth aspect of the present disclosure, which may be used in combination with any one, or more, or all of the other aspects described herein, the device program screen allows for a template to be recalled for populating a plurality of the parameters with preselected values.

In a thirteenth aspect of the present disclosure, which may be used in combination with any one, or more, or all of the other aspects described herein, the clinician portion of the website includes a patient settings screen, the patient settings screen enabling clinicians to set at least one treatment display aspect.

In a fourteenth aspect of the present disclosure, which may be used in combination with any one, or more, or all of the other aspects described herein, the clinician portion of the website includes a clinician dashboard including a list of patients; and a notification associated with each patient indicating whether a predefined treatment condition or alert occurred during a treatment.

In a fifteenth aspect of the present disclosure, which may be used in combination with any one, or more, or all of the other aspects described herein, the dashboard associates each patient in the list of patients with at least one of (i) a treatment summary providing detailed treatment data about the patient or (ii) a patient snapshot providing historical treatment data about the patient.

In a sixteenth aspect of the present disclosure, which may be used in combination with any one, or more, or all of the other aspects described herein, the system includes a product development client in communication with the system hub, the product development client capable of providing a firmware upgrade that can be downloaded over the system hub and the connectivity server to the home therapy machine.

In a seventeenth aspect of the present disclosure, which may be used in combination with any one, or more, or all of the other aspects described herein, the system includes a service personnel director in communication with the system hub, the service personnel director enabled to approve the firmware upgrade for one or more of the plurality of home therapy machines before the firmware upgrade is downloaded to the approved home therapy machine.

In an eighteenth aspect of the present disclosure, which may be used in combination with any one, or more, or all of the other aspects described herein, the system includes at least one service personnel in communication with the system hub, each service personnel dedicated to at least one of the plurality of home therapy machines, the at least one service personnel enabled to determine when the firmware upgrade, after approval by the service personnel director, is delivered to the at least one dedicated home therapy machine.

In a nineteenth aspect of the present disclosure, which may be used in combination with any one, or more, or all of the other aspects described herein, the connectivity server is configured to provide a check that at least one of (i) all data in a packet of data is actually sent or (ii) data is sent to the proper home therapy machine.

In a twentieth aspect of the present disclosure, any one, or more, or all of the first to nineteenth aspects may be used in combination with any one, or more, or all of the other of the first to nineteenth aspects.

In a twenty-first aspect of the present disclosure, which may be used in combination with any one, or more, or all of the other aspects described herein, a method for personalizing a therapy machine includes: generating a unique patient ID for a patient; generating information about the patient, the information including therapy machine settings based upon a prescription; and linking the therapy machine to the patient by entering the patient ID and a second patient identifier into the therapy machine, the linking causing the information to be sent to the therapy machine.

In a twenty-second aspect of the present disclosure, which may be used in combination with any one, or more, or all of the other aspects described herein, the therapy machine is a second therapy machine, and further comprising: providing a first therapy machine in a clinic; training a patient to operate the first therapy machine to perform a renal therapy in the clinic; and sending the second therapy machine to the patient's home, the linking occurring after sending the second therapy machine to the patient's home.

In a twenty-third aspect of the present disclosure, which may be used in combination with any one, or more, or all of the other aspects described herein, a clinician enters the patient ID into the second therapy machine.

In a twenty-fourth aspect of the present disclosure, which may be used in combination with any one, or more, or all of the other aspects described herein, the therapy machine is a second therapy machine, and wherein the linking is performed after a first therapy machine used by a patient malfunctions.

In a twenty-fifth aspect of the present disclosure, which may be used in combination with any one, or more, or all of the other aspects described herein, the second patient identifier is the patient's birth date.

In a twenty-sixth aspect of the present disclosure, which may be used in combination with any one, or more, or all of the other aspects described herein, the second therapy machine operates initially according to the therapy machine settings.

In a twenty-seventh aspect of the present disclosure, any one, or more, or all of the twenty-first to twenty-sixth aspects may be used in combination with any one, or more, or all of the other of the twenty-first to twenty-sixth aspects.

In a twenty-eighth aspect of the present disclosure, which may be used in combination with any one, or more, or all of the other aspects described herein, a method for performing renal therapy at a home or dwelling of a patient using a renal therapy machine includes: retrieving a doctor's prescription for renal therapy; based on the doctor's prescription, selecting supplies, including a dialyzer, at a first location other than the patient's home; and sending the supplies and the renal therapy machine to the patient's home or dwelling.

In a twenty-ninth aspect of the present disclosure, which may be used in combination with any one, or more, or all of the other aspects described herein, a method for performing renal therapy at a home of a patient using a renal therapy machine includes: retrieving a doctor's prescription for renal therapy; based on the doctor's prescription, selecting settings at a first location other than the patient's home or dwelling for operating the renal therapy machine; and performing renal therapy on the patient according to the settings.

In a thirtieth aspect of the present disclosure, which may be used in combination with any one, or more, or all of the other aspects described herein, the method further includes: modifying the settings at the first location for operating the renal therapy machine; and performing renal therapy on the patient at the patient's home or dwelling according to the modified settings.

In a thirty-first aspect of the present disclosure, which may be used in combination with any one, or more, or all of the other aspects described herein, the settings include a parameter and an allowed range of values for the parameter.

In a thirty-second aspect of the present disclosure, which may be used in combination with any one, or more, or all of the other aspects described herein, the settings further include a patient editable setting for the parameter, and wherein if the patient editable setting is enabled, the patient can modify the value of the parameter within the allowed range of values for the parameter.

In a thirty-third aspect of the present disclosure, any one, or more, or all of the twenty-ninth to thirty-second aspects may be used in combination with any one, or more, or all of the other of the twenty-ninth to thirty-second aspects.

In a thirty-fourth aspect of the present disclosure, which may be used in combination with any one, or more, or all of the other aspects described herein, a method for operating a home therapy machine includes: performing treatment using the home therapy machine; storing log files relating to the treatment; and using system communications to send the log files to a connectivity server.

In a thirty-fifth aspect of the present disclosure, which may be used in combination with any one, or more, or all of the other aspects described herein, the method further includes: before performing the treatment using the home therapy machine, querying the connectivity server for updated settings for the home therapy machine; and if updated settings exist, sending the updated settings to the home therapy machine via system communications.

In a thirty-sixth aspect of the present disclosure, which may be used in combination with any one, or more, or all of the other aspects described herein, the method includes performing at least one post-treatment operation after storing the log files relating to the treatment and before sending the log files to the connectivity server.

In a thirty-seventh aspect of the present disclosure, any one, or more, or all of the thirty-fourth to thirty-sixth aspects may be used in combination with any one, or more, or all of the other of the thirty-fourth to thirty-sixth aspects.

In a thirty-eighth aspect of the present disclosure, which may be used in combination with any one, or more, or all of the other aspects described herein, a method of upgrading firmware on a home therapy machine includes: generating upgraded firmware for a plurality of home therapy machines; approving the upgraded firmware for the plurality of home therapy machines; uploading the upgraded firmware to a first location; determining which of the approved home therapy machines should receive the upgraded firmware; and for each home therapy machine that should receive the upgraded firmware (i) uploading the upgraded firmware from the first location to a connectivity server associated with each home therapy machine that should receive the upgraded firmware; (ii) selecting a time to send the upgraded firmware to each home therapy machine that should receive the upgraded firmware; and (iii) sending the upgraded firmware at the selected time from the connectivity server to each home therapy machine that should receive the upgraded firmware.

In a thirty-ninth aspect of the present disclosure, which may be used in combination with any one, or more, or all of the other aspects described herein, the method includes prompting each patient associated with the home therapy machines receiving the upgraded firmware whether to install the upgraded firmware.

In a fortieth aspect of the present disclosure, which may be used in combination with any one, or more, or all of the other aspects described herein, the method includes a determination by the home therapy machines receiving the upgraded firmware whether to install the upgraded firmware.

In a forty-first aspect of the present disclosure, which may be used in combination with any one, or more, or all of the other aspects described herein, the method includes prompting each patient associated with the home therapy machines receiving the upgraded firmware to approve installing the upgraded firmware and a determination by the home therapy machines receiving the upgraded firmware whether the upgraded firmware has been approved.

In a forty-second aspect of the present disclosure, any one, or more, or all of the thirty-eighth to forty-first aspects may be used in combination with any one, or more, or all of the other of the thirty-eighth to forty-first aspects.

In a forty-third aspect of the present disclosure, which may be used in combination with any one, or more, or all of the other aspects described herein, a therapy entry, modification and reporting system includes: a website for displaying therapy entry, modification and reporting information; and a system hub for managing a flow of the information between the website and a plurality of home therapy machines that perform a home therapy on a patient, wherein the website includes a therapy prescription screen for specifying supplies needed at the patient's home for operating one of the home therapy machines, a device program screen for setting parameters by which one of the home therapy machines operates, and a clinician dashboard having a list of patients and a notification associated with each patient indicating whether a predefined treatment condition or alert occurred during a treatment.

In a forty-fourth aspect of the present disclosure, which may be used in combination with any one, or more, or all of the other aspects described herein, the device program screen includes a first parameter and a second parameter, and wherein values that can be entered into the second parameter depend upon values entered into the first parameter.

In a forty-fifth aspect of the present disclosure, which may be used in combination with any one, or more, or all of the other aspects described herein, the device program screen is a first device program screen, and which includes a second device program screen, wherein the first parameter appears on the first device program screen and the second parameter appears on the second device program screen.

In a forty-sixth aspect of the present disclosure, which may be used in combination with any one, or more, or all of the other aspects described herein, a clinician's access to the second device program screen depends upon values entered into parameters on the first device program screen.

In a forty-seventh aspect of the present disclosure, any one, or more, or all of the forty-third to forty-sixth aspects may be used in combination with any one, or more, or all of the other of the forty-third to forty-sixth aspects.

In a forty-eighth aspect of the present disclosure, which may be used in combination with any one, or more, or all of the other aspects described herein, a method of verifying supplies used by a home therapy machine having a user interface includes retrieving a doctor's prescription for home therapy; connecting a supply to the home therapy machine, the supply including a code indicating information about the supply; obtaining the code using the user interface of the home therapy machine; determining the information about the supply from the obtained code; comparing the determined information about the supply with the prescription; and performing home therapy if the determined information about the supply comports with the prescription.

In a forty-ninth aspect of the present disclosure, which may be used in combination with any one, or more, or all of the other aspects described herein, the supply includes a container of a medical substance, wherein the prescription includes a concentration of the medical substance that should be used in the home therapy, and wherein the code indicates the actual concentration of the medical substance in the container.

In a fiftieth aspect of the present disclosure, which may be used in combination with any one, or more, or all of the other aspects described herein, the supply includes a dialyzer, wherein the prescription includes a type of dialyzer, and wherein the code indicates the type of dialyzer.

In a fifty-first aspect of the present disclosure, which may be used in combination with any one, or more, or all of the other aspects described herein, the user interface communicates wirelessly with the home therapy machine.

In a fifty-second aspect of the present disclosure, which may be used in combination with any one, or more, or all of the other aspects described herein, the user interface includes a camera operable to read the code.

In a fifty-third aspect of the present disclosure, any one, or more, or all of the forty-eighth to fifty-second aspects may be used in combination with any one, or more, or all of the other of the forty-eighth to fifty-second aspects.

In a fifty-fourth aspect of the present disclosure, which may be used in combination with any one, or more, or all of the other aspects described herein, a computer readable medium storing instructions is structured to cause a home therapy machine to: allow patient selection of a prescription from a plurality of prescriptions stored on the home therapy machine; perform treatment using the home therapy machine according to the selected prescription; disinfect the home therapy machine; and generate log files documenting the treatment performed by the home therapy machine.

In a fifty-fifth aspect of the present disclosure, which may be used in combination with any one, or more, or all of the other aspects described herein, the instructions are further structured to cause the home therapy machine to: send the log files to a system hub; and query the system hub for at least one of (i) an update for one of the prescriptions from the plurality of prescriptions or (ii) a new prescription.

In a fifty-sixth aspect of the present disclosure, which may be used in combination with any one, or more, or all of the other aspects described herein, the instructions are further structured to cause the home therapy machine to receive data from at least one of a water treatment device, a weight scale, a blood pressure cuff, or a tablet.

In a fifty-seventh aspect of the present disclosure, which may be used in combination with any one, or more, or all of the other aspects described herein, the home therapy machine is connected wirelessly to at least one of the weight scale, the blood pressure cuff, or the tablet.

In a fifty-eighth aspect of the present disclosure, any one, or more, or all of the fifty-fourth to fifty-seventh aspects may be used in combination with any one, or more, or all of the other of the fifty-fourth to fifty-seventh aspects.

In a fifty-ninth aspect of the present disclosure, which may be used in combination with any one, or more, or all of the other aspects described herein, a computer readable medium storing instructions is structured to cause a computing device to display a clinician user interface that enables a clinician to manage a plurality of home therapy machines, the clinician user interface including (i) a device program screen for setting parameters by which one of the home therapy machines performs treatments, and a clinician dashboard including (a) a list of patients, and (b) a notification associated with each patient indicating whether a predefined condition occurred during a treatment.

In a sixtieth aspect of the present disclosure, which may be used in combination with any one, or more, or all of the other aspects described herein, the instructions are further structured to cause the computing device to store a first value entered into a first parameter on the device program screen, and determine, based upon the first value, whether a second value can be entered into a second parameter on the device program screen.

In a sixty-first aspect of the present disclosure, which may be used in combination with any one, or more, or all of the other aspects described herein, the instructions are further structured to cause the computing device to store templates that can be recalled for populating preselected values into at least one of the device program screen, a therapy prescription screen for ordering supplies for one of the home therapy machines, a patient settings screen for controlling how treatments appear to patients, or a system settings screen for controlling settings other than how treatments are performed on the home therapy machines.

In a sixty-second aspect of the present disclosure, which may be used in combination with any one, or more, or all of the other aspects described herein, the instructions are further structured to cause the computing device to display a rules screen listing treatment events that can occur during the treatments, store conditions related to the treatment events entered by the clinician into the rules screen, and evaluate log files received from the home therapy machines based upon the conditions to generate the notification.

In a sixty-third aspect of the present disclosure, which may be used in combination with any one, or more, or all of the other aspects described herein, the instructions are further structured to cause the computing device to display an indicator indicating whether the same or a different clinician has reviewed the condition associated with the notification In a sixty-fourth aspect of the present disclosure, any one, or more, or all of the fifty-ninth to sixty-third aspects may be used in combination with any one, or more, or all of the other of the fifty-ninth to sixty-third aspects.

In a sixty-fifth aspect any of the structure and functionality illustrated and described in connection with FIGS. 1 to 46B may be used in combination with any aspect or combination of aspects listed herein.

It should be understood that various changes and modifications to the presently preferred embodiments described herein will be apparent to those skilled in the art. Such changes and modifications can be made without departing from the spirit and scope of the present subject matter and The invention is claimed as follows:

1. A renal therapy system comprising:
a dialysis fluid pump;
a control processor for controlling a treatment performed by the dialysis fluid pump, the control processor configured to operate using a current version of firmware;
a user interface device in operable communication with the control processor, the user interface device including a display and an input device configured to receive a patient selection; and
a connectivity agent communicatively coupled to a remotely located connectivity server via a network, the connectivity agent including an activated mode and a deactivated mode, the connectivity agent configured to after transitioning from the deactivated mode to the activated mode, transmit a message indicative of the activated mode to the connectivity server causing the connectivity server to transmit a new version of firmware,
wherein the connectivity agent is in the deactivated mode while the control processor controls a treatment performed by the dialysis fluid pump.

2. The renal therapy system of claim 1, wherein when the connectivity agent is in the deactivated mode, the connectivity agent is unable to receive the new version of firmware from the connectivity server.

3. The renal therapy system of claim 1, wherein the control processor is configured to operate using the new version of firmware.

4. The renal therapy system of claim 1, wherein the user interface device is configured to cause the display to show a prompt for a patient to install the new version of firmware, and
wherein the input device is configured to receive the patient selection causing the new version of firmware to replace the current version of firmware.

5. The renal therapy system of claim 1, wherein the control processor causes the new version of firmware to replace the current version of firmware.

6. The renal therapy system of claim 5, wherein the control processor is configured to:
determine the new version of firmware is corrupt; and
revert back to the current version of firmware.

7. The renal therapy system of claim 6, wherein the control processor determines the new version of firmware is corrupt after at least one treatment is performed by the dialysis fluid pump.

8. The renal therapy system of claim 1, wherein the connectivity agent is communicatively coupled to a user device, and
wherein the connectivity agent receives the new version of firmware from the connectivity server via the user device when the connectivity agent is in the activated mode.

9. The renal therapy system of claim 8, wherein the user device includes at least one of a smartphone or a tablet computer.

10. The renal therapy system of claim 1, wherein the dialysis fluid pump, the control processor, the user interface device and the connectivity agent are included within at least one of (i) a hemodialysis machine, (ii) a peritoneal dialysis machine, (iii) a hemofiltration machine, (iv) a hemodiafiltration machine, (v) a continuous renal replacement machine, (vi) a medical fluid delivery machine, or (vii) a machine running a nutritional therapy.

11. A method for upgrading firmware on a renal therapy machine, the method comprising:
receiving, in a connectivity server, a new version of firmware;
receiving, in the connectivity server, identifiers of renal therapy machines that are to receive the new version of firmware;
receiving, in the connectivity server, a message from a connectivity agent of a renal therapy machine indicative that the renal therapy machine is in an activated mode, the message including an identifier of the renal therapy machine;
determining, via the connectivity server, the identifier of the renal therapy machine matches at least one of the identifiers of renal therapy machines that are to receive the new version of firmware; and
transmitting, via the connectivity server, the new version of firmware to the renal therapy machine causing the renal failure machine to operate using the new version of firmware instead of a current version of firmware,
wherein the connectivity agent includes a deactivated mode where the connectivity server is unable to transmit the new version of firmware while the renal therapy machine is performing a treatment.

12. The method of claim 11, further comprising:
determining, via the connectivity server, the renal therapy machine is scheduled to undergo maintenance; and
refraining from transmitting the new version of firmware to the renal therapy machine until indications are received of the maintenance being completed and the renal therapy machine being in the activated mode.

13. The method of claim 11, wherein the identifiers of renal therapy machines that are to receive the new version of firmware are associated with at least one of a geographic location or a model number.

14. The method of claim 11, further comprising:
receiving, in the connectivity server from the connectivity agent of the renal therapy machine, an indication the new version of firmware was installed; and
storing, via the connectivity server, the indication to a firmware log.

15. The method of claim 11, further comprising:
receiving, in the connectivity server from the connectivity agent of the renal therapy machine, an indication the new version of firmware is corrupt; and
storing, via the connectivity server, the indication to a firmware log.

16. The method of claim 11, further comprising:
receiving, in the connectivity server from the connectivity agent of the renal therapy machine, an indication a patient has not accepted the new version of firmware; and
storing, via the connectivity server, the indication to a firmware log.

17. The method of claim 11, wherein the new version of firmware is received by the connectivity server from a system hub after the new version of firmware has been approved for distribution.

18. The method of claim 11, further comprising transmitting, via the connectivity server, an indication of the new version of firmware to service personnel that are associated with the renal therapy machine.

19. The method of claim 11, wherein the connectivity server is communicatively coupled to a user device, and wherein the connectivity server transmits the new version of firmware to the user device for transferring to the connectivity agent of the renal therapy machine.

20. The method of claim 11, wherein the renal therapy machine includes at least one of (i) a hemodialysis machine, (ii) a peritoneal dialysis machine, (iii) a hemofiltration machine, (iv) a hemodiafiltration machine, (v) a continuous renal replacement machine, (vi) a medical fluid delivery machine, or (vii) a machine running a nutritional therapy.

* * * * *